US009006487B2

(12) United States Patent
Anderson et al.

(10) Patent No.: US 9,006,487 B2
(45) Date of Patent: Apr. 14, 2015

(54) AMINE-CONTAINING LIPIDS AND USES THEREOF

(75) Inventors: Daniel G. Anderson, Framingham, MA (US); Andreas Zumbuehl, Cambridge, MA (US); Elizaveta Sergeyevna Leshchiner (Turkhanova), Watertown, MA (US); Robert S. Langer, Newton, MA (US); Michael Goldberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 846 days.

(21) Appl. No.: 11/453,222

(22) Filed: Jun. 14, 2006

(65) Prior Publication Data

US 2011/0009641 A1 Jan. 13, 2011

Related U.S. Application Data

(60) Provisional application No. 60/690,608, filed on Jun. 15, 2005, provisional application No. 60/785,176, filed on Mar. 23, 2006.

(51) Int. Cl.
| | | |
|---|---|---|
| C07C 239/00 | (2006.01) |
| C07C 229/00 | (2006.01) |
| C12N 15/88 | (2006.01) |
| A61K 31/785 | (2006.01) |
| C07B 53/00 | (2006.01) |
| G01N 33/92 | (2006.01) |
| A61K 48/00 | (2006.01) |
| A61K 9/16 | (2006.01) |
| C07C 229/12 | (2006.01) |
| C07C 229/14 | (2006.01) |
| C07C 229/16 | (2006.01) |
| C07C 229/18 | (2006.01) |
| C07C 237/06 | (2006.01) |
| C07D 211/26 | (2006.01) |
| C07D 233/61 | (2006.01) |
| C07D 243/08 | (2006.01) |
| C07D 295/12 | (2006.01) |
| C07D 307/14 | (2006.01) |
| C07D 317/28 | (2006.01) |

(52) U.S. Cl.
CPC ............ *A61K 48/0033* (2013.01); *A61K 9/1617* (2013.01); *C07C 229/12* (2013.01); *C07C 229/14* (2013.01); *C07C 229/16* (2013.01); *C07C 229/18* (2013.01); *C07C 237/06* (2013.01); *C07D 211/26* (2013.01); *C07D 233/61* (2013.01); *C07D 243/08* (2013.01); *C07D 295/12* (2013.01); *C07D 307/14* (2013.01); *C07D 317/28* (2013.01); *C12N 15/88* (2013.01)

(58) Field of Classification Search
USPC ........................................................ 564/197
See application file for complete search history.

(56) References Cited

U.S. PATENT DOCUMENTS

| 2,647,121 | A | * | 7/1953 | Jacoby .......................... 544/400 |
| 2,717,909 | A | | 9/1955 | Kosmin |
| 2,819,718 | A | | 1/1958 | Goldman |
| 2,844,629 | A | | 7/1958 | William et al. |
| 3,096,560 | A | | 7/1963 | Liebig |
| 3,535,289 | A | | 10/1970 | Yoshihara et al. |
| 3,614,954 | A | | 10/1971 | Mirowski et al. |
| 3,614,955 | A | | 10/1971 | Mirowski |
| 3,656,185 | A | | 4/1972 | Carpentier |
| 3,805,301 | A | | 4/1974 | Liebig |
| 3,945,052 | A | | 3/1976 | Liebig |
| 3,995,623 | A | | 12/1976 | Blake et al. |
| 4,013,507 | A | | 3/1977 | Rembaum |
| 4,072,146 | A | | 2/1978 | Howes |
| 4,096,860 | A | | 6/1978 | McLaughlin |
| 4,099,528 | A | | 7/1978 | Sorenson et al. |
| 4,106,129 | A | | 8/1978 | Carpentier et al. |
| 4,134,402 | A | | 1/1979 | Mahurkar |

(Continued)

FOREIGN PATENT DOCUMENTS

| CA | 2518132 A1 | 3/2006 |
| DE | 2430998 A1 | 1/1975 |

(Continued)

OTHER PUBLICATIONS

Martell et al., Journal of the American Chemical Society (1950), 72, 5357-61.*
Database CAS Online on STN. Chem. Abstr., Accession No. 1965:44520, FR 1378382, Hofer et al, Nov. 13, 1964, abstract.*
Li et al. Macromolecules (2003) 36(16) 6028-6035.*
Bourque et al. J. Am. Chem. Soc. (2000), 122, 956-957.*
Allison, The mode of action of immunological adjuvants. Dev Biol Stand. 1998;92:3-11. Review.
Anderson, Human gene therapy. Nature. Apr. 30, 1998;392(6679 Suppl):25-30. Review.
Behr et al., Synthetic gene-transfer vectors. Acc Chem Res. 1993;26:274-278.

(Continued)

*Primary Examiner* — Nyeemah A Grazier
(74) *Attorney, Agent, or Firm* — Wolf, Greenfield & Sacks, P.C.; C. Hunter Baker; Wei Zhang

(57) ABSTRACT

Nitrogen-containing lipids prepared from the conjugate addition of amines to acrylates, acrylamides, or other carbon-carbon double bonds conjugated to electron-withdrawing groups are described. Methods of preparing these lipids from commercially available starting materials are also provided. These amine-containing lipids or salts forms of these lipids are preferably biodegradable and biocompatible and may be used in a variety of drug delivery systems. Given the amino moiety of these lipids, they are particularly suited for the delivery of polynucleotides. Complexes or nanoparticles containing the inventive lipid and polynucleotide have been prepared. The inventive lipids may also be used to in preparing microparticle for drug delivery. They are particularly useful in delivering labile agents given their ability to buffer the pH of their surroundings.

25 Claims, 7 Drawing Sheets

(56) References Cited

U.S. PATENT DOCUMENTS

| | | |
|---|---|---|
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,946,857 A | 8/1990 | Kanehira et al. |
| 4,960,409 A | 10/1990 | Catalano |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,176,661 A | 1/1993 | Evard et al. |
| 5,197,977 A | 3/1993 | Hoffman, Jr. et al. |
| 5,200,395 A | 4/1993 | Eto et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A * | 12/1997 | Fujii et al. ............ 423/220 |
| 5,736,573 A | 4/1998 | Galat |
| 5,772,694 A | 6/1998 | Bokros et al. |
| 5,776,165 A | 7/1998 | Ripart |
| 5,776,747 A | 7/1998 | Schinstine et al. |
| 5,874,105 A | 2/1999 | Watkins et al. |
| 5,910,168 A | 6/1999 | Myers et al. |
| 5,916,208 A | 6/1999 | Luther et al. |
| 5,976,569 A | 11/1999 | Milstein |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,696,424 B1 | 2/2004 | Wheeler |
| 6,756,055 B2 | 6/2004 | McDonald et al. |
| 6,821,530 B2 | 11/2004 | Koob et al. |
| 6,887,665 B2 | 5/2005 | Trulson et al. |
| 7,022,214 B2 | 4/2006 | Olech |
| 7,084,303 B2 | 8/2006 | Watanabe et al. |
| 7,507,859 B2 | 3/2009 | Grinstaff et al. |
| 7,556,684 B2 | 7/2009 | Bury et al. |
| 7,972,435 B2 | 7/2011 | Bury et al. |
| 8,450,298 B2 | 5/2013 | Mahon et al. |
| 2002/0022721 A1 | 2/2002 | Trulson et al. |
| 2002/0094528 A1 | 7/2002 | Salafsky |
| 2002/0192721 A1 | 12/2002 | Rizzuto et al. |
| 2002/0193622 A1 | 12/2002 | Watanabe et al. |
| 2003/0215395 A1 | 11/2003 | Yu et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0228404 A1 | 10/2006 | Anderson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |
| 2010/0331234 A1 | 12/2010 | Mahon et al. |
| 2011/0293703 A1 | 12/2011 | Mahon et al. |
| 2012/0009222 A1 | 1/2012 | Nguyen et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0161830 A1 | 6/2014 | Anderson et al. |

FOREIGN PATENT DOCUMENTS

| | | |
|---|---|---|
| EP | 1 912 679 A2 | 4/2008 |
| EP | 2 045 251 A1 | 4/2009 |
| EP | 2 476 756 A1 | 7/2012 |
| FR | 1 378 382 | 11/1964 |
| FR | 2235112 A1 | 1/1975 |
| GB | 1072118 A | 6/1967 |
| JP | S48-022365 | 3/1973 |
| JP | S49-127908 A | 12/1974 |
| JP | 50-24216 A | 3/1975 |
| JP | S51-023537 A | 2/1976 |
| JP | 51-125144 | 11/1976 |
| JP | S52-010847 A | 1/1977 |
| JP | 63-125144 | 5/1988 |
| JP | 63-154788 A | 6/1988 |
| JP | 4108173 A | 4/1992 |
| JP | H07-053535 A | 2/1995 |
| JP | H09-505593 A | 6/1997 |
| JP | 11-005786 A | 1/1999 |
| JP | 11-080142 A | 3/1999 |
| JP | 2001-523215 A | 11/2001 |
| JP | 2002-167368 A | 6/2002 |
| JP | 2003-519199 A | 6/2003 |
| WO | WO 93/18229 A1 | 9/1993 |
| WO | WO 93/18754 A1 | 9/1993 |
| WO | WO 95/11004 A1 | 4/1995 |
| WO | WO 95/14651 A1 | 6/1995 |
| WO | WO 96/26179 A1 | 8/1996 |

(56) References Cited

FOREIGN PATENT DOCUMENTS

| | | |
|---|---|---|
| WO | WO 96/36314 A2 | 11/1996 |
| WO | WO 00/03044 A1 | 1/2000 |
| WO | WO 01/15726 A2 | 3/2001 |
| WO | WO 02/097068 A2 | 12/2002 |
| WO | WO 03/040288 A2 | 5/2003 |
| WO | WO 03/070735 A2 | 8/2003 |
| WO | WO 2004/043588 A2 | 5/2004 |
| WO | WO 2004/048345 A2 | 6/2004 |
| WO | WO 2005/028619 A2 | 3/2005 |
| WO | WO 2006/082088 A1 | 8/2006 |
| WO | WO 2006/138380 A2 | 12/2006 |
| WO | WO 2008/113364 A2 | 9/2008 |
| WO | WO 2009/046220 A2 | 4/2009 |
| WO | WO 2010/045512 A2 | 4/2010 |
| WO | WO 2010/053572 A2 | 5/2010 |
| WO | WO 2010/114789 A1 | 10/2010 |
| WO | WO 2010/129709 A1 | 11/2010 |
| WO | WO 2011/012746 A2 | 2/2011 |
| WO | WO 2012/027675 A2 | 3/2012 |

OTHER PUBLICATIONS

Boussif et al., A versatile vector for gene and oligonucleotide transfer into cells in culture and in vivo: polyethylenimine. Proc Natl Acad Sci U S A. Aug. 1, 1995;92(16):7297-301.
Byk et al., Synthesis, activity, and structure—activity relationship studies of novel cationic lipids for DNA transfer. J Med Chem. 1998;41(2):224-235.
Chan et al., Triplex DNA: fundamentals, advances, and potential applications for gene therapy. J Mol Med. Apr. 1997;75(4):267-82. Review.
Cotten et al., Receptor-mediated transport of DNA into eukaryotic cells. Methods Enzymol. 1993;217:618-44.
Crooke, Evaluating the mechanism of action of antiproliferative antisense drugs. Antisense Nucleic Acid Drug Dev. Apr. 2000;10(2):123-6; discussion 127.
Crooke, Molecular mechanisms of action of antisense drugs. Biochim Biophys Acta. Dec. 10, 1999;1489(1):31-44. Review.
Crystal, Transfer of genes to humans: early lessons and obstacles to success. Science. Oct. 20, 1995;270(5235):404-10. Review.
Deshmukh et al., Liposome and polylysine mediated gene therapy. New J Chem. 1997;21:113-124.
Discher et al., Polymersomes: tough vesicles made from diblock copolymers. Science. May 14, 1999;284(5417):1143-6.
Discher et al., Polymer vesicles. Science. Aug. 9, 2002;297(5583):967-73. Review.
Fire et al., Potent and specific genetic interference by double-stranded RNA in *Caenorhabditis elegans*. Nature. Feb. 19, 1998;391(6669):806-11.
Gonzalez et al., New class of polymers for the delivery of macromolecular therapeutics. Bioconjug Chem. Nov.-Dec. 1999;10(6):1068-74.
Haensler et al., Polyamidoamine cascade polymers mediate efficient transfection of cells in culture. Bioconjug Chem. Sep.-Oct. 1993;4(5):372-9.
Hofland et al., Formation of stable cationic lipid/DNA complexes for gene transfer. Proc Natl Acad Sci USA. Jul. 9, 1996;93(14):7305-9.
Hope et al., Cationic Lipids, Phosphatidylethanolamine and the Intracellular Delivery of Polymeric, Nucleic Acid-Based Drugs. Molecular Membrane Technology. 1998;15:1-14.
Kabanov et al., DNA complexes with polycations for the delivery of genetic material into cells. Bioconjug Chem. Jan.-Feb. 1995;6(1):7-20.
Kukowska-Latallo et al., Efficient transfer of genetic material into mammalian cells using Starburst polyamidoamine dendrimers. Proc Natl Acad Sci USA. May 14, 1996;93(10):4897-902.
Lim, et al., A self-destroying polycationic polymer: biodegradable poly(4-hydroxy-1-proline ester. J. Am. Chem. Soc. 1999;121:5633-5639.
Lukyanov et al., Micelles from lipid derivatives of water-soluble polymers as delivery systems for poorly soluble drugs. Adv Drug Deliv Rev. May 7, 2004;56(9):1273-89.
Luo et al., Synthetic DNA delivery systems. Nat Biotechnol. Jan. 2000;18(1):33-7. Review.
Mathiowitz et al., Novel microcapsules for delivery systems. Reactive Polymers. 1987;6:275-283.
Mathiowitz et al., Polyanhydride microspheres as drug darriers I. Hot-melt microencapsulation. J Control Release. 1987;5:13-22.
Mathiowitz et al., Polyanhydride Mocrospheres as Drug Carriers. II. Microencapsulation by Solvent Removal. J Appl Polymer Sci. 1988;35:755-774.
Miller et al., Cationic Liposomes for Gene Therapy. Angew. Chem. Int. Ed. 1998;37:1768-1785.
Mulligan, The basic science of gene therapy. Science. May 14, 1993;260(5110):926-32. Review.
Narang et al., Cationic lipids with increased DNA binding affinity for nonviral gene transfer in dividing and nondividing cells. Bioconjug Chem. Jan.-Feb. 2005;16(1):156-68.
Phillips et al., Enhanced antibody response to liposome-associated protein antigens: preferential stimulation of IgG2a/b production. Vaccine. 1992;10(3):151-8.
Putnam et al., Poly(4-hydroxy-L-proline ester): Low-Temperature Polycondensation and Plasmid. Macromolecules. 1999;32:3658-3662.
Sanford et al., The biolistic process. Trends Biotechnol. 1988;6:288-302.
Szoka et al., Comparative properties and methods of preparation of lipid vesicles (liposomes). Annu Rev Biophys Bioeng. 1980;9:467-508.
Tang et al., In vitro gene delivery by degraded polyamidoamine dendrimers. Bioconjug Chem. Nov.-Dec. 1996;7(6):703-14.
Tranchant et al., Physicochemical optimisation of plasmid delivery by cationic lipids. J Gene Med. Feb. 2004;6 Suppl 1:S24-35.
Unkeless et al., Structure and function of human and murine receptors for IgG. Annu Rev Immunol. 1988;6:251-81.
Van Balen et al., Liposome/water lipophilicity: methods, information content, and pharmaceutical applications. Med Res Rev. May 2004;24(3):299-324.
Wu et al., Cationic lipid polymerization as a novel approach for constructing new DNA delivery agents. Bioconjug Chem. Mar.-Apr. 2001;12(2):251-7.
Zauner et al., Polylysine-based transfection systems utilizing receptor-mediated delivery. Adv Drug Deliv Rev. Mar. 2, 1998;30(1-3):97-113.
Extended European Search Report for EP06784878.8 mailed Jun. 29, 2009.
International Search Report and Written Opinion for PCT/US2009/005810, mailed Jun. 16, 2010.
Akinc et al., A combinatorial library of lipid-like materials for delivery of RNAi therapeutics. Nat Biotech. 2008;26(5):561-69.
Ali et al., Derivation of type II alveolar epithelial cells from murine embryonic stem cells. Tissue Eng. Aug. 2002;8(4):541-50.
Anderson et al., Nanoliter-scale synthesis of arrayed biomaterials and application to human embryonic stem cells. Nat Biotechnol. Jul. 2004;22(7):863-6. Epub Jun. 13, 2004.
Ballermann et al., Shear stress and the endothelium. Kidney Int Suppl. Sep. 1998;67:S100-8.
Bartel, MicroRNAs: Genomics, Biogenesis, Mechanism, and Function. Cell. 2004;116:281-97.
Braun et al., Structure/function relationships of polyamidoamine/DNA dendrimers as gene delivery vehicles. J Pharm Sci. Feb. 2005;94(2):423-36.
Campbell et al., Application of cytokeratin 7 and 20 immunohistochemistry to diagnostic pathology. Current Diagnostic Pathology. 2001;7:113-22.
Carter et al., Mechanobiology of skeletal regeneration. Clin Orthop Relat Res. Oct. 1998;(355 Suppl):S41-55.
Chakraborty, Potentiality of Small Interfering RNAs (siRNA) as Recent Therapeutic Targets for Gene-Silencing. Curr Drug Targets. 2007;8:469-82.
Chen et al., Polymeric growth factor delivery strategies for tissue engineering. Pharm Res. Aug. 2003;20(8):1103-12.
Chu et al., Cytokeratin 7 and cytokeratin 20 expression in epithelial neoplasms: a survey of 435 cases. Mod Pathol. Sep. 2000;13(9):962-72.

(56) References Cited

OTHER PUBLICATIONS

Conley et al., Derivation, propagation and differentiation of human embryonic stem cells. Int J Biochem Cell Biol. Apr. 2004;36(4):555-67.
Dushnik-Levinson et al., Embryogenesis in vitro: study of differentiation of embryonic stem cells. Biol Neonate. 1995;67(2):77-83.
Elbashir et al., RNA interference is mediated by 21- and 22-nucleotide RNAs. Genes Dev. 2001;15:188-200.
Fisher et al., Photoinitiated Polymerization of Biomaterials. Annu Rev Mater Res. 2001;31:171-81.
Gardner, Stem cells and regenerative medicine: principles, prospects and problems. C R Biol. Jun.-Jul. 2007;330(6-7):465-73. Epub Feb. 15, 2007.
Guan et al., Embryonic stem cell-derived neurogenesis. Retinoic acid induction and lineage selection of neuronal cells. Cell Tissue Res. Aug. 2001;305(2):171-6.
Guan et al., Surface photo-grafting of polyurethane with 2-hydroxyethyl acrylate for promotion of human endothelial cell adhesion and growth. J Biomater Sci Polym Ed. 2000;11(5):523-36.
Hammond et al., An RNA-directed nuclease mediates post-transcriptional gene silencing in *Drosophila* cells. Nature. 2000;404:293-96.
Hasan et al., Identification of cytokeratin 1 as a binding protein and presentation receptor for kininogens on endothelial cells. Proc Natl Acad Sci U S A. Mar. 31, 1998;95(7):3615-20.
Hill et al., Enantioselective Epoxidation of Allylic Alcohols: (2S,3S)-3-Propyloxiranemethanol. Org Syn. 1990;7:461.
Ingber et al., Mechanochemical switching between growth and differentiation during fibroblast growth factor-stimulated angiogenesis in vitro: role of extracellular matrix. J Cell Biol. Jul. 1989;109(1):317-30.
Ito, Surface micropatterning to regulate cell functions. Biomaterials. Dec. 1999;20(23-24):2333-42.
Itskovitz-Eldor et al., Differentiation of human embryonic stem cells into embryoid bodies compromising the three embryonic germ layers. Mol Med. Feb. 2000;6(2):88-95.
Jia et al., Demonstration of two novel methods for predicting functional siRNA efficiency. BMC Bioinformatics. 2006;7:271.
Jiang et al., Electrochemically controlled release of lipid/DNA complexes: a new tool for synthetic gene delivery system. Electrochem Commun. 2004;6:576-82.
Johansson et al., Evidence for involvement of activin A and bone morphogenetic protein 4 in mammalian mesoderm and hematopoietic development. Mol Cell Biol. Jan. 1995;15(1):141-51.
Katsuki et al., Chapter 1. Asymmetric Epoxidation of Allylic Alcohols: The Katsuki-Sharpless Epoxidation Reaction. Org React 1996;48:1-299.
Katsuki et al., The First Practical Method for Asymmetric Epoxidation. J Am Chem Soc. 1980:102;5974-76.
Kaufman et al., Hematopoietic colony-forming cells derived from human embryonic stem cells. Proc Natl Acad Sci U S A. Sep. 11, 2001;98(19):10716-21. Epub Sep. 4, 2001.
Levenberg et al., Differentiation of human embryonic stem cells on three-dimensional polymer scaffolds. Proc Natl Acad Sci U S A. Oct. 28, 2003;100(22):12741-6. Epub Oct. 15, 2003.
Li et al., Defining the optimal parameters for hairpin-based knockdown constructs. RNA. 2007;13:1765-74.
Li et al., Plasticity of the urothelial phenotype: effects of gastro-intestinal mesenchyme/stroma and implications for urinary tract reconstruction. Differentiation. Oct. 2000;66(2-3):126-35.
Lyle et al., Cytokeratin 15 (K15) as an Epithelial Stem Cell Marker: Implications for Aging and Carcinogenesis. J Invest Derma. 1999;112(4):623. Abstract #606.
MacBeath et al., Printing proteins as microarrays for high-throughput function determination. Science. Sep. 8, 2000;289(5485):1760-3.
MacBeath et al., Printing Small Molecules as Microarrays and Detecting Protein-Ligand Interactions en Masse. J Am Chem Soc. 1999;121:7967-68.
Mattey et al., Demonstration of cytokeratin in endothelial cells of the synovial microvasculature in situ and in vitro. Br J Rheumatol. Aug. 1993;32(8):676-82.
Moll et al., The human keratins: biology and pathology. Histochem Cell Biol. Jun. 2008; 129(6):705-33. Epub May 7, 2008.
Moll, [Cytokeratins as markers of differentiation. Expression profiles in epithelia and epithelial tumors] Veroff Pathol. 1993;142:1-197. German.
Morris et al., Lentiviral-mediated delivery of siRNAs for antiviral therapy. Gene Ther. 2006;13:553-58.
Naito et al., siVirus: web-based antiviral siRNA design software for highly divergent viral sequences. Nucleic Acids Res. 2006;34:W448-450.
Novina et al., The RNAi revolution. Nature. 2004;430:161-64.
Odorico et al., Multilineage differentiation from human embryonic stem cell lines. Stem Cells. 2001;19(3):193-204.
Pera et al., Human embryonic stem cells. J Cell Sci. Jan. 2000;113 ( Pt 1):5-10.
Reynolds et al., Rational siRNA design for RNA interference. Nat Biotechnol. 2004;22(3):326-30.
Sakiyama-Elbert et al., Functional Biomaterials: Design of Novel Biomaterials. Ann Rev Mater Res. 2001;31:183-201.
Saltzman, Cell Interactions with Polymers. In: Principles of Tissue Engineering, 2d ed., Chapter 19. 2000:221-35.
Sawarf et al., [Cytokeratins, markers of epithelial cell differentiation: expression in normal epithelia.] Pathol Biol (Paris). 1992;40:655-65. French.
Schaus et al., Highly Selective Hydrolytic Kinetic Resolution of Terminal Epoxides Catalyzed by Chiral (salen)Co$^{III}$ Complexes. Practical Synthesis of Enantioenriched Terminal Epoxides and 1,2-Biols. J Am Chem Soc. 2002;124(7):1307-15.
Schena et al., Quantitative monitoring of gene expression patterns with a complementary DNA microarray. Science. Oct. 20, 1995;270(5235):467-70.
Schuldiner et al., Effects of eight growth factors on the differentiation of cells derived from human embryonic stem cells. Proc Natl Acad Sci U S A. Oct. 10, 2000;97(21):11307-12.
Schweizer et al., Synthetic Studies towards the Total Synthesis of Providencin. Synthesis. 2007;24:3807-14.
Spradling et al., Stem cells find their niche. Nature. Nov. 1, 2001;414(6859):98-104.
Stocum, Stem cells in regenerative biology and medicine. Wound Repair Regen. Nov.-Dec. 2001;9(6):429-42.
Streuli, Extracellular matrix remodeling and cellular differentiation. Curr Opin Cell Biol. 1999;11:634-40.
Swali et al., Solid-Phase Dendrimer Synthesis and the Generation of Super-High-Loading Resin Beads for Combinatorial Chemistry. J Org Chem Am Chem Soc. 1997;62:4902-03.
Tabara et al., The *rde-1* Gene, RNA Interference, and Transposon Silencing in *C. elegans*. Cell. 1999;99:123-32.
Thomson et al., Embryonic stem cell lines derived from human blastocysts. Science. Nov. 6, 1998;282(5391):1145-7.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002:28(6):470-86.
Wang et al, The functions of microRNAs in plants. Front Biosci. 2007;12:3975-82.
Wobus, Potential of embryonic stem cells. Mol Aspects Med. Jun. 2001;22(3):149-64.
Yaffee et al., Serial passaging and differentiation of myogenic cells isolated from dystrophic mouse muscle. Nature. 1977;270:725-27.
Yiu et al., Filtering of Ineffective siRNAs and Improved siRNA Design Tool. Bioinformatics. 2005;21(2):144-51.
Zamore et al., RNAi: Double-Stranded RNA Directs the ATP-Dependent Cleavage of mRNA at 21 to 23 Nucleotide Intervals. Cell. 2000;101:25-33.
Zhao et al., A developmental view of microRNA function. Trends Biochem. 2007;32(4):189-97.
International Search Report and Written Opinion for PCT/US2006/023171 mailed May 29, 2008.
International Preliminary Report on Patentability for PCT/US2006/023171 mailed Jul. 3, 2008.
International Search Report and Written Opinion for PCT/US2009/006018 mailed May 25, 2010.

(56) References Cited

OTHER PUBLICATIONS

International Preliminary Report on Patentability for PCT/US2009/006018 mailed May 19, 2011.
International Preliminary Report on Patentability for PCT/US2009/005810 mailed May 12, 2011.
Office Action, mailed Jun. 13, 2011, for U.S. Appl. No. 12/716,732.
Akinc et al., Exploring polyethylenimine-mediated DNA transfection and the proton sponge hypothesis. J Gene Med. May 2005;7(5):657-63.
Akira et al., Functions of toll-like receptors: lessons from KO mice. C R Biol. Jun. 2004;327(6):581-9.
Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.
U.S. Appl. No. 61/377,348, filed Aug. 26, 2010, Ma et al.
U.S. Appl. No. 61/468,455, filed Mar. 28, 2011, Dahlman et al.
Anderson, Biological Responses to Materials. Annu Rev Mater Res. 2001;31:81-110.
Anderson, Chapter 4. Mechanisms of Inflammation and Infection With Implanted Devices. Cardiovasc Pathol. 1993;2:33S-41S.
Bajaj et al., Synthesis and gene transfection efficacies of PEI-cholesterol-based lipopolymers. Bioconjug Chem. Aug. 2008;19(8):1640-51. Epub Jul. 11, 2008
Berge et al., Pharmaceutical salts. J Pharm Sci. Jan. 1977;66(1):1-19.
Boudou et al., Multiple functionalities of polyelectrolyte multilayer films: new biomedical applications. Adv Mater. Jan. 26, 2010;22(4):441-67.
Bratlie et al., Rapid biocompatibility analysis of materials via in vivo fluorescence imaging of mouse models. PLoS One. Apr. 6, 2010;5(4):e10032.
Breunig et al., Breaking up the correlation between efficacy and toxicity for nonviral gene delivery. Proc Natl Acad Sci U S A. Sep. 4, 2007;104(36):14454-9. Epub Aug. 28, 2007.
Breunig et al., Mechanistic investigation of poly(ethylene imine)-based siRNA delivery: disulfide bonds boost intracellular release of the cargo. J Control Release. Aug. 25, 2008;130(1):57-63. Epub May 24, 2008.
Brodbeck et al., Biomaterial surface chemistry dictates adherent monocyte/macrophage cytokine expression in vitro. Cytokine. Jun. 21, 2002;18(6):311-9.
Chang, Therapeutic applications of polymeric artificial cells. Nat Rev Drug Discov. Mar. 2005;4(3):221-35.
Creusat et al., Proton sponge trick for pH-sensitive disassembly of polyethylenimine-based siRNA delivery systems. Bioconjug Chem. May 19, 2010;21(5):994-1002.
Cristofaro et al., Role of Toll-like receptors in infection and immunity: clinical implications. Drugs. 2006;66(1):15-29.
Davis et al., Evidence of RNAi in humans from systemically administered siRNA via targeted nanoparticles. Nature. Apr. 15, 2010;464(7291):1067-70. Epub Mar. 21, 2010.
Decher, Fuzzy Nanoassemblies: Toward Layered Polymeric Multicomposites. Science. 1997;277;1232-37.
Diebold et al., Innate antiviral responses by means of TLR7-mediated recognition of single-stranded RNA. Science. Mar. 5, 2004;303(5663):1529-31. Epub Feb. 19, 2004.
Ewert et al., Cationic lipid-DNA complexes for gene therapy: understanding the relationship between complex structure and gene delivery pathways at the molecular level. Curr Med Chem. Jan. 2004;11(2):133-49.
Forsbach et al., Identification of RNA sequence motifs stimulating sequence-specific TLR8-dependent immune responses. J Immunol. Mar. 15, 2008;180(6):3729-38.
Friedmann, Human gene therapy—an immature genie, but certainly out of the bottle. Nat Med. Feb. 1996;2(2):144-7.
Furgeson et al., Modified linear polyethylenimine-cholesterol conjugates for DNA complexation. Bioconjug Chem. Jul.-Aug. 2003;14(4):840-7.
Furgeson et al., Novel water insoluble lipoparticulates for gene delivery. Pharm Res. Apr. 2002;19(4):382-90.

Ghosh et al., Toll-like receptor (TLR) 2-9 agonists-induced cytokines and chemokines: I. Comparison with T cell receptor-induced responses. Cell Immunol. Sep. 2006;243(1):48-57. Epub Jan. 23, 2007.
Godbey et al., Size matters: molecular weight affects the efficiency of poly(ethylenimine) as a gene delivery vehicle. J Biomed Mater Res. Jun. 5, 1999;45(3):268-75.
Grayson et al., Biophysical and structural characterization of polyethylenimine-mediated siRNA delivery in vitro. Pharm Res. Aug. 2006;23(8):1868-76.
Gross et al., Bioluminescence imaging of myeloperoxidase activity in vivo. Nat Med. Apr. 2009;15(4):455-61. Epub Mar. 22, 2009.
Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517-23.
Grzelinski et al., RNA interference-mediated gene silencing of pleiotrophin through polyethylenimine-complexed small interfering RNAs in vivo exerts antitumoral effects in glioblastoma xenografts. Hum Gene Ther. Jul. 2006;17(7):751-66.
Harder et al., Molecular Conformation in Oligo(ethylene glycol)-Terminated Self-Assembled Monolayers on Gold and Silver Surfaces Determines Their Ability to Resist Protein Adsorpotion. J Phys Chem B. 1998;102:426-36.
Heil et al., Species-specific recognition of single-stranded RNA via toll-like receptor 7 and 8. Science. Mar. 5, 2004;303(5663):1526-9. Epub Feb. 19, 2004.
Hemmi et al., Small anti-viral compounds activate immune cells via the TLR7 MyD88-dependent signaling pathway. Nat Immunol. Feb. 2002;3(2):196-200. Epub Jan. 22, 2000.
Holmlin et al., Zwitterionic SAMs that Resist Nonspecific Adsorption of Protein from Aqueous Buffer. Langmuir. 2001;17:2841-50.
Hornung et al., Quantitative expression of toll-like receptor 1-10 mRNA in cellular subsets of human peripheral blood mononuclear cells and sensitivity to CpG oligodeoxynucleotides. J Immunol. May 1, 2002;168(9):4531-7.
Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.
Howard, Delivery of RNA interference therapeutics using polycation-based nanoparticles. Adv Drug Deliv Rev. Jul. 25, 2009;61(9):710-20. Epub Apr. 5, 2009.
Hunt et al., Effect of biomaterial surface charge on the inflammatory response: evaluation of cellular infiltration and TNF alpha production. J Biomed Mater Res. May 1996;31(1):139-44.
Incani et al., Lipid and hydrophobic modification of cationic carriers on route to superior gene vectors. Soft Matter. 2010;6:2124-38.
Irwin et al., Modulus-dependent macrophage adhesion and behavior. J Biomater Sci Polym Ed. 2008;19(10):1363-82.
Iwasaki et al., Toll-like receptor control of the adaptive immune responses. Nat Immunol. Oct. 2004;5(10):987-95.
Jarrossay et al., Specialization and complementarity in microbial molecule recognition by human myeloid and plasmacytoid dendritic cells. Eur J Immunol. Nov. 2001;31(11):3388-93.
Jiang et al., Hyaluronic acid-polyethyleneimine conjugate for target specific intracellular delivery of siRNA. Biopolymers. Jul. 2008;89(7):635-42.
Jiang et al., Ultralow-fouling, functionalizable, and hydrolyzable zwitterionic materials and their derivatives for biological applications. Adv Mater. Mar. 5, 2010;22(9):920-32.
Jon et al., Degradable poly(amino alcohol esters) as potential DNA vectors with low cytotoxicity. Biomacromolecules. Nov.-Dec. 2003;4(6):1759-62.
Judge et al., Design of noninflammatory synthetic siRNA mediating potent gene silencing in vivo. Mol Ther. Mar. 2006;13(3):494-505. Epub Dec. 15, 2005.
Kamath et al., Surface chemistry influences implant-mediated host tissue responses. J Biomed Mater Res A. Sep. 2008;86(3):617-26.
Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.

(56) References Cited

OTHER PUBLICATIONS

Kim et al., Efficient siRNA delivery using water soluble lipopolymer for anti-angiogenic gene therapy. J Control Release. Apr. 23, 2007;118(3):357-63. Epub Jan. 9, 2007.
Kim et al., Local and systemic delivery of VEGF siRNA using polyelectrolyte complex micelles for effective treatment of cancer. J Control Release. Jul. 14, 2008;129(2):107-16. Epub Mar. 14, 2008.
Kleinman et al., Sequence- and target-independent angiogenesis suppression by siRNA via TLR3. Nature. Apr. 3, 2008;452(7187):591-7. Epub Mar. 26, 2008.
Krieg et al., CpG motifs in bacterial DNA trigger direct B-cell activation. Nature. Apr. 6, 1995;374(6522):546-9.
Krieg et al., Toll-like receptors 7, 8, and 9: linking innate immunity to autoimmunity. Immunol Rev. Dec. 2007;220:251-69.
Kwon et al., Application of an HIV gp41-derived peptide for enhanced intracellular trafficking of synthetic gene and siRNA delivery vehicles. Bioconjug Chem. Apr. 2008;19(4):920-7. Epub Apr. 1, 2008.
Lan et al., Stabilized immune modulatory RNA compounds as agonists of Toll-like receptors 7 and 8. Proc Natl Acad Sci U S A. Aug. 21, 2007;104(34):13750-5. Epub Aug. 14, 2007.
Langer, Perspectives and challenges in tissue engineering and regenerative medicine. Adv Mater. Sep. 4, 2009;21(32-33):3235-6.
Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.
Love et al., Lipid-like materials for low-dose, in vivo gene silencing. Proc Natl Acad Sci U S A. Feb. 2, 2010;107(5):1864-9. Epub Jan. 11, 2010.
Ma et al., Development of Cationic Polymer Coatings to Regulate Foreign Body Responses. Adv Mater. 2011;23:H189-94.
Marques et al., Activation of the mammalian immune system by siRNAs. Nat Biotechnol. Nov. 2005;23(11):1399-405.
Marshak-Rothstein, Toll-like receptors in systemic autoimmune disease. Nat Rev Immunol. Nov. 2006;6(11):823-35.
Mendelsohn et al., Rational design of cytophilic and cytophobic polyelectrolyte multilayer thin films. Biomacromolecules. Jan.-Feb. 2003;4(1):96-106.
Morrissey et al., Potent and persistent in vivo anti-HBV activity of chemically modified siRNAs. Nat Biotechnol. Aug. 2005;23(8):1002-7. Epub Jul. 24, 2005.
Nahrendorf et al., Dual channel optical tomographic imaging of leukocyte recruitment and protease activity in the healing myocardial infarct. Circ Res. Apr. 27, 2007;100(8):1218-25. Epub Mar. 22, 2007.
Neamnark et al., Aliphatic lipid substitution on 2 kDa polyethylenimine improves plasmid delivery and transgene expression. Mol Pharm. Nov.-Dec. 2009;6(6):1798-815.
Nguyen et al., A novel high-throughput cell-based method for integrated quantification of type I interferons and in vitro screening of immunostimulatory RNA drug delivery. Biotechnol Bioeng. Jul. 1, 2009;103(4):664-75.
Nguyen et al., Drug delivery-mediated control of RNA immunostimulation. Mol Ther. Sep. 2009;17(9):1555-62. Epub Jul. 7, 2009.
Novak et al., Biomimetic strategies based on viruses and bacteria for the development of immune evasive biomaterials. Biomaterials. Apr. 2009;30(11):1989-2005. Epub Jan. 29, 2009.
Onuki et al., A review of the biocompatibility of implantable devices: current challenges to overcome foreign body response. J Diabetes Sci Technol. Nov. 2008;2(6):1003-15.
Orive et al., Cell encapsulation: promise and progress. Nat Med. Jan. 2003;9(1):104-7.
Ostuni et al., A Survey of Structure-Property Relationships of Surfaces that Resist the Adsorption of Protein. Langmuir. 2001;17:5605-20.
Pashine et al., Targeting the innate immune response with improved vaccine adjuvants. Nat Med. Apr. 2005;11(4 Suppl):S63-8.
Paul et al., Topographical control of human macrophages by a regularly microstructured polyvinylidene fluoride surface. Biomaterials. Oct. 2008;29(30):4056-64. Epub Jul. 29, 2008.
Peer et al., Nanocarriers as an emerging platform for cancer therapy. Nat Nanotechnol. Dec. 2007;2(12):751-60.
Peppas et al., Hydrogels in Biology and Medicine: From Molecular Principles to Bionanotechnology. Mater. 2006;18:1345-60.
Philipp et al., Hydrophobically modified oligoethylenimines as highly efficient transfection agents for siRNA delivery. Bioconjug Chem. Nov. 2009;20(11):2055-61.
Putnam, Polymers for gene delivery across length scales. Nat Mater. Jun. 2006;5(6):439-51.
Ratner et al., Biomaterials: where we have been and where we are going. Annu Rev Biomed Eng. 2004;6:41-75.
Refai et al., Effect of titanium surface topography on macrophage activation and secretion of proinflammatory cytokines and chemokines. J Biomed Mater Res A. Aug. 1, 2004;70(2):194-205.
Robbins et al., siRNA and innate immunity. Oligonucleotides. Jun. 2009;19(2):89-102.
Sahay et al., Endocytosis of nanomedicines. J Control Release. Aug. 3, 2010;145(3):182-95. Epub Mar. 10, 2010.
Scheel et al., Therapeutic anti-tumor immunity triggered by injections of immunostimulating single-stranded RNA. Eur J Immunol. Oct. 2006;36(10):2807-16.
Schön et al.. TLR7 and TLR8 as targets in cancer therapy. Oncogene. Jan. 7, 2008;27(2):190-9.
Schutte et al., Cytokine profiling using monocytes/macrophages cultured on common biomaterials with a range of surface chemistries. J Biomed Mater Res A. Jan. 2009;88(1):128-39.
Sioud, Induction of inflammatory cytokines and interferon responses by double-stranded and single-stranded siRNAs is sequence-dependent and requires endosomal localization. J Mol Biol. May 20, 2005;348(5):1079-90. Epub Mar. 22, 2005.
Sioud, Single-stranded small interfering RNA are more immunostimulatory than their double-stranded counterparts: a central role for 2'-hydroxyl uridines in immune responses. Eur J Immunol. May 2006;36(5):1222-30.
Steinman et al., Taking dendritic cells into medicine. Nature. Sep. 27, 2007;449(7161):419-26.
Suh et al., Ionization of Poly(ethylenimine) and Poly(allylamine) at Various PHS. Bioorg Chem. 1994;22:318-27.
Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.
Urban-Klein et al., RNAi-mediated gene-targeting through systemic application of polyethylenimine (PEI)-complexed siRNA in vivo. Gene Ther. Mar. 2005;12(5):461-6.
Von Harpe et al., Characterization of commercially available and synthesized polyethylenimines for gene delivery. J Control Release. Nov. 3, 2000;69(2):309-22.
Walde et al., Preparation of Vesicles (Liposomes). In: Encyclopedia of Nanoscience and Nanotechnology. Nalwa, ed. American Scientific Publishers: Los Angeles. 2004;9:43-79.
Ward, A Review of the Foreing-body Response to Subcutaneously-implanted Devices: The Role of Macrophages and Cytokines in Biofouling and Fibrosis. J Diabetes Sci Technol. 2008;2:768-77.
Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.
White et al., Poly(hydroxyaminoethers): A New Family of Epoxy-Based Thermoplastics. Adv Mater. 2000;12:1791-1800.
White et al., Step-growth polymerization of 10,11-epoxyundecanoic acid. Synthesis and properties of a new hydroxy-functionalized thermopastic polyester. Adv Mater. 2007;48:3990-98.
Whitehead et al., Knocking down barriers: advances in siRNA delivery. Nat Rev Drug Discov. Feb. 2009;8(2):129-38.
Wilen et al., Strategies in Optical Resolutions. Tetrahedron. 1977;33:2725-36.
Williams, On the mechanisms of biocompatibility. Biomaterials. Jul. 2008;29(20):2941-53. Epub Apr. 28, 2008.

(56) References Cited

OTHER PUBLICATIONS

Yoshioka et al., Epoxy-based Electroactive Polymer Gels. Experimental Mechanics. 2002;42:404-08.

Zhang et al., Human Toll-like receptor-dependent induction of interferons in protective immunity to viruses. Immunol Rev. Dec. 2007;220:225-36.

Zintchenko et al., Simple modifications of branched PEI lead to highly efficient siRNA carriers with low toxicity. Bioconjug Chem. Jul. 2008;19(7):1448-55. Epub Jun. 14, 2008.

Extended European Search Report for EP 11186795.8, mailed Jun. 19, 2012.

International Search Report and Written Opinion for PCT/US2011/049360, mailed Mar. 20, 2012.

Invitation to Pay Additional Fees for PCT/US2012/030349, mailed on Jul. 24, 2012.

Navarro et al., Phospholipid—polyethylenimine conjugate-based micelle-like nanoparticles for siRNA delivery. Drug Deliv and Trans Res. 2011; 25-33.

Office Action, mailed Apr. 4, 2012, for U.S. Appl. No. 12/716,732.

Office Action, mailed Dec. 16, 2011, for U.S. Appl. No. 12/716,732.

Invitation to Pay Additional Fees for PCT/US2012/062222, mailed Dec. 14, 2012.

International Search Report and Written Opinion for PCT/US2012/062222, mailed Mar. 27, 2013.

International Preliminary Report on Patentability for PCT/US2011/049360, mailed Mar. 7, 2013.

International Search Report and Written Opinion for PCT/US2012/030349, mailed on Oct. 5, 2012.

Office Action, mailed Sep. 28, 2012, for U.S. Appl. No. 12/716,732.

Notice of Allowance, mailed Feb. 1, 2013, for U.S. Appl. No. 12/716,732.

Adami et al., An amino acid-based amphoteric liposomal delivery system for systemic administration of siRNA. Mol Ther. Jun. 2011;19(6):1141-51.

Astle et al., A VEGFR2 Antagonist and Other Peptoids Evade Immune Recognition. Int J Pept Res Ther. 2008;14(3):223-227.

Dern et al., Toxicity studies of pyrimethamine (daraprim). Am J Trop Med Hyg. Mar. 1955;4(2):217-20.

Hoekenga, The treatment of malaria with hydroxychloroquine. Am J Trop Med Hyg. Mar. 1955;4(2): 221-3.

Ichimaru et al., Synthesis and characterization of new piperazine-type inhibitors for mitochondrial NADH-ubiquinone oxidoreductase (complex I). Biochemistry. Oct. 7, 2008;47(40):10816-26. Epub Sep. 10, 2008.

Jolck et al., Solid-phase synthesis of PEGylated lipopeptides using click chemistry. Bioconjug Chem. May 19, 2010;21(5):807-10.

Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.

Mintzer et al., Nonviral vectors for gene delivery. Chem Rev. Feb. 2009;109(2):259-302.

Parrish et al., Five- and six-membered ring opening of pyroglutamic diketopiperazine. J Org Chem. Mar. 22, 2002;67(6):1820-6.

Prata et al., Lipophilic peptides for gene delivery. Bioconjug Chem. Feb. 2008;19(2):418-20.

Thompson et al., Antiamebic action of 5-chloro-7-diethylaminomethyl-8-quinolinol and of other substituted 8-quinolinols in vitro and in experimental animals. Am J Trop Med Hyg. Mar. 1955;4(2):224-48.

Vandenbroucke et al., Prolonged gene silencing in hepatoma cells and primary hepatocytes after small interfering RNA delivery with biodegradable poly(beta-amino esters). J Gene Med. Jul. 2008;10(7):783-94.

Zaugg et al., 3-Carboxy-2,5-piperazinedione and Derivatives. J Amer Chem Soc. Jun. 5, 1956;78(11):2626-2631.

Extended European Search Report for European Application No. 09825132.5, dated Jul. 16, 2013.

International Preliminary Report on Patentability for PCT/US2012/030349, mailed on Oct. 10, 2013.

Bossle et al., Synthesis and biological activity of new 2-substituted analogs of fluphenazine. J Med Chem. Mar. 1, 1976;19(3):370-3.

Ryng et al., Synthesis and Structure Elucidation of 5-Aminomethinimino-3-methyl-4-isoxazolecarboxylic Acid Phenylamides and Their Immunological Activity. Archiv der Pharmazie Jan. 1, 1997;330(11):319-26.

Wintermantel et al., Blocked polyurethane prepolymers as component A in reactive adhesives. STN International HCAPLUS Database. 2006. Accession No. 2006:215601.

Invitation to Pay Additional Fees for PCT/US2013/054726, mailed Oct. 31, 2013.

International Search Report and Written Opinion for PCT/US2013/054726, mailed Jan. 7, 2014.

Asokan et al., Cytosolic delivery of macromolecules. 3. Synthesis and characterization of acid-sensitive bis-detergents. Bioconjug Chem. Nov.-Dec. 2004;15(6):1166-73.

Conte et al., Regioselective ring opening of [(perfluoroalkyemethyl] oxiranes with N-nucleophiles. J Fluorine Chem. 2005;126(9-10):1274-80.

Fourneau et al., Two new series of local anesthetics derived from piperazine. Bulletin de la Societe Chimique de France. 1930;47:1003-16. French.

Pollard et al., Ether amino alcohols. II. J Org Chem. 1952;17:1-3.

Zagridullin et al., Monobasic amines. II. Cycloalkylation and hydroxyalkylation of cyclic and acyclic di- and polyamines.. Zhurnal Organicheskoi Khimii. 1990;26(1):184-88. Russian.

\* cited by examiner

NMR DATA: PROOF OF THE STRUCTURE

AMINE-CONTAINING LIPIDS AND USES THEREOF

RELATED APPLICATIONS

The present application claims priority under 35 U.S.C. §119(e) to U.S. provisional patent applications, U.S. Ser. No. 60/690,608, filed Jun. 15, 2005, and U.S. Ser. No. 60/785,176, filed Mar. 23, 2006, each of which is incorporated herein by reference.

GOVERNMENT SUPPORT

This invention was made with Government support under grant no. R01-EB000244 awarded by the National Institutes of Health. The Government has certain rights in the invention.

BACKGROUND OF THE INVENTION

The treatment of human diseases through the application of nucleotide-based drugs such as DNA and RNA has the potential to revolutionize the medical field (Anderson *Nature* 392 (Suppl.):25-30, 1996; Friedman *Nature Med.* 2:144-147, 1996; Crystal *Science* 270:404-410, 1995; Mulligan *Science* 260:926-932, 1993; each of which is incorporated herein by reference). Thus far, the use of modified viruses as gene transfer vectors has generally represented the most clinically successful approach to gene therapy. While viral vectors are currently the most efficient gene transfer agents, concerns surrounding the overall safety of viral vectors, which include the potential for unsolicited immune responses, have resulted in parallel efforts to develop non-viral alternatives (for leading references, see: Luo et al. *Nat. Biotechnol.* 18:33-37, 2000; Behr *Acc. Chem. Res.* 26:274-278, 1993; each of which is incorporated herein by reference). Current alternatives to viral vectors include polymeric delivery systems (Zauner et al. *Adv. Drug Del. Rev.* 30:97-113, 1998; Kabanov et al. *Bioconjugate Chem.* 6:7-20, 1995; each of which is incorporated herein by reference), liposomal formulations (Miller *Angew. Chem. Int. Ed.* 37:1768-1785, 1998; Hope et al. *Molecular Membrane Technology* 15:1-14, 1998; Deshmukh et al. *New J. Chem.* 21:113-124, 1997; each of which is incorporated herein by reference), and "naked" DNA injection protocols (Sanford *Trends Biotechnol.* 6:288-302, 1988; incorporated herein by reference). While these strategies have yet to achieve the clinical effectiveness of viral vectors, the potential safety, processing, and economic benefits offered by these methods (Anderson *Nature* 392(Suppl.):25-30, 1996; incorporated herein by reference) have ignited interest in the continued development of non-viral approaches to gene therapy (Boussif et al. *Proc. Natl. Acad. Sci. USA* 92:7297-7301, 1995; Putnam et al. *Macromolecules* 32:3658-3662, 1999; Lim et al. *J. Am. Chem. Soc.* 121:5633-5639, 1999; Gonzalez et al. *Bioconjugate Chem.* 10:1068-1074, 1999; Kukowska-Latallo et al. *Proc. Natl. Acad. Sci. USA* 93:4897-4902, 1996; Tang et al. *Bioconjugate Chem.* 7:703-714, 1996; Haensler et al. *Bioconjugate Chem.* 4:372-379, 1993; each of which is incorporated herein by reference).

There exists a continuing need for non-toxic, biodegradable, biocompatible lipids that can be used to transfect nucleic acids and that are easily prepared efficiently and economically. Such lipids would have several uses, including the delivery of nucleic acids in gene therapy as well as in the packaging and/or delivery of diagnostic, therapeutic, and prophylactic agents.

SUMMARY OF THE INVENTION

The present invention provides novel lipids of the formula (I):

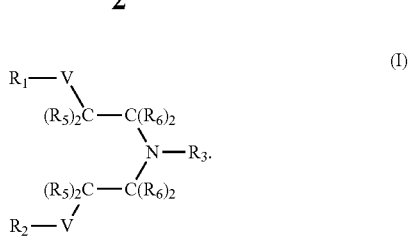

These lipids may be prepared by the addition of a primary amine to a double bond conjugated with an electron withdrawing groups such as a carbonyl moiety. Two equivalents of an α,β-unsaturated ketone such as an acrylate are reacted with one equivalent of a primary amine to prepare the inventive lipids as shown in the scheme below:

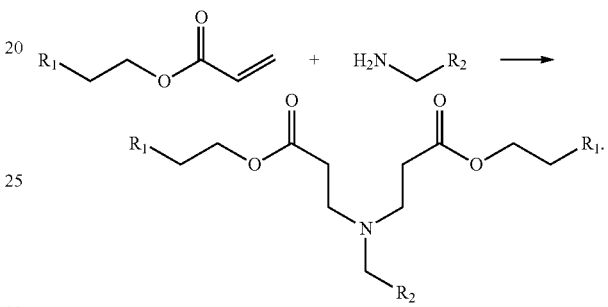

These lipids typically have a hydrophobic half and a hydrophilic half. The hydrophobic portion is typically provided by fatty acid moieties attached to the acrylate, and the hydrophilic portion is provided by the esters, amines, and side chain of the amine. The fatty acid groups may be straight chain alkyl groups ($C_1$-$C_{30}$) with no substitutions. In certain embodiments, the fatty acid groups are substituted and/or branched. The amine may be protonated or alkylated thereby forming a positively charged amine. These lipids may be used in the delivery of therapeutic agents to a subject. The inventive lipids are particularly useful in delivering negatively charged agents given the tertiary amine available for protonation thus forming a positive charge. For example, these lipids may be used to delivery DNA, RNA, or other polynucleotides to a subject or to a cell. As would be appreciated by one of skill in the art, the above reaction may result in a mixture with some lipids have one acrylate tail and other having two acrylate tails. Also, two different acrylates may be used in the reaction mixture to prepare a lipid with two different acrylate tails.

In another aspect, the invention provides lipids of the formula (II):

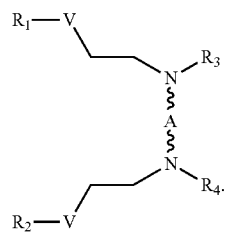

Lipids of the formula (II) are prepared by the addition of a primary or secondary diamine to a double bond conjugated to an electron-withdrawing group such as a carbonyl. The lipids of formula (II) have two amines per lipid molecule as compared to the one amine per lipid molecule in the lipids of formula (I). These amines may be protonated or alkylated to form positively charged amino groups. These lipids may also be used to deliver DNA, RNA, or other polynucleotides. As with the primary amine, the acrylate tails may be the same or different. Also, the lipid may include any where from one acrylate tail to as many acrylate tails as is chemically possible.

In another aspect, the invention provides lipids of the formulae (III) or (IV):

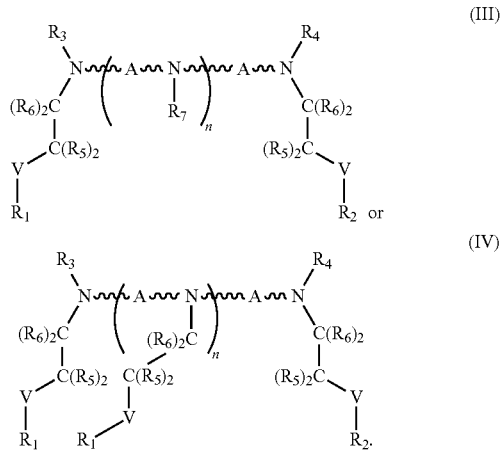

Lipids of the formulae (III) or (IV) are prepared by the addition of primary or secondary amino groups to a double bond conjugated to an electron-withdrawing groups as a carbonyl. The lipids of formulae (III) and (IV) have multiple amino groups per lipid molecule. In certain embodiments, the number of amino groups per lipid molecule is 3, 4, 5, 6, 7, 8, 9, or 10. These amines may be protonated or alkylated to form positively charged amino groups. The acrylate tails may all be the same or they may be different. Any number of acrylate tails may be present on the molecule. The lipids may be used to delivery DNA, RNA, or other polynucleotides.

In one aspect of the invention, the inventive lipids are combined with an agent to form microparticles, liposomes, or micelles. The agent to be delivered by the microparticles, liposomes, or micelles may be in the form of a gas, liquid, or solid, and the agent may be a polynucleotide, protein, peptide, or small molecule. The inventive lipids may be combined with other lipids, polymers, surfactants, cholesterol, carbohydrates, proteins, etc. to form the particles. These particles may be combined with a pharmaceutically excipient to form pharmaceutical compositions.

The invention also provides methods of making the inventive lipids. One or more equivalents of an acrylate are allowed to react with one equivalent of a primary amine, diamine, or polyamine under suitable conditions to form a lipid of the formula (I), (II), (III), or (IV). In certain embodiments, all the amino groups of the amine are fully reacted with acrylates to form tertiary amines. In other embodiments, all the amino groups of the amine are not fully reacted with acrylate to form tertiary amines thereby resulting in primary or secondary amines in the lipid molecule. These primary or secondary amines are left as is or may be reacted with another electrophile such as a different acrylate. As will be appreciated by one of skill in this art, reacting an amine with less than an excess of acrylate will result in a plurality of different lipid amines. Certain molecules may include a full complement of acrylate moieties while other molecules will not include a full complement of acrylates. For example, a diamine or polyamine may include only one, two, three, four, five, or six acrylate moieties off the various amino moieties of the molecule resulting in primary, secondary, and tertiary amines. In certain embodiments, it is preferred that all the amino groups not be fully functionalized. In certain embodiments, the two of the same type of acrylate are used. In other embodiments, two or more different acrylates are used. The synthesis of the lipid may be performed with or without solvent, and the synthesis may be performed at temperatures ranging from 25° C. to 100° C., preferably approximately 95° C. The prepared lipids may be optionally purified. For example, the mixture of lipids may be purified to yield a lipid with a certain number of acrylate moieties. The lipids may also be alkylated using an alkyl halide (e.g., methyl iodide) or other alkylating agent.

The invention also provides libraries of lipids prepared by the inventive methods. These lipids may be prepared and/or screened using high-throughput techniques involving liquid handlers, robots, microtiter plates, computers, etc. In certain embodiments, the lipids are screened for their ability to transfect DNA, RNA, or other polynucleotides into the cell.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BQC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chlorop-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups.

An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" as used herein refers to saturated, straight- or branched-chain hydrocarbon radicals derived from a hydrocarbon moiety containing between one and twenty carbon atoms by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkenyl" denotes a monovalent group derived from a hydrocarbon moiety having at least one carbon-carbon double bond by the removal of a single hydrogen atom. Alkenyl groups include, for example, ethenyl, propenyl, butenyl, 1-methyl-2-buten-1-yl, and the like.

The term "alkynyl" as used herein refers to a monovalent group derived form a hydrocarbon having at least one carbon-carbon triple bond by the removal of a single hydrogen atom. Representative alkynyl groups include ethynyl, 2-propynyl (propargyl), 1-propynyl, and the like.

The term "alkoxy", or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "carboxylic acid" as used herein refers to a group of formula —$CO_2H$.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limted to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Carbocycle": The term "carbocycle", as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^{2}H$, $^{3}H$, $^{32}P$, $^{35}S$, $^{67}Ga$, $^{99m}Tc$ (Tc-99m), $^{111}In$, $^{123}I$, $^{125}I$, $^{169}Yb$ and $^{186}Re$; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

The terms halo and halogen as used herein refer to an atom selected from fluorine, chlorine, bromine, and iodine.

The term "heterocyclic", as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term "heteroaryl", as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl) piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The terms "substituted," whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The following are more general terms used throughout the present application:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. For example, the effective amount of microparticles containing an antigen to be delivered to immunize an individual is the amount that results in an immune response sufficient to prevent infection with an organism having the administered antigen.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2% fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

DETAILED DESCRIPTION OF CERTAIN PREFERRED EMBODIMENTS OF THE INVENTION

Figure 1A:
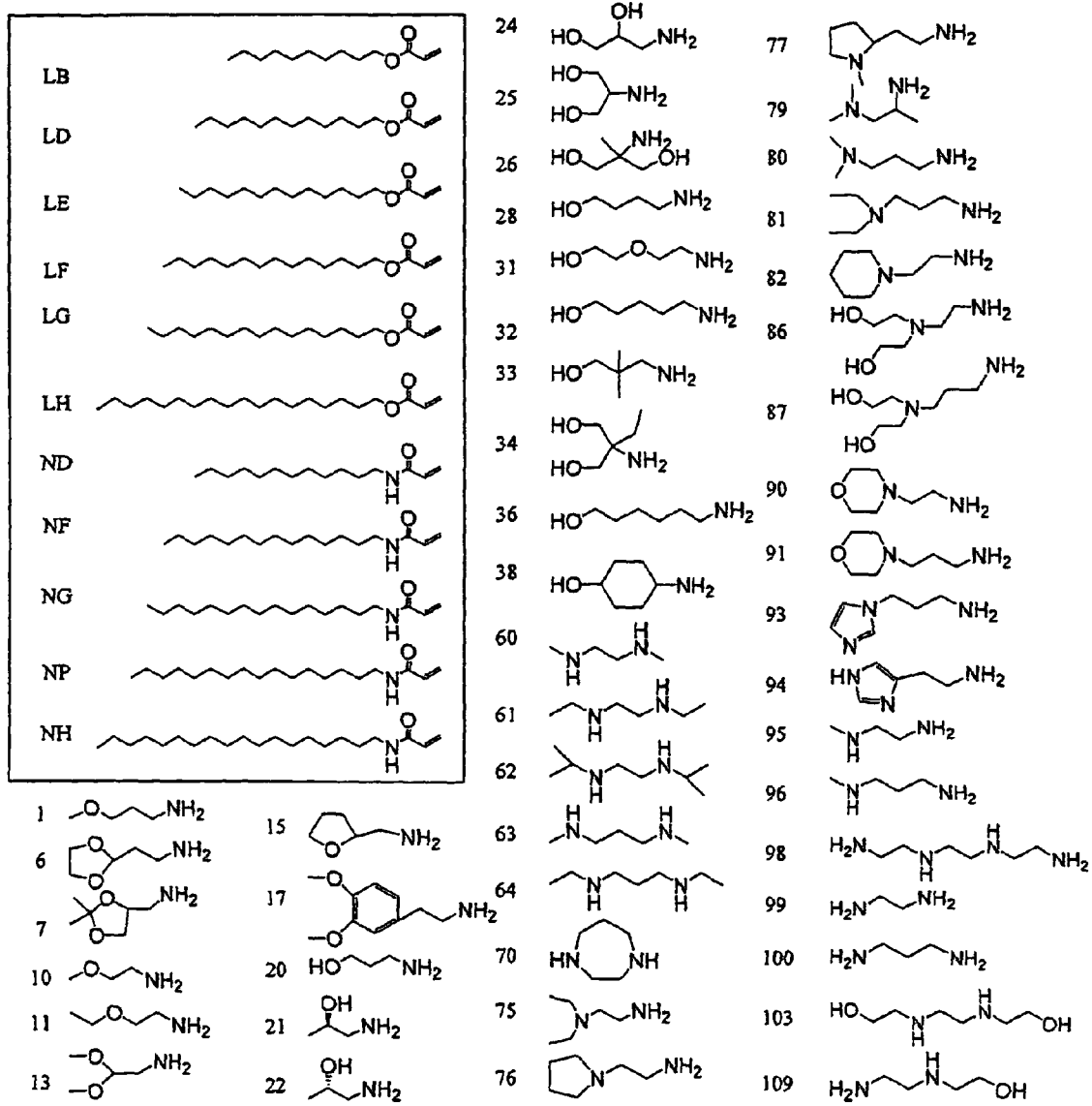
FIG. 1 shows acrylates and amines used in the synthesis of exemplary amine-containing lipids.

The present invention provides novel lipids and delivery systems based on the use of amino lipids. The system may be used in the pharmaceutical/drug delivery arts to delivery polynucleotides, proteins, small molecules, peptides, antigen, drugs, etc. to a patient, tissue, organ, cell, etc.

The amino lipids of the present invention provide for several different uses in the drug delivery art. The lipids with their amine-containing hydrophilic portion may be used to complex polynucleotides and thereby enhance the delivery of polynucleotide and prevent their degradation. The lipids may also be used in the formation of nanoparticles, microparticles, liposomes, and micelles containing the agent to be delivered. Preferably, the lipids are biocompatible and biodegradable, and the formed particles are also biodegradable and biocompatible and may be used to provide controlled, sustained release of the agent. These lipids and their corresponding particles may also be responsive to pH changes given that these lipids are protonated at lower pH.

Lipids

The lipids of the present invention are lipids containing primary, secondary, or tertiary amines and salts thereof. In a particularly preferred embodiment, the inventive lipids are relatively non-cytotoxic. In another particularly preferred embodiment, the inventive lipids are biocompatible and biodegradable. In a particularly preferred embodiment, the lipids of the present invention have $pK_a$s in the range of 5.5 to 7.5, more preferably between 6.0 and 7.0. In another particularly preferred embodiment, the lipid may be designed to have a desired $pK_a$ between 3.0 and 9.0, more preferably between 5.0 and 8.0. The inventive lipids are particularly attractive for drug delivery for several reasons: 1) they contain amino groups for interacting with DNA, RNA, other polynucleotides, and other negatively charged agents, for buffering the pH, for causing endosomolysis, etc.; 2) they can be synthesized from commercially available starting materials; and 3) they are pH responsive and can be engineered with a desired $pK_a$.

In certain embodiments, the lipids of the present invention are of the formula (I):

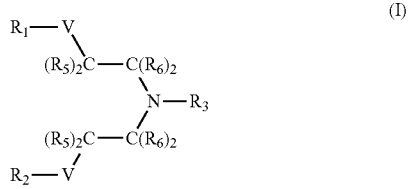

(I)

wherein each occurrence of V is independently selected from the group consisting of C=O, C=S, S=O, and SO$_2$;

R$_1$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO$_2$R$_A$; —CN; —SCN; —SR$_A$; —SOR$_A$; —SO$_2$R$_A$; —NO$_2$; —N$_3$; —N(R$_A$)$_2$; —NHC(=O)R$_A$; —NR$_A$C(=O)N(R$_A$)$_2$; —OC(=O)OR$_A$; —OC(=O)R$_A$; —OC(=O)N(R$_A$)$_2$; —NR$_A$C(=O)OR$_A$; or —C(R$_A$)$_3$; wherein each occurrence of R$_A$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

R$_2$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO$_2$R$_B$; —CN; —SCN; —SR$_B$; —SOR$_B$; —SO$_2$R$_B$; —NO$_2$; —N$_3$; —N(R$_B$)$_2$; —NHC(=O)R$_B$; —NR$_B$C(=O)N(R$_B$)$_2$; —OC(=O)OR$_B$; —OC(=O)R$_B$; —OC(=O)N(R$_B$)$_2$; —NR$_B$C(=O)OR$_B$; or —C(R$_B$)$_3$; wherein each occurrence of R$_B$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

wherein R$_1$ and R$_2$ may be taken together to form a cyclic structure;

R$_3$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —CN; —SCN; —SR$_C$; —SOR$_C$; —SO$_2$R$_C$; —NO$_2$; —N$_3$; —N(R$_C$)$_2$; —NHC(=O)R$_C$; —NR$_C$C(=O)N(R$_C$)$_2$; —OC(=O)OR$_C$; —OC(=O)R$_C$; —OC(=O)N(R$_C$)$_2$; —NR$_C$C(=O)OR$_C$; or —C(R$_C$)$_3$; wherein each occurrence of R$_C$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety; each occurrence of R$_5$ is independently selected from the group consisting of hydrogen and C$_1$-C$_6$ alkyl;

each occurrence of R$_6$ is independently selected from the group consisting of hydrogen and C$_1$-C$_6$ alkyl; and salts thereof.

In certain embodiments, the tertiary amine of formula (I) is protonated or alkylated to form a compound of formula (Ia):

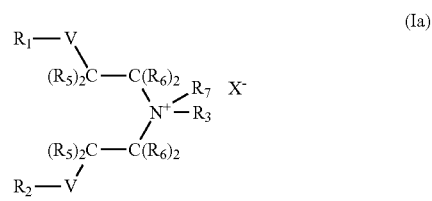

(Ia)

wherein R$_1$, R$_2$, R$_3$, R$_5$, R$_6$, and V are defined above;

R$_7$ is hydrogen or C$_1$-C$_6$ aliphatic, preferably C$_1$-C$_6$ alkyl, more preferably hydrogen or methyl; and X is any anion. Possible anions include fluoride, chloride, bromide, iodide, sulfate, bisulfate, phosphate, nitrate, acetate, fumarate, oleate, citrate, valerate, maleate, oxalate, isonicotinate, lactate, salicylate, tartrate, tannate, pantothenate, bitartrate, ascorbate, succinate, gentisinate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate).

In certain embodiments, V is C=O. In other embodiments, V is C=S. In yet other embodiments, V is S=O. In still other embodiments, V is SO$_2$.

In certain embodiments, R$_1$ is hydrogen. In other embodiments, R$_1$ is a cyclic or acyclic, substituted or unsubstituted, branched or un branched aliphatic or heteroaliphatic moiety. In certain embodiments, R$_1$ is a substituted or unsubstituted aryl or heteroaryl moiety. Preferably, the aryl or heteroaryl moiety is a monocyclic 5- or 6-membered ring system. In certain embodiments, R$_1$ is —OR$_A$, —SR$_A$, —NR$_A$)$_2$, or —NHR$_A$. In certain embodiments, R$_1$ is —OR$_A$. In other embodiments, R$_1$ is —N(R$_A$)$_2$ or —NHR$_A$. In certain embodiments, R$_A$ is hydrogen. In other embodiments, R$_A$ is a cyclic or acyclic, substituted or unsubstituted, branched or unbranched aliphatic or heteroaliphatic moiety. In certain embodiments, R$_A$ is an acyclic, substituted or unsubstituted aliphatic moiety. In certain other embodiments, R$_A$ is an acyclic, unsubstituted, unbranched aliphatic moiety, preferably C$_6$-C$_{30}$, more preferably C$_{10}$-C$_{20}$. In certain embodiments, R$_A$ is an unsubstituted, straight chain alkyl group with at least 5 carbons. In certain embodiments, R$_A$ is an unsubstituted, straight chain alkyl group, preferably C$_6$-C$_{30}$, more preferably C$_{10}$-C$_{20}$. In certain embodiments, R$_1$ is —OR$_A$, wherein R$_A$ is an unsubstituted, unbranched C$_9$ alkyl chain. In certain embodiments, R$_1$ is —OR$_A$, wherein R$_A$ is an unsubstituted, unbranched C$_{10}$ alkyl chain. In certain embodiments, R$_1$ is —OR$_A$, wherein R$_A$ is an unsubstituted, unbranched C$_{11}$ alkyl chain. In certain embodiments, $R_1$ is $-OR_A$, wherein $R_A$ is an unsubstituted, unbranched $C_{12}$ alkyl chain. In certain embodiments, $R_1$ is $-OR_A$, wherein $R_A$ is an unsubstituted, unbranched $C_{13}$ alkyl chain. In certain embodiments, $R_1$ is $-OR_A$, wherein $R_A$ is an unsubstituted, unbranched $C_{14}$ alkyl chain. In certain embodiments, $R_1$ is $-OR_A$, wherein $R_A$ is an unsubstituted, unbranched $C_{15}$ alkyl chain. In certain embodiments, $R_1$ is $-OR_A$, wherein $R_A$ is an unsubstituted, unbranched $C_{16}$ alkyl chain. In certain embodiments, $R_1$ is $-OR_A$, wherein $R_A$ is an unsubstituted, unbranched $C_{17}$ alkyl chain. In certain embodiments, $R_1$ is $-OR_A$, wherein $R_A$ is an unsubstituted, unbranched $C_{18}$ alkyl chain. In certain embodiments, $R_1$ is $-OR_A$, wherein $R_A$ is an unsubstituted, unbranched $C_{19}$ alkyl chain. In certain embodiments, $R_1$ is $-OR_A$, wherein $R_A$ is an unsubstituted, unbranched $C_{20}$ alkyl chain. In yet other embodiments, $R_A$ is a substituted or unsubstituted aryl or heteroaryl moiety.

In certain embodiments, $R_2$ is hydrogen. In other embodiments, $R_2$ is a cyclic or acyclic, substituted or unsubstituted, branched or unbranched aliphatic or heteroaliphatic moiety. In certain embodiments, $R_2$ is a substituted or unsubstituted aryl or heteroaryl moiety. Preferably, the aryl or heteroaryl moiety is a monocyclic 5- or 6-membered ring system. In certain embodiments, $R_2$ is $-OR_B$, $-SR_B$, $-N(R_B)_2$, or $-NHR_B$. In certain embodiments, $R_2$ is $-OR_B$. In other embodiments, $R_2$ is $-N(R_B)_2$ or $-NHR_B$. In certain embodiments, $R_B$ is hydrogen. In other embodiments, $R_B$ is a cyclic or acyclic, substituted or unsubstituted, branched or unbranched aliphatic or heteroaliphatic moiety. In certain embodiments, $R_B$ is an acyclic, substituted or unsubstituted aliphatic moiety. In certain embodiments, $R_B$ is an unsubstituted, straight chain alkyl group with at least 5 carbons. In certain other embodiments, $R_B$ is an acyclic, unsubstituted, unbranched aliphatic moiety, preferably $C_6$-$C_{30}$, more preferably $C_{10}$-$C_{20}$. In certain embodiments, $R_B$ is an unsubstituted, straight chain alkyl group, preferably $C_6$-$C_{30}$, more preferably $C_{10}$-$C_{20}$. In certain embodiments, $R_2$ is $-OR_B$, wherein $R_B$ is an unsubstituted, unbranched $C_9$ alkyl chain. In certain embodiments, $R_2$ is $-OR_B$, wherein $R_B$ is an unsubstituted, unbranched $C_{10}$ alkyl chain. In certain embodiments, $R_2$ is $-OR_B$, wherein $R_B$ is an unsubstituted, unbranched $C_{11}$ alkyl chain. In certain embodiments, $R_2$ is $-OR_B$, wherein $R_B$ is an unsubstituted, unbranched $C_{12}$ alkyl chain. In certain embodiments, $R_2$ is $-OR_B$, wherein $R_B$ is an unsubstituted, unbranched $C_{13}$ alkyl chain. In certain embodiments, $R_2$ is $-OR_B$, wherein $R_B$ is an unsubstituted, unbranched $C_{14}$ alkyl chain. In certain embodiments, $R_2$ is $-OR_B$, wherein $R_B$ is an unsubstituted, unbranched $C_{15}$ alkyl chain. In certain embodiments, $R_2$ is $-OR_A$, wherein $R_B$ is an unsubstituted, unbranched $C_{16}$ alkyl chain. In certain embodiments, $R_2$ is $-OR_A$, wherein $R_B$ is an unsubstituted, unbranched $C_{17}$ alkyl chain. In certain embodiments, $R_2$ is $-OR_A$, wherein $R_B$ is an unsubstituted, unbranched $C_{18}$ alkyl chain. In certain embodiments, $R_2$ is $-OR_B$, wherein $R_B$ is an unsubstituted, unbranched $C_{19}$ alkyl chain. In certain embodiments, $R_2$ is $-OR_B$, wherein $R_B$ is an unsubstituted, unbranched $C_{20}$ alkyl chain. In yet other embodiments, $R_B$ is a substituted or unsubstituted aryl or heteroaryl moiety.

Figure 1B:
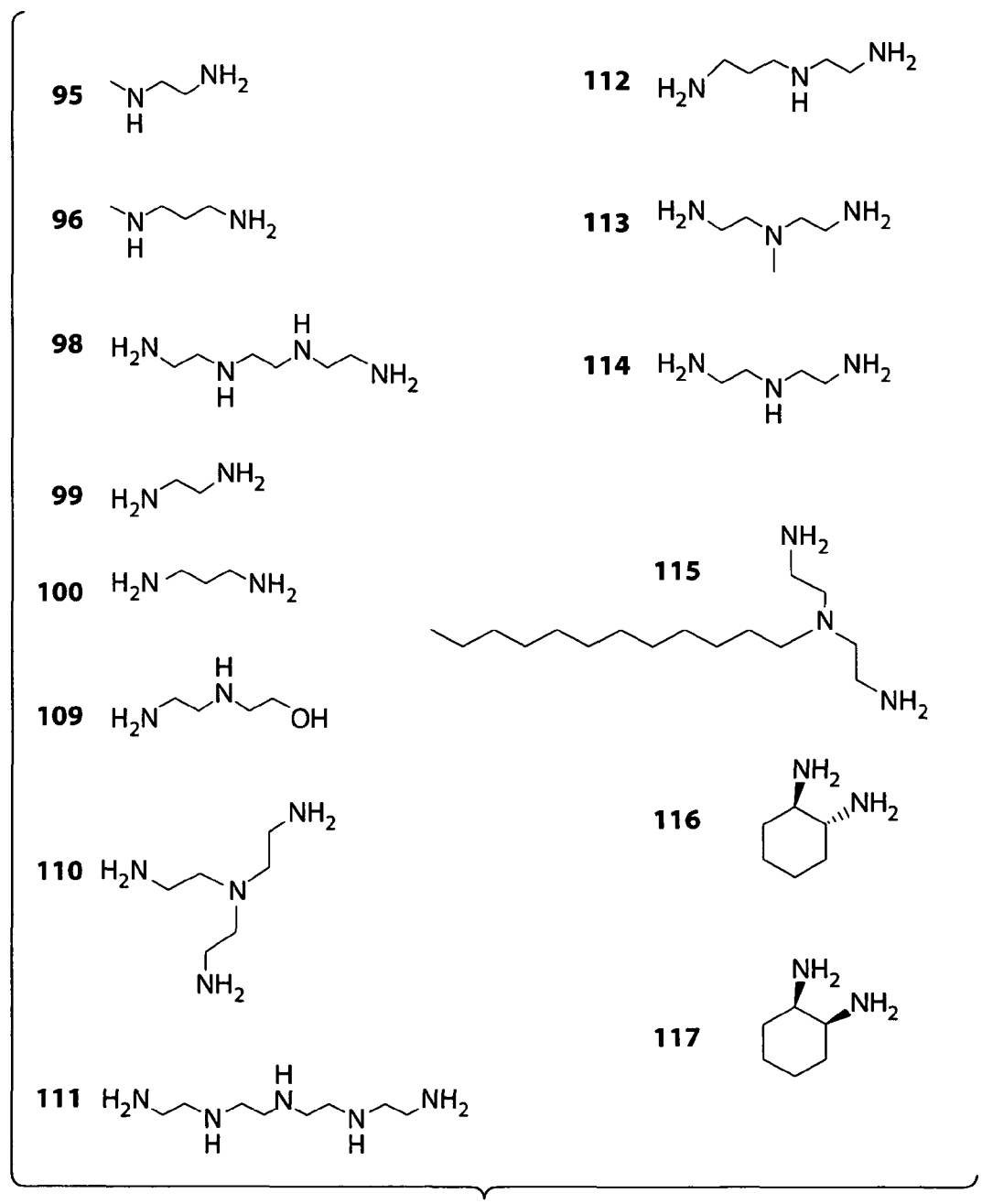
Figure 2A:
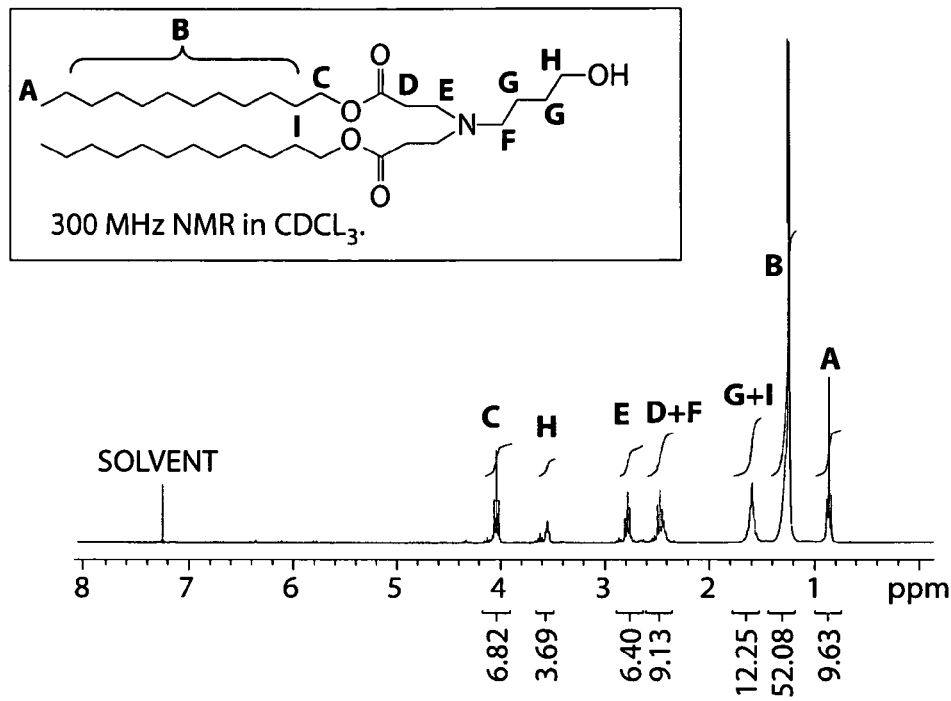
FIG. 2 shows $^1$H NMR spectra of lipids LD28 (A), LD86 (B), LD87 (C), ND32 (D), ND86 (E), and ND87 (F).
Figure 2B:
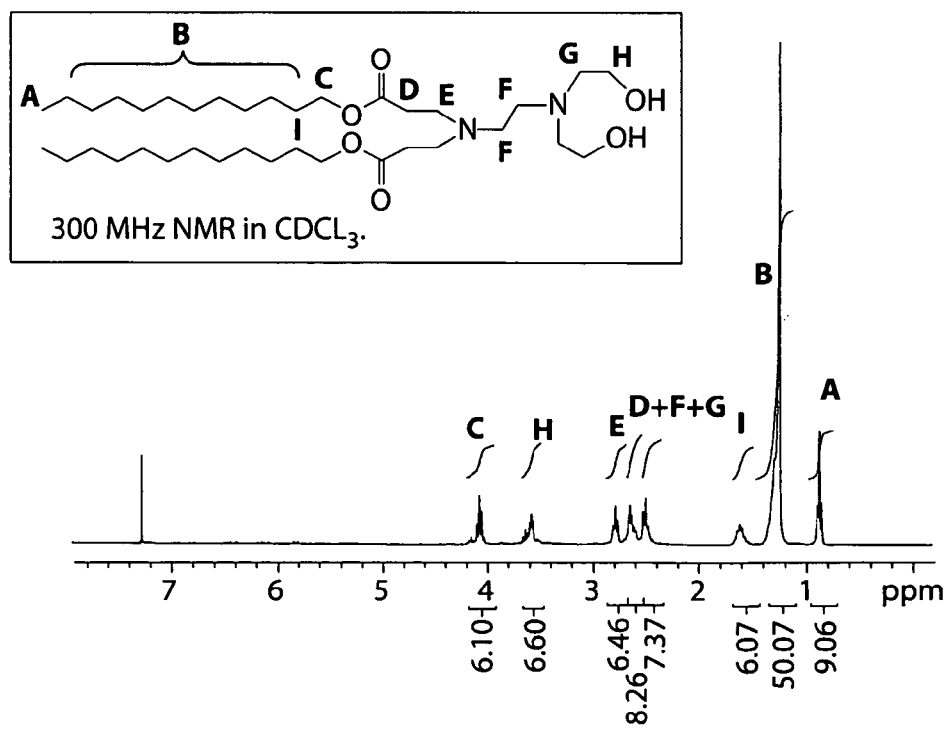
Figure 2C:
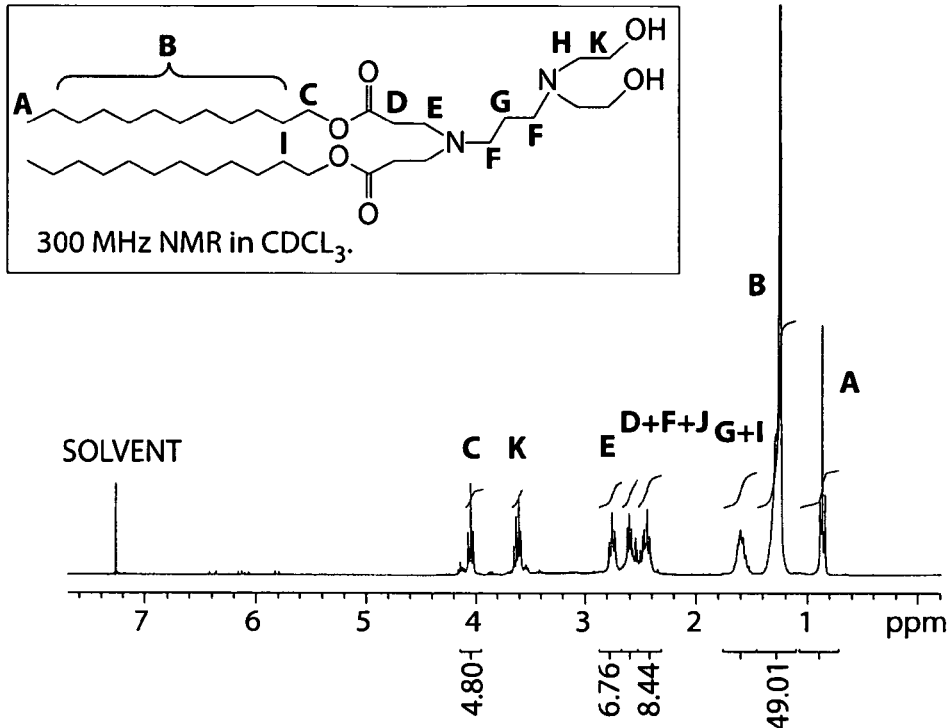
Figure 2D:
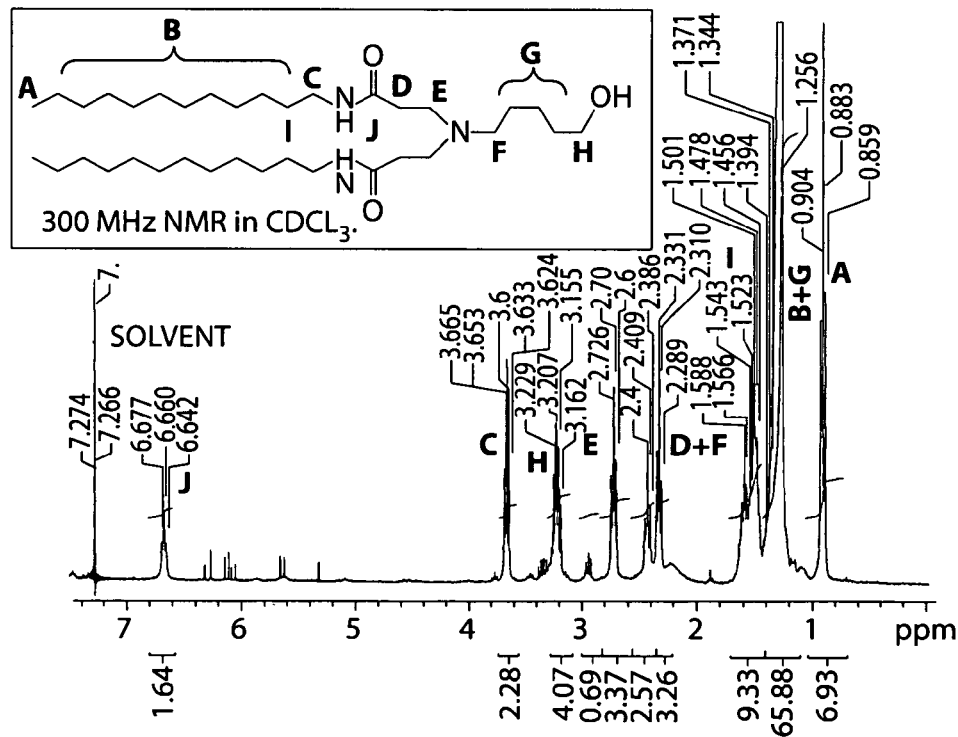
Figure 2E:
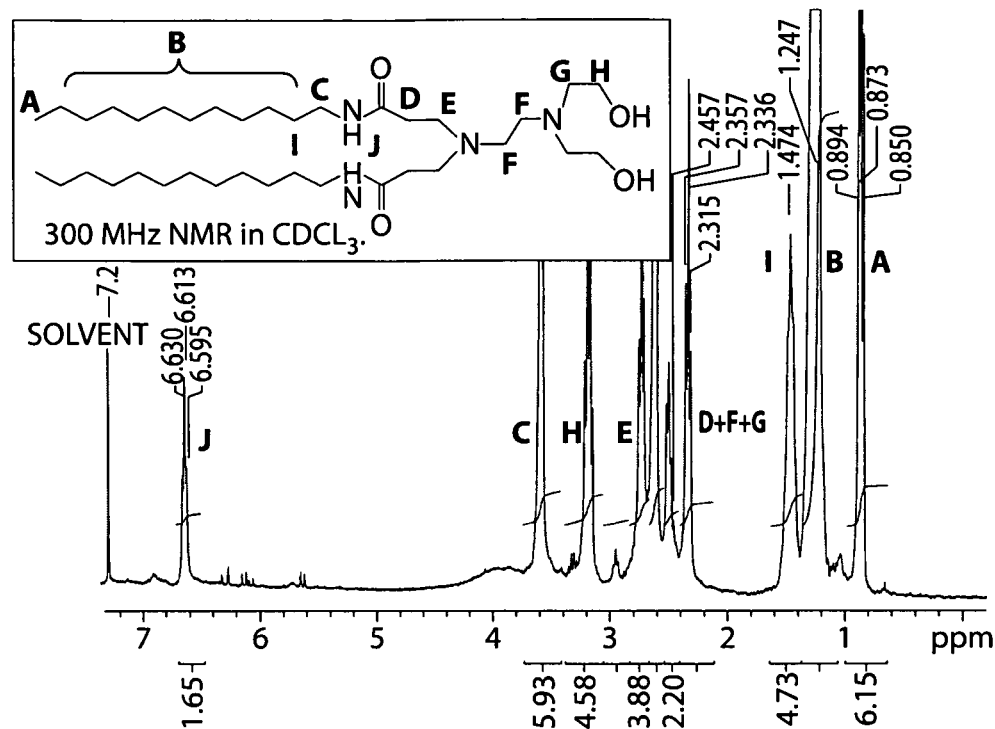
Figure 2F:
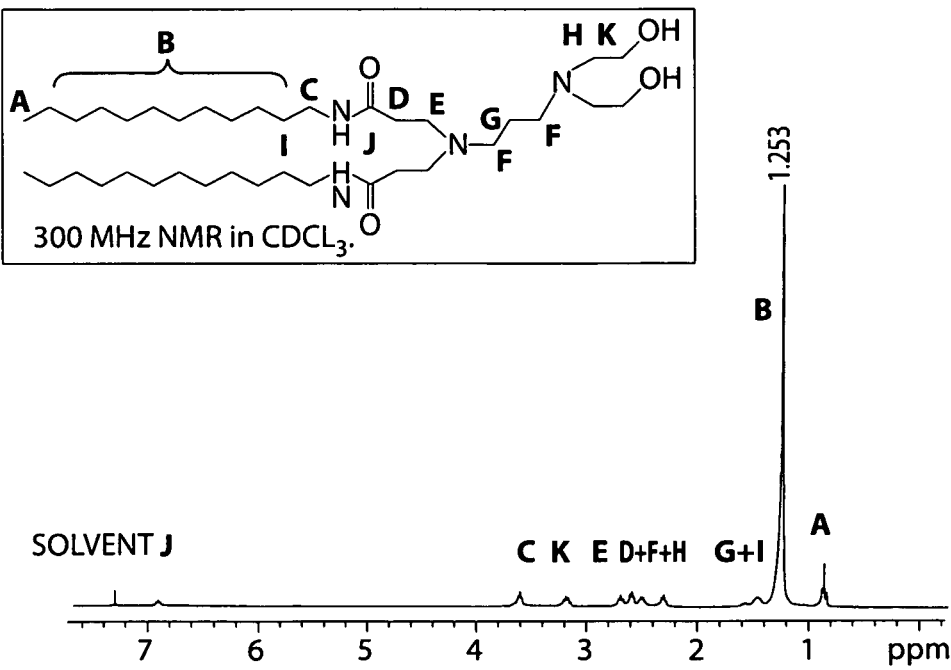
Figure 3:
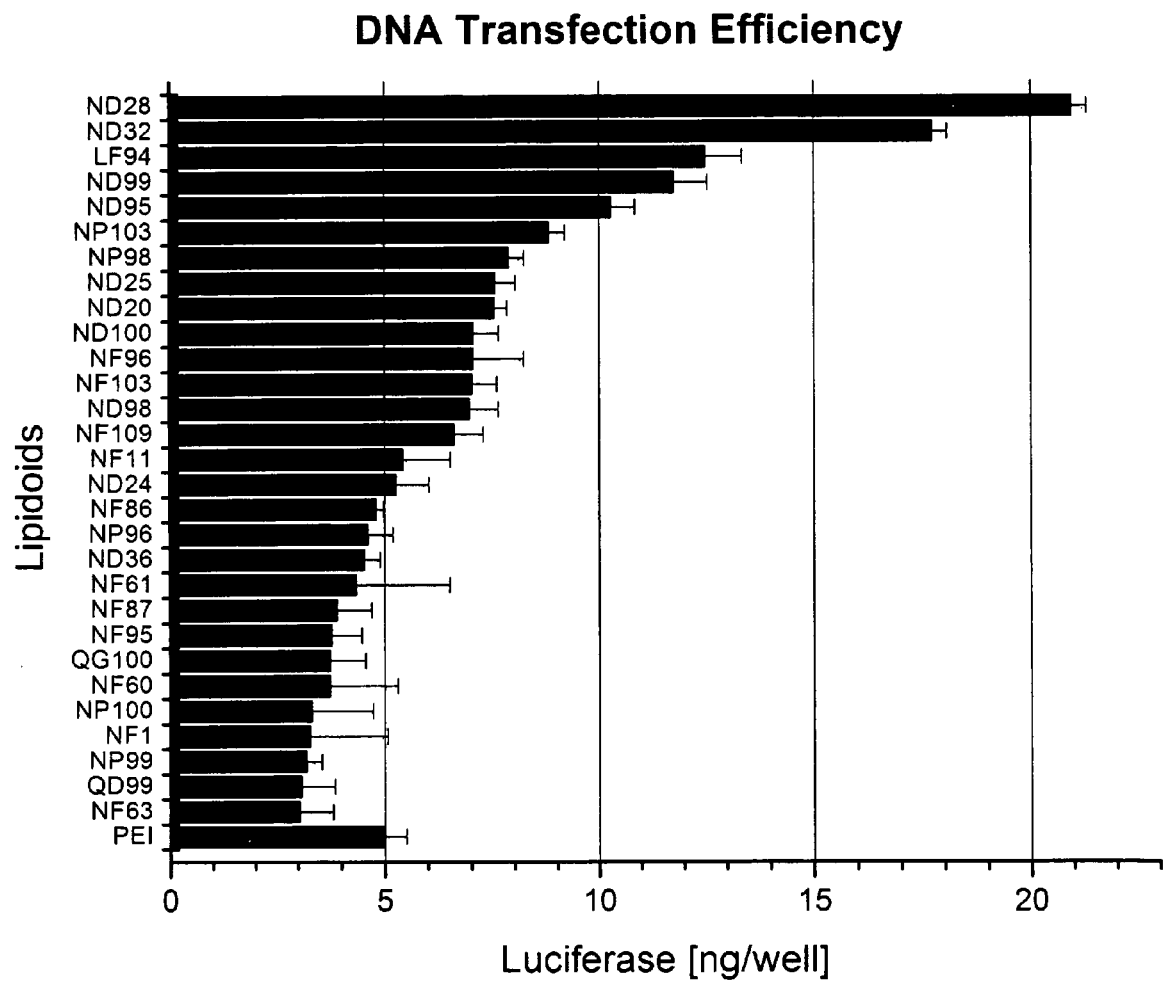
FIG. 3 shows the DNA transfection efficiency of several of the inventive amine-containing lipids.
Figure 4:
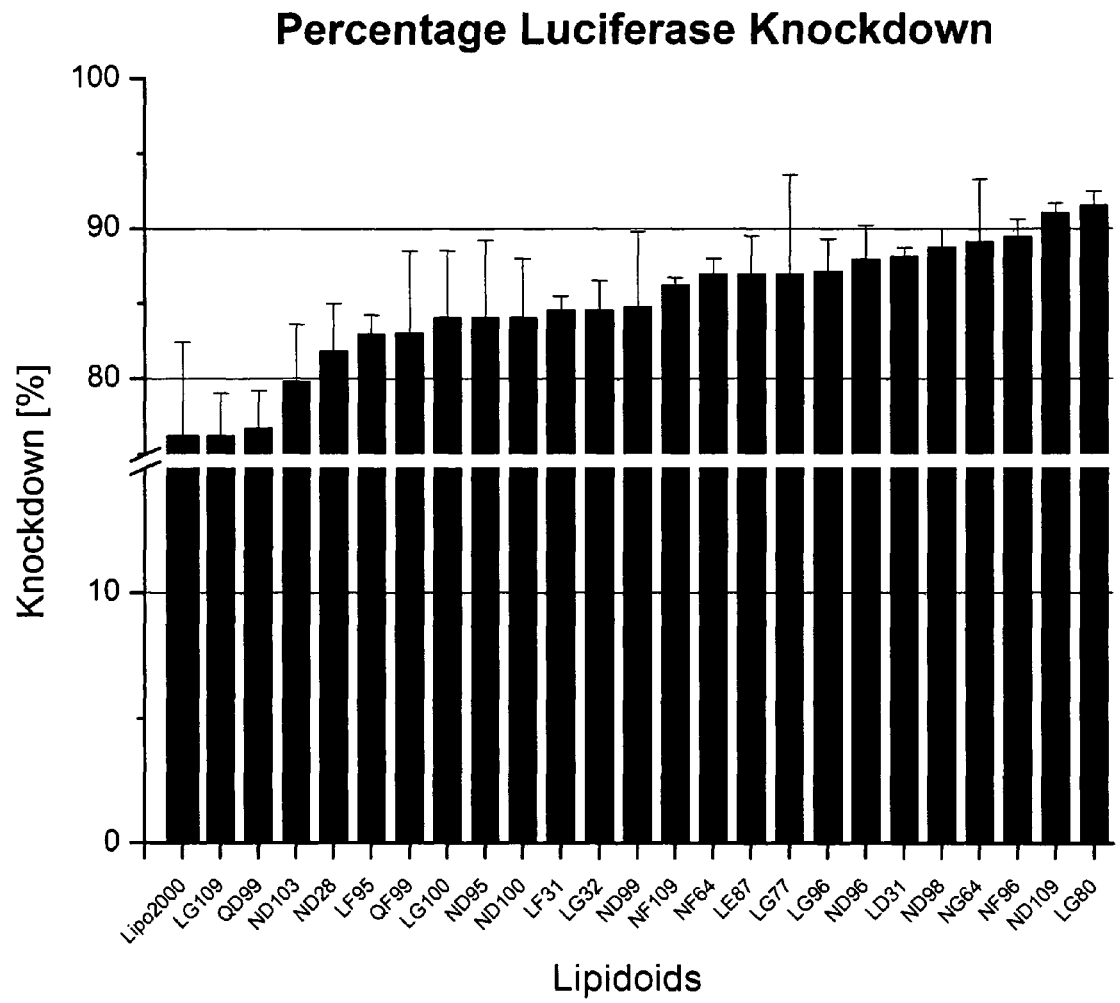
FIG. 4 shows the percentage of luciferase knockdown for several of the inventive lipids.

In certain embodiments, $R_3$ is a cyclic or acyclic, substituted or unsubstituted, branched or unbranched aliphatic moiety. In other embodiments, $R_3$ is a cyclic or acyclic, substituted or unsubstituted, branched or unbranched heteroaliphatic moiety. In certain embodiments, $R_3$ is a polyethylene glycol moiety. In certain embodiments, $R_3$ is an aliphatic moiety substituted with one or more hydroxyl groups. In other embodiments, $R_3$ is an aliphatic moiety substituted with one or more amino, alkylamino, or dialkylamino groups. In certain embodiments, $R_3$ is a heteroaliphatic moiety. In certain embodiments, $R_3$ is cyclic aliphatic, preferably a monocyclic ring system with a 5- or 6-membered ring. In other embodiments, $R_3$ is aryl or heteroaryl, preferably a monocyclic ring system with a 5- or 6-membered ring. In certain embodiments, the lipids are prepared from the primary amines 1, 11, 20, 24, 25, 28, 31, 32, 36, 76, 77, 80, 86, 87, 93, 94, 95, 96, 99, or 100 shown in FIG. 1. In certain other embodiments the lipids are prepared from the primary amines 31, 93, or 94 as shown in FIG. 1.

In certain embodiments, each occurrence of $R_5$ is hydrogen. In certain embodiments, at least one occurrence of $R_5$ is methyl and the other occurrences are hydrogen. In certain embodiments, at least two occurrences of $R_5$ are methyl, and the other occurrences are hydrogen. In other embodiments, at least two occurrences of $R_5$ are hydrogen.

In certain embodiments, each occurrence of $R_6$ is hydrogen. In certain other embodiments, at least two occurrences of $R_6$ are hydrogen. In certain embodiments, at least one occurrence of $R_6$ is methyl, and the other occurrences are hydrogen. In certain embodiments, at least two occurrences of $R_6$ are methyl, and the other occurrences are hydrogen.

In certain embodiments,

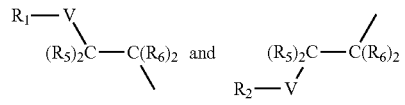

which are

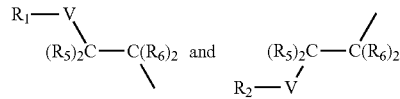

attached to N, are the same. In other embodiments, which are attached to N are the same and are different than $R_3$. In yet other embodiments,

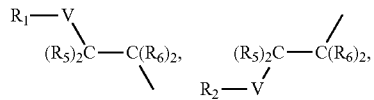

and $R_3$ are all different.

In certain subclasses of lipids, the lipids are of the formula:

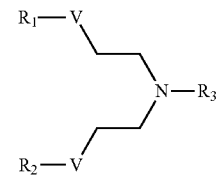

wherein V, $R_1$, $R_2$, and $R_3$ are defined as above; and all occurrences of $R_5$ and $R_6$ are hydrogen. In certain embodiments, $R_1$ and $R_2$ are the same. In other embodiments, $R_1$ and $R_2$ are different. In certain embodiments, V is C=O as shown in the formula:

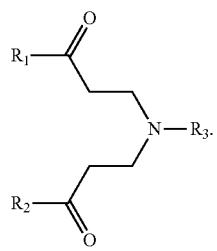

In certain embodiments, $R_1$ and $R_2$ are the same. In other embodiments, $R_1$ and $R_2$ are different. In certain embodiments, $R_1$ is —$OR_A$ and $R_2$ is —$OR_B$, as shown in the formula below:

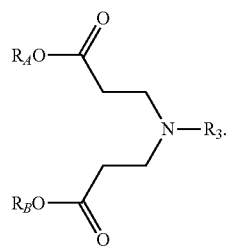

In certain embodiments, $R_A$ and $R_B$ are the same. In other embodiments, $R_A$ and $R_B$ are different. In certain embodiments, at least one of $R_A$ and $R_B$ is an unsubstituted, straight chain alkyl group with at least 5 carbons. In certain embodiments, both of $R_A$ and $R_B$ are an unsubstituted, straight chain alkyl group with at least 5 carbons. In certain embodiments, $R_A$ and $R_B$ are $C_6$-$C_{30}$ straight chain alkyl groups, or $C_{21}$-$C_{30}$ straight chain alkyl groups, preferably $C_9$-$C_{20}$ straight chain alkyl groups. In certain embodiments, $R_A$ and $R_B$ are $C_6$-$C_{30}$ straight chain alkenyl groups, or $C_{21}$-$C_{30}$ straight chain alkenyl groups, preferably $C_9$-$C_{20}$ straight chain alkenyl groups. In certain embodiments, $R_A$ and $R_B$ are $C_6$-$C_{30}$ straight chain alkynyl groups, or $C_{21}$-$C_{30}$ straight chain alkynyl groups, preferably $C_9$-$C_{20}$ straight chain alkynyl groups. In certain embodiments, when $R_A$ and $R_B$ are the same, $R_A$ and $R_B$ are not methyl, ethyl, n-propyl,

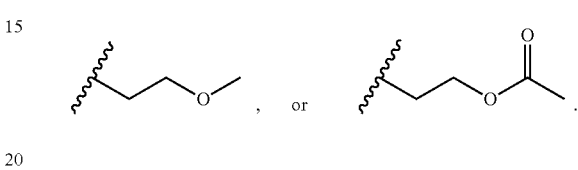

In other embodiments, when $R_A$ and $R_B$ are the same, $R_A$ and $R_B$ each comprise at least 4 carbon atoms. In other embodiments, when $R_A$ and $R_B$ are the same, $R_A$ and $R_B$ each comprise at least 5 carbon atoms. In other embodiments, when $R_A$ and $R_B$ are the same, $R_A$ and $R_B$ each comprise at least 6 carbon atoms. In other embodiments, $R_A$ and $R_B$ each comprise at least 4 carbon atoms. In other embodiments, $R_A$ and $R_B$ each comprise at least 5 carbon atoms. In other embodiments, $R_A$ and $R_B$ each comprise at least 6 carbon atoms. Exemplary classes of the above formula include:

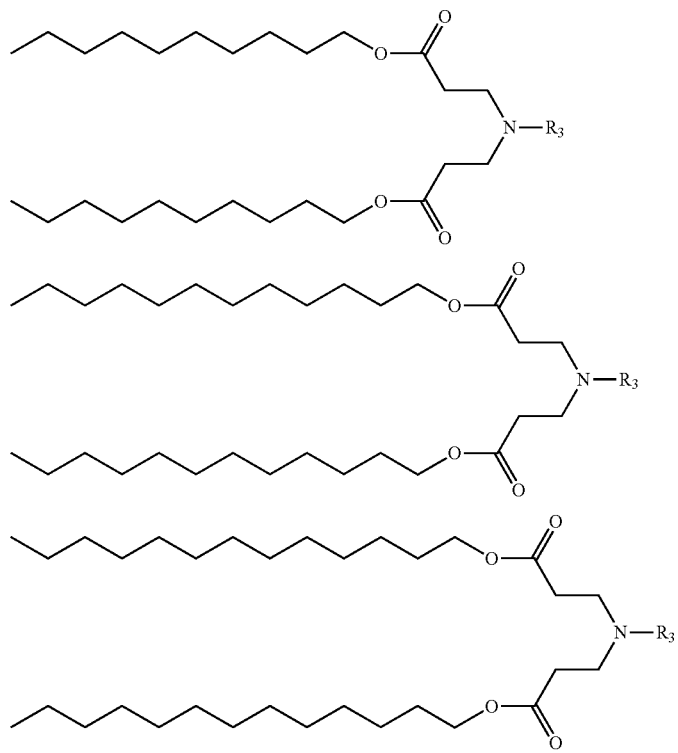

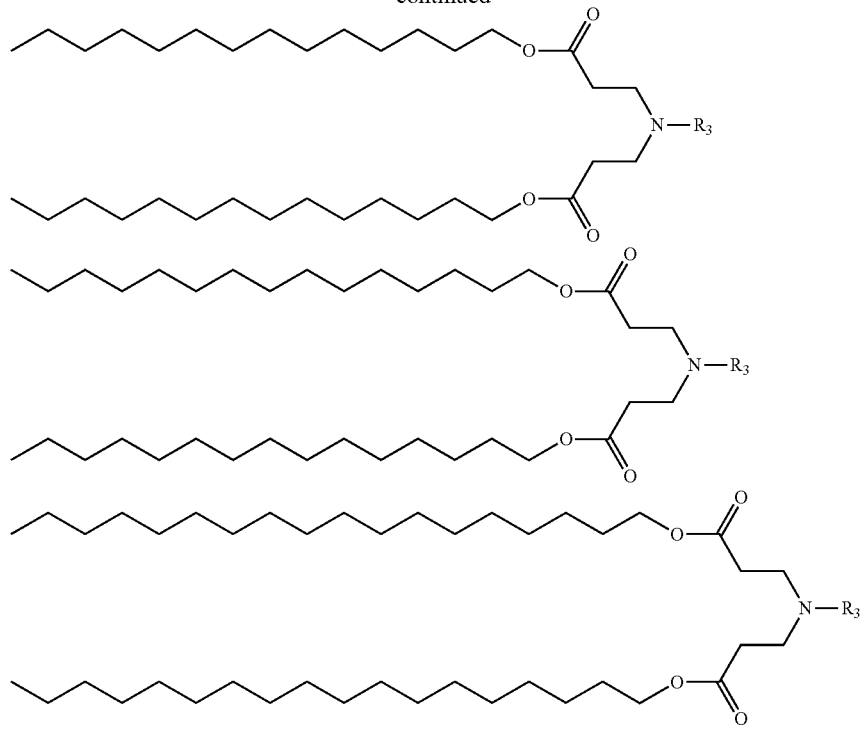

In certain embodiments, the acrylate used in the synthesis of the lipid is acrylate LD, LF, or LG in FIG. 1. In certain embodiments the acrylate is acrylate LF in FIG. 1. In certain embodiments the acrylate is acrylate LG in FIG. 1.

In certain embodiments, $R_3$ is not

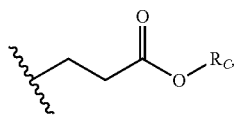

wherein $R_C$ is defined as above. In certain embodiments, $R_3$ is not —$CH_2CH_2OR_C'$, wherein $R_C'$ is methyl, ethyl, propyl, isopropyl, butyl, s-butyl, isobutyl, t-butyl, pentyl, cyclopentyl, hexyl, cyclohexyl, decyl, methoxymethyl, 2-methoxyethyl, 1-ethoxyethyl, 2-ethoxyethyl, (2-methoxyethoxy)methyl, 2-tetrahydrofuranyl, 2-tetrahydropyranyl, tetrahydrofurfuryl, formyl, acetyl, propionyl, butyryl, isobutyryl, pivaloyl, valeryl, methoxyacetyl, ethoxyacetyl, acetoxyacetyl, 2-formyloxyethyl, 2-acetoxyethyl, 2-oxopropyl, 2-oxobutyl, 2-oxocyclopentyl, 2-oxo-3-tetrahydrofuranyl, 2-oxo-3-tetrahydropyranyl, methoxycarbonyl, ethoxycarbonyl, and t-butoxycarbonyl. In yet other embodiments, $R_3$ is not —$CH_2CH_2OR_C''$, wherein $R_C''$ is a straight chain, branched or cyclic alkyl group of 1 to 20 carbons atoms, which may contain an ether, carbonyl, or carbonyloxy group. In yet other embodiments, $R_3$ is not —$CH_2CH_2OR_C''$, wherein $R_C''$ is a straight chain, branched or cyclic alkyl group of 1 to 10 carbons atoms, which may contain an ether, carbonyl, or carbonyloxy group. In certain particular embodiments, $R_3$ is not —$CH_2CH_2OR_C''$, wherein $R_C''$ is formyl; acetyl; or methyl group.

In other embodiments, $R_1$ is —$NR_A$ and $R_2$ is —$NR_B$, as shown in the formula below:

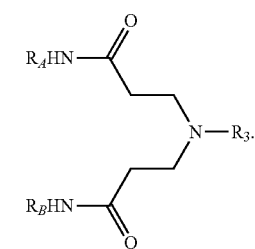

In certain embodiments, $R_A$ and $R_B$ are the same. In other embodiments, $R_A$ and $R_B$ are different. In certain embodiments, $R_A$ and $R_B$ are $C_6$-$C_{30}$ straight chain alkyl groups, or $C_{21}$-$C_{30}$ straight chain alkyl groups, preferably $C_9$-$C_{20}$ straight chain alkyl groups. In certain embodiments, $R_A$ and $R_B$ are $C_6$-$C_{30}$ straight chain alkenyl groups, or $C_{21}$-$C_{30}$ straight chain alkenyl groups, preferably $C_9$-$C_{20}$ straight chain alkenyl groups. In certain embodiments, $R_A$ and $R_B$ are $C_6$-$C_{30}$ straight chain alkynyl groups, or $C_{21}$-$C_{30}$ straight chain alkynyl groups, preferably $C_9$-$C_{20}$ straight chain alkynyl groups. In certain embodiments, when $R_A$ and $R_B$ are the same, $R_A$ and $R_B$ are not methyl, ethyl, n-propyl,

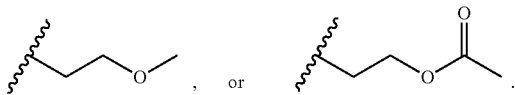

In other embodiments, when $R_A$ and $R_B$ are the same, $R_A$ and $R_B$ each comprise at least 4 carbon atoms. In other embodiments, when $R_A$ and $R_B$ are the same, $R_A$ and $R_B$ each comprise at least 5 carbon atoms. In other embodiments, when $R_A$ and $R_B$ are the same, $R_A$ and $R_B$ each comprise at least 6 carbon atoms. In other embodiments, $R_A$ and $R_B$ each comprise at least 4 carbon atoms. In other embodiments, $R_A$ and $R_B$ each comprise at least 5 carbon atoms. In other embodiments, $R_A$ and $R_B$ each comprise at least 6 carbon atoms. Exemplary classes of the above formula include:

In certain embodiments, the acrylate used in the synthesis of the lipid is acrylate ND, NF, NG, or NP in FIG. 1. In certain embodiments the acrylate is acrylate ND in FIG. 1. In certain embodiments the acrylate is acrylate NF in FIG. 1. In certain embodiments the acrylate is acrylate NP in FIG. 1.

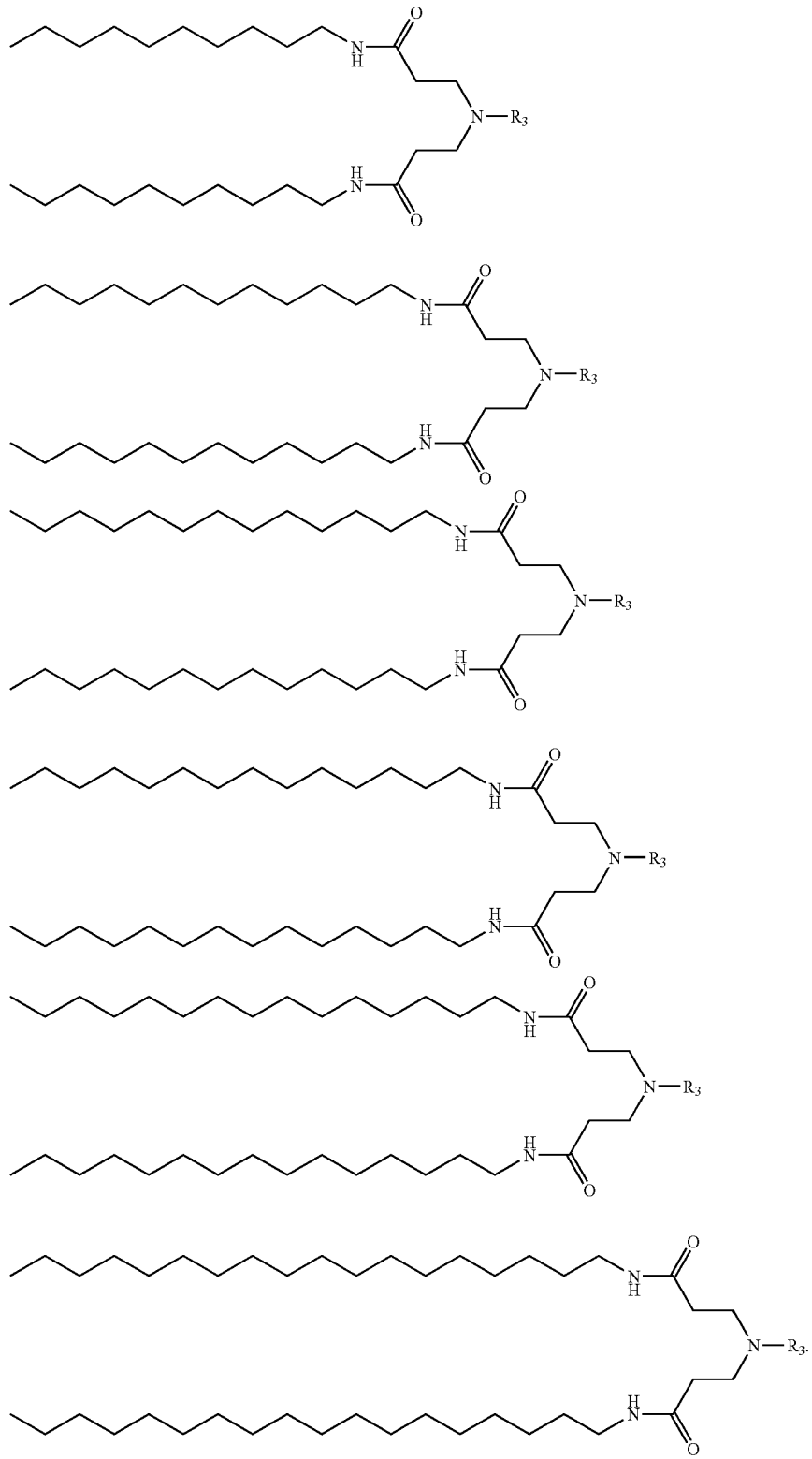

Particular exemplary compounds include:
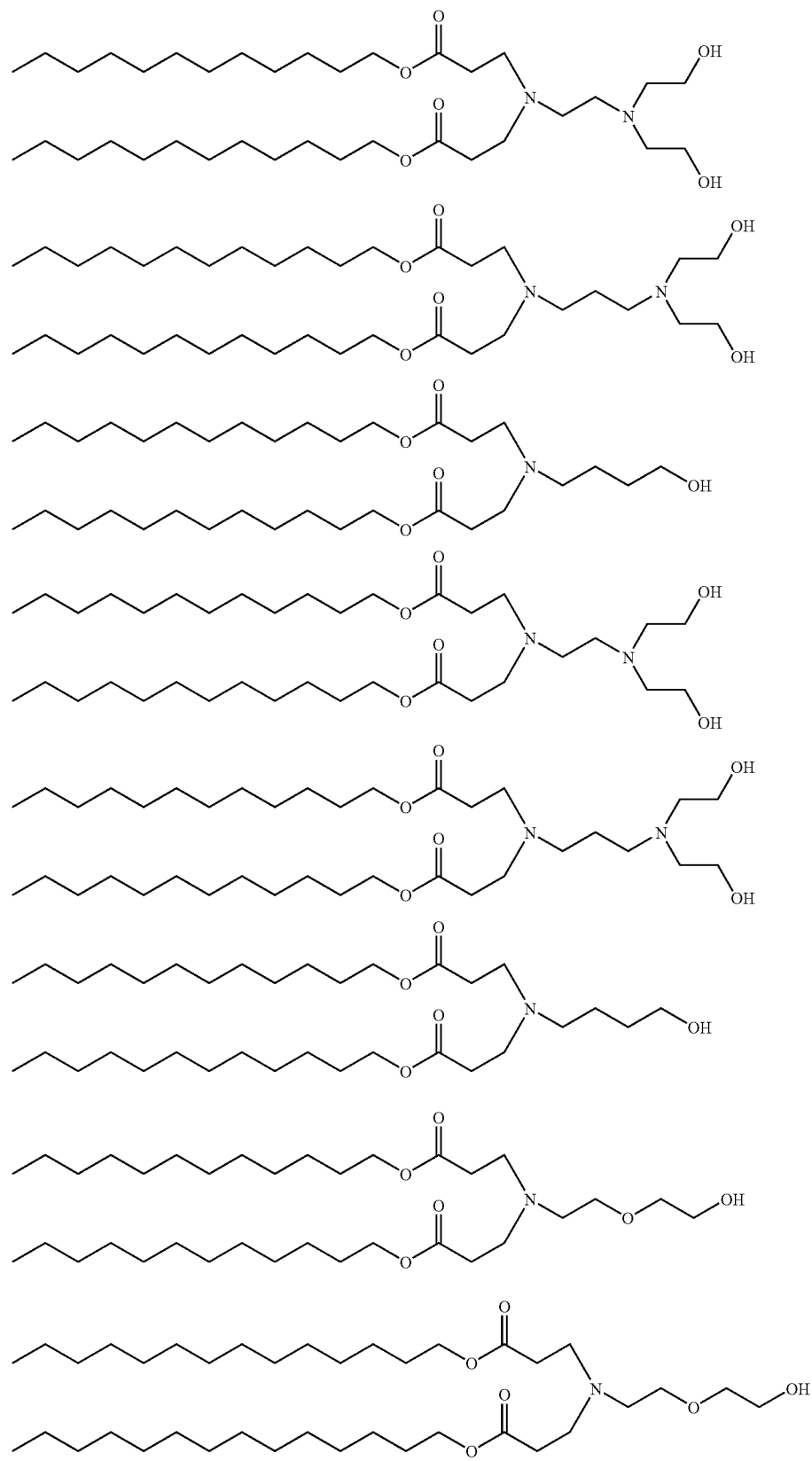

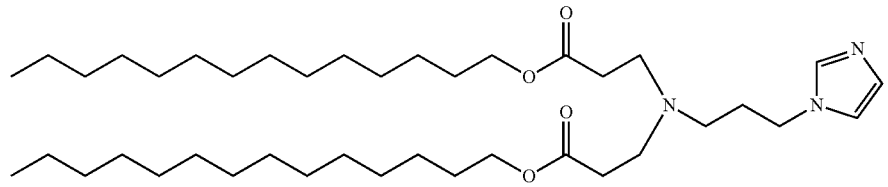
LF93
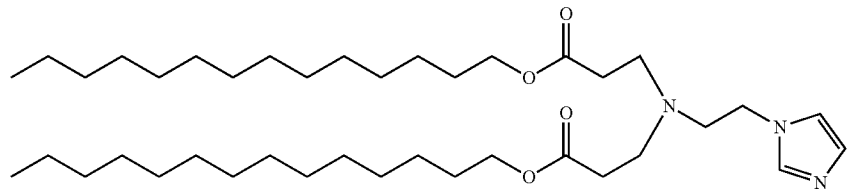
LF94
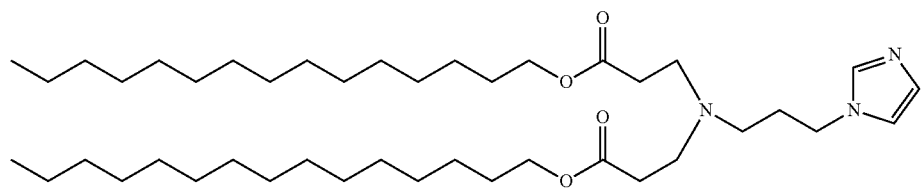
LG93
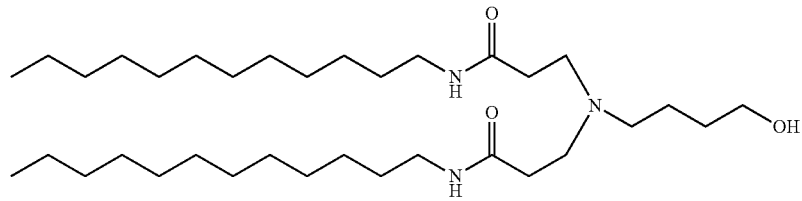
ND28
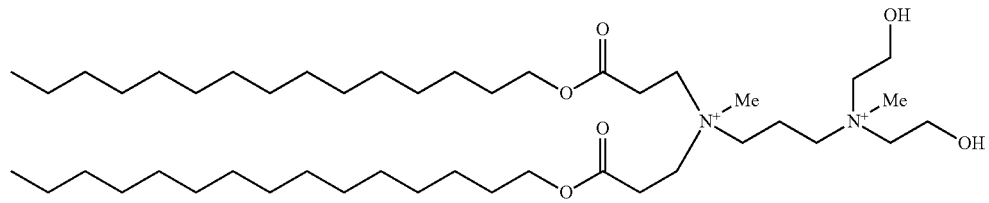
QG87
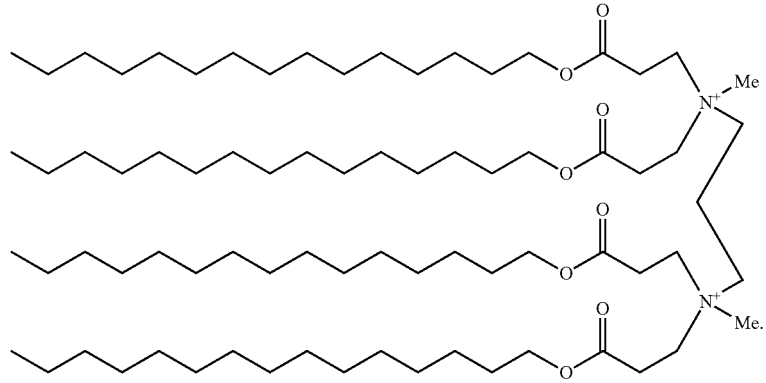
QG100

In other subclasses of lipids, the lipids are of the formula:

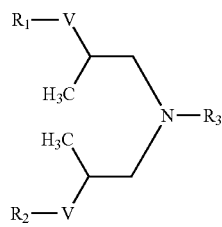

wherein V, $R_1$, and $R_3$ are defined as above; all occurrences of $R_6$ are hydrogen; and $R_5$ is defined as in the formula. In certain embodiments, $R_1$ and $R_2$ are the same. In certain embodiments, V is C=O as shown in the formula:

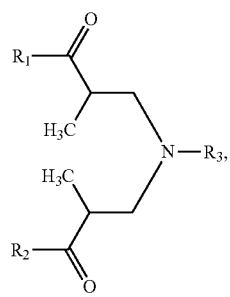

preferably $R_1$ and $R_2$ are the same.

In certain embodiments, $R_1$ is —$OR_A$ and $R_2$ is —$OR_B$, as shown in the formula below:

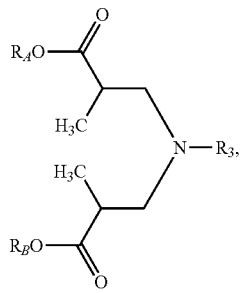

preferably $R_A$ and $R_B$ are the same. In certain embodiments, $R_A$ and $R_B$ are $C_6$-$C_{30}$ straight chain alkyl groups, preferably $C_9$-$C_{20}$ straight chain alkyl groups. In other embodiments, $R_1$ is —$NR_A$ and $R_2$ is —$NR_B$, as shown in the formula below:

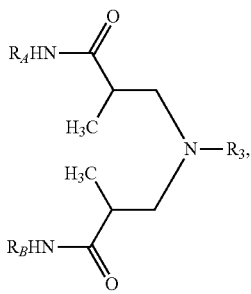

preferably $R_A$ and $R_B$ are the same. In certain embodiments, $R_A$ and $R_B$ are $C_6$-$C_{30}$ straight chain alkyl groups, preferably $C_9$-$C_{20}$ straight chain alkyl groups.

In certain embodiments,

in formulae (I) and (Ia) are selected from the group consisting of:

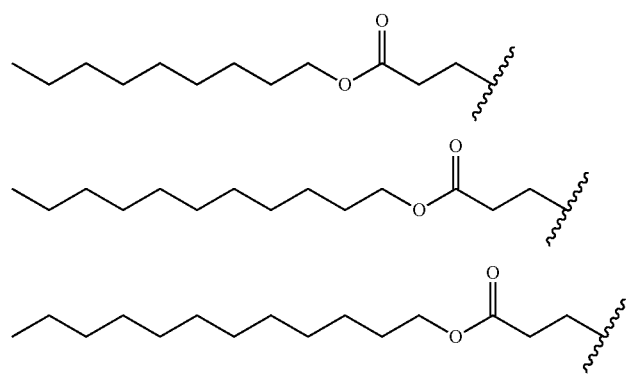

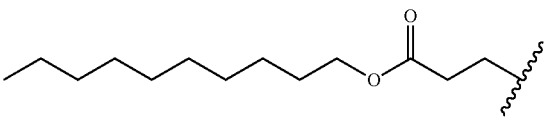

-continued
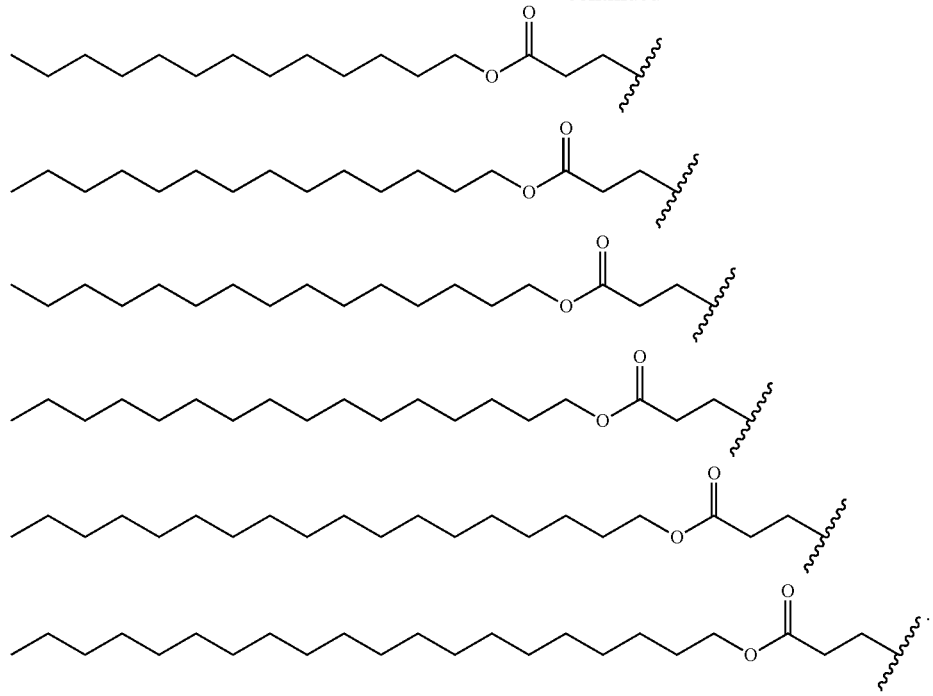
In certain embodiments, the lipids are prepared using acrylates LC, LD, LE, LF, and LG in FIG. 1.
In certain embodiments,
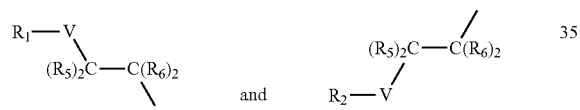
in formulae (I) and (Ia) are selected from the group consisting of:
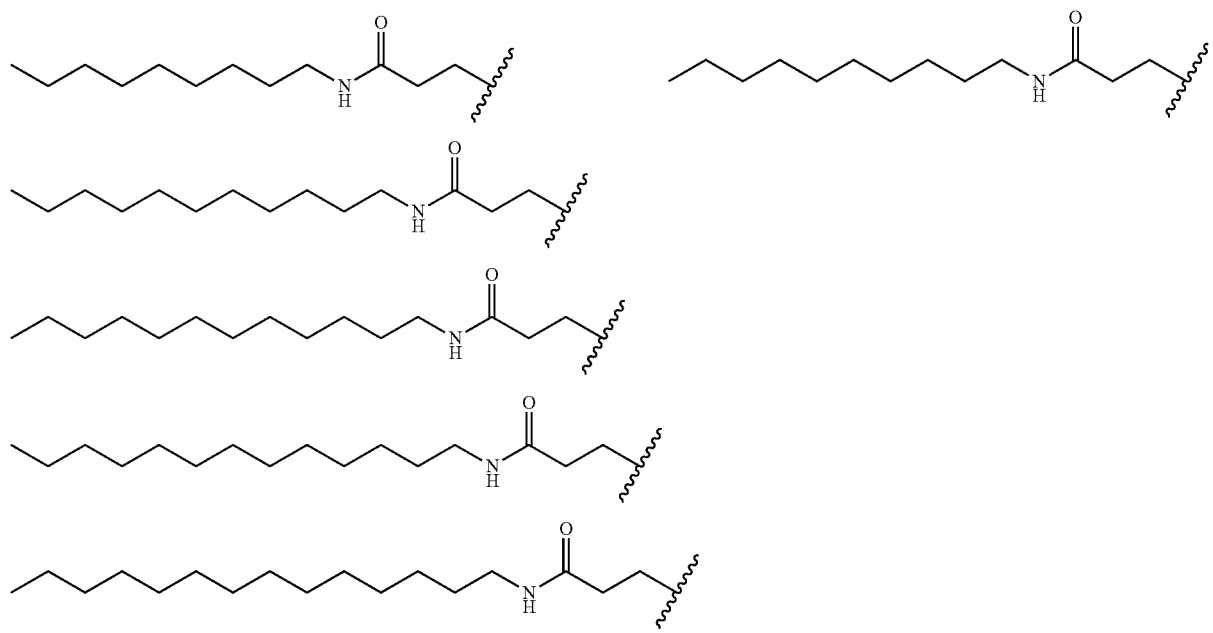

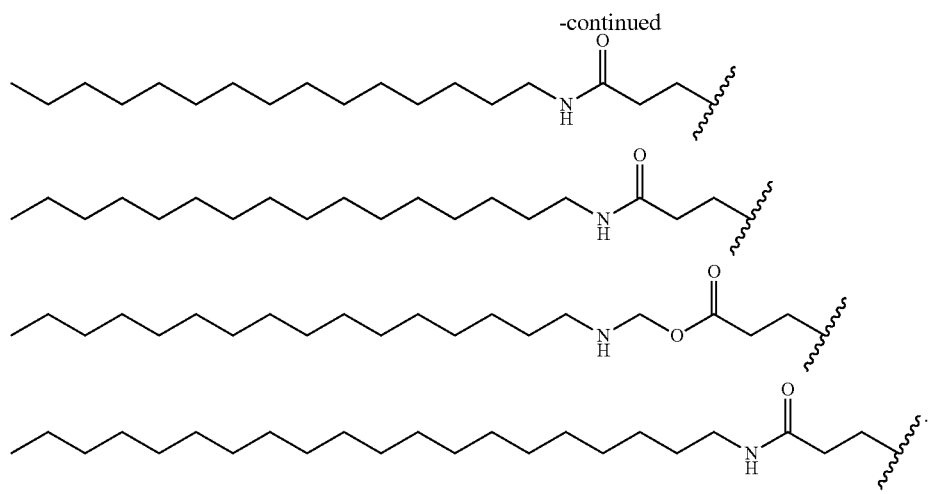
In certain embodiments, the lipids are prepared using acrylates NC, ND, NF, NG, or NP in FIG. 1. In certain embodiments, the lipids are prepared using acrylate ND. In other embodiments, the lipids are prepared using acrylate NF.
In certain embodiments,
is selected from the group consisting of:
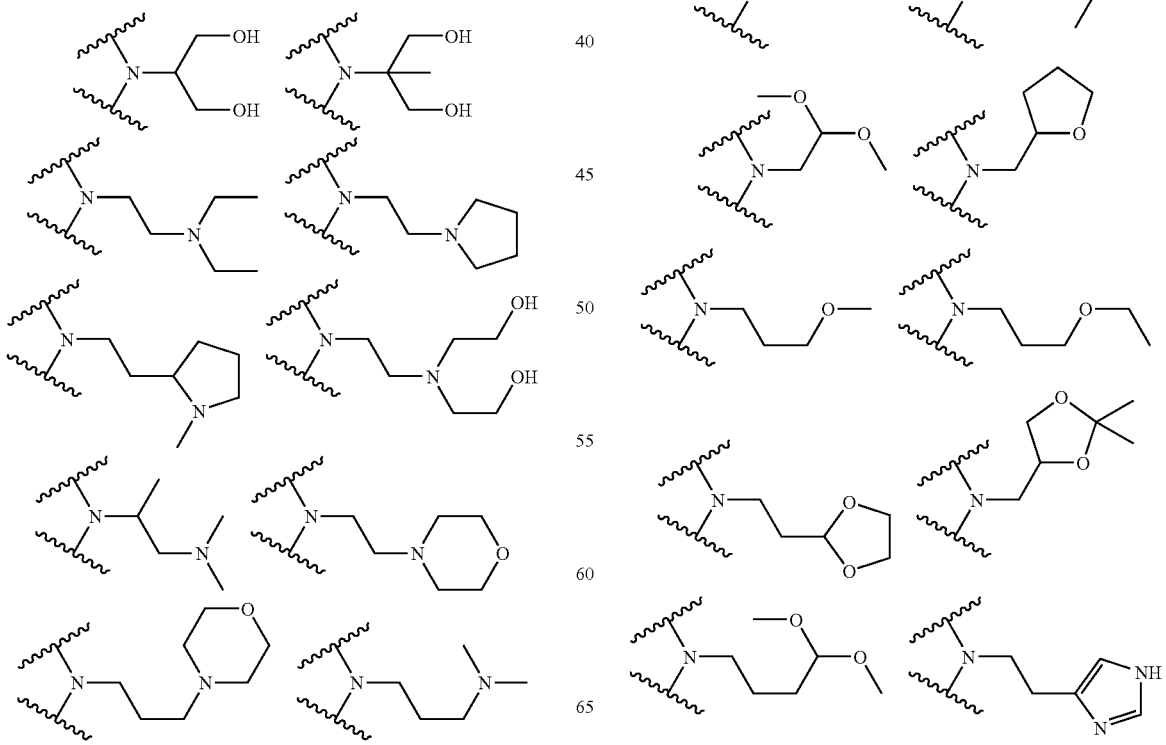

-continued

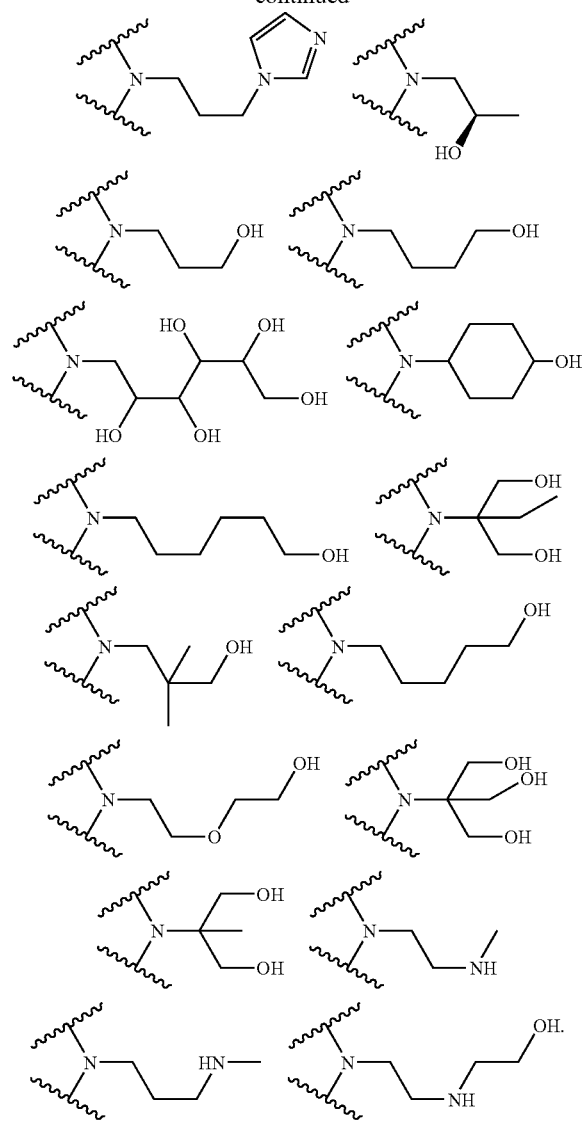

In certain embodiments,

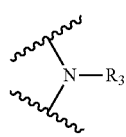

is selected from the group consisting of:

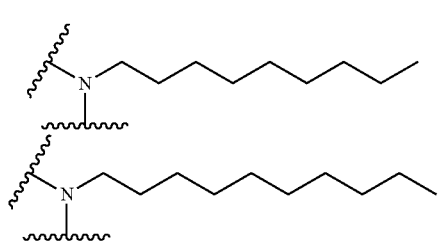

-continued

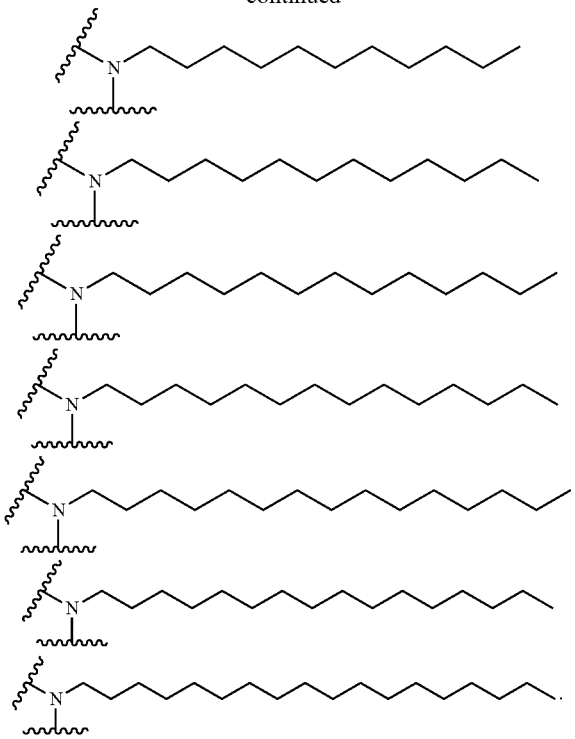

In certain embodiments,

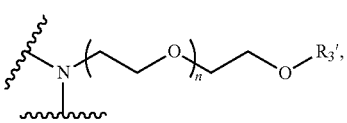

is wherein n is an integer between 0 and 10, inclusive; and $R_3'$ is hydrogen, aliphatic, heteroaliphatic, carbocyclic, heterocyclic, aryl, acyl, or heteroaryl. In certain embodiments, $R_3'$ is hydrogen, In other embodiments, $R_3'$ is $C_1$-$C_6$ alkyl. In yet other embodiments, $R_3'$ is acyl (e.g., acetyl).

In certain embodiments, the inventive lipid is of formula:

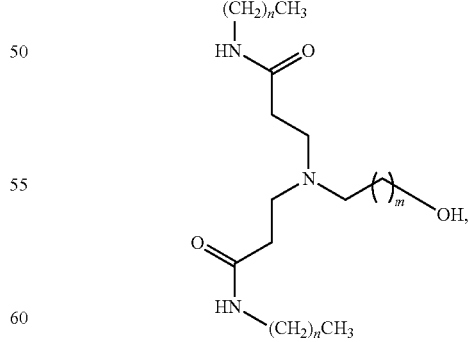

wherein
n is an integer between 5 and 20, inclusive; and
m is an integer between 1 and 10, inclusive; and pharmaceutically acceptable salts thereof. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

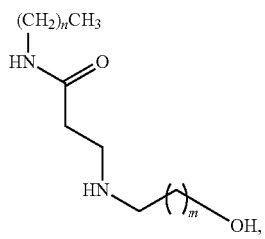

wherein n is an integer between 5 and 20, inclusive; and m is an integer between 1 and 10, inclusive; and pharmaceutically acceptable salts thereof. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

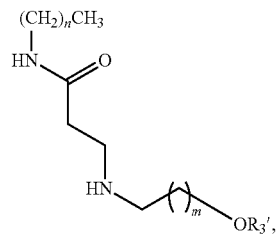

wherein $R_3'$ is $C_{1-6}$alkyl;

n is an integer between 5 and 20, inclusive; and m is an integer between 1 and 10, inclusive; and pharmaceutically acceptable salts thereof. In certain embodiments, $R_3'$ is methyl. In other embodiments, $R_3'$ is ethyl. In other embodiments, $R_3'$ is n-propyl. In still other embodiments, $R_3'$ is iso-propyl. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

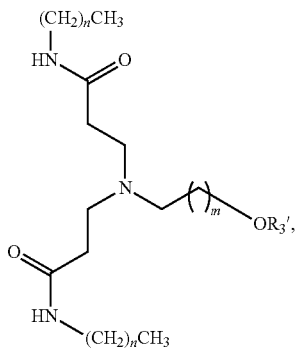

wherein $R_3'$ is $C_{1-6}$alkyl;

n is an integer between 5 and 20, inclusive; and m is an integer between 1 and 10, inclusive; and pharmaceutically acceptable salts thereof. In certain embodiments, $R_3'$ is methyl. In other embodiments, $R_3'$ is ethyl. In other embodiments, $R_3'$ is n-propyl. In still other embodiments, $R_3'$ is iso-propyl. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

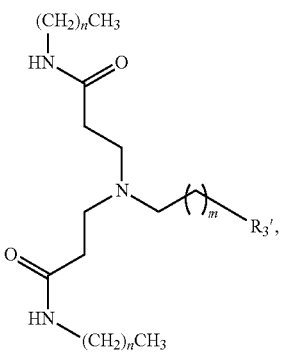

wherein $R_3'$ is carbocyclic; heterocyclic; aryl or heteroaryl;

n is an integer between 5 and 20, inclusive; and m is an integer between 1 and 10, inclusive; and pharmaceutically acceptable salts thereof. In certain embodiments, $R_3'$ is phenyl. In other embodiments, $R_3'$ is heteroaryl. In other embodiments, $R_3'$ is aryl. In still other embodiments, $R_3'$ is histidine. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

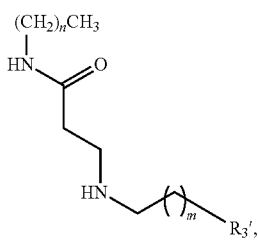

wherein $R_3'$ is carbocyclic; heterocyclic; aryl or heteroaryl;

n is an integer between 5 and 20, inclusive; and m is an integer between 1 and 10, inclusive; and pharmaceutically acceptable salts thereof. In certain embodiments, $R_3'$ is phenyl. In other embodiments, $R_3'$ is heteroaryl. In other embodiments, $R_3'$ is aryl. In still other embodiments, $R_3'$ is histidine. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

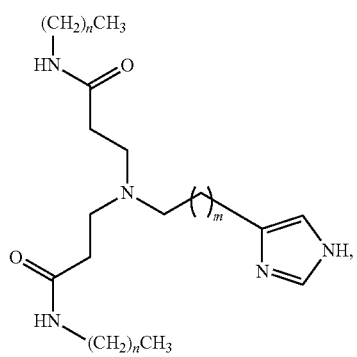

wherein n is an integer between 5 and 20, inclusive; and m is an integer between 1 and 10, inclusive; and pharmaceutically acceptable salts thereof. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

In certain embodiments, the inventive lipid is of formula:

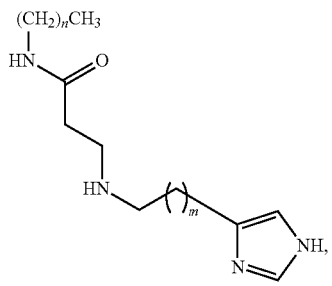

wherein n is an integer between 5 and 20, inclusive; and m is an integer between 1 and 10, inclusive; and pharmaceutically acceptable salts thereof. In certain embodiments, n is 11. In other embodiments, n is 12. In yet other embodiments, n is 13. In still other embodiments, n is 14. In certain embodiments, m is 1. In other embodiments, m is 2. In other embodiments, m is 3. In other embodiments, m is 4. In other embodiments, m is 5. In other embodiments, m is 6.

The present invention also provides amino lipids prepared from reacting acrylates with diamines, triamines, or polyamines. The amino moieties are completely or partially reacted with acrylate or acrylamides. Also, as would be appreciated by one of skill in this art, amino lipids with different number of acrylate or acrylamide tails will result in various isomers. These various forms of the linventive lipids are prepared individually, or the lipid is prepared as a mixture and then purified from the other forms. A single form mya be used in a composition, or a mixture of forms may be used.

The tails of the inventive amino lipids may also be the same or different. Non-exhaustively reacted amino groups may be reacted with a second acrylate, second acrylamide, or other electrophiles to created a mixed amino lipid. Again, various isomeric forms may be prepared and may optionally be purified.

In certain embodiments, the lipids of the present invention are of the formula (II):

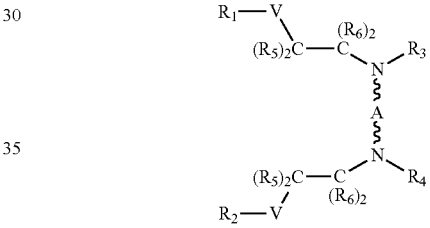

wherein A is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; and substituted or unsubstituted, branched or unbranched heteroaryl;

V is selected from the group consisting of C=O, C=S, S=O, and $SO_2$;

$R_1$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —C(=O)$R_A$; —$CO_2R_A$; —CN; —SCN; —$SR_A$; —$SOR_A$; —$SO_2R_A$; —$NO_2$; —$N_3$; —$N(R_A)_2$; —NHC(=O)$R_A$; —$NR_AC$(=O)$N(R_A)_2$; —OC(=O)$OR_A$; —OC(=O)$R_A$; —OC(=O)$N(R_A)_2$; —$NR_AC$(=O)$OR_A$; and —C($R_A)_3$;

wherein each occurrence of $R_A$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy;

alkylthio; arylthio; amino, alkylamino, dialkylamino, heteroaryloxy; or heteroarylthio moiety;

$R_2$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —CN; —SCN; —$SR_B$; —$SOR_B$; —$SO_2R_B$; —$NO_2$; —$N_3$; —$N(R_B)_2$; —$NHC(=O)R_B$; —$NR_BC(=O)N(R_B)_2$; —$OC(=O)OR_B$; —$OC(=O)R_B$; —$OC(=O)N(R_B)_2$; —$NR_BC(=O)OR_B$; or —$C(R_B)_3$; wherein each occurrence of $R_B$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

wherein $R_1$ and $R_2$ may be taken together to form a cyclic structure;

$R_3$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N_3$; —$N(R_C)_2$; —$NHC(=O)R_C$; —$NR_CC(=O)N(R_C)_2$; —$OC(=O)OR_C$; —$OC(=OC)R_C$; —$OC(=O)N(R_C)_2$; —$NR_CC(=O)OR_C$; or —$C(R_C)_3$; wherein each occurrence of $R_C$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

$R_4$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —CN; —SCN; —$SR_D$; —$SOR_D$; —$SO_2R_D$; —$NO_2$; —$N_3$; —$N(R_D)_2$; —$NHC(=O)R_D$; —$NR_CC(=O)N(R_D)_2$; —$OC(=O)OR_D$; —$OC(=O)R_D$; —$OC(=O)N(R_D)_2$; —$NR_CC(=O)OR_D$; or —$C(R_D)_3$; wherein each occurrence of $R_D$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

wherein $R_3$ and $R_4$ may be taken together to form a cyclic structure;

each occurrence of $R_5$ is independently selected from the group consisting of hydrogen and $C_1$-$C_6$ alkyl;

each occurrence of $R_6$ is independently selected from the group consisting of hydrogen and $C_1$-$C_6$ alkyl; and salts thereof. In certain embodiments, the lipid is prepared using amine 95, 96, 99, 100, 103, and 109 in FIG. 1. In certain embodiments, the lipid is prepared using amine 99 in FIG. 1. In certain embodiments, the lipid is prepared using amine 100 in FIG. 1. In certain embodiments, the lipid is prepared using acrylate ND, NF, NP, LF, and LG in FIG. 1. In certain embodiments, the lipid is prepared using acrylate ND in FIG. 1. In certain embodiments, the lipid is prepared using acrylate NF in FIG. 1. In certain embodiments, the lipid is prepared using acrylate NP in FIG. 1.

In certain embodiments, the tertiary amine of formula (II) is protonated or alkylated to form a compound of formula (IIa):

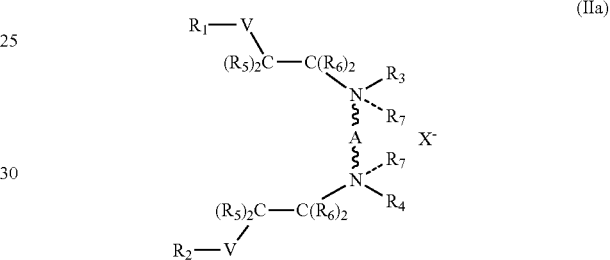

(IIa)

wherein $R_1$, $R_2$, $R_3$, $R_4$, $R_5$, $R_6$, and V are defined above;

each occurrence of $R_7$ is hydrogen or $C_1$-$C_6$ aliphatic, preferably $C_1$-$C_6$ alkyl, more preferably hydrogen or methyl;

each dashed line represents a bond or the absence of a bond, wherein when the dashed line represents a bond, the attached nitrogen is positively charged; and X is any anion. Possible anions include fluoride, chloride, bromide, iodide, sulfate, bisulfate, phosphate, nitrate, acetate, fumarate, oleate, citrate, valerate, maleate, oxalate, isonicotinate, lactate, salicylate, tartrate, tannate, pantothenate, bitartrate, ascorbate, succinate, gentisinate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate). In certain embodiments, both dashed lines presents bonds, and both nitrogen atoms are positively charged.

In certain embodiments, A is a cyclic or acyclic, substituted or unsubstituted, branched or unbranched aliphatic or heteroaliphatic group. In certain embodiments, A is a substituted or unsubstituted, branched or unbranched aliphatic group. In certain particular embodiments, A is a substituted or unsubstituted, branched or unbranched alkyl group. In certain embodiments, A is an unsubstituted, $C_1$-$C_6$ straight chain alkyl group. In other embodiments, A is a polyethylene group. In yet other embodiments, A is a polyethylene glycol moiety. In certain embodiments, A, the two nitrogen atoms attached to A, $R_3$ and $R_4$ form a heterocyclic ring. In certain embodiments, the ring is aromatic. In other embodiments, the ring is non-aromatic. In certain embodiments,

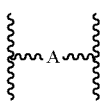

is selected from the group consisting of:

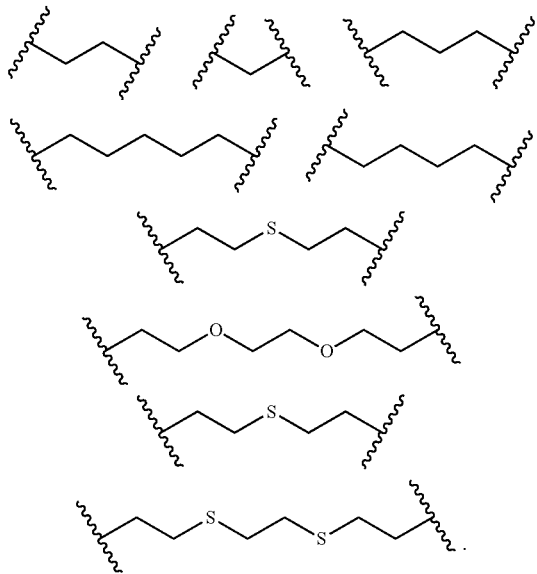

In certain embodiments,

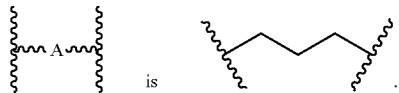

In certain particular embodiments,

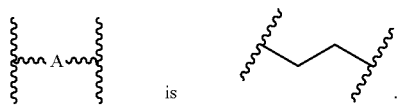

In certain embodiments, A is

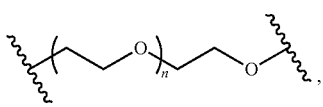

wherein n is an integer between 0 and 10, inclusive.

In certain embodiments, V is C=O. In other embodiments, V is C=S. In yet other embodiments, V is S=O. In still other embodiments, V is $SO_2$.

In certain embodiments, $R_1$ is hydrogen. In other embodiments, $R_1$ is a cyclic or acyclic, substituted or unsubstituted, branched or unbranched aliphatic or heteroaliphatic moiety. In certain embodiments, $R_1$ is a substituted or unsubstituted aryl or heteroaryl moiety. Preferably, the aryl or heteroaryl moiety is a monocyclic 5- or 6-membered ring system. In certain embodiments, $R_1$ is —$OR_A$, —$SR_A$, —$N(R_A)_2$, or —$NHR_A$. In certain embodiments, $R_1$ is —$OR_A$. In other embodiments, $R_1$ is —$N(R_A)_2$ or —$NHR_A$. In certain embodiments, $R_A$ is hydrogen. In certain embodiments, $R_A$ is not hydrogen. In other embodiments, $R_A$ is a cyclic or acyclic, substituted or unsubstituted, branched or unbranched aliphatic or heteroaliphatic moiety. In certain embodiments, $R_A$ is an acyclic, substituted or unsubstituted aliphatic moiety. In certain embodiments, $R_A$ is an unsubstituted, straight chain alkyl group with at least 5 carbons. In certain other embodiments, $R_A$ is an acyclic, unsubstituted, unbranched aliphatic moiety, preferably $C_6$-$C_{30}$, more preferably $C_{10}$-$C_{20}$. In certain embodiments, $R_A$ is an unsubstituted, straight chain alkyl group, preferably $C_6$-$C_{30}$, more preferably $C_{10}$-$C_{20}$. In certain embodiments, $R_1$ is —$OR_A$, wherein $R_A$ is an unsubstituted, unbranched $C_9$ alkyl chain. In certain embodiments, $R_1$ is —$OR_A$, wherein $R_A$ is an unsubstituted, unbranched $C_{10}$ alkyl chain. In certain embodiments, $R_1$ is —$OR_A$, wherein $R_A$ is an unsubstituted, unbranched $C_{11}$ alkyl chain. In certain embodiments, $R_1$ is —$OR_A$, wherein $R_A$ is an unsubstituted, unbranched $C_{12}$ alkyl chain. In certain embodiments, $R_1$ is —$OR_A$, wherein $R_A$ is an unsubstituted, unbranched $C_{13}$ alkyl chain. In certain embodiments, $R_1$ is —$OR_A$, wherein $R_A$ is an unsubstituted, unbranched $C_{14}$ alkyl chain. In certain embodiments, $R_1$ is —$OR_A$, wherein $R_A$ is an unsubstituted, unbranched $C_{15}$ alkyl chain. In certain embodiments, $R_1$ is —$OR_A$, wherein $R_A$ is an unsubstituted, unbranched $C_{16}$ alkyl chain. In certain embodiments, $R_1$ is —$OR_A$, wherein $R_A$ is an unsubstituted, unbranched $C_{17}$ alkyl chain. In certain embodiments, $R_1$ is —$OR_A$, wherein $R_A$ is an unsubstituted, unbranched $C_{18}$ alkyl chain. In certain embodiments, $R_1$ is —$OR_A$, wherein $R_A$ is an unsubstituted, unbranched $C_{19}$ alkyl chain. In certain embodiments, $R_1$ is —$OR_A$, wherein $R_A$ is an unsubstituted, unbranched $C_{20}$ alkyl chain. In yet other embodiments, $R_A$ is a substituted or unsubstituted aryl or heteroaryl moiety.

In certain embodiments, $R_2$ is hydrogen. In other embodiments, $R_2$ is a cyclic or acyclic, substituted or unsubstituted, branched or un branched aliphatic or heteroaliphatic moiety. In certain embodiments, $R_2$ is a substituted or unsubstituted aryl or heteroaryl moiety. Preferably, the aryl or heteroaryl moiety is a monocyclic 5- or 6-membered ring system. In certain embodiments, $R_2$ is —$OR_B$, —$SR_B$, —$N(R_B)_2$, or —$NHR_B$. In certain embodiments, $R_2$ is —$OR_B$. In other embodiments, $R_2$ is —$N(R_B)_2$ or —$NHR_B$. In certain embodiments, $R_B$ is hydrogen. In certain embodiments, $R_B$ is not hydrogen. In other embodiments, $R_B$ is a cyclic or acyclic, substituted or unsubstituted, branched or unbranched aliphatic or heteroaliphatic moiety. In certain embodiments, $R_B$ is an acyclic, substituted or unsubstituted aliphatic moiety. In certain embodiments, $R_B$ is an unsubstituted, straight chain alkyl group with at least 5 carbons. In certain other embodiments, $R_B$ is an acyclic, unsubstituted, unbranched aliphatic moiety, preferably $C_6$-$C_{30}$, more preferably $C_{10}$-$C_{20}$. In certain embodiments, $R_B$ is an unsubstituted, straight chain alkyl group, preferably $C_6$-$C_{30}$, more preferably $C_{10}$-$C_{20}$. In certain embodiments, $R_2$ is —$OR_B$, wherein $R_B$ is an unsubstituted, unbranched $C_9$ alkyl chain. In certain embodiments, $R_2$ is —$OR_B$, wherein $R_B$ is an unsubstituted, unbranched $C_{10}$ alkyl chain. In certain embodiments, $R_2$ is —$OR_B$, wherein $R_B$ is an unsubstituted, unbranched $C_{11}$ alkyl chain. In certain embodiments, $R_2$ is —$OR_B$, wherein $R_B$ is an unsubstituted, unbranched $C_{12}$ alkyl chain. In certain embodiments, $R_2$ is —$OR_B$, wherein $R_B$ is an unsubstituted, unbranched $C_{13}$ alkyl chain. In certain embodiments, $R_2$ is —$OR_B$, wherein $R_B$ is an unsubstituted, unbranched $C_{14}$ alkyl chain. In certain embodiments, $R_2$ is —$OR_B$, wherein $R_B$ is an unsubstituted, unbranched $C_{15}$ alkyl chain. In certain embodiments, $R_2$ is —$OR_A$, wherein $R_B$ is an unsubstituted, unbranched $C_{16}$ alkyl chain. In certain embodiments, $R_2$ is —$OR_A$, wherein $R_B$ is an unsubstituted, unbranched $C_{17}$ alkyl chain. In certain embodiments, $R_2$ is —$OR_A$, wherein $R_B$ is an unsubstituted, unbranched $C_{18}$ alkyl chain. In certain embodiments, $R_2$ is —$OR_B$, wherein $R_B$ is an unsubstituted, unbranched $C_{19}$ alkyl chain. In certain embodiments, $R_2$ is —$OR_B$, wherein $R_B$ is an unsubstituted, unbranched $C_{20}$ alkyl chain. In yet other embodiments, $R_B$ is a substituted or unsubstituted aryl or heteroaryl moiety.

In certain embodiments, $R_3$ is a cyclic or acyclic, substituted or unsubstituted, branched or unbranched aliphatic moiety. In other embodiments, $R_3$ is a cyclic or acyclic, substituted or unsubstituted, branched or unbranched heteroaliphatic moiety. In certain embodiments, $R_3$ is an aliphatic moiety substituted with one or more hydroxyl groups. In other embodiments, $R_3$ is an aliphatic moiety substituted with one or more amino, alkylamino, or dialkylamino groups. In certain embodiments, $R_3$ is $C_1$-$C_6$ alkyl. In certain embodiments, $R_3$ is methyl. In certain embodiments, $R_3$ is ethyl. In other embodiments, $R_3$ is n-propyl. In other embodiments, $R_3$ is iso-propyl. In certain embodiments, $R_3$ is hydrogen. In certain embodiments, $R_3$ is a heteroaliphatic moiety. In certain embodiments, $R_3$ is cyclic aliphatic, preferably a monocyclic ring system with a 5- or 6-membered ring. In other embodiments, $R_3$ is aryl or heteroaryl, preferably a monocyclic ring system with a 5- or 6-membered ring. In certain embodiments, $R_3$ is

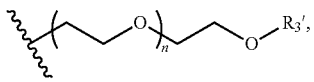

wherein n is an integer between 0 and 10, inclusive; and $R_3'$ is hydrogen, aliphatic, heteroaliphatic, carbocyclic, heterocyclic, aryl, acyl, or heteroaryl. In certain embodiments, $R_3'$ is hydrogen, In other embodiments, $R_3'$ is $C_1$-$C_6$ alkyl. In yet other embodiments, $R_3'$ is acyl (e.g., acetyl). In certain embodiments, $R_3$ is

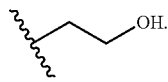

In other embodiments, $R_3$ is

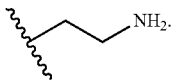

In certain embodiments, $R_4$ is a cyclic or acyclic, substituted or unsubstituted, branched or unbranched aliphatic moiety. In other embodiments, $R_4$ is a cyclic or acyclic, substituted or unsubstituted, branched or unbranched heteroaliphatic moiety. In certain embodiments, $R_4$ is an aliphatic moiety substituted with one or more hydroxyl groups. In other embodiments, $R_4$ is an aliphatic moiety substituted with one or more amino, alkylamino, or dialkylamino groups. In certain embodiments, $R_4$ is $C_1$-$C_6$ alkyl. In certain embodiments, $R_3$ is methyl. In certain embodiments, $R_3$ is ethyl. In other embodiments, $R_3$ is n-propyl. In other embodiments, $R_3$ is iso-propyl. In certain embodiments, $R_4$ is hydrogen. In certain embodiments, $R_4$ is a heteroaliphatic moiety. In certain embodiments, $R_3$ is cyclic aliphatic, preferably a monocyclic ring system with a 5- or 6-membered ring. In other embodiments, $R_4$ is aryl or heteroaryl, preferably a monocyclic ring system with a 5- or 6-membered ring. In certain embodiments, $R_4$ is

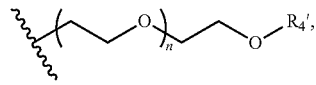

wherein n is an integer between 0 and 10, inclusive; and $R_4'$ is hydrogen, aliphatic, heteroaliphatic, carbocyclic, heterocyclic, aryl, acyl, or heteroaryl. In certain embodiments, $R_4'$ is hydrogen, In other embodiments, $R_4'$ is $C_1$-$C_6$ alkyl. In yet other embodiments, $R_4'$ is acyl (e.g., acetyl). In certain embodiments, $R_4$ is

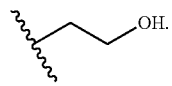 [SMILES: *CCO]

In other embodiments, $R_4$ is

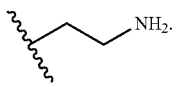

In certain embodiments, $R_3$ and $R_4$ are the same. In other embodiments, $R_3$ and $R_4$ are different.

In certain embodiments, each occurrence of $R_5$ is hydrogen. In certain embodiments, at least one occurrence of $R_5$ is methyl and the other occurrences are hydrogen. In certain embodiments, at least two occurrences of $R_5$ are methyl, and the other occurrences are hydrogen. In other embodiments, at least two occurrences of $R_5$ are hydrogen.

In certain embodiments, each occurrence of $R_6$ is hydrogen. In certain other embodiments, at least two occurrences of $R_6$ are hydrogen. In certain embodiments, at least one occurrence of $R_6$ is methyl, and the other occurrences are hydrogen. In certain embodiments, at least two occurrences of $R_6$ are methyl, and the other occurrences are hydrogen.

In certain embodiments,

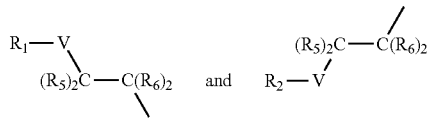

which are attached to N are the same. In other embodiments,

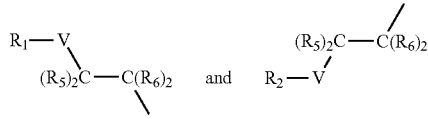

which are attached to N are the same and are different than $R_3$. In yet other embodiments,

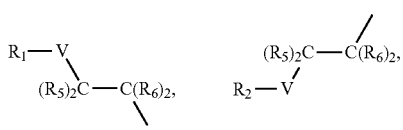
and $R_3$ are all different.
In certain embodiments,
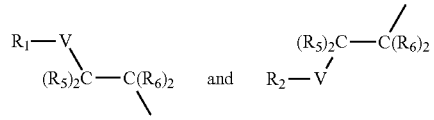
in formulae (II) and (IIa) are selected from the group consisting of:
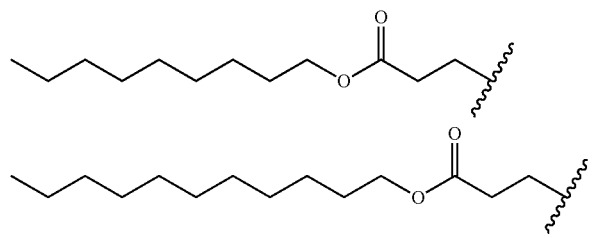
In certain embodiments, the lipids are prepared using acrylates LC, LD, LE, LF, and LG in FIG. 1.
In certain embodiments,
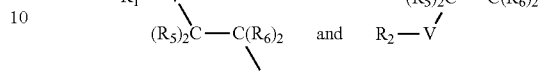
in formulae (II) and (IIa) are selected from the group consisting of:
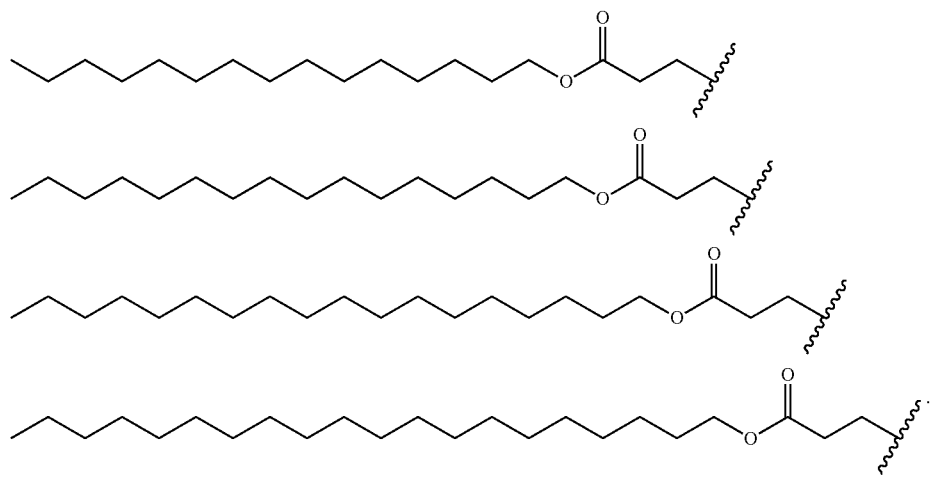

51                                                                  52

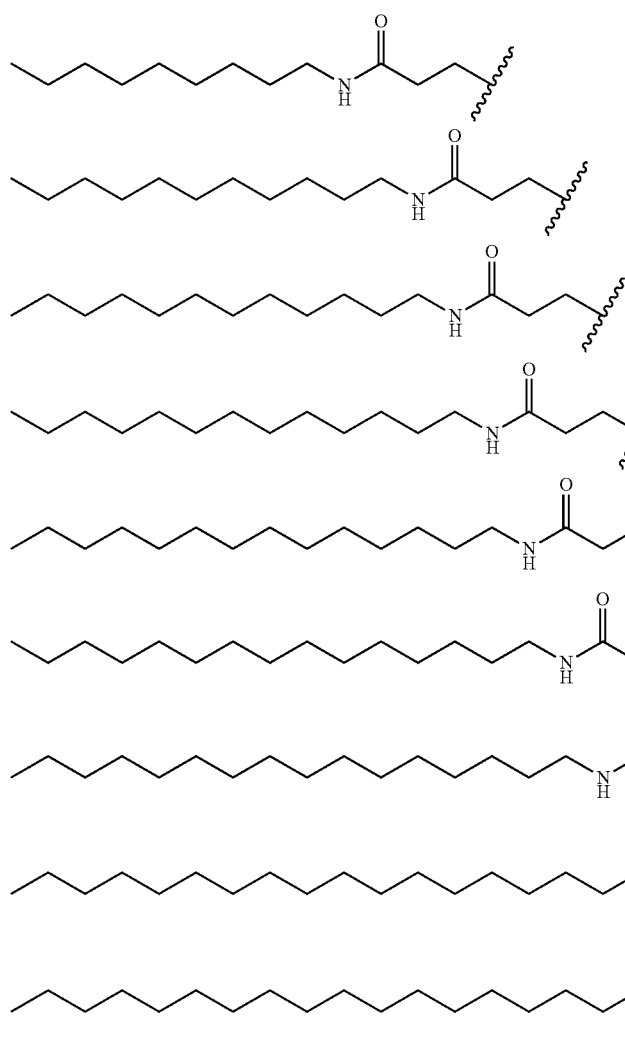

In certain embodiments, the lipids are prepared using acrylates NC, ND, NF, NO, or NP in FIG. 1. In certain embodiments, the lipids are prepared using acrylate ND. In other embodiments, the lipids are prepared using acrylate NF. In other embodiments, the lipids are prepared using acrylate NP.

In certain embodiments,

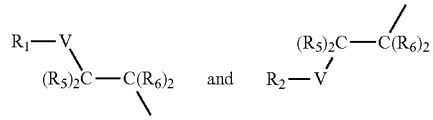

in formulae (II) and (IIa) are the same. In other embodiments,

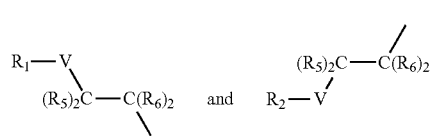

in formulae (II) and (IIa) are different.

In certain embodiments,

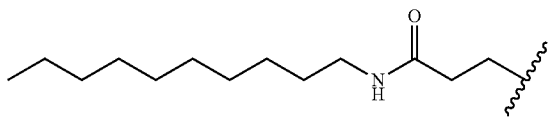

is selected from the group consisting of:

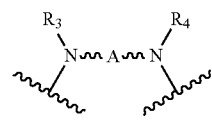 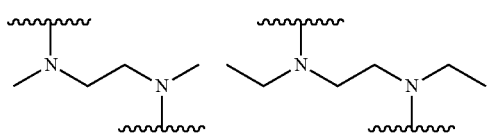

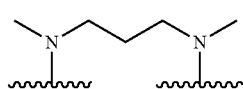

-continued

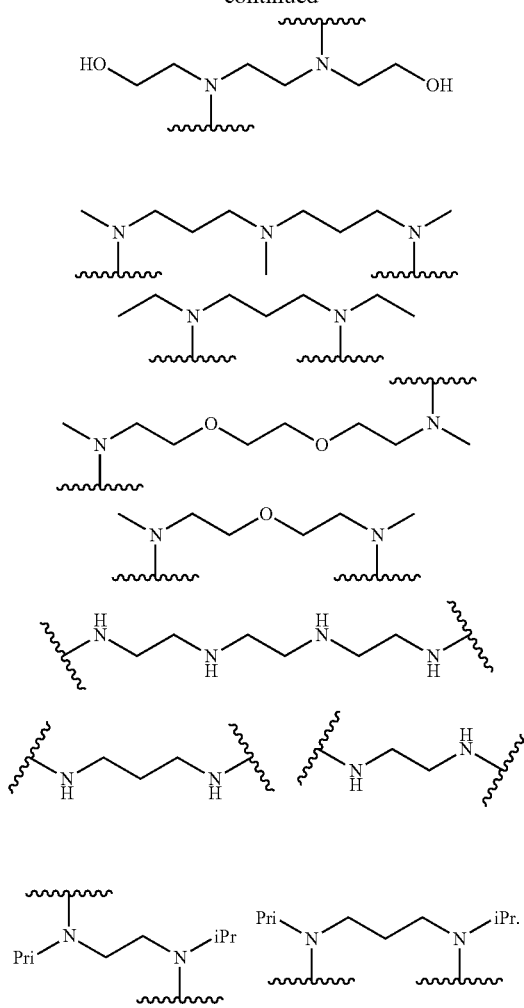

In certain embodiments,

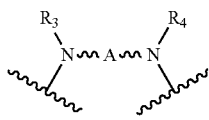

is selected from the group consisting of:

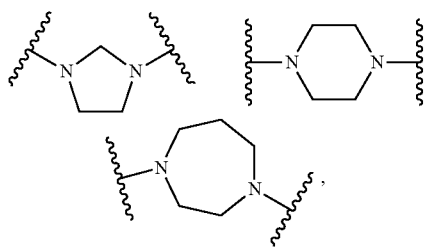

wherein $R_3$ and $R_4$ form a cyclic structure.

In other embodiments, the lipids of the present invention are of the formula (III):

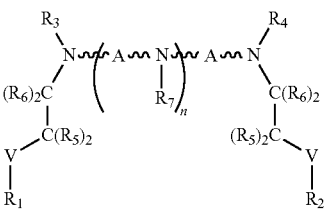

(III)

wherein

A is selected from the group consisting of cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; and substituted or unsubstituted, branched or unbranched heteroaryl;

V is selected from the group consisting of C=O, C=S, S=O, and SO$_2$;

n is an integer between 0 and 10, inclusive;

$R_1$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_A$; —C(=O)R$_A$; —CO$_2$R$_A$; —CN; —SCN; —SR$_A$; —SOR$_A$; —SO$_2$R$_A$; —NO$_2$; —N$_3$; —N(R$_A$)$_2$; —NHC(=O) R$_A$; —NR$_A$C(=O)N(R$_A$)$_2$; —OC(=O)OR$_A$; —OC(=O) R$_A$; —OC(=O)N(R$_A$)$_2$; —NR$_A$C(=O)OR$_A$; and —C(R$_A$)$_3$; wherein each occurrence of R$_A$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

$R_2$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_a$; —CO$_2$R$_B$; —CN; —SCN; —SR$_B$; —SOR$_B$; —SO$_2$R$_B$; —NO$_2$; —N$_3$; —N(R$_B$)$_2$; —NHC(=O) R$_B$; —NR$_B$C(=O)N(R$_B$)$_2$; —OC(=O)OR$_B$; —OC(=O) R$_B$; —OC(=O)N(R$_B$)$_2$; —NR$_B$C(=O)OR$_B$; or —C(R$_B$)$_3$; wherein each occurrence of R$_B$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

wherein $R_1$ and $R_2$ may be taken together to form a cyclic structure;

R₃ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO₂R$_C$; —CN; —SCN; —SR$_C$; —SOR$_C$; —SO₂R$_C$; —NO₂; —N₃; —N(R$_C$)₂; —NHC(=O)R$_C$; —NR$_C$C(=O)N(R$_C$)₂; —OC(=O)OR$_C$; —OC(=O)R$_C$; —OC(=O)N(R$_C$)₂; —NR$_C$C(=O)OR$_C$; or —C(R$_C$)₃; wherein each occurrence of R$_C$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

R₄ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO₂R$_D$; —CN; —SCN; —SR₁); —SOR$_D$; —SO₂R$_D$; —NO₂; —N₃; —N(R$_D$)₂; —NHC(=O)R$_D$; —NR$_C$C(=O)N(R$_D$)₂; —OC(=O)OR$_D$; —OC(=O)R$_D$; —OC(=O)N(R$_D$)₂; —NR$_C$C(=O)OR$_D$; or —C(R$_D$)₃; wherein each occurrence of R$_D$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

wherein R₃ and R₄ may be taken together to form a cyclic structure;

each occurrence of R₅ is independently selected from the group consisting of hydrogen and C₁-C₆ alkyl;

each occurrence of R₆ is independently selected from the group consisting of hydrogen and C₁-C₆ alkyl;

R₇ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_G$; —C(=OC)R$_G$; —CO₂R$_G$; —CN; —SCN; —SR$_G$; —SOR$_G$; —SO₂R$_O$; —NO₂; —N₃; —N(R$_G$)₂; —NHC(=O)R$_G$; —NR$_G$C(=O)N(R$_G$)₂; —OC(=O)OR$_G$; —OC(=O)R$_G$; —OC(=O)N(R$_G$)₂; —NR$_G$C(=O)OR$_G$; and —C(R$_G$)₃; wherein each occurrence of R$_G$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety and salts thereof. In certain embodiments, n is 0. In other embodiments, n is 1. In still other embodiments, n is 2. In other embodiments, n is 3. In yet other embodiments, n is 4. In other embodiments, n is 5. In other embodiments, n is 6. In certain embodiments, the lipid is prepared using amine 98. In other embodiments, the lipid is prepared using amine 100.

In certain embodiments, the tertiary amine of formula (III) is protonated or alkylated to form a compound of formula (IIIa):

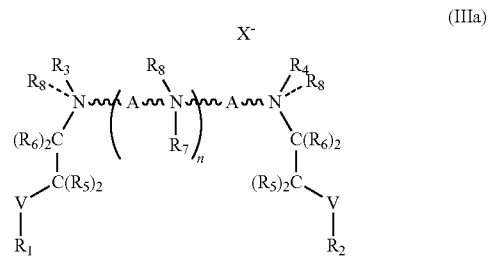

(IIIa)

wherein R₁, R₂, R₃, R₄, R₅, R₆, R₇, n, and V are defined above;

each occurrence of R₈ is hydrogen or C₁-C₆ aliphatic, preferably C₁-C₆ alkyl, more preferably hydrogen or methyl;

each dashed line represents a bond or the absence of a bond, wherein when the dashed line represents a bond, the attached nitrogen is positively charged; and X is any anion. Possible anions include fluoride, chloride, bromide, iodide, sulfate, bisulfate, phosphate, nitrate, acetate, fumarate, oleate, citrate, valerate, maleate, oxalate, isonicotinate, lactate, salicylate, tartrate, tannate, pantothenate, bitartrate, ascorbate, succinate, gentisinate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate). In certain embodiments, both dashed lines presents bonds, and both nitrogen atoms are positively charged.

In certain embodiments, A is a cyclic or acyclic, substituted or unsubstituted, branched or unbranched aliphatic or heteroaliphatic group. In certain embodiments, A is a substituted or unsubstituted, branched or unbranched aliphatic group. In certain particular embodiments, A is a substituted or unsubstituted, branched or unbranched alkyl group. In certain embodiments, A is an unsubstituted, C₁-C₆ straight chain alkyl group. In other embodiments, A is a polyethylene group. In yet other embodiments, A is a polyethylene glycol moiety. In certain embodiments, A, the two nitrogen atoms attached to A, R₃ and R₄ form a heterocyclic ring. In certain embodiments, the ring is aromatic. In other embodiments, the ring is non-aromatic.

In certain embodiments, V is C=O. In other embodiments, V is C=S. In yet other embodiments, V is S=O. In still other embodiments, V is SO₂.

In certain embodiments, R₁ is hydrogen. In other embodiments, R₁ is a cyclic or acyclic, substituted or unsubstituted, branched or un branched aliphatic or heteroaliphatic moiety. In certain embodiments, R₁ is a substituted or unsubstituted aryl or heteroaryl moiety. Preferably, the aryl or heteroaryl moiety is a monocyclic 5- or 6-membered ring system. In certain embodiments, R₁ is —OR$_A$, —SR$_A$, —N(R$_A$)₂, or —NHR$_A$. In certain embodiments, R₁ is —OR$_A$. In other embodiments, R₁ is —N(R$_A$)₂ or —NHR$_A$. In certain embodiments, $R_A$ is hydrogen. In other embodiments, $R_A$ is a cyclic or acyclic, substituted or unsubstituted, branched or unbranched aliphatic or heteroaliphatic moiety. In certain embodiments, $R_A$ is an acyclic, substituted or unsubstituted aliphatic moiety. In certain other embodiments, $R_A$ is an acyclic, unsubstituted, unbranched aliphatic moiety, preferably $C_6$-$C_{30}$, more preferably $C_{10}$-$C_{20}$. In certain embodiments, $R_A$ is an unsubstituted, straight chain alkyl group, preferably $C_6$-$C_{30}$, more preferably $C_{10}$-$C_{20}$. In certain embodiments, $R_1$ is —$OR_A$, wherein $R_A$ is an unsubstituted, unbranched $C_9$ alkyl chain. In certain embodiments, $R_1$ is —$OR_A$, wherein $R_A$ is an unsubstituted, unbranched $C_{10}$ alkyl chain. In certain embodiments, $R_1$ is —$OR_A$, wherein $R_A$ is an unsubstituted, unbranched $C_{11}$ alkyl chain. In certain embodiments, $R_1$ is —$OR_A$, wherein $R_A$ is an unsubstituted, unbranched $C_{12}$ alkyl chain. In certain embodiments, $R_1$ is —$OR_A$, wherein $R_A$ is an unsubstituted, unbranched $C_{13}$ alkyl chain. In certain embodiments, $R_1$ is —$OR_A$, wherein $R_A$ is an unsubstituted, unbranched $C_{14}$ alkyl chain. In certain embodiments, $R_1$ is —$OR_A$, wherein $R_A$ is an unsubstituted, unbranched $C_{15}$ alkyl chain. In certain embodiments, $R_1$ is —$OR_A$, wherein $R_A$ is an unsubstituted, unbranched $C_{16}$ alkyl chain. In certain embodiments, $R_1$ is —$OR_A$, wherein $R_A$ is an unsubstituted, unbranched $C_{17}$ alkyl chain. In certain embodiments, $R_1$ is —$OR_A$, wherein $R_A$ is an unsubstituted, unbranched $C_{18}$ alkyl chain. In certain embodiments, $R_1$ is —$OR_A$, wherein $R_A$ is an unsubstituted, unbranched $C_{19}$ alkyl chain. In certain embodiments, $R_1$ is —$OR_A$, wherein $R_A$ is an unsubstituted, unbranched $C_{20}$ alkyl chain. In yet other embodiments, $R_A$ is a substituted or unsubstituted aryl or heteroaryl moiety.

In certain embodiments, $R_2$ is hydrogen. In other embodiments, $R_2$ is a cyclic or acyclic, substituted or unsubstituted, branched or unbranched aliphatic or heteroaliphatic moiety. In certain embodiments, $R_2$ is a substituted or unsubstituted aryl or heteroaryl moiety. Preferably, the aryl or heteroaryl moiety is a monocyclic 5- or 6-membered ring system. In certain embodiments, $R_2$ is —$OR_B$, —$SR_B$, —$N(R_B)_2$, or —$NHR_B$. In certain embodiments, $R_2$ is —$OR_B$. In other embodiments, $R_2$ is —$N(R_B)_2$ or —$NHR_B$. In certain embodiments, $R_B$ is hydrogen. In other embodiments, $R_B$ is a cyclic or acyclic, substituted or unsubstituted, branched or unbranched aliphatic or heteroaliphatic moiety. In certain embodiments, $R_B$ is an acyclic, substituted or unsubstituted aliphatic moiety. In certain other embodiments, $R_B$ is an acyclic, unsubstituted, unbranched aliphatic moiety, preferably $C_6$-$C_{30}$, more preferably $C_{10}$-$C_{20}$. In certain embodiments, $R_B$ is an unsubstituted, straight chain alkyl group, preferably $C_6$-$C_{30}$, more preferably $C_{10}$-$C_{20}$. In certain embodiments, $R_2$ is —$OR_B$, wherein $R_B$ is an unsubstituted, unbranched $C_9$ alkyl chain. In certain embodiments, $R_2$ is —$OR_B$, wherein $R_B$ is an unsubstituted, unbranched $C_{10}$ alkyl chain. In certain embodiments, $R_2$ is —$OR_B$, wherein $R_B$ is an unsubstituted, unbranched $C_{11}$ alkyl chain. In certain embodiments, $R_2$ is —$OR_B$, wherein $R_B$ is an unsubstituted, unbranched $C_{12}$ alkyl chain. In certain embodiments, $R_2$ is —$OR_B$, wherein $R_B$ is an unsubstituted, unbranched $C_{13}$ alkyl chain. In certain embodiments, $R_2$ is —$OR_B$, wherein $R_B$ is an unsubstituted, unbranched $C_{14}$ alkyl chain. In certain embodiments, $R_2$ is —$OR_B$, wherein $R_B$ is an unsubstituted, unbranched $C_{15}$ alkyl chain. In certain embodiments, $R_2$ is —$OR_A$, wherein $R_B$ is an unsubstituted, unbranched $C_{16}$ alkyl chain. In certain embodiments, $R_2$ is —$OR_A$, wherein $R_B$ is an unsubstituted, unbranched $C_{17}$ alkyl chain. In certain embodiments, $R_2$ is —$OR_A$, wherein $R_B$ is an unsubstituted, unbranched $C_{18}$ alkyl chain. In certain embodiments, $R_2$ is —$OR_B$, wherein $R_B$ is an unsubstituted, unbranched $C_{19}$ alkyl chain. In certain embodiments, $R_2$ is —$OR_B$, wherein $R_B$ is an unsubstituted, unbranched $C_{20}$ alkyl chain. In yet other embodiments, $R_B$ is a substituted or unsubstituted aryl or heteroaryl moiety.

In certain embodiments, $R_3$ is hydrogen. In certain embodiments, $R_3$ is a cyclic or acyclic, substituted or unsubstituted, branched or unbranched aliphatic moiety. In other embodiments, $R_3$ is a cyclic or acyclic, substituted or unsubstituted, branched or unbranched heteroaliphatic moiety. In certain embodiments, $R_3$ is an aliphatic moiety substituted with one or more hydroxyl groups. In other embodiments, $R_3$ is an aliphatic moiety substituted with one or more amino, alkylamino, or dialkylamino groups. In certain embodiments, $R_3$ is $C_1$-$C_6$ alkyl. In certain embodiments, $R_3$ is hydrogen. In certain embodiments, $R_3$ is a heteroaliphatic moiety. In certain embodiments, $R_3$ is cyclic aliphatic, preferably a monocyclic ring system with a 5- or 6-membered ring. In other embodiments, $R_3$ is aryl or heteroaryl, preferably a monocyclic ring system with a 5- or 6-membered ring. In certain embodiments, $R_3$ is

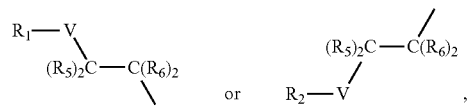

wherein $R_1$, $R_2$, $R_5$, $R_6$, and V are defined as above.

In other embodiments, $R_4$ is hydrogen. In certain embodiments, $R_4$ is a cyclic or acyclic, substituted or unsubstituted, branched or unbranched aliphatic moiety. In other embodiments, $R_4$ is a cyclic or acyclic, substituted or unsubstituted, branched or unbranched heteroaliphatic moiety. In certain embodiments, $R_4$ is an aliphatic moiety substituted with one or more hydroxyl groups. In other embodiments, $R_4$ is an aliphatic moiety substituted with one or more amino, alkylamino, or dialkylamino groups. In certain embodiments, $R_4$ is $C_1$-$C_6$ alkyl. In certain embodiments, $R_4$ is hydrogen. In certain embodiments, $R_4$ is a heteroaliphatic moiety. In certain embodiments, $R_3$ is cyclic aliphatic, preferably a monocyclic ring system with a 5- or 6-membered ring. In other embodiments, $R_4$ is aryl or heteroaryl, preferably a monocyclic ring system with a 5- or 6-membered ring. In certain embodiments, $R_4$ is

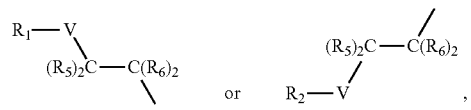

wherein $R_1$, $R_2$, $R_5$, $R_6$, and V are defined as above.

In certain embodiments, $R_3$ and $R_4$ are the same. In other embodiments, $R_3$ and $R_4$ are different. In certain embodiments, both $R_3$ and $R_4$ are hydrogen. In certain embodiments, only one of $R_3$ and $R_4$ is hydrogen. In certain embodiments, both $R_3$ and $R_4$ are

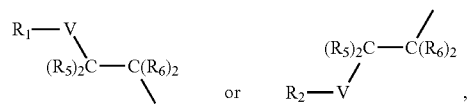

wherein $R_1$, $R_2$, $R_5$, $R_6$, and V are defined as above. In certain embodiments, one of $R_3$ and $R_4$ is

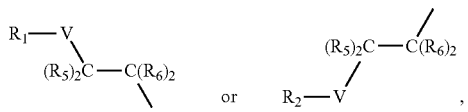 or 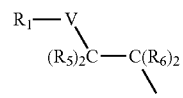, wherein $R_1$, $R_2$, $R_5$, $R_6$, and V are defined as above; and the other is hydrogen. In certain embodiments, both $R_3$ and $R_4$ are

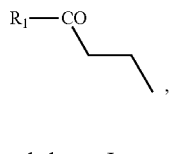

wherein $R_1$ is as defined above. In certain embodiments, one of $R_3$ and $R_4$ is

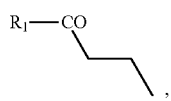

wherein $R_1$ is defined as above; and the other is hydrogen.

In certain embodiments, each occurrence of $R_5$ is hydrogen. In certain embodiments, at least one occurrence of $R_5$ is methyl and the other occurrences are hydrogen. In certain embodiments, at least two occurrences of $R_5$ are methyl, and the other occurrences are hydrogen. In other embodiments, at least two occurrences of $R_5$ are hydrogen.

In certain embodiments, each occurrence of $R_6$ is hydrogen. In certain other embodiments, at least two occurrences of $R_6$ are hydrogen. In certain embodiments, at least one occurrence of $R_6$ is methyl, and the other occurrences are hydrogen. In certain embodiments, at least two occurrences of $R_6$ are methyl, and the other occurrences are hydrogen.

In certain embodiments, $R_7$ is

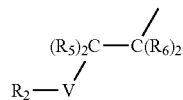

wherein $R_1$, $R_2$, $R_5$, $R_6$, and V are defined as above. In certain embodiments, $R_7$,

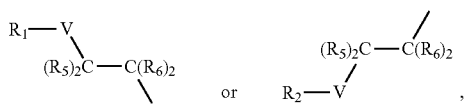

are the same. In other embodiments, $R_7$,

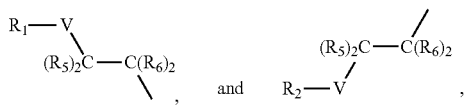

are different. In certain embodiments, $R_7$ and

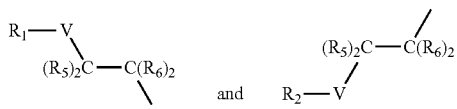

are the same.

In other embodiments, $R_7$ and

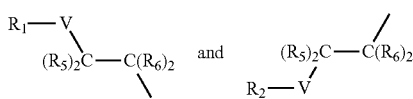

are the same. In certain embodiments, all $R_7$ are the same.

In certain embodiments,

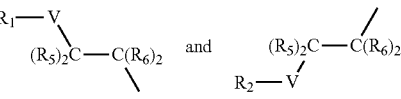

which are attached to N are the same. In other embodiments,

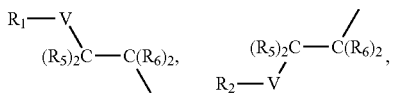

which are attached to N are the same and are different than $R_3$ or $R_4$. In yet other embodiments,

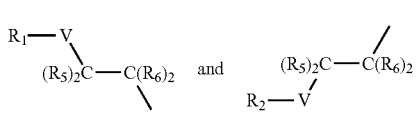

$R_3$, and $R_4$ are all different. In certain embodiments, $R_3$ and $R_4$ are the same. In other embodiments, $R_3$ and $R_4$ are different.

In certain embodiments,

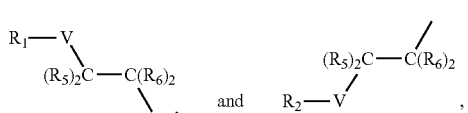

in formulae (III) and (IIIa) are selected from the group consisting of:

61 62
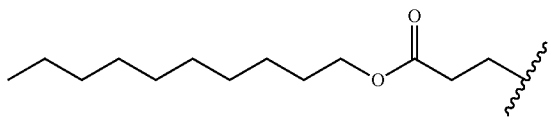
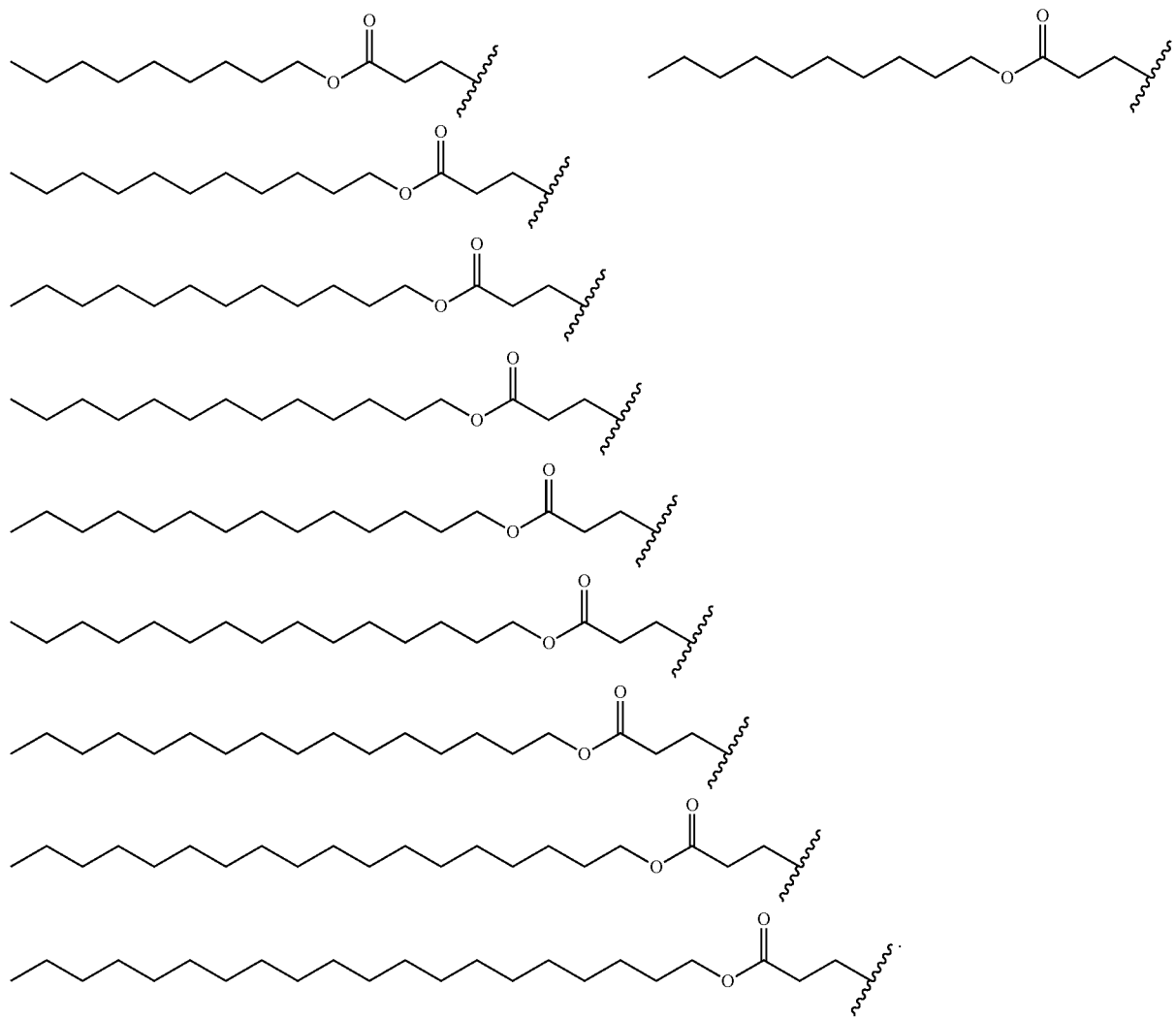
In certain embodiments, the lipids are prepared using acrylates LC, LD, LE, LF, and LG in FIG. 1.
In certain embodiments,
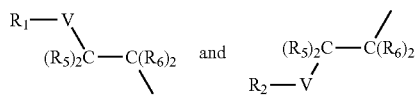
in formulae (III) and (IIIa) are selected from the group consisting of:
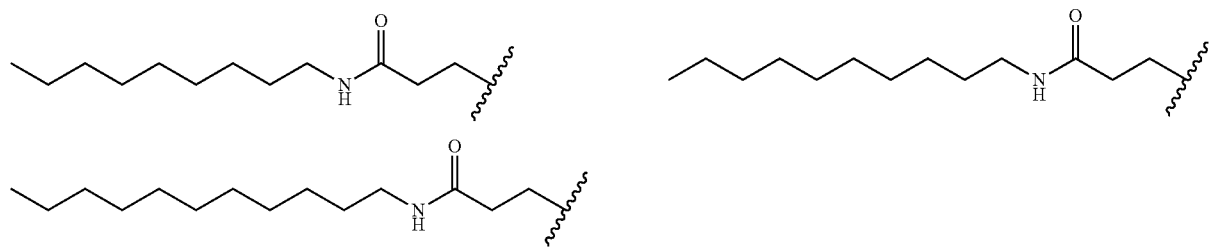

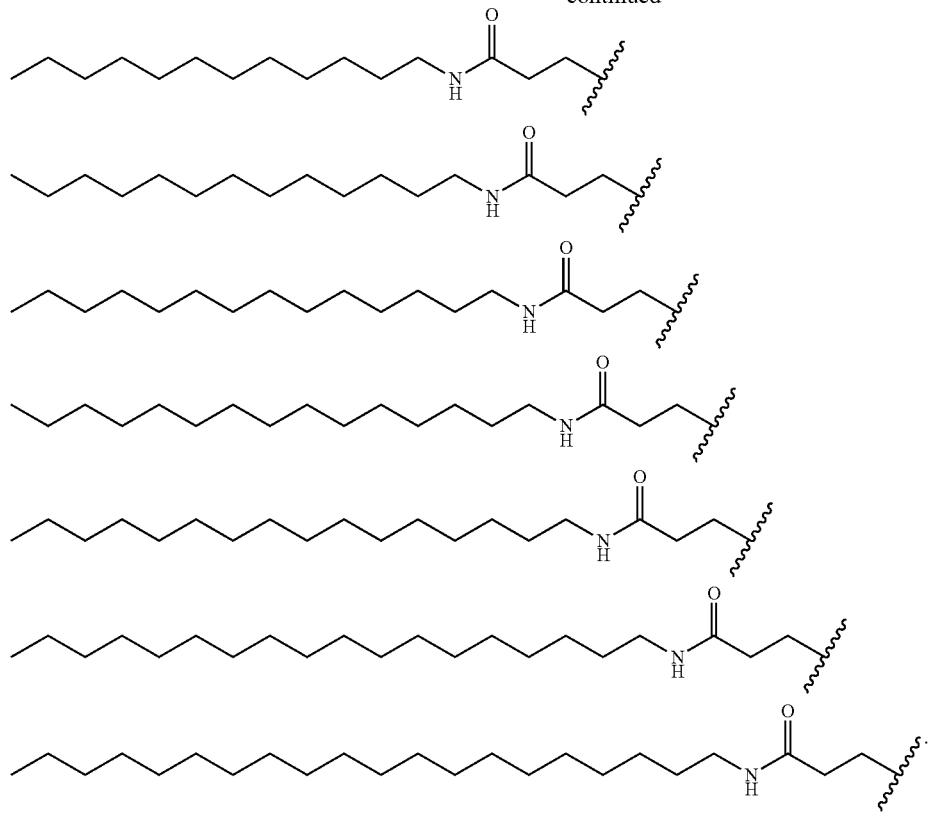

In certain embodiments, the lipids are prepared using acrylates NC, ND, NF, NG, and NP in FIG. 1. In certain embodiments, the lipids are prepared using acrylate ND. In other embodiments, the lipids are prepared using acrylate NF.

In certain embodiments,

is selected from the group consisting of:

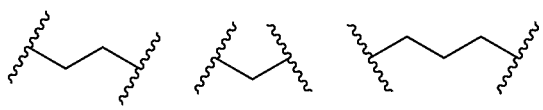

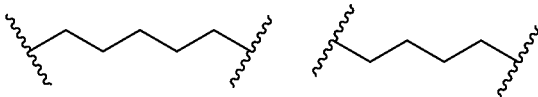

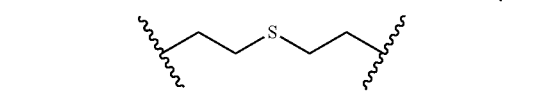

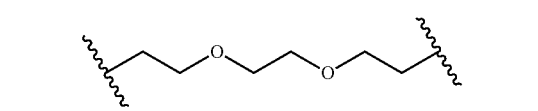

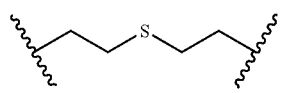

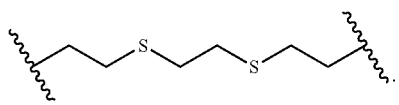

In certain particular embodiments,

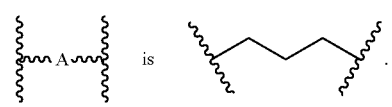

In certain particular embodiments,

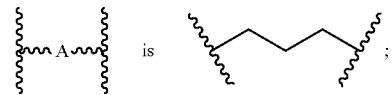

and n is 0, 1, 2, 3, 4, 5, or 6. In certain particular embodiments,

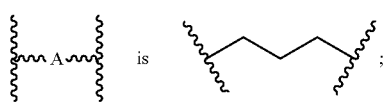

and n is 2.
In certain embodiments,

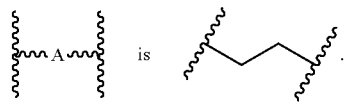

In certain embodiments,

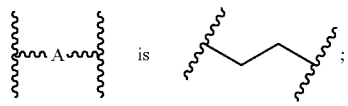

and n is 0, 1, 2, 3, 4, 5, or 6. In certain embodiments,

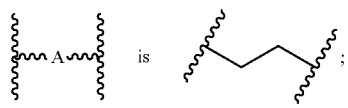

and n is 2.
In certain embodiments, the lipid is of the formula (IV):

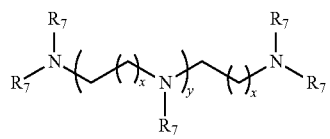

wherein each occurrence of x is an integer between 1 and 10, inclusive; preferably, between 1 and 6, inclusive;

y is an integer between 0 and 10, inclusive; preferably, between 0 and 6, inclusive;

each occurrence of $R_7$ is hydrogen; substituted or unsubstituted, branched or unbranched aliphatic; substituted or unsubstituted, branched or unbranched heteroaliphatic; substituted or unsubstituted aryl; substituted or unsubstituted heteroaryl; or

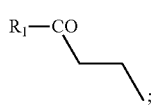

$R_1$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(\!=\!O)R_A$; —$CO_2R_A$; —CN; —SCN; —$SR_A$; —$SOR_A$; —$SO_2R_A$; —$NO_2$; —$N_3$; —$N(R_A)_2$; —NHC(=O) $R_A$; —$NR_AC(\!=\!O)N(R_A)_2$; —OC(=O)$OR_A$; —OC(=O) $R_A$; —OC(=O)N($R_A$)$_2$; —$NR_AC(\!=\!O)OR_A$; and —C($R_A$)$_3$; wherein each occurrence of $R_A$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety; and salts thereof. In certain embodiments, x is 1, 2, 3, 4, or 5. In certain particular embodiments, x is 1. In other particular embodiments, x is 2. In certain embodiments, y is 0. In certain embodiments, y is 1. In other embodiments, y is 2. In yet other embodiments, y is 3. In still other embodiments, y is 4. In certain embodiments, $R_1$ is —$OR_A$. In other embodiments, $R_1$ is —$N_1HR_A$. In certain embodiments, at least one $R_1$ is $C_1$-$C_{20}$ alkyl. In certain embodiments, all $R_7$ are of the formula

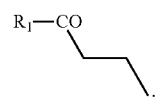

In certain embodiments, at least one $R_7$ is branched or unbranched, substituted or unsubstituted aliphatic. In certain embodiments, at least one $R_7$ is $C_1$-$C_{20}$ alkyl. In certain embodiments, at least one $R_7$ is $C_1$-$C_{12}$ alkyl. In certain embodiments, at least one $R_7$ is branched or unbranched, substituted or unsubstituted heteroaliphatic. In certain embodiments, at least one $R_7$ is

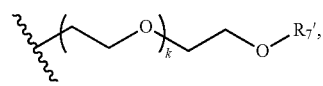

wherein k is an integer between 0 and 10, inclusive, and $R_7'$ is hydrogen or $C_{1-6}$alkyl. In certain embodiments, at least one $R_7$ is

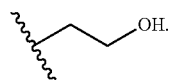 [SMILES: *CCO]

In other embodiments, at least one $R_7$ is

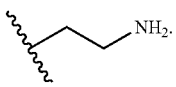

In other embodiments, at least one $R_7$ is a hydrogen. In other embodiments, at least two $R_7$ are each hydrogen. In still other embodiments, at least three $R_7$ are each hydrogen. In still further embodiments, at least four $R_7$ are each hydrogen.

In certain embodiments, each $R_7$ in formulae (IV) is independently selected from the group consisting of hydrogen and

67                                                      68
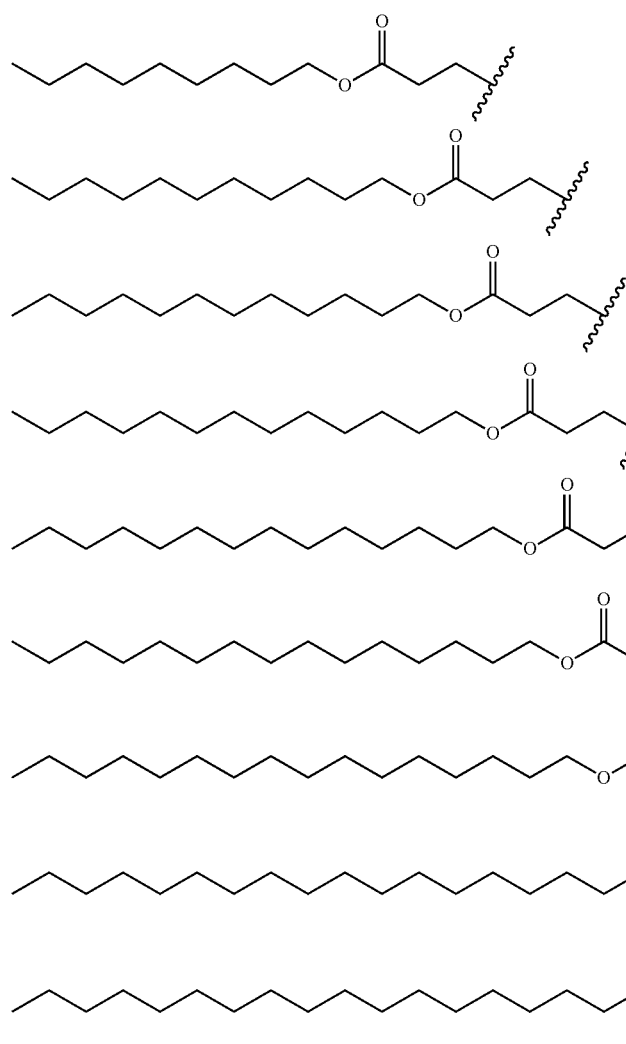 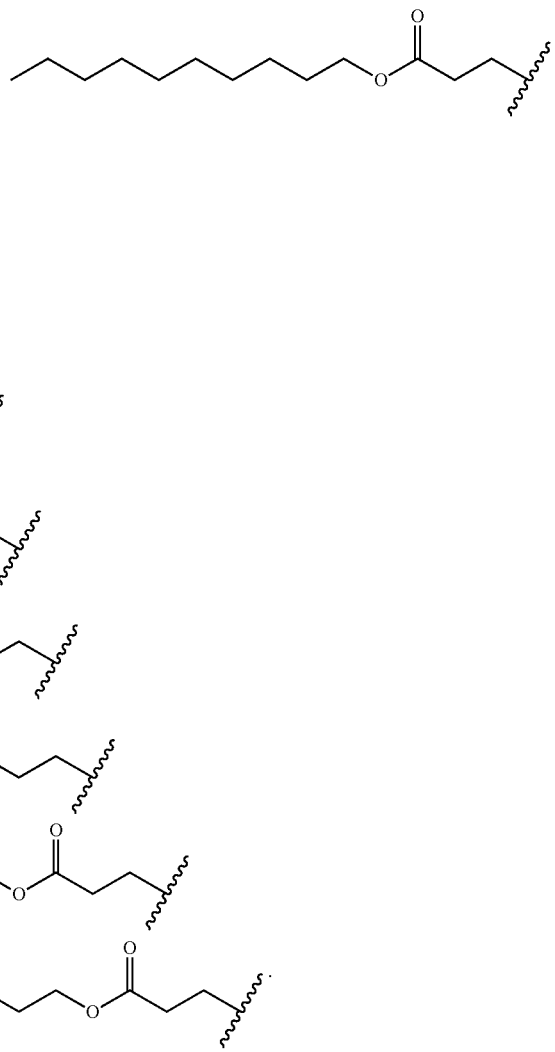
In certain embodiments, each $R_7$ in formulae (IV) is independently selected from the group consisting of hydrogen and
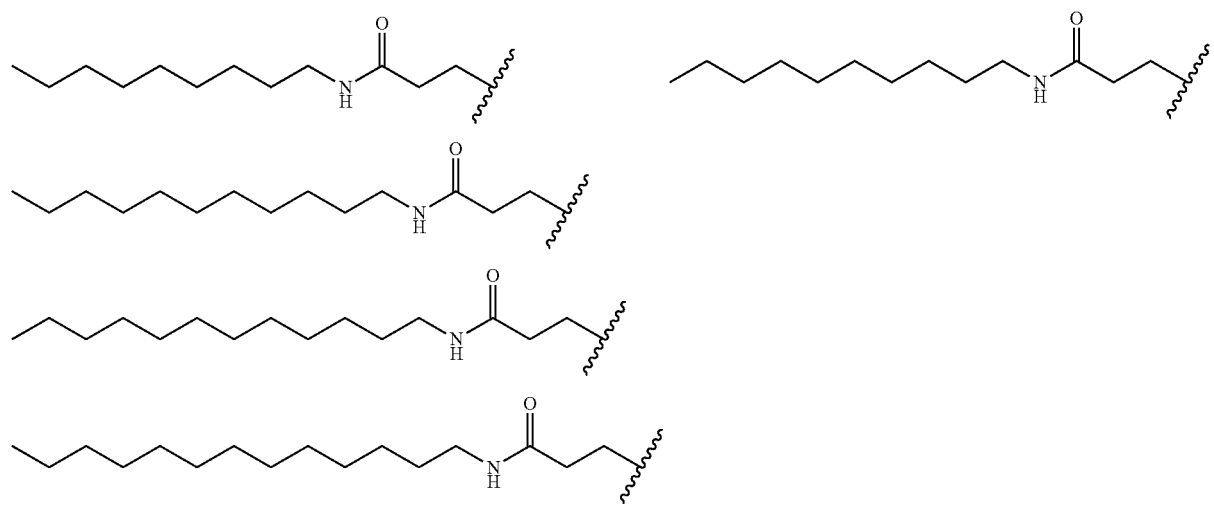

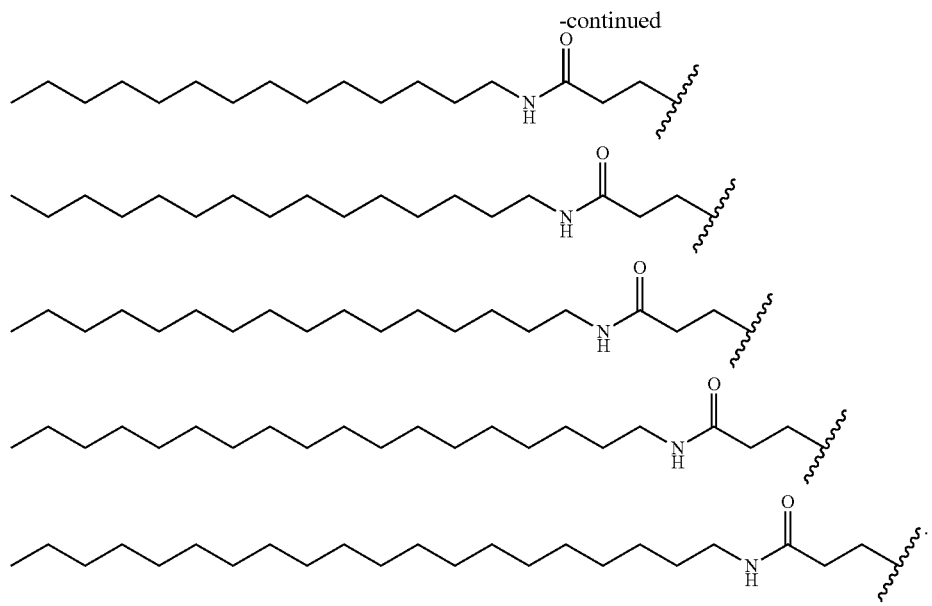

In certain embodiments, the lipid is of the formula (V), (VI), or (VII):

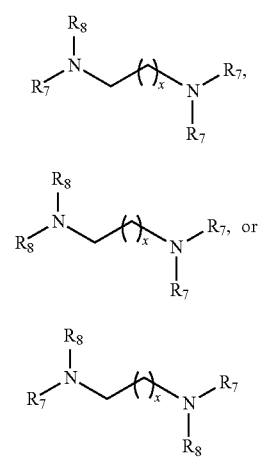

wherein x is an integer between 1 and 10, inclusive; preferably, between 1 and 6, inclusive; more preferably, between 1 and 3, inclusive;

each occurrence of $R_7$ is hydrogen or

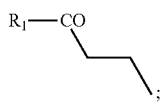

$R_1$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N_3$; —$N(R_A)_2$; —$NR_AC(=O)N(R_A)_2$; —$OC(=O)OR_A$; $OC(=O)R_A$; —$OC(=O)N(R_A)_2$; —$NR_AC(=O)OR_A$; and —$C(R_A)_3$; wherein each occurrence of $R_A$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; an acyl moiety; alkoxy; aryloxy; alkylthio; arylthio; amino, alkylamino, dialkylamino, heteroaryloxy; or heteroarylthio moiety;

each occurrence of $R_8$ is independently hydrogen, $C_1$-$C_6$ alkyl, hydroxy-$C_1$-$C_6$-alkyl; or

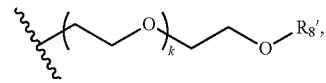

wherein k is an integer between 0 and 10, inclusive, and $R_8{'}$ is hydrogen or $C_{1-6}$ alkyl; and salts thereof. In certain embodiments, x is 1, 2, 3, 4, or 5. In certain particular embodiments, x is 1. In other particular embodiments, x is 2. In other embodiments, x is 3. In certain embodiments, $R_1$ is —$OR_A$. In other embodiments, $R_1$ is —$NHR_A$. In certain embodiments, all $R_7$ are of the formula

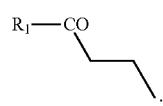

In other embodiments, at least one $R_7$ is a hydrogen. In other embodiments, at least two $R_7$ are each hydrogen. In still other embodiments, at least three $R_7$ are each hydrogen. In still further embodiments, at least four $R_7$ are each hydrogen. In certain embodiments, all $R_8$ are the same. In certain particular embodiments, $R_8$ is hydrogen. In certain embodiments, $R_8$ is methyl. In other embodiments, $R_8$ is ethyl. In yet other embodiments, $R_8$ is hydroxymethyl. In still other embodiments, $R_8$ is hydroxyethyl.

In certain embodiments, each $R_7$ in formula (V), (VI), or (VII) is independently selected from the group consisting of hydrogen and

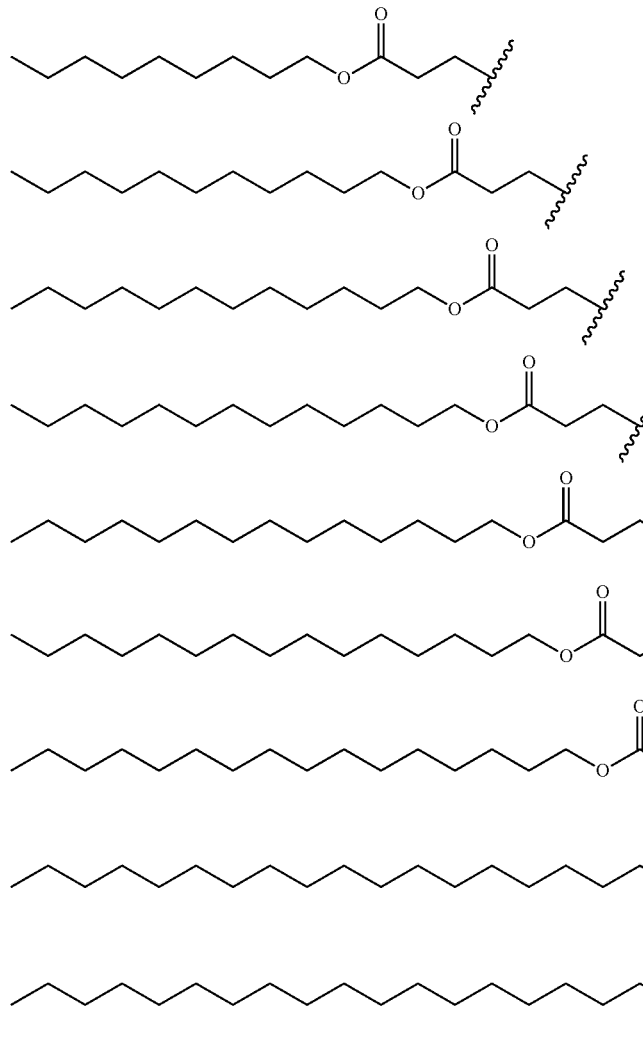
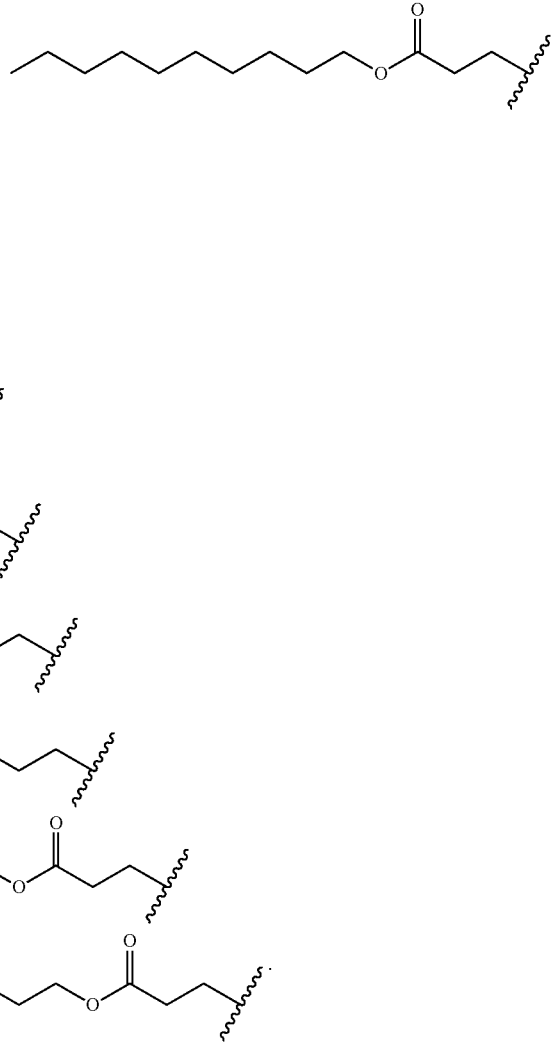

In certain embodiments, each $R_7$ in formula (V), (VI), or (VII) is independently selected from the group consisting of hydrogen and

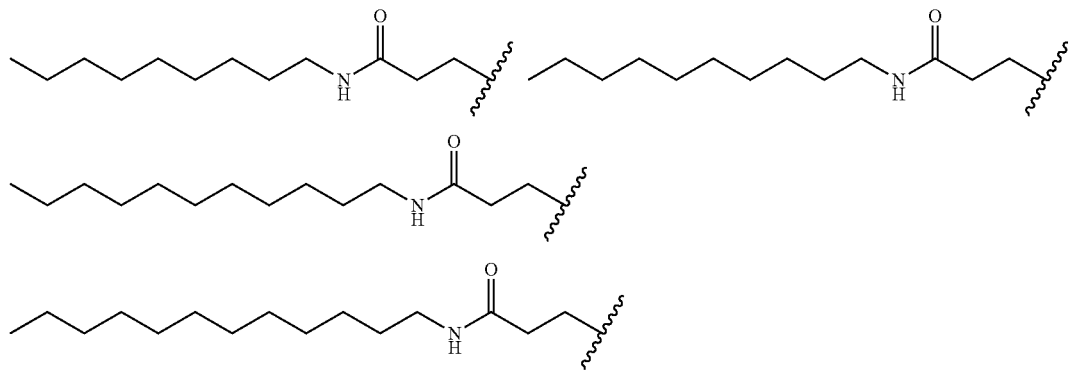

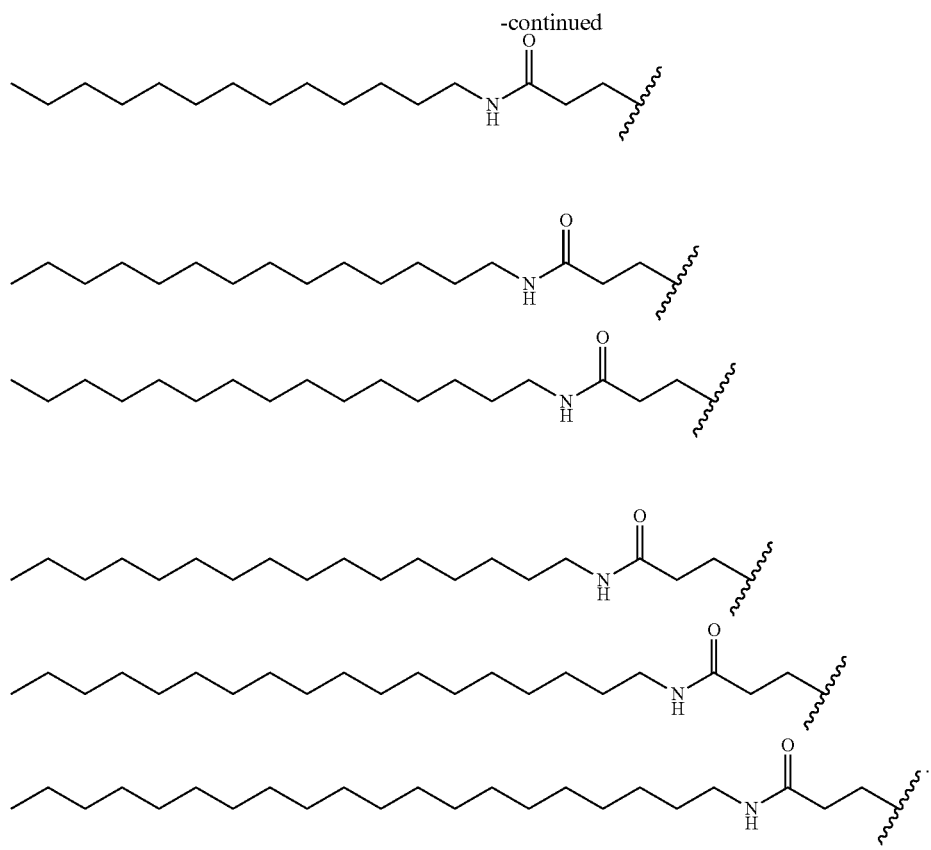
Exemplary compounds of the formulae (V), (VI), and (VII) are of the formula:
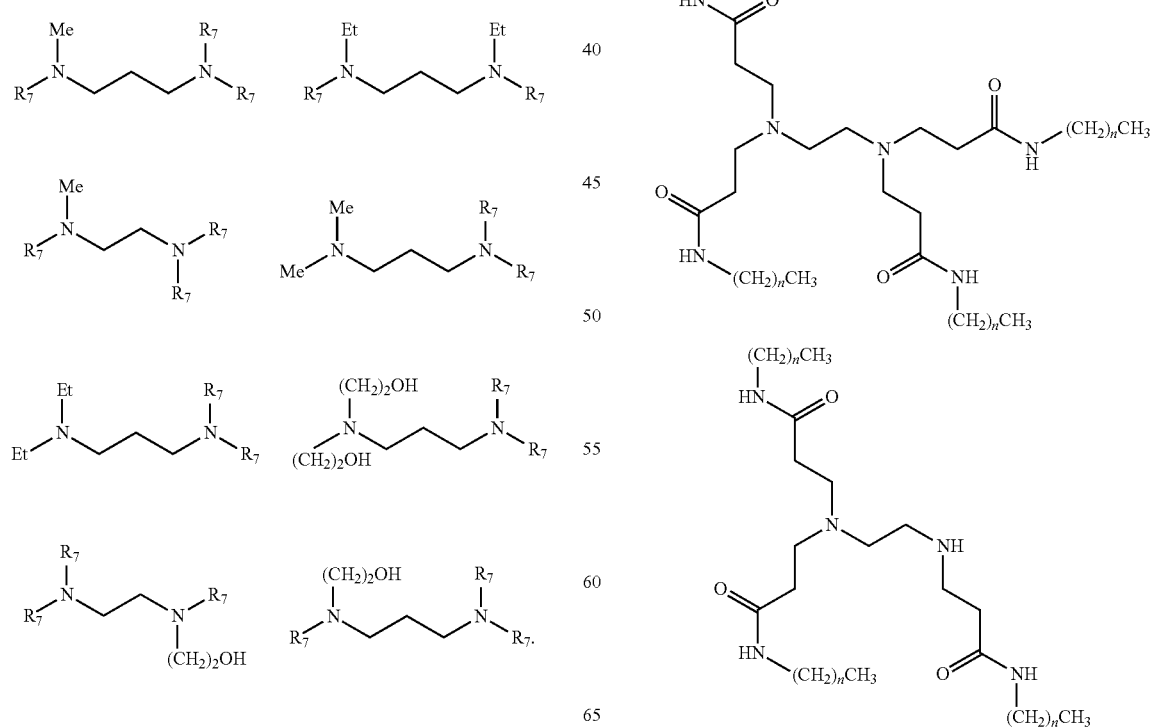
In certain embodiments, the lipid is one of the formulae:

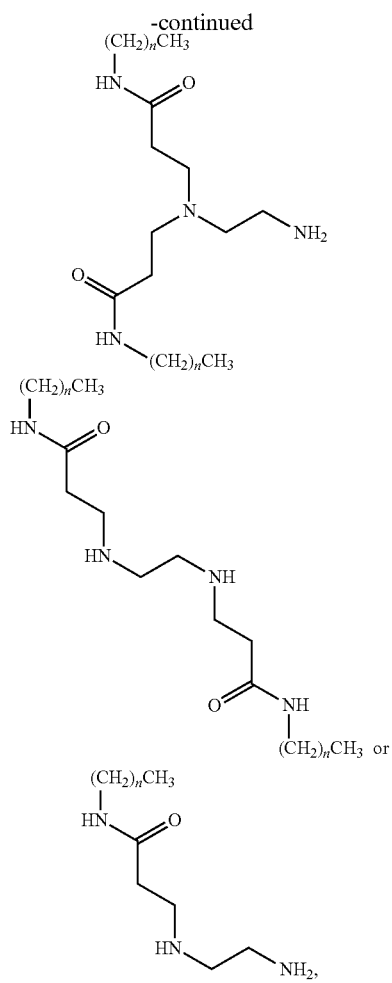

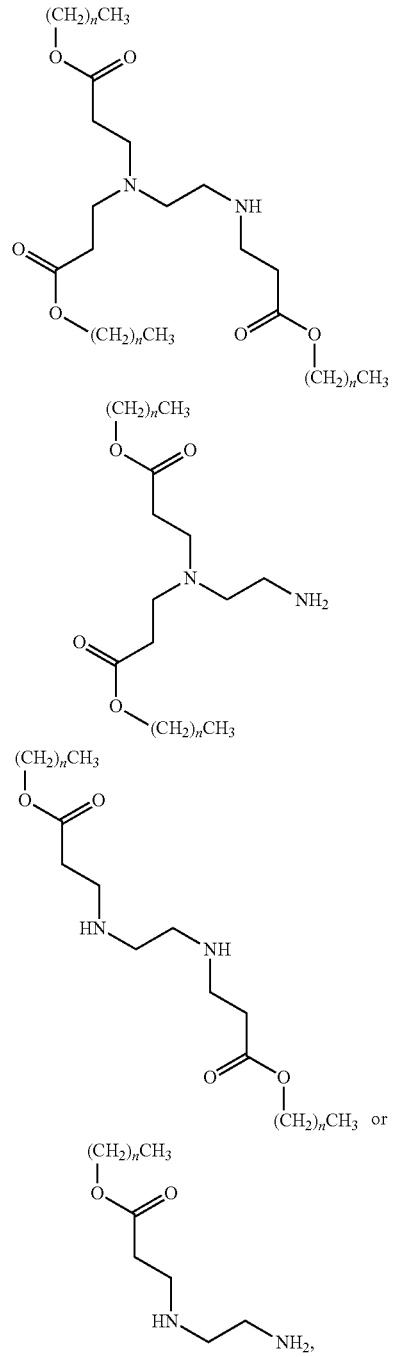

wherein n is an integer ranging from 1 to 15, inclusive; preferably, n is an integer ranging from 6 to 12, inclusive, or 1 to 6, inclusive. In certain embodiments, n is 1, 2, 3, 4, 5, 6, 7, 8, 9, 10, 11, 12, 13, 14, or 15. In certain particular embodiments, n is 10, 11, or 12. In certain embodiments, n is 11. In other embodiments, n is 10. In certain embodiments, each n is independently an integer ranging from 1 to 15, inclusive. In other embodiments, all n are the same integer. In certain embodiments, one n is different from the other n in the compound.

In other embodiments, the compound is of one of the formulae:

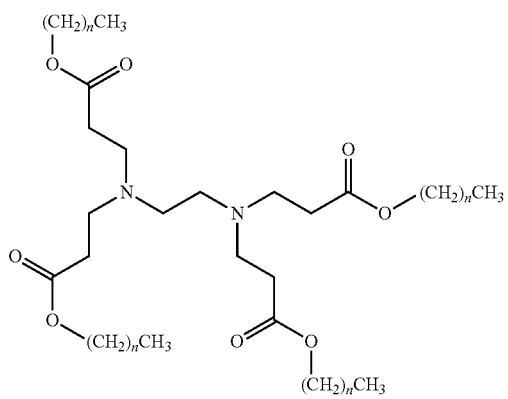

wherein n is an integer ranging from 1 to 15, inclusive; preferably, n is an integer ranging from 6 to 12, inclusive, or 1 to 6, inclusive. In certain embodiments, n is 1, 2, 3, 4, 5, 6, 7, 8, 9, 10, 11, 12, 13, 14, or 15. In certain particular embodiments, n is 10, 11, or 12. In certain embodiments, n is 11. In other embodiments, n is 10. In certain embodiments, each n is independently an integer ranging from 1 to 15, inclusive. In other embodiments, all n are the same integer. In certain embodiments, one n is different from the other n in the compound.

In certain embodiments, the lipid is of one of the formulae:

77

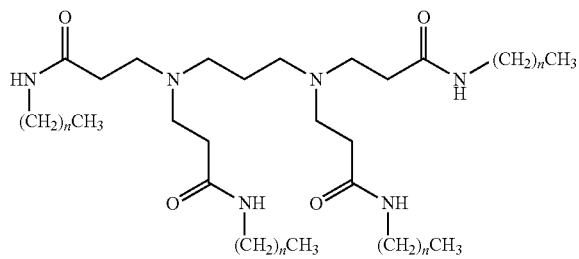

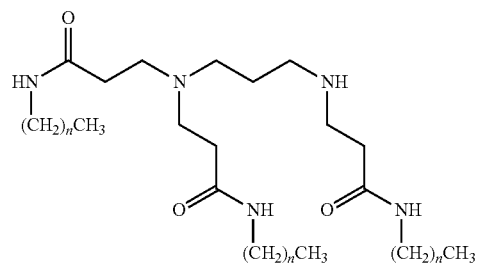

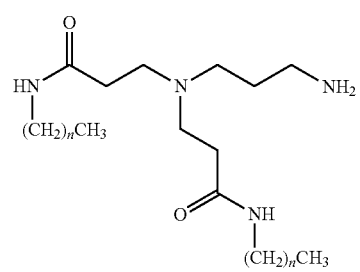

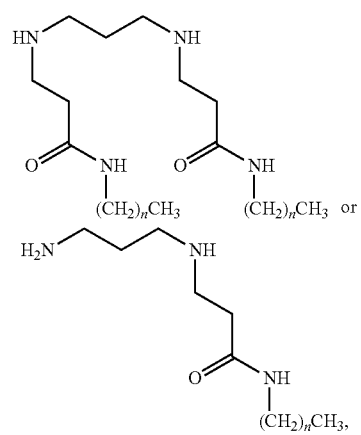

wherein n is an integer ranging from 1 to 15, inclusive; preferably, n is an integer ranging from 6 to 12, inclusive, or 1 to 6, inclusive. In certain embodiments, n is 1, 2, 3, 4, 5, 6, 7, 8, 9, 10, 11, 12, 13, 14, or 15. In certain particular embodiments, n is 10, 11, or 12. In certain embodiments, n is 11. In other embodiments, n is 10. In certain embodiments, each n is independently an integer ranging from 1 to 15, inclusive. In other embodiments, all n are the same integer. In certain embodiments, one n is different from the other n in the compound.

In certain embodiments, the lipid is of one of the formulae:

78

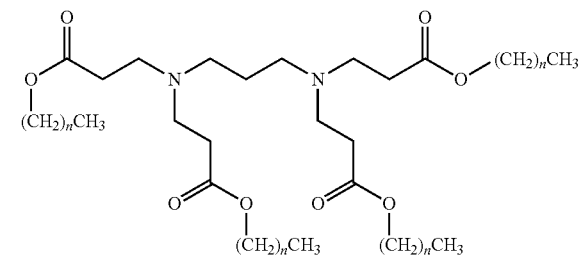

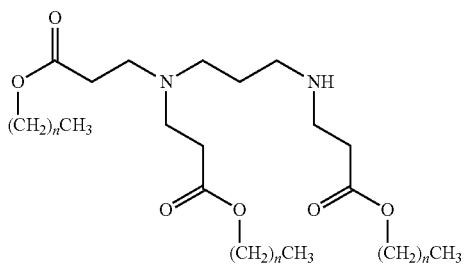

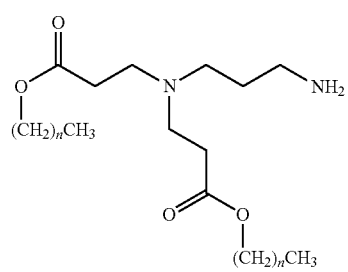

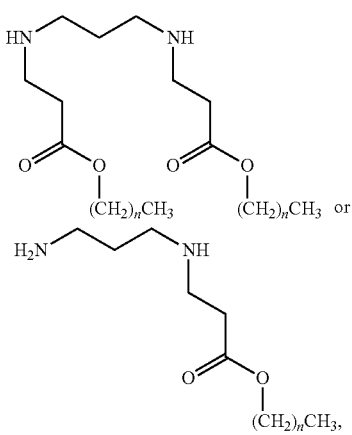

wherein n is an integer ranging from 1 to 15, inclusive; preferably, n is an integer ranging from 6 to 12, inclusive, or 1 to 6, inclusive. In certain embodiments, n is 1, 2, 3, 4, 5, 6, 7, 8, 9, 10, 11, 12, 13, 14, or 15. In certain particular embodiments, n is 10, 11, or 12. In certain embodiments, n is 11. In other embodiments, n is 10. In certain embodiments, each n is independently an integer ranging from 1 to 15, inclusive. In other embodiments, all n are the same integer. In certain embodiments, one n is different from the other n in the compound.

In certain embodiments, the lipid is of one of the formulae:

79
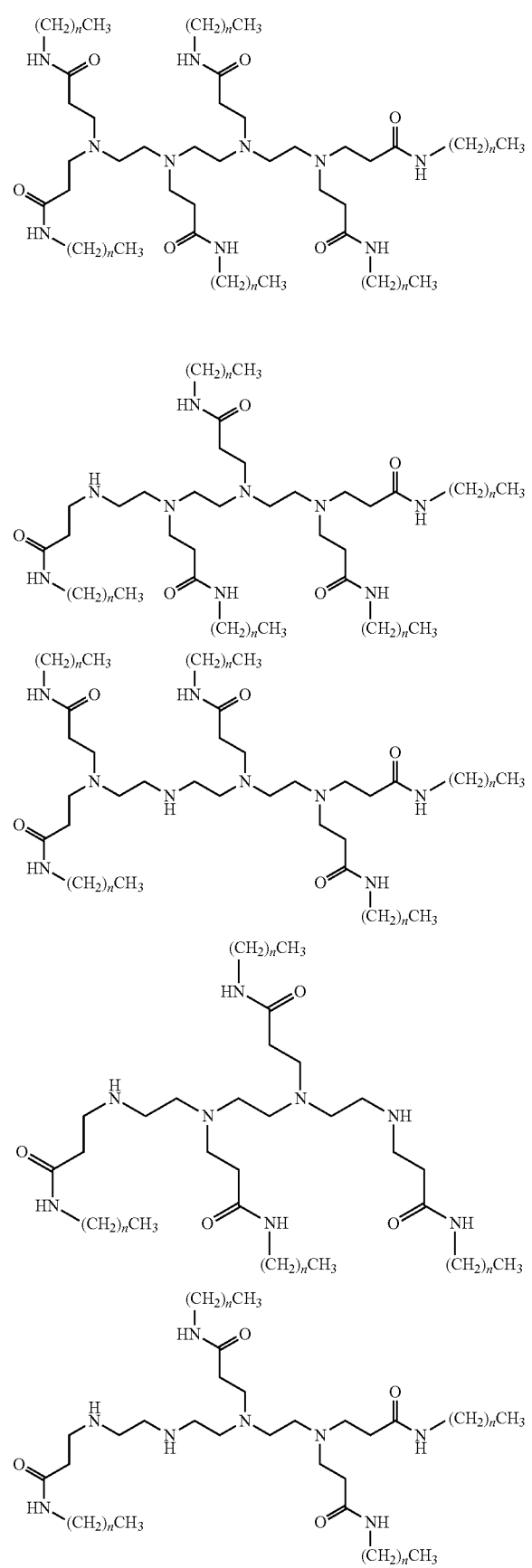
80
-continued
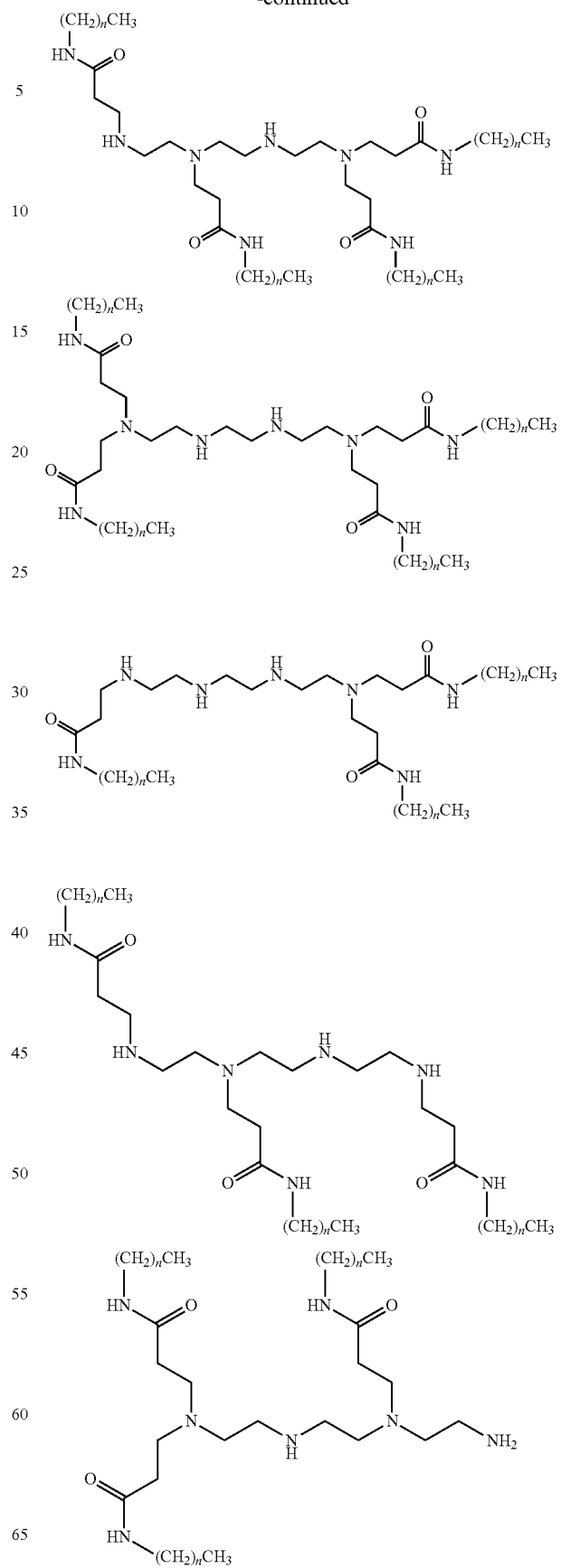

-continued

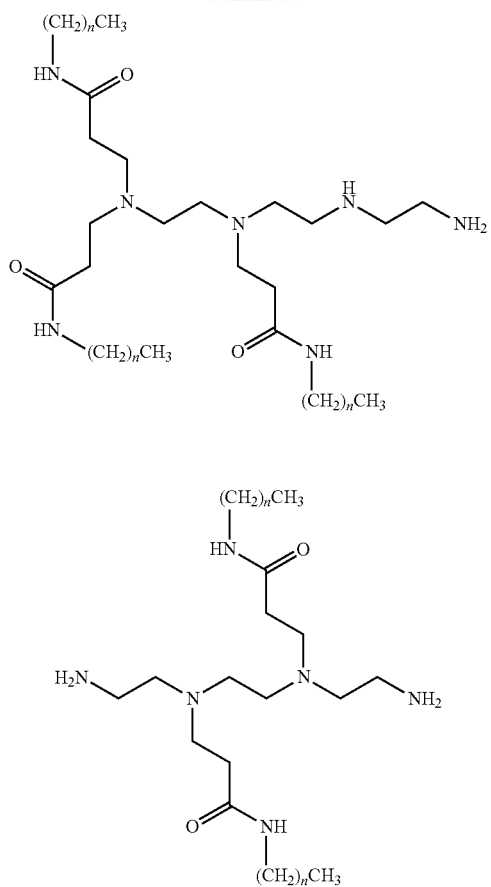

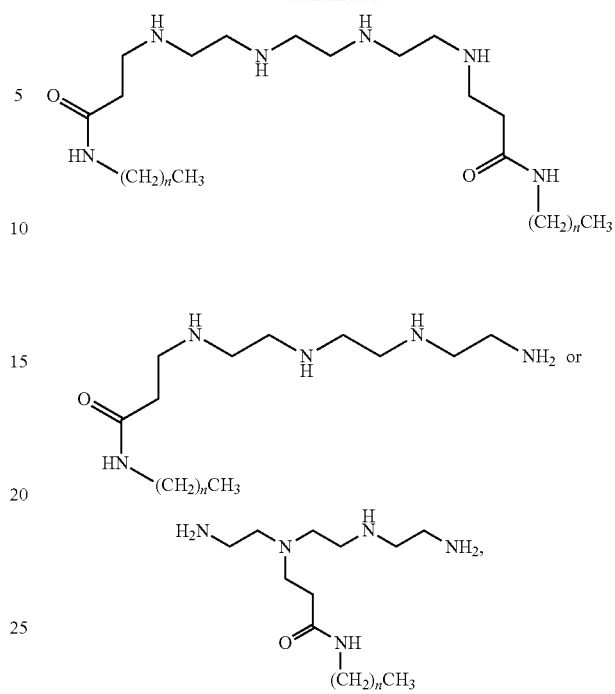

-continued wherein n is an integer ranging from 1 to 15, inclusive; preferably, n is an integer ranging from 6 to 12, inclusive, or 1 to 6, inclusive. In certain embodiments, n is 1, 2, 3, 4, 5, 6, 7, 8, 9, 10, 11, 12, 13, 14, or 15. In certain particular embodiments, n is 10, 11, or 12. In certain embodiments, n is 11. In other embodiments, n is 10. In certain embodiments, each n is independently an integer ranging from 1 to 15, inclusive. In other embodiments, all n are the same integer. In certain embodiments, one n is different from the other n in the compound.

In certain embodiments, the lipid is of one of the formulae:

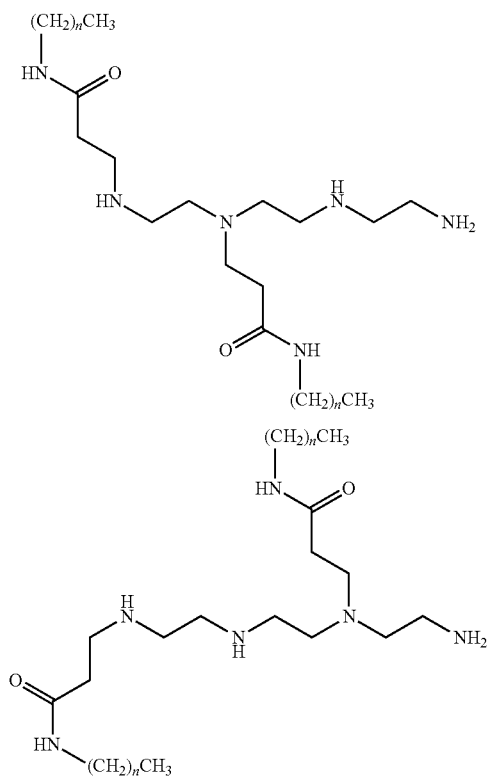

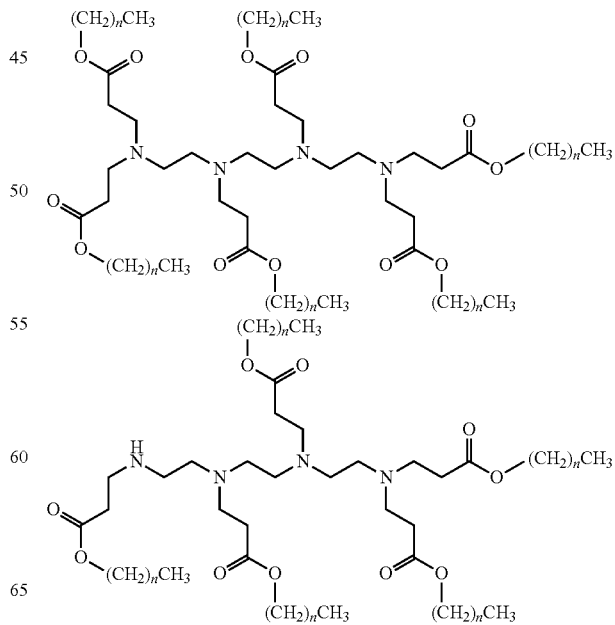

83
-continued
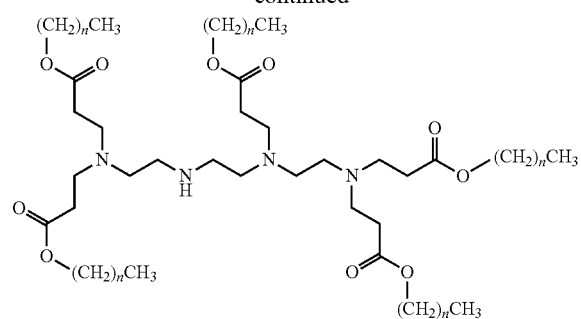
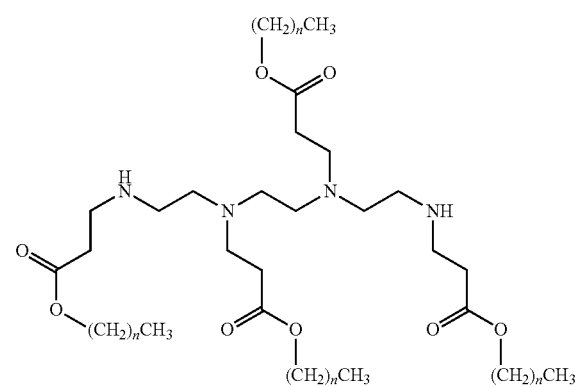
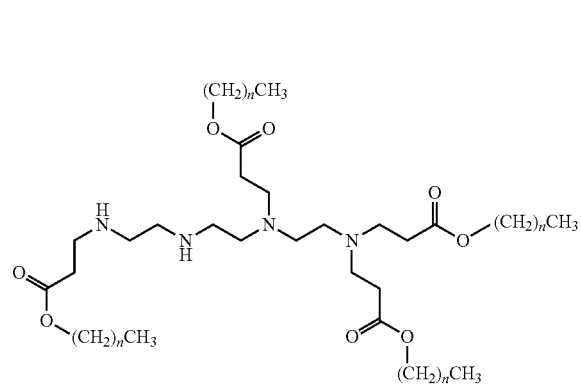
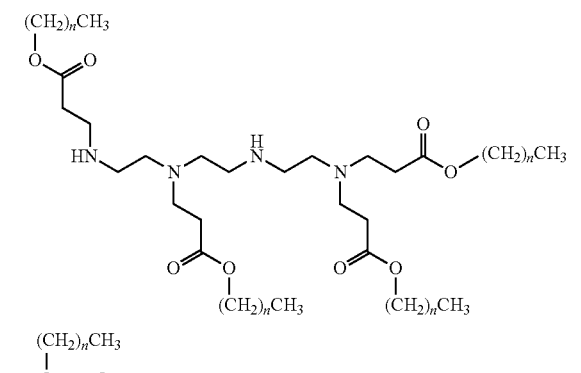
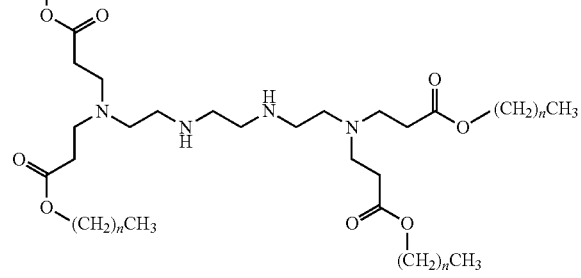
84
-continued
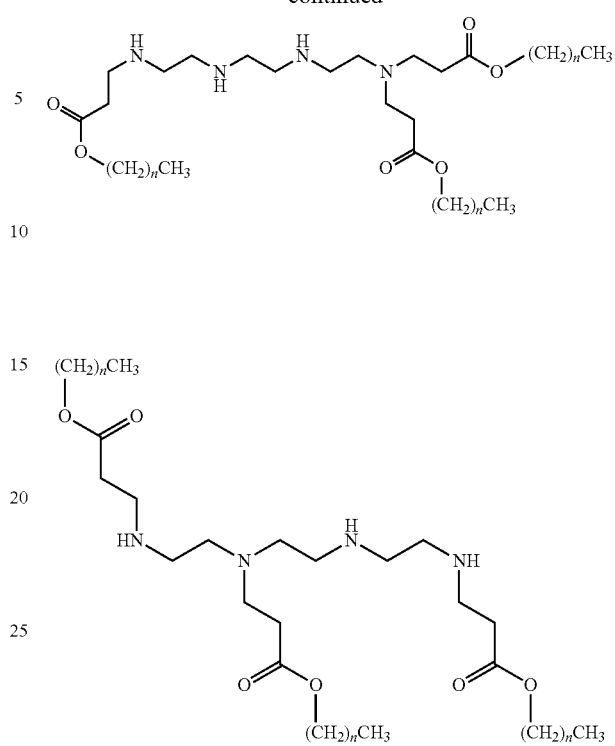
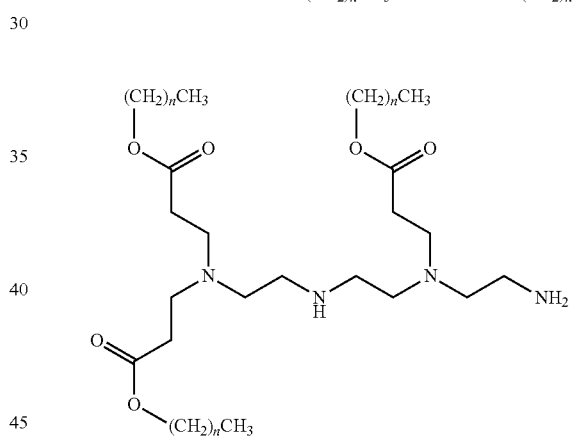
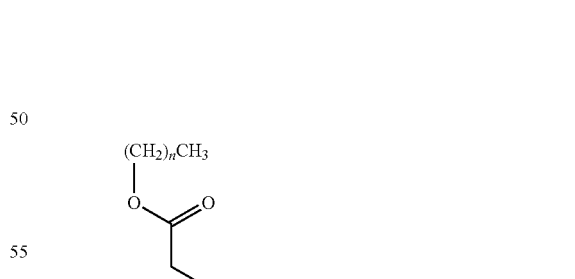
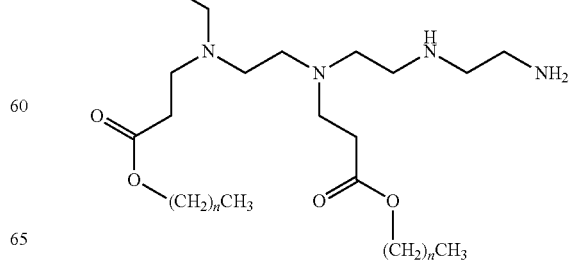

wherein n is an integer ranging from 1 to 15, inclusive; preferably, n is an integer ranging from 6 to 12, inclusive, or 1 to 6, inclusive. In certain embodiments, n is 1, 2, 3, 4, 5, 6, 7, 8, 9, 10, 11, 12, 13, 14, or 15. In certain particular embodiments, n is 10, 11, or 12. In certain embodiments, n is 11. In other embodiments, n is 10. In certain embodiments, each n is independently an integer ranging from 1 to 15, inclusive. In other embodiments, all n are the same integer. In certain embodiments, one n is different from the other n in the compound.

In another aspect of the invention, the lipid or composition of lipids of the invention is lipid or composition prepared by reacting an amine of one of the formula (1-117):

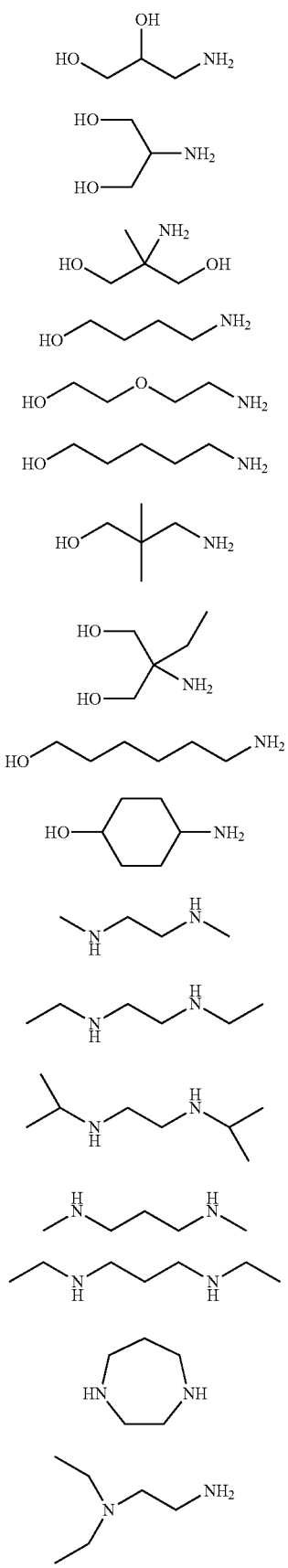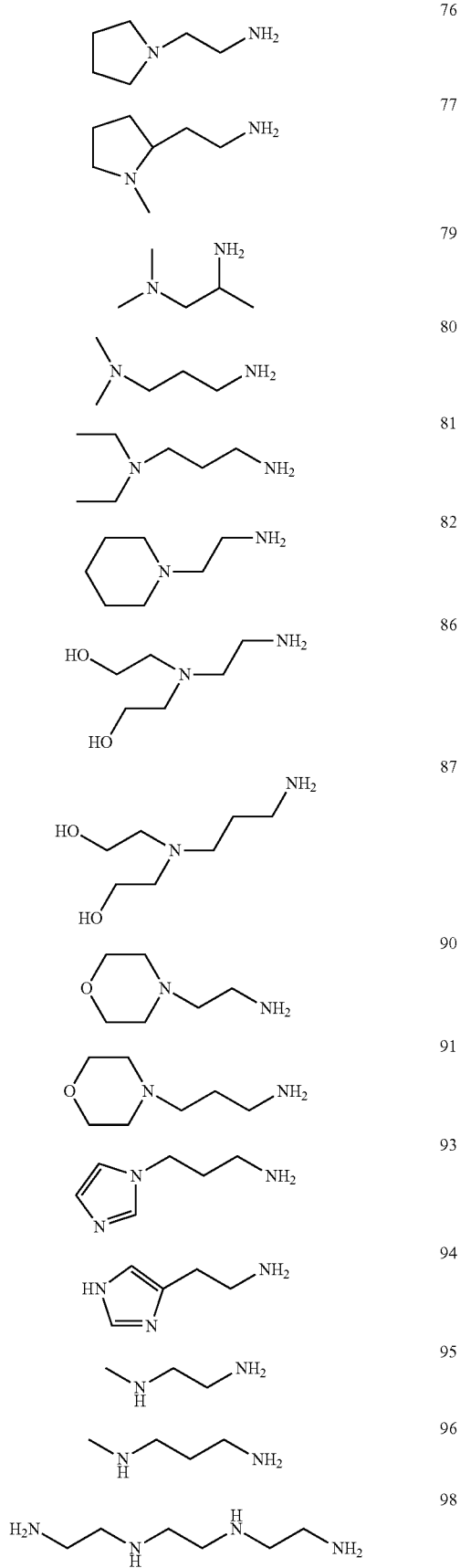

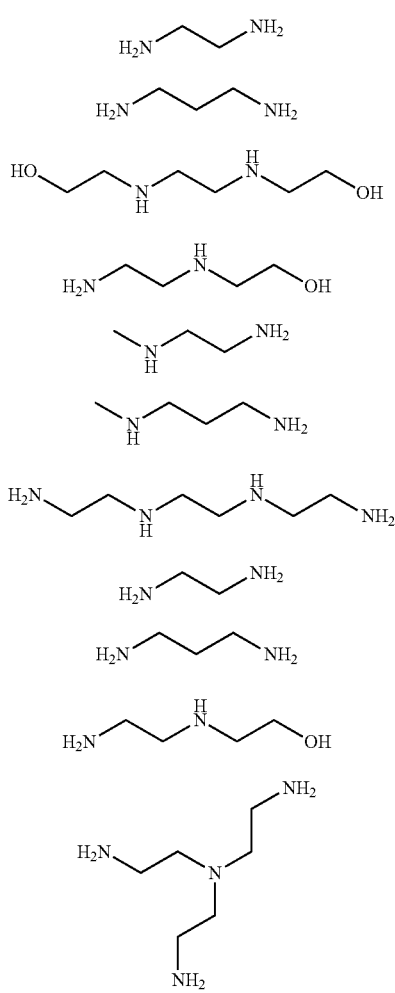
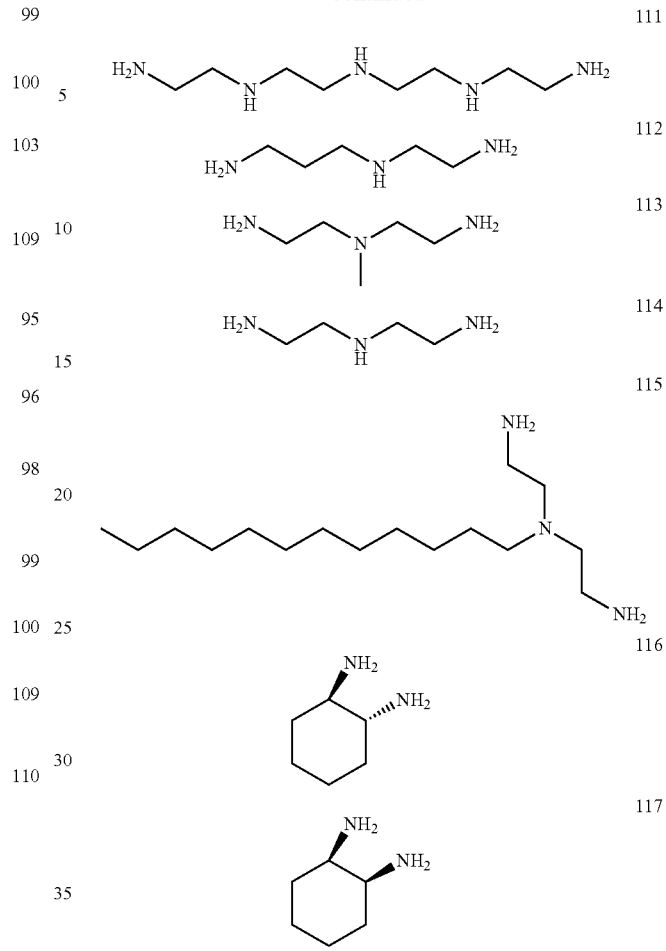
with an acrylate of formula:
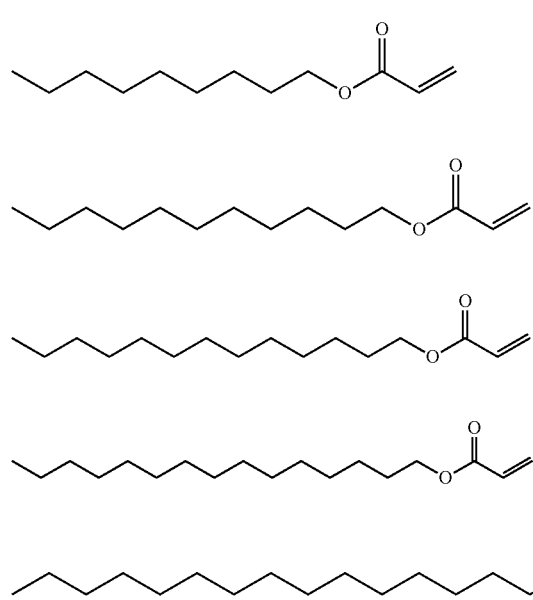
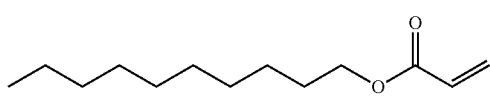
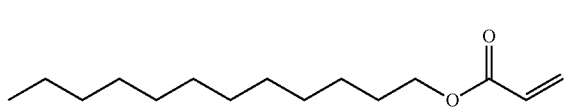
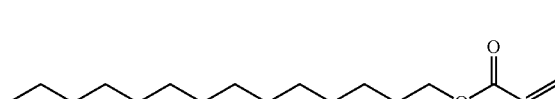
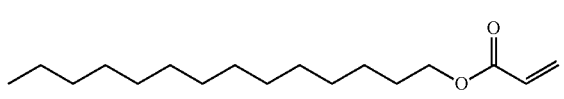
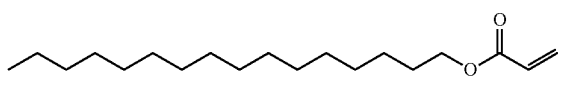

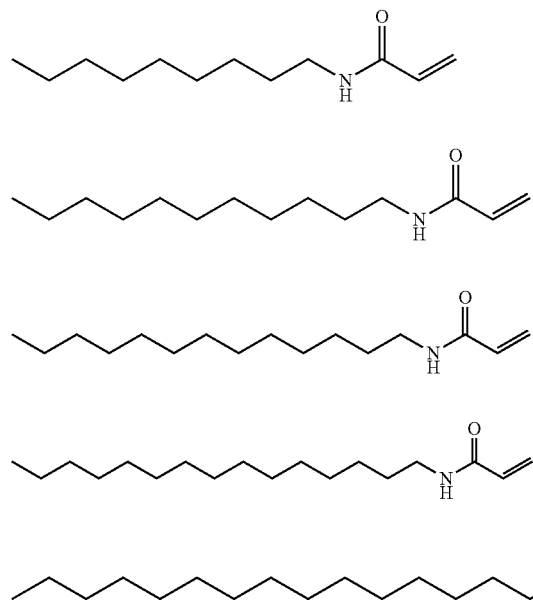
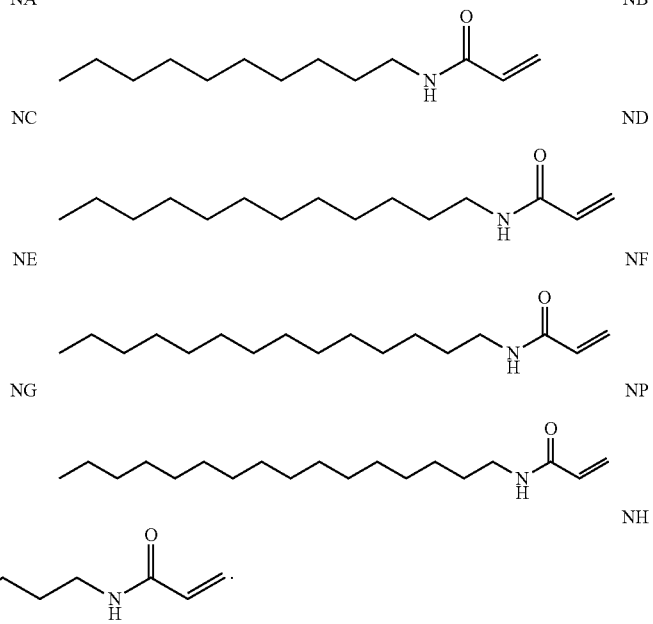

In certain embodiments, one equivalent of amine is reacted with one equivalent of acrylate. In certain embodiments, one equivalent of amine is reacted with one, two, three, four, five, six, or more equivalents of acrylate. In certain embodiments, the amount of acrylate is limiting to prevent the functionalization of all amino groups. The resulting lipid or lipid composition in these instances contain secondary amino groups or primary amino groups. Lipids having secondary amines are particular useful in certain instances. In certain embodiments, amine-containing lipids that have not been fully functionalize are further reacted with another electrophile (e.g., an acrylate, acrylamide, alkylating agent, acylating agent, etc.). Such further functionalization of the amines of the lipid results in lipids with different tails. One, two, three, four, five, or more tails may be different from the other tails of the lipid.

In certain embodiments, the amine and acrylate are reacted together neat. In other embodiments, the reaction is done in a solvent (e.g., THF, CH$_2$Cl$_2$, MeOH, EtOH, CHCl$_3$, hexanes, toluene, benzene, CCl$_4$, glyme, diethyl ether, etc.). In certain embodiments, the reaction mixture is heated. In a particularly preferred embodiment, the reaction mixture is heated to temperature ranging from 50-150° C. In another particularly preferred embodiment, the reaction mixture is heated to approximately 95° C. The reaction may also be catalyzed. For example, the reaction may be catalyzed by the addition of an acid, base, or metal. The reaction may be allowed to proceed for hours, days, or weeks. In certain embodiments, the reaction is allowed to proceed for 1-7 days, preferably 7 days. The resulting composition may be used with or without purification. In certain embodiments, the lipids are subsequently subjected to an alkylation step (e.g., reaction with methyl iodide) to form quanternary amine salts. Optionally, various salt forms of the lipids may be prepared. In certain embodiments, the salts are pharmaceutically acceptable salts.

In certain embodiments, the lipid is prepared by reacting amine 98 with acrylate NC to form lipid NC98. In certain embodiments, the lipid NC98 is of one of the formulae below:

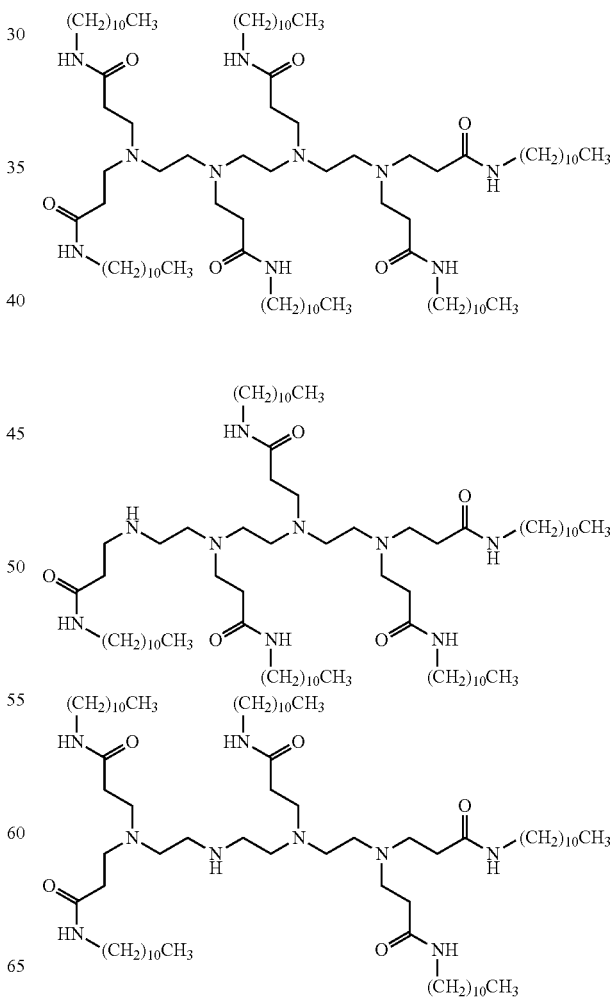

93
94
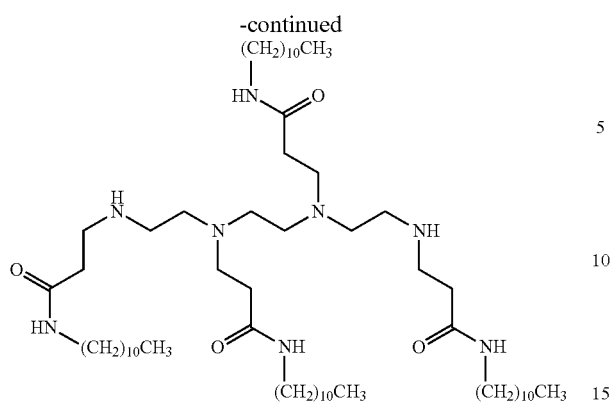
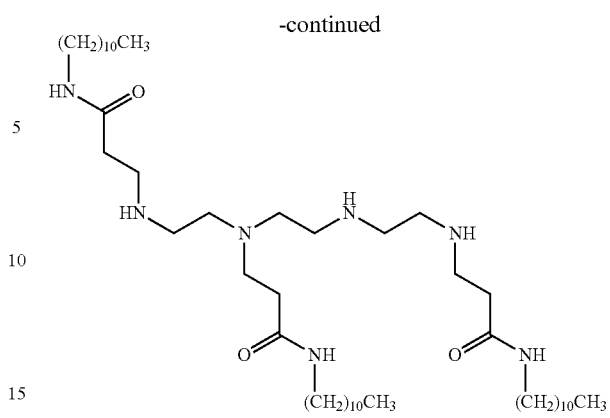
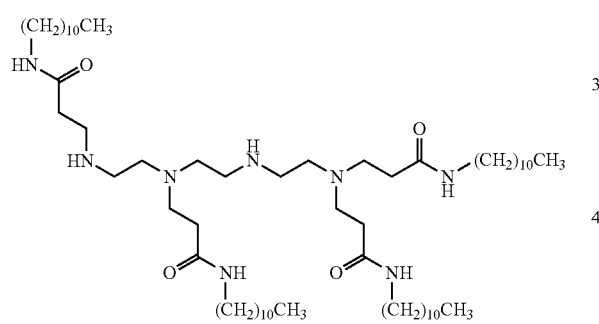
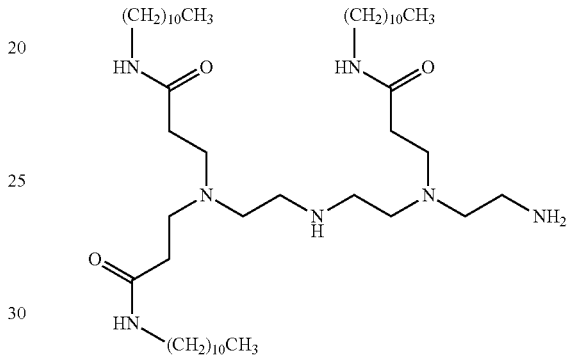
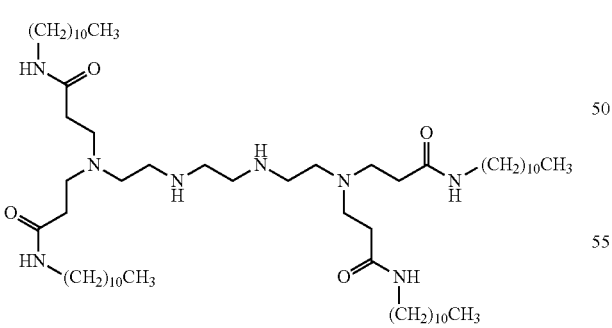
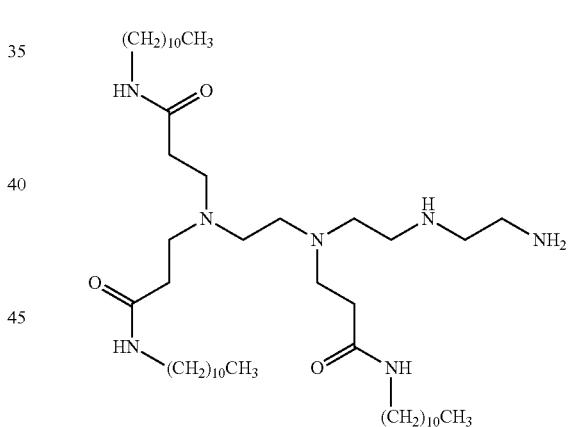
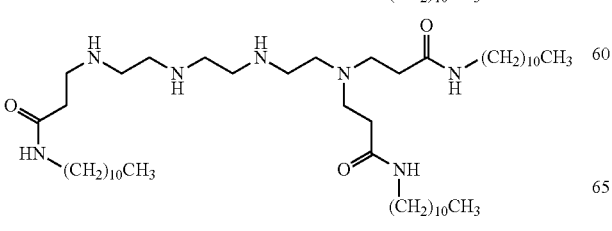
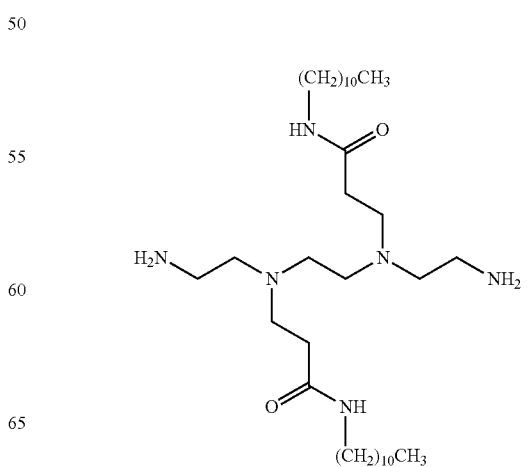

95
-continued
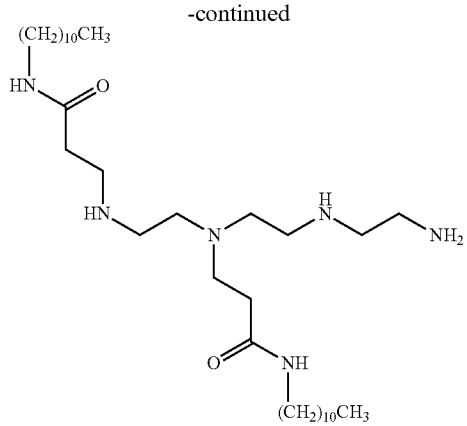
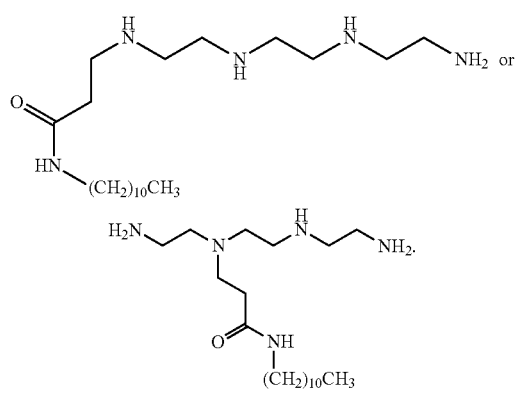
96
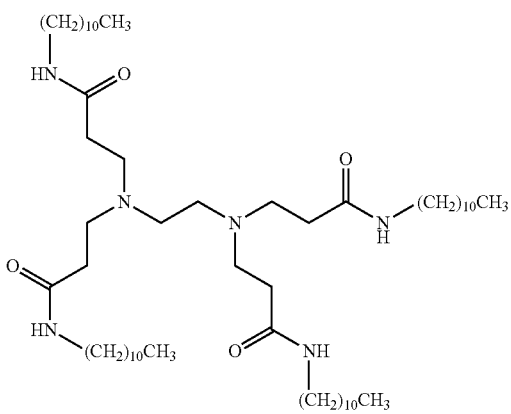
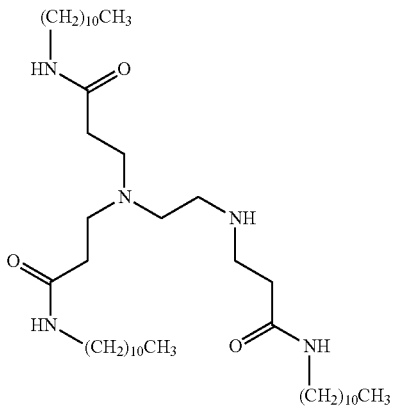
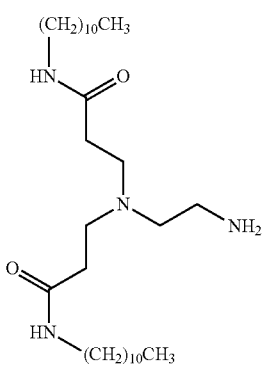
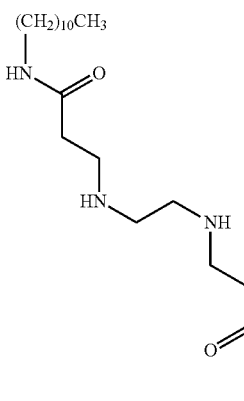
In other embodiments, the lipid is a composition of one or more of the above lipids.
In certain embodiments, the lipid is prepared by reacting amine 99 with acrylate NC to form lipid NC99. In certain embodiments, the lipid NC99 is of one of the formulae below:

-continued

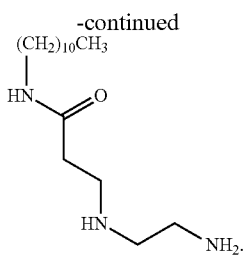

In other embodiments, the lipid is a composition of one or more of the above lipids.

In certain embodiments, the lipid is prepared by reacting amine 100 with acrylate NC to form lipid NC 100. In certain embodiments, the lipid NC 100 is of one of the formulae below:

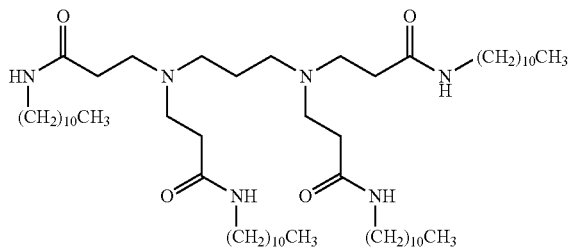

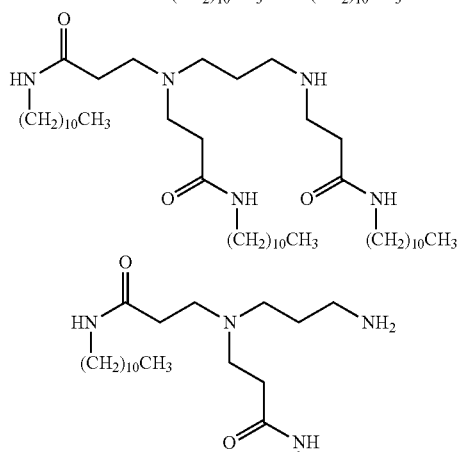

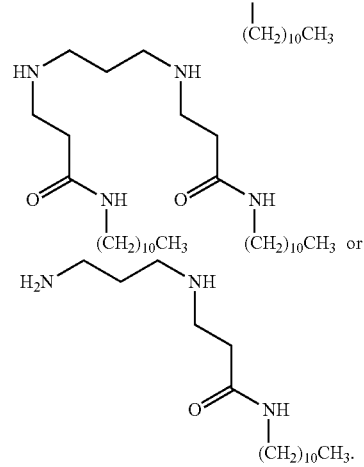

In other embodiments, the lipid is a composition of one or more of the above lipids.

In certain embodiments, the lipid is prepared by reacting amine 20 with acrylate ND to form lipid ND20. In certain embodiments, the lipid $ND_{20}$ is of one of the formulae below:

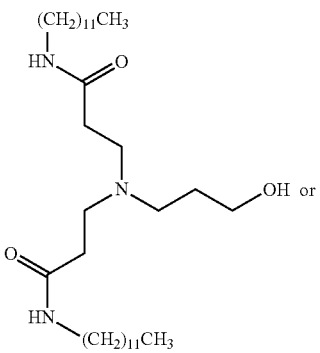

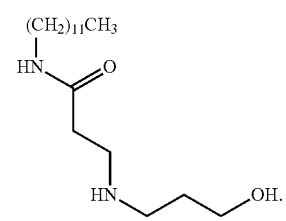

In other embodiments, the lipid is a composition of one or more of the above lipids.

In certain embodiments, the lipid is prepared by reacting amine 24 with acrylate ND to form lipid ND24. In certain embodiments, the lipid ND24 is of one of the formulae below:

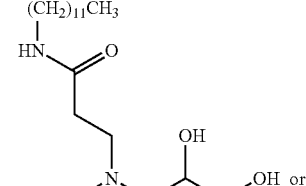

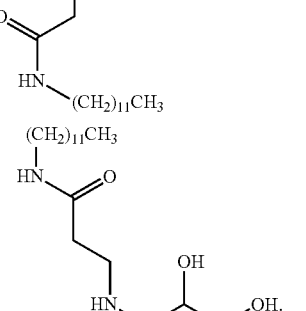

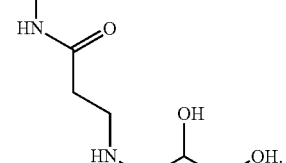

In other embodiments, the lipid is a composition of one or more of the above lipids.

In certain embodiments, the lipid is prepared by reacting amine 25 with acrylate ND to form lipid ND25. In certain embodiments, the lipid ND25 is of one of the formulae below:

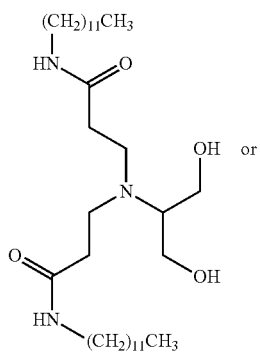

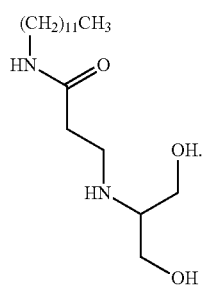

In other embodiments, the lipid is a composition of one or more of the above lipids.

In certain embodiments, the lipid is prepared by reacting amine 28 with acrylate ND to form lipid ND28. In certain embodiments, the lipid ND28 is of one of the formulae below:

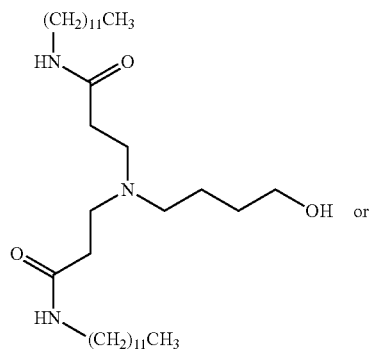

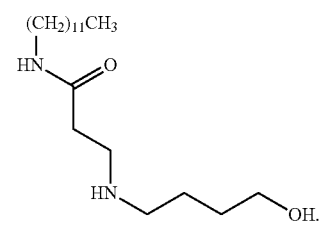

In other embodiments, the lipid is a composition of one or more of the above lipids.

In certain embodiments, the lipid is prepared by reacting amine 32 with acrylate ND to form lipid ND32. In certain embodiments, the lipid ND32 is of one of the formulae below:

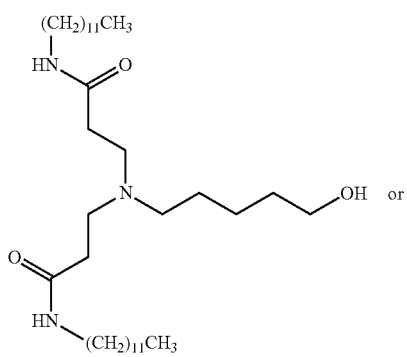

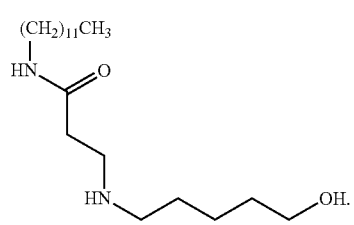

In other embodiments, the lipid is a composition of one or more of the above lipids.

In certain embodiments, the lipid is prepared by reacting amine 36 with acrylate ND to form lipid ND36. In certain embodiments, the lipid ND36 is of one of the formulae below:

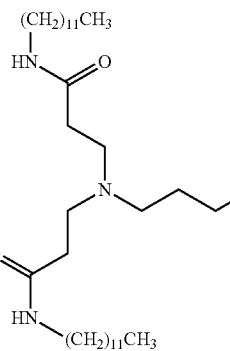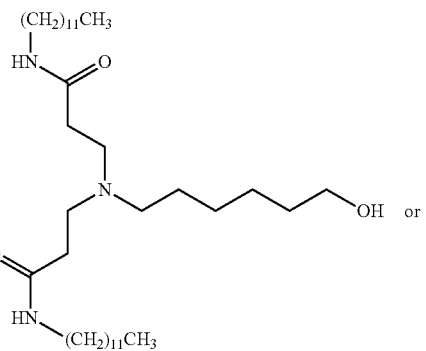

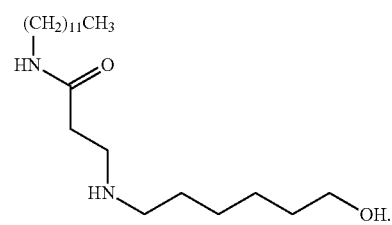

In other embodiments, the lipid is a composition of one or more of the above lipids.

In certain embodiments, the lipid is prepared by reacting amine 98 with acrylate ND to form lipid ND98. In certain embodiments, the lipid ND98 is of one of the formulae below:

101
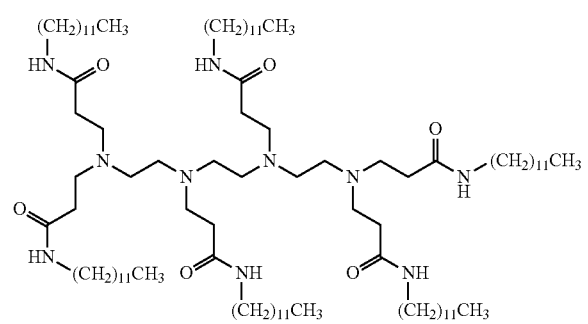
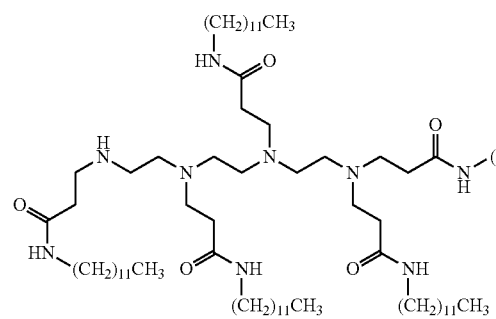
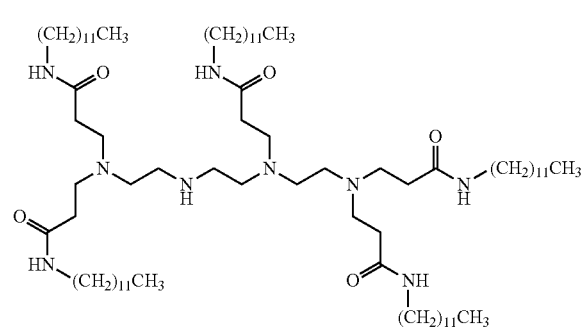
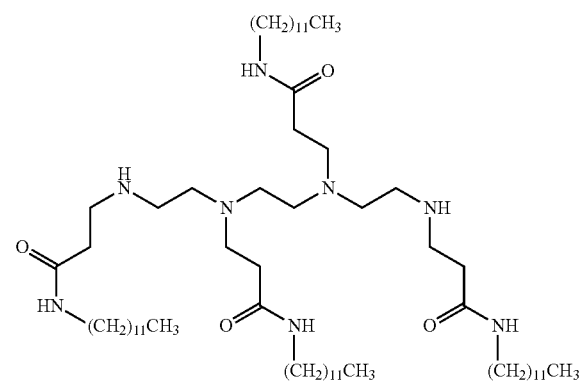
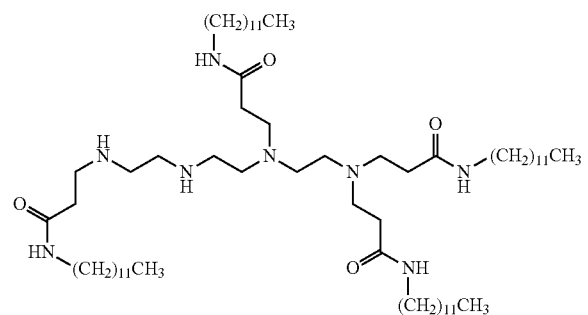
102
-continued
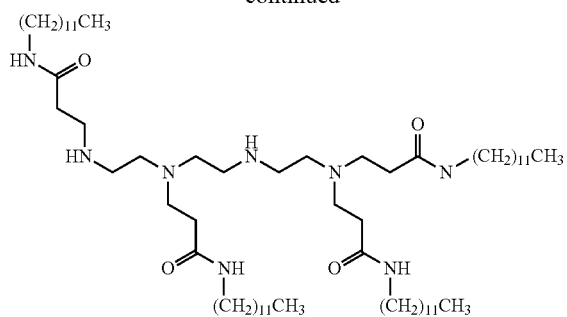
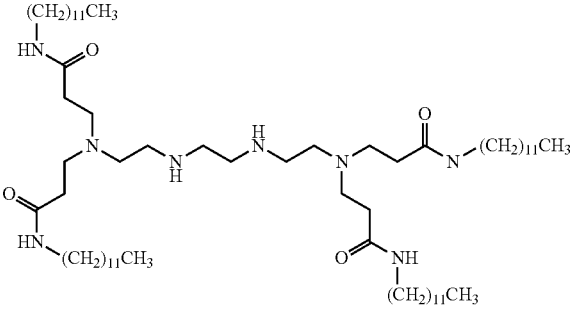
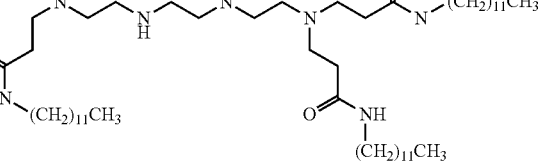
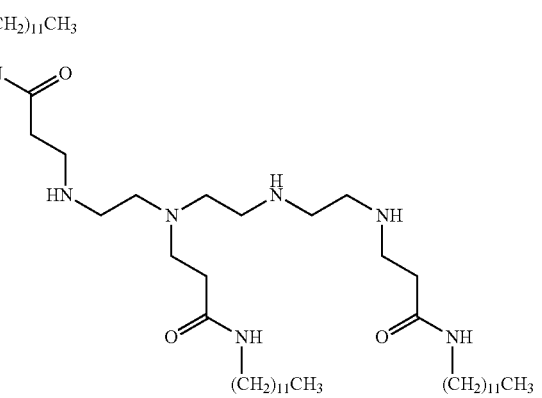
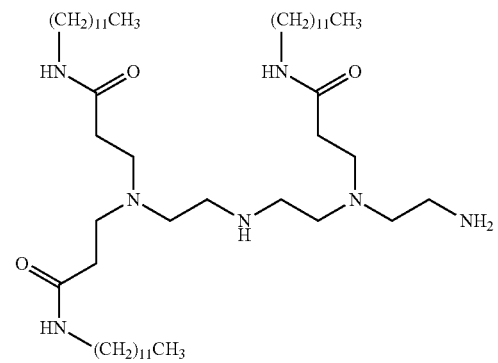

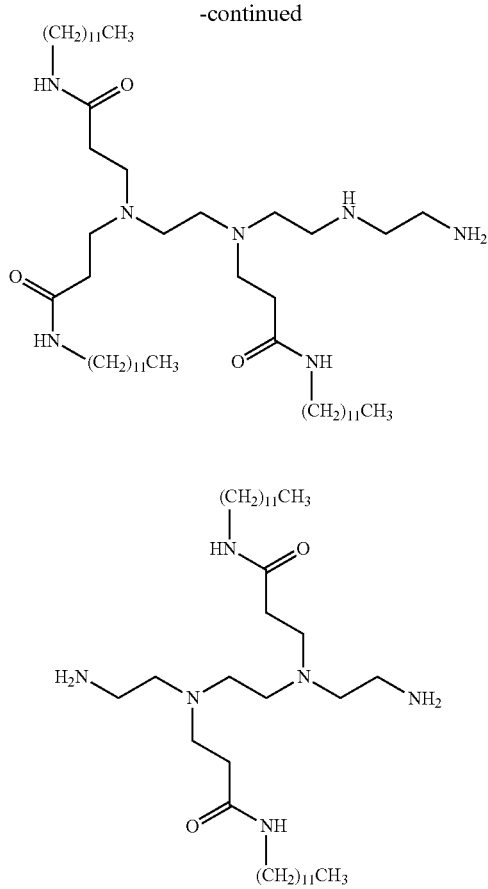
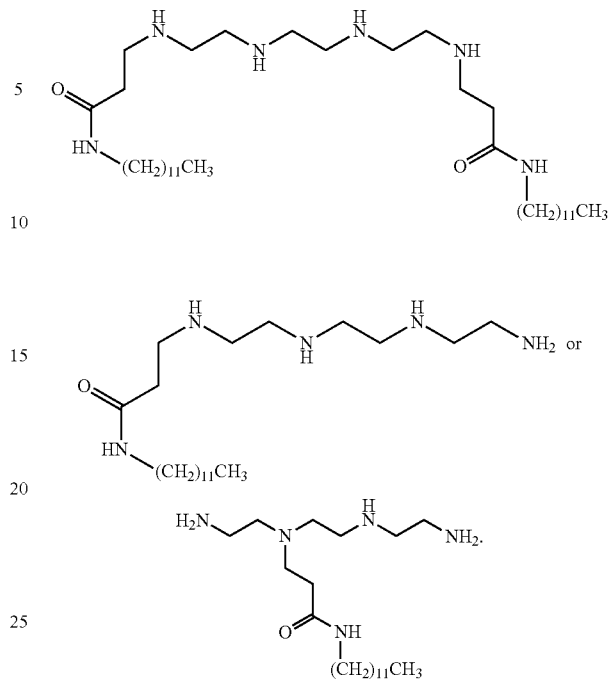
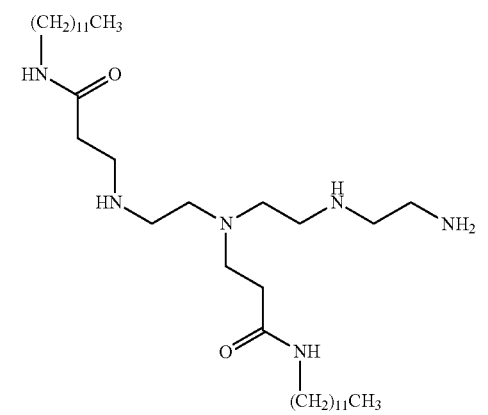

In other embodiments, the lipid is a composition of one or more of the above lipids.

In certain embodiments, the lipid is prepared by reacting amine 94 with acrylate ND to form lipid ND94. In certain embodiments, the lipid ND94 is of one of the formulae below:

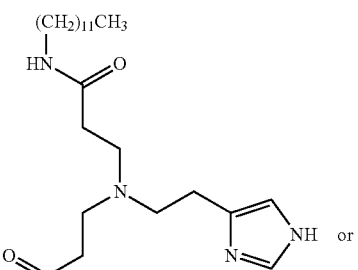

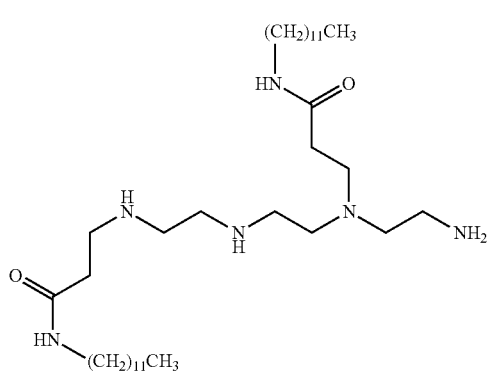

In other embodiments, the lipid is a composition of one or more of the above lipids.

In certain embodiments, the lipid is prepared by reacting amine 95 with acrylate ND to form lipid ND95. In certain embodiments, the lipid ND95 is of one of the formulae below:

105

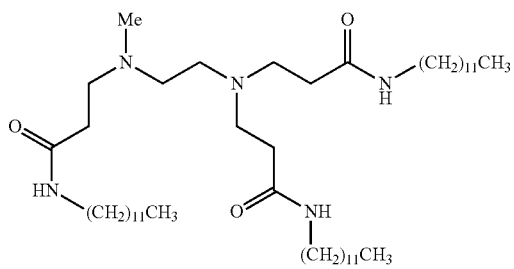

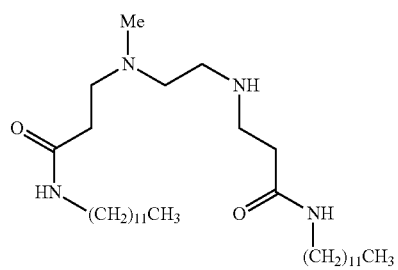

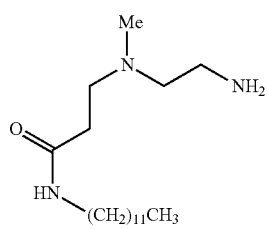

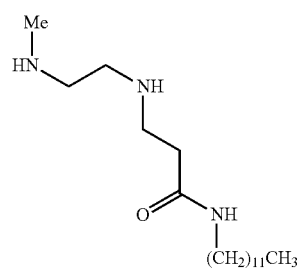

or

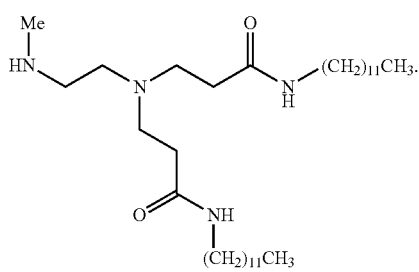

In other embodiments, the lipid is a composition of one or more of the above lipids.

In certain embodiments, the lipid is prepared by reacting amine 96 with acrylate ND to form lipid ND96. In certain embodiments, the lipid ND96 is of one of the formulae below:

106

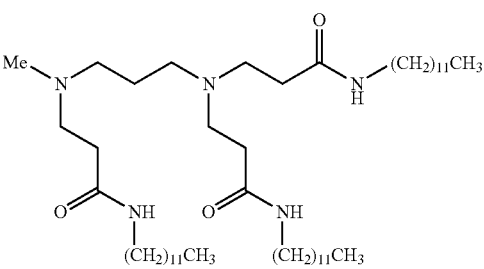

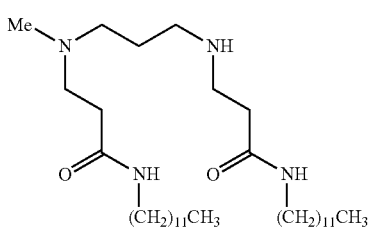

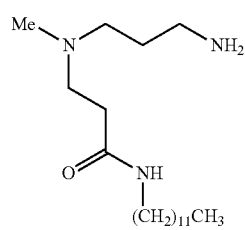

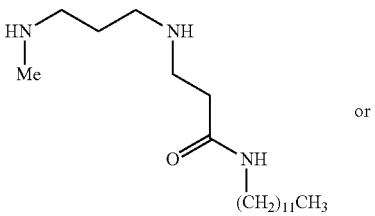

or

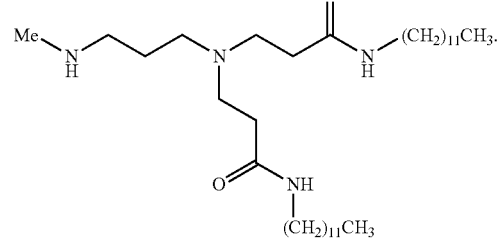

In other embodiments, the lipid is a composition of one or more of the above lipids.

In certain embodiments, the lipid is prepared by reacting amine 99 with acrylate ND to form lipid ND99. In certain embodiments, the lipid ND99 is of one of the formulae below:

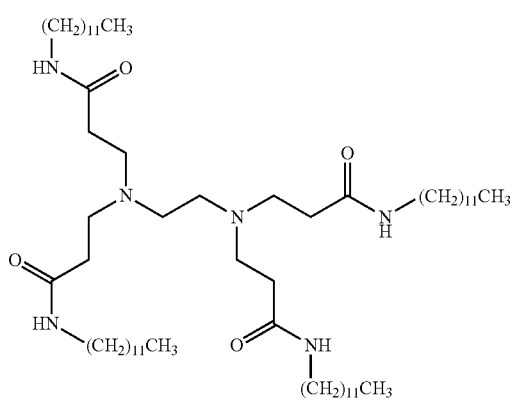
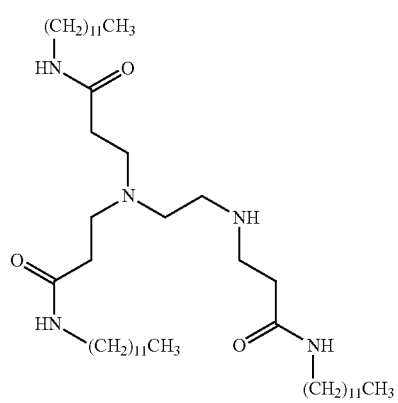
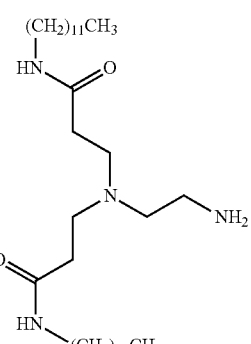
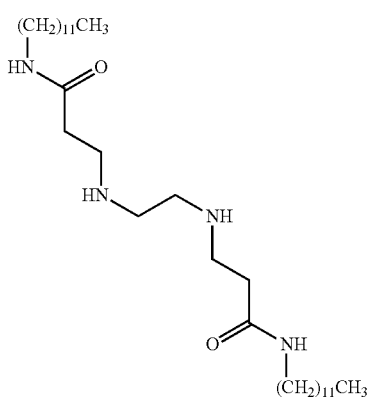
or
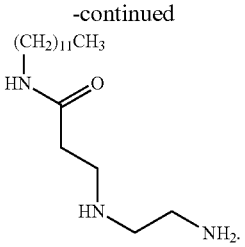
In other embodiments, the lipid is a composition of one or more of the above lipids. In certain embodiments, ND99 is treated with MeI or another alkylating agent to form lipids of the formulae:
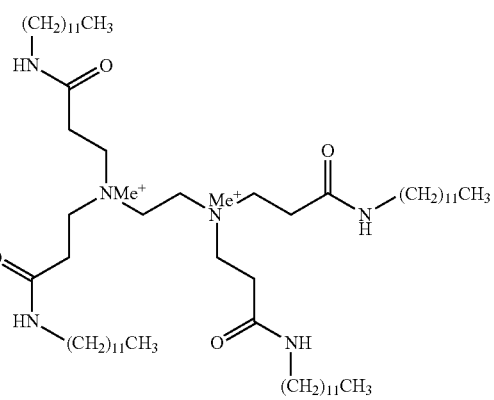
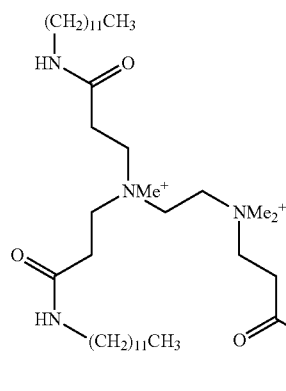
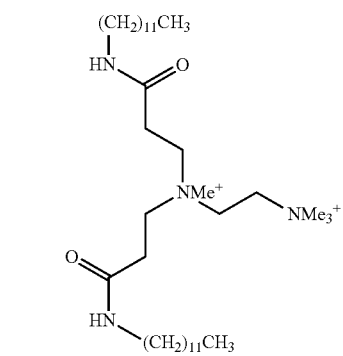

109
-continued

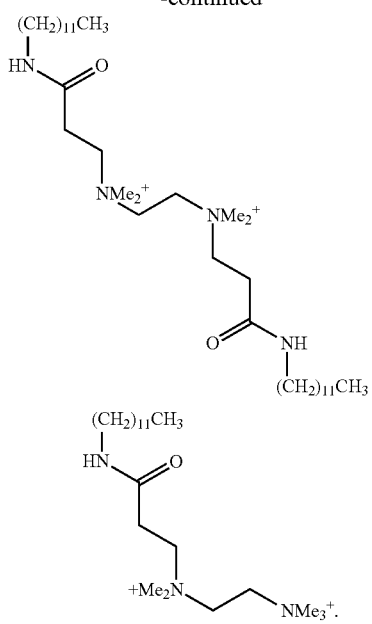

or

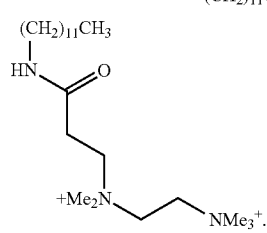

In certain embodiments, the lipid is prepared by reacting amine 100 with acrylate ND to form lipid ND100. In certain embodiments, the lipid ND100 is of one of the formulae below:

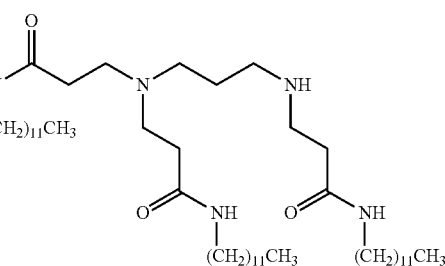

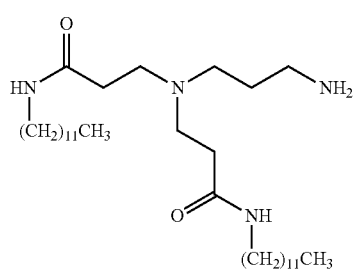

110
-continued

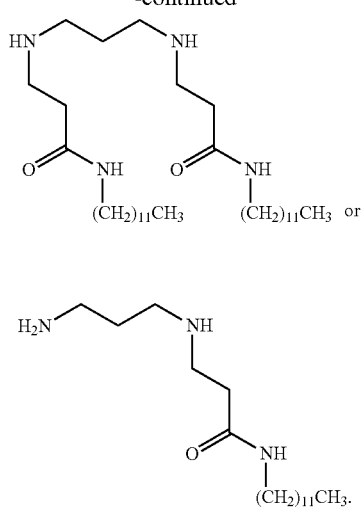

or

In other embodiments, the lipid is a composition of one or more of the above lipids.

In certain embodiments, the lipid is prepared by reacting amine 103 with acrylate ND to form lipid ND103. In certain embodiments, the lipid ND103 is of one of the formulae below:

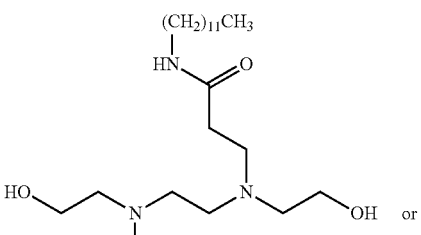

or

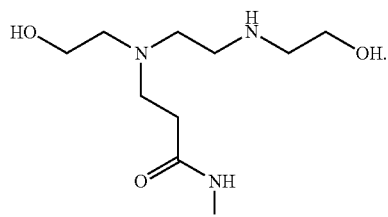

In other embodiments, the lipid is a composition of one or more of the above lipids.

In certain embodiments, the lipid is prepared by reacting amine 109 with acrylate ND to form lipid ND109. In certain embodiments, the lipid ND109 is of one of the formulae below:

111
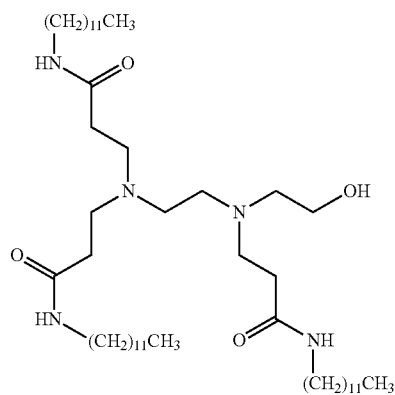
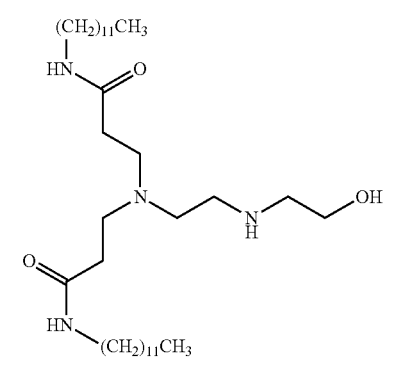
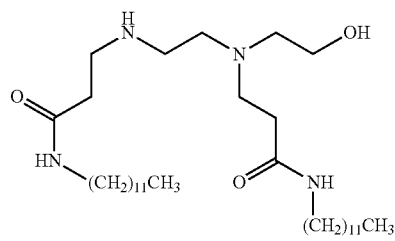
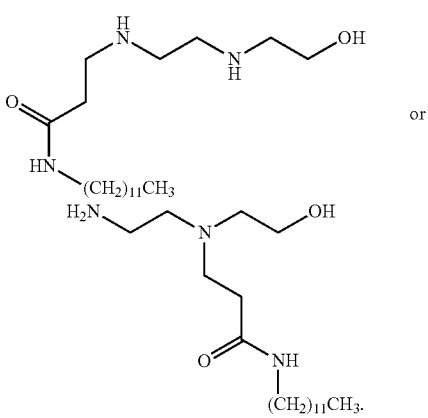
112
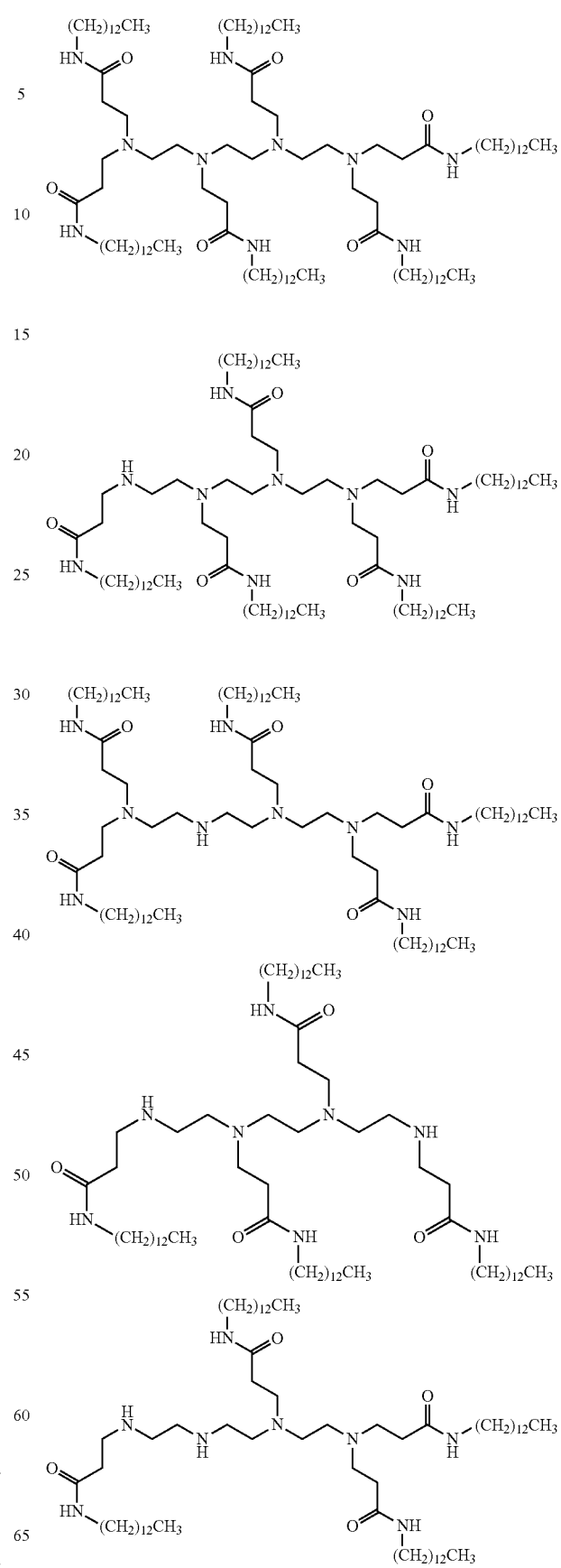
In other embodiments, the lipid is a composition of one or more of the above lipids.
In certain embodiments, the lipid is prepared by reacting amine 98 with acrylate NE to form lipid NE98. In certain embodiments, the lipid NE98 is of one of the formulae below:

113
-continued
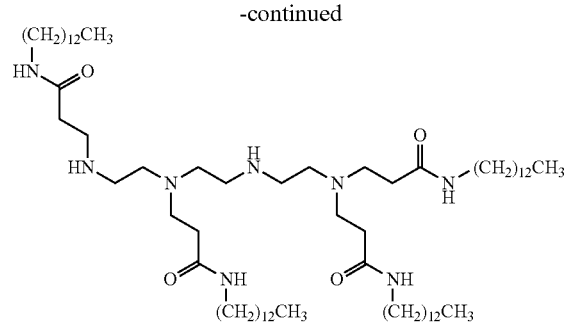
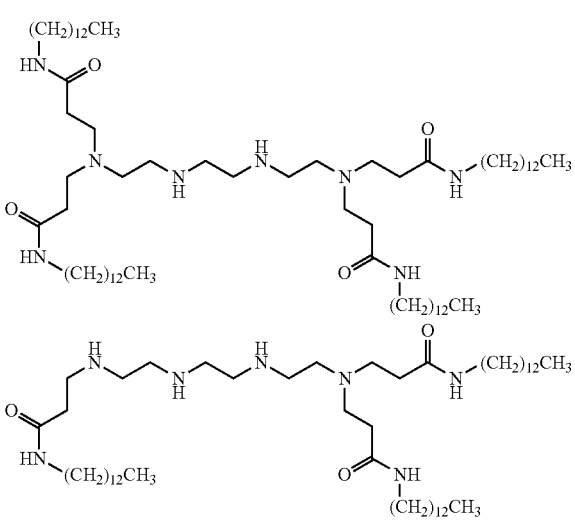
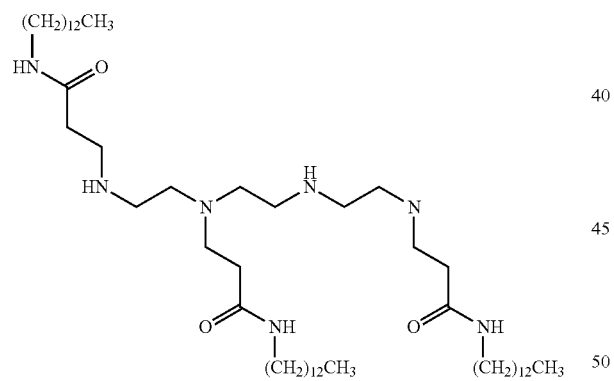
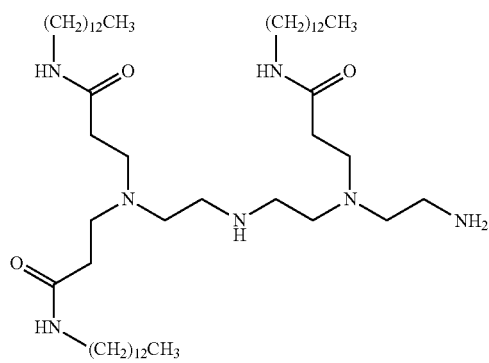
114
-continued
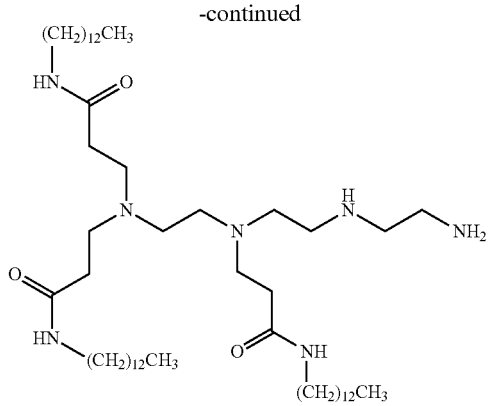
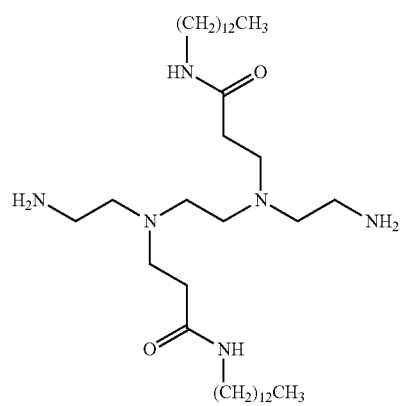
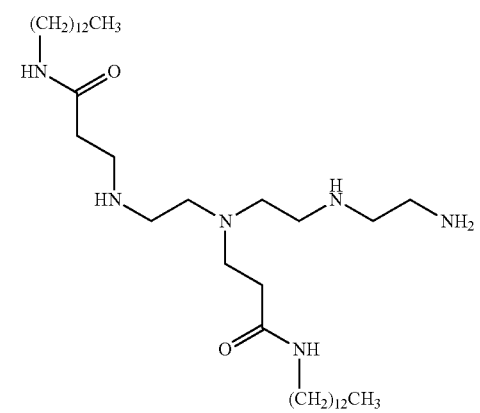
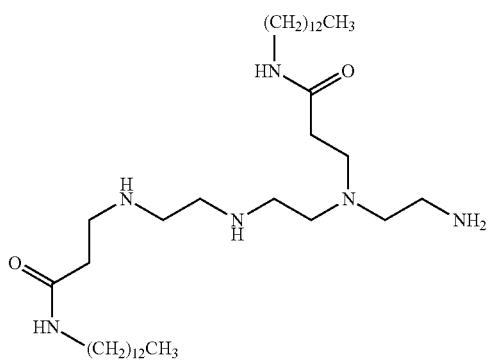

-continued

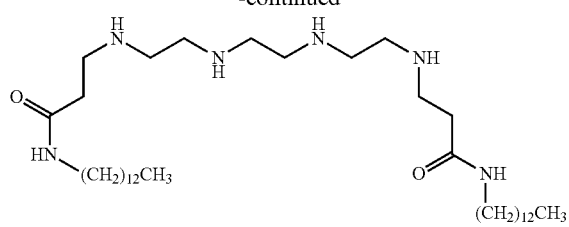

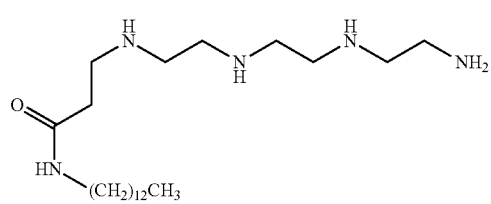

or

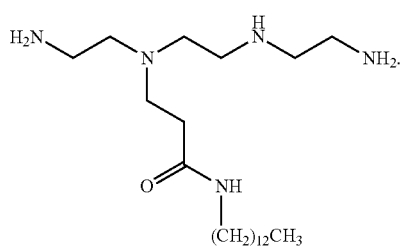

In other embodiments, the lipid is a composition of one or more of the above lipids.

In certain embodiments, the lipid is prepared by reacting amine 94 with acrylate NE to form lipid NE94. In certain embodiments, the lipid NE94 is of one of the formulae below:

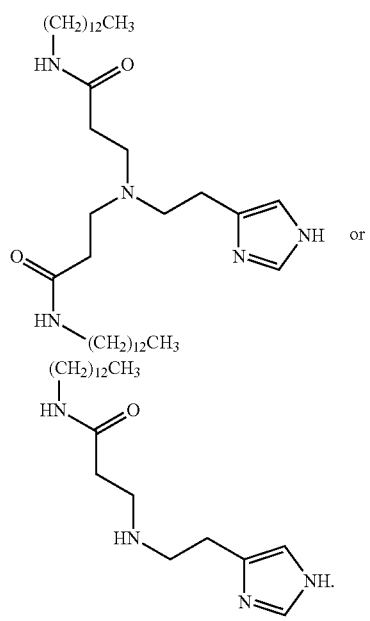

In other embodiments, the lipid is a composition of one or more of the above lipids.

In certain embodiments, the lipid is prepared by reacting amine 95 with acrylate NE to form lipid NE95. In certain embodiments, the lipid NE95 is of one of the formulae below:

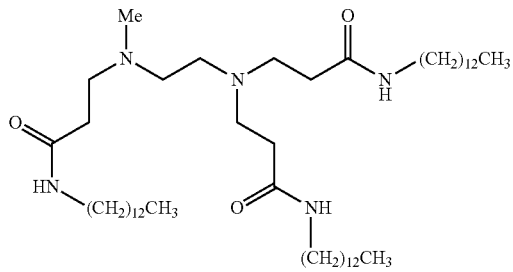

or

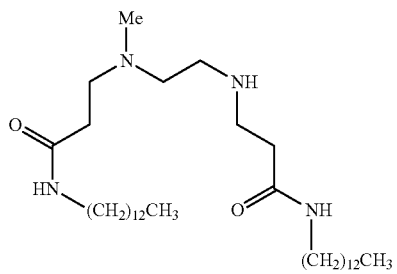

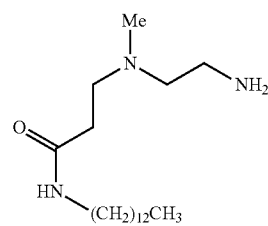

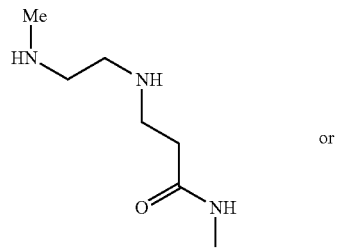

or

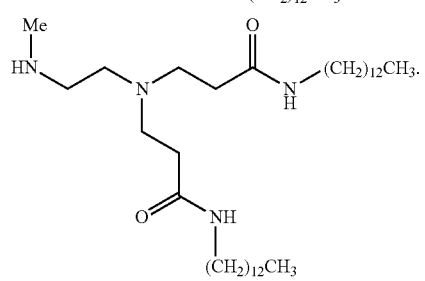

In other embodiments, the lipid is a composition of one or more of the above lipids.

In certain embodiments, the lipid is prepared by reacting amine 96 with acrylate NE to form lipid NE96. In certain embodiments, the lipid NE96 is of one of the formulae below:

117
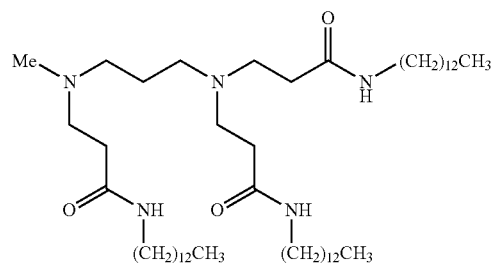
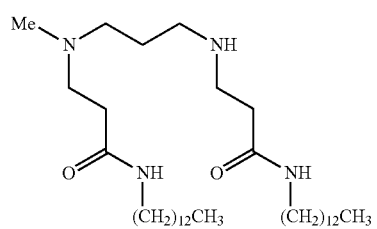
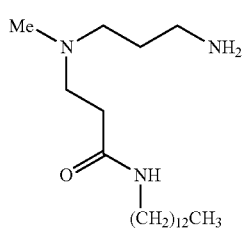
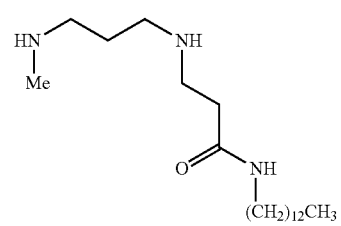
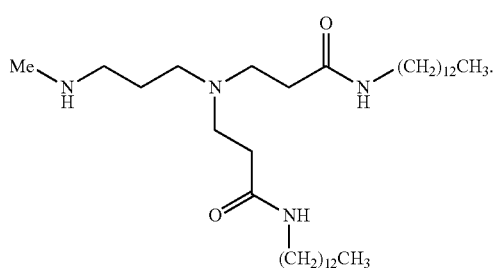
In other embodiments, the lipid is a composition of one or more of the above lipids.
In certain embodiments, the lipid is prepared by reacting amine 99 with acrylate NE to form lipid NE99. In certain embodiments, the lipid NE99 is of one of the formulae below:
118
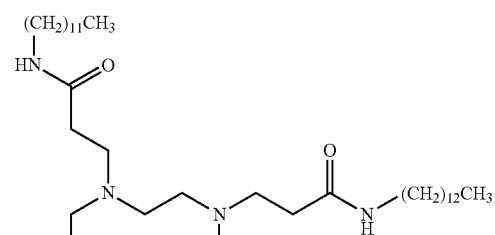
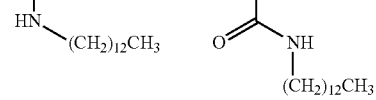
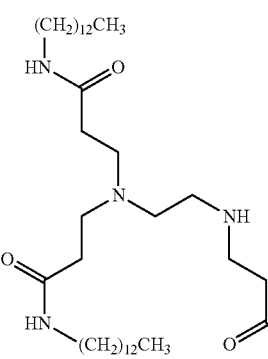
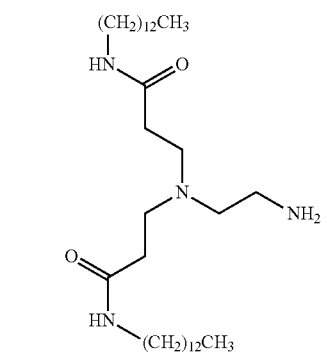
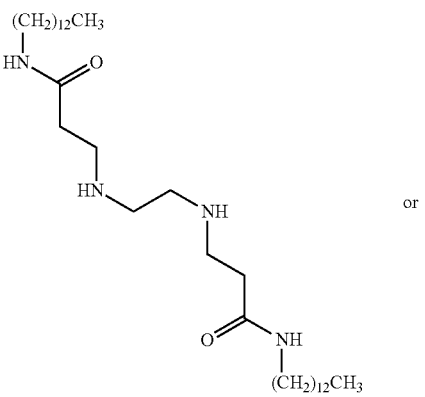
or -continued

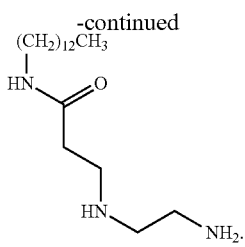

In other embodiments, the lipid is a composition of one or more of the above lipids. In certain embodiments, NE99 is treated with MeI or another alkylating agent to form lipids of the formulae:

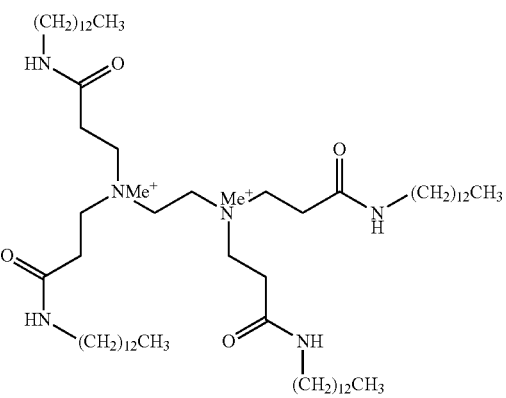

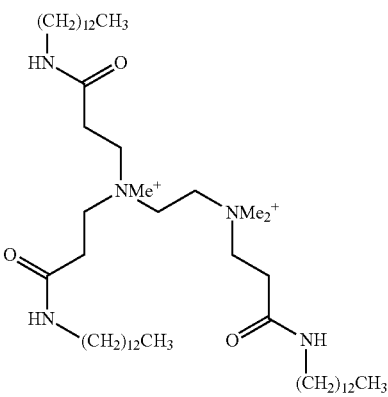

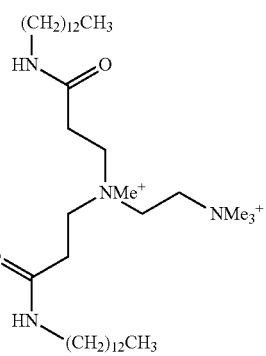

-continued

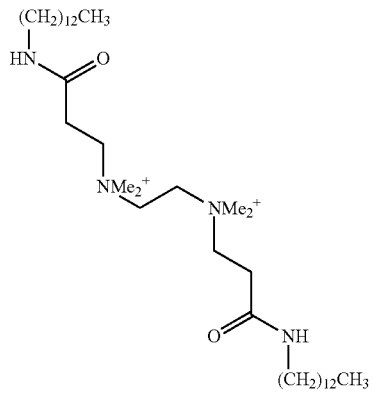

or

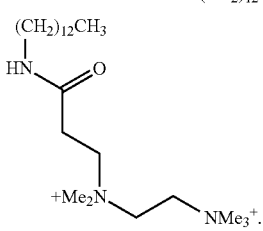

In certain embodiments, the lipid is prepared by reacting amine 100 with acrylate NE to form lipid NE100. In certain embodiments, the lipid NE100 is of one of the formulae below:

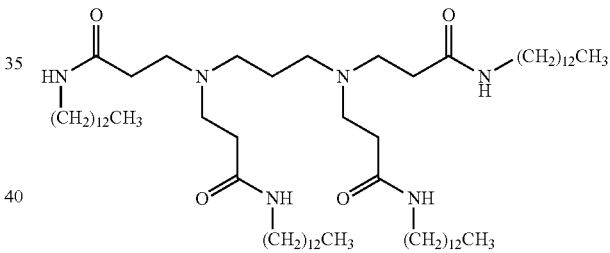

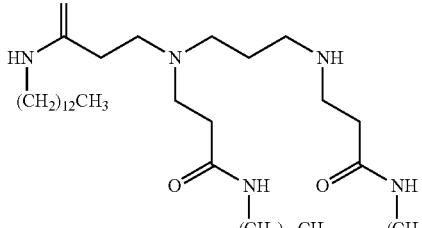

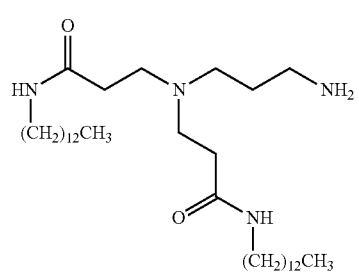

121

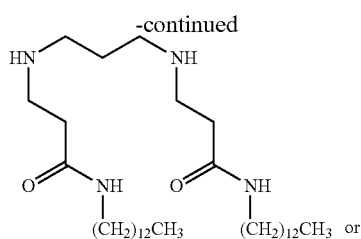

or

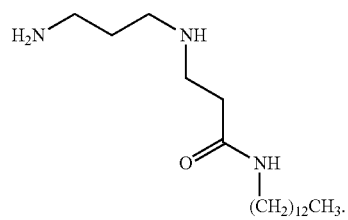

In other embodiments, the lipid is a composition of one or more of the above lipids.

In certain embodiments, the lipid is prepared by reacting amine 103 with acrylate NE to form lipid NE103. In certain embodiments, the lipid NE103 is of one of the formulae below:

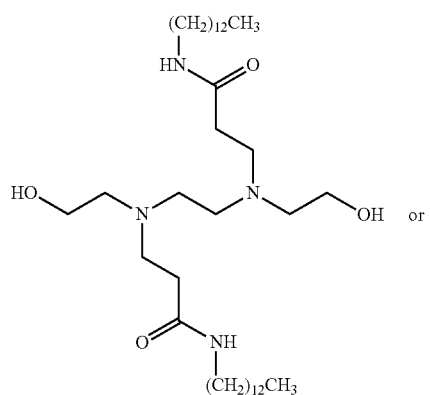

or

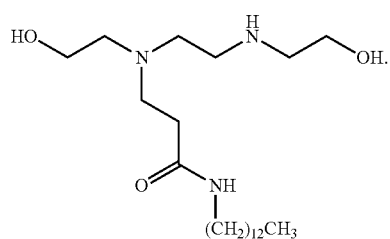

In other embodiments, the lipid is a composition of one or more of the above lipids.

In certain embodiments, the lipid is prepared by reacting amine 109 with acrylate NE to form lipid NE109. In certain embodiments, the lipid NE109 is of one of the formulae below:

122

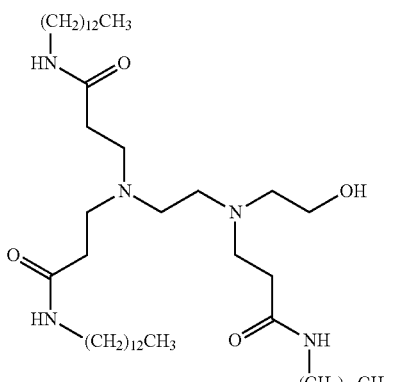

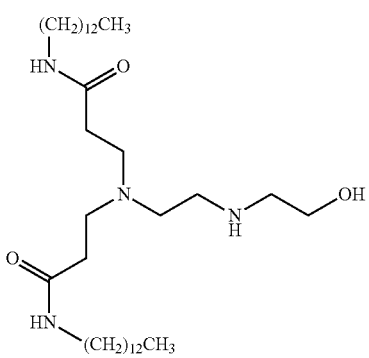

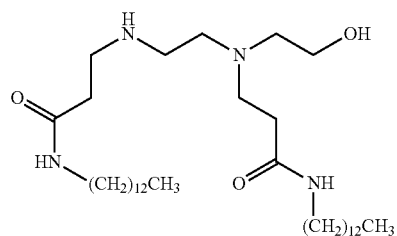

or

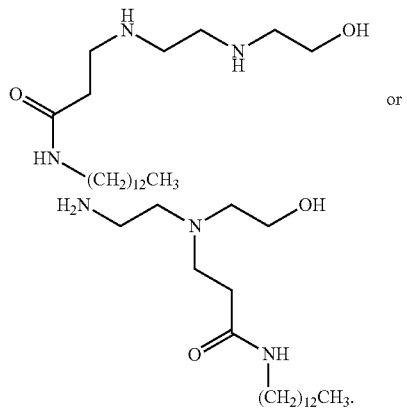

In other embodiments, the lipid is a composition of one or more of the above lipids.

In certain embodiments, the lipid is prepared by reacting amine 1 with acrylate NF to form lipid NF1. In certain embodiments, the lipid NF1 is of one of the formulae below:

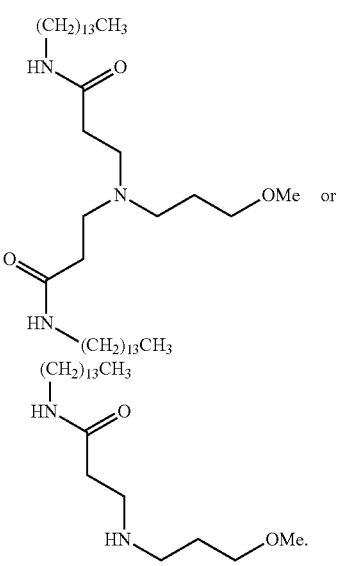

In other embodiments, the lipid is a composition of one or more of the above lipids.

In certain embodiments, the lipid is prepared by reacting amine 10 with acrylate NF to form lipid NF10. In certain embodiments, the lipid NF10 is of one of the formulae below:

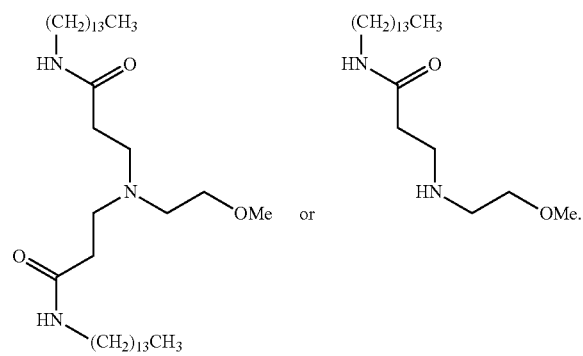

In other embodiments, the lipid is a composition of one or more of the above lipids.

In certain embodiments, the lipid is prepared by reacting amine 11 with acrylate NF to form lipid NF11. In certain embodiments, the lipid NF10 is of one of the formulae below:

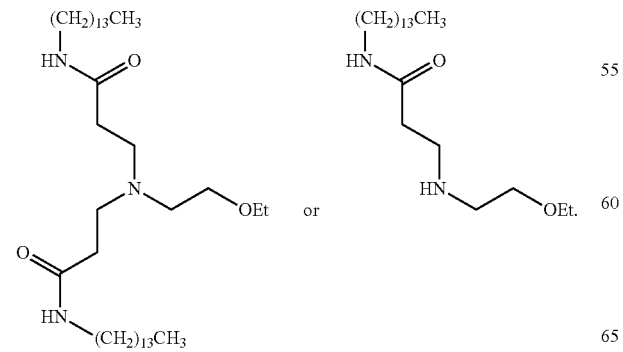

In other embodiments, the lipid is a composition of one or more of the above lipids.

In certain embodiments, the lipid is prepared by reacting amine 20 with acrylate NF to form lipid NF20. In certain embodiments, the lipid NF20 is of one of the formulae below:

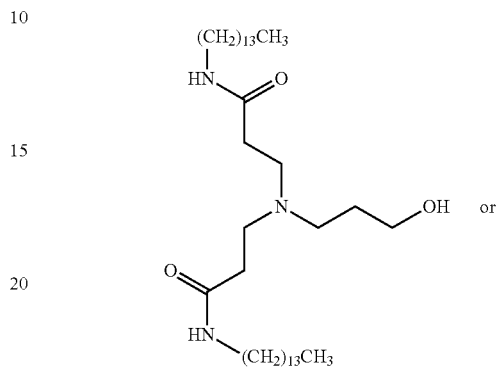

In other embodiments, the lipid is a composition of one or more of the above lipids.

In certain embodiments, the lipid is prepared by reacting amine 25 with acrylate NF to form lipid NF25. In certain embodiments, the lipid NF25 is of one of the formulae below:

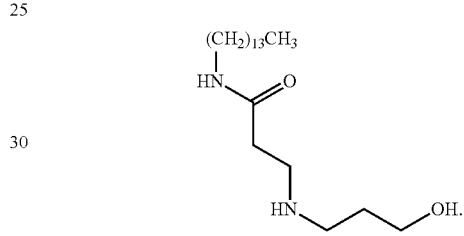

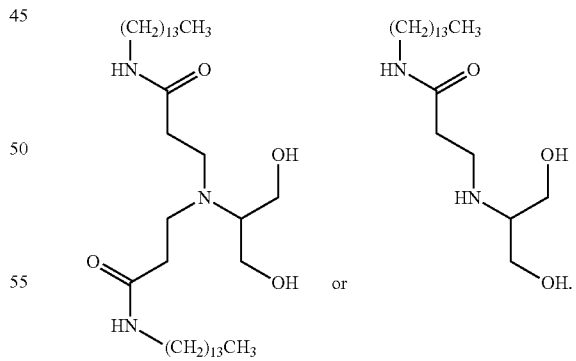

In other embodiments, the lipid is a composition of one or more of the above lipids.

In certain embodiments, the lipid is prepared by reacting amine 28 with acrylate NF to form lipid NF28. In certain embodiments, the lipid NF28 is of one of the formulae below:

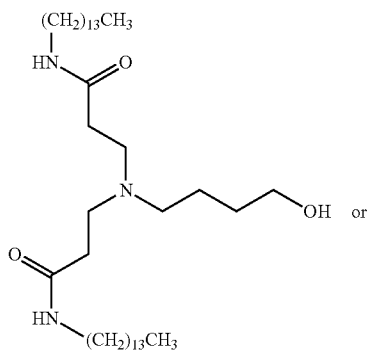

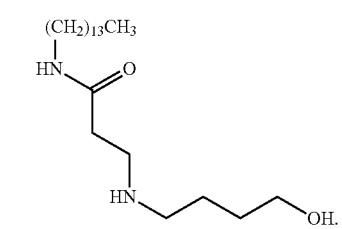

In other embodiments, the lipid is a composition of one or more of the above lipids.

In certain embodiments, the lipid is prepared by reacting amine 32 with acrylate NF to form lipid NF32. In certain embodiments, the lipid NF32 is of one of the formulae below:

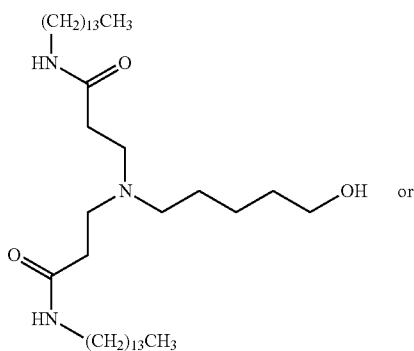

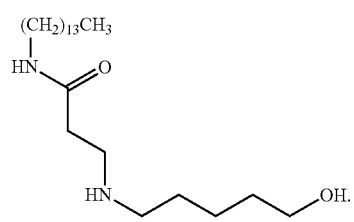

In other embodiments, the lipid is a composition of one or more of the above lipids.

In certain embodiments, the lipid is prepared by reacting amine 36 with acrylate NF to form lipid NF36. In certain embodiments, the lipid NF36 is of one of the formulae below:

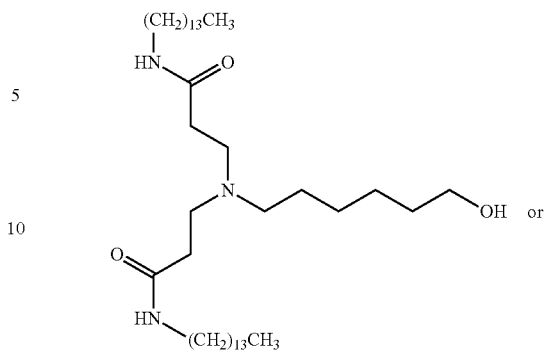

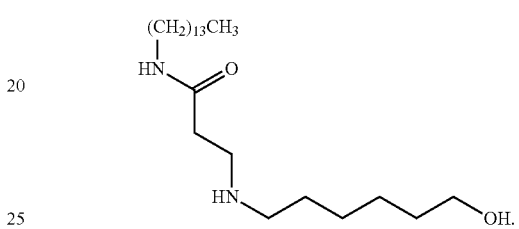

In other embodiments, the lipid is a composition of one or more of the above lipids.

In certain embodiments, the lipid is prepared by reacting amine 60 with acrylate NF to form lipid NF60. In certain embodiments, the lipid NF60 is of one of the formulae below:

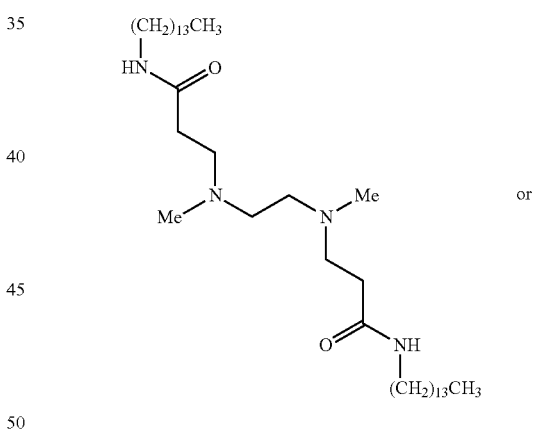

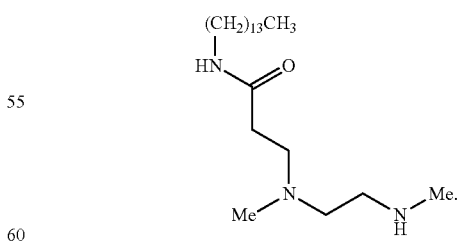

In other embodiments, the lipid is a composition of one or more of the above lipids.

In certain embodiments, the lipid is prepared by reacting amine 61 with acrylate NF to form lipid NF61. In certain embodiments, the lipid NF61 is of one of the formulae below:

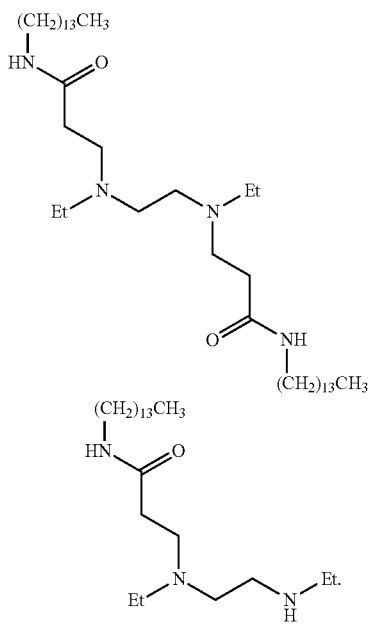

In other embodiments, the lipid is a composition of one or more of the above lipids.

In certain embodiments, the lipid is prepared by reacting amine 63 with acrylate NF to form lipid NF63. In certain embodiments, the lipid NF63 is of one of the formulae below:

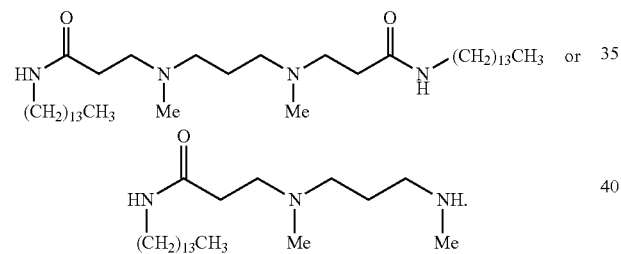

In other embodiments, the lipid is a composition of one or more of the above lipids.

In certain embodiments, the lipid is prepared by reacting amine 64 with acrylate NF to form lipid NF64. In certain embodiments, the lipid NF64 is of one of the formulae below:

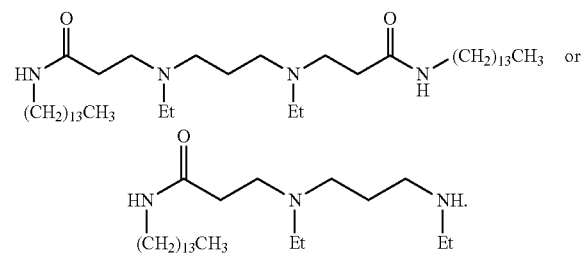

In other embodiments, the lipid is a composition of one or more of the above lipids.

In certain embodiments, the lipid is prepared by reacting amine 61 with acrylate NF to form lipid NF70. In certain embodiments, the lipid NF70 is of one of the formulae below:

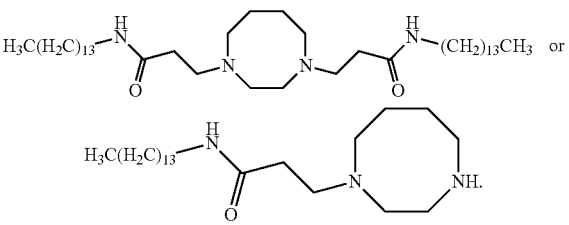

In other embodiments, the lipid is a composition of one or more of the above lipids.

In certain embodiments, the lipid is prepared by reacting amine 86 with acrylate NF to form lipid NF86. In certain embodiments, the lipid NF86 is of one of the formulae below:

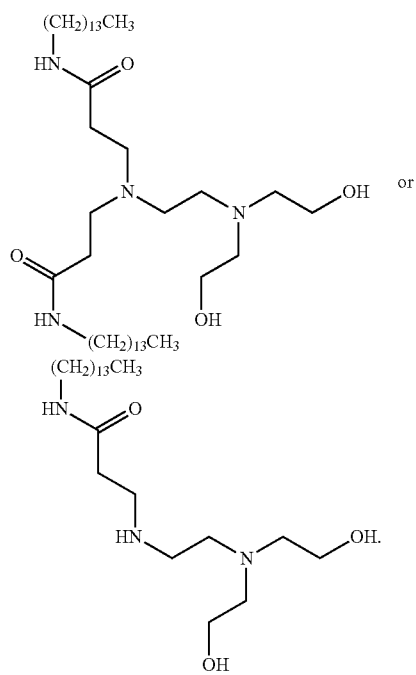

In other embodiments, the lipid is a composition of one or more of the above lipids.

In certain embodiments, the lipid is prepared by reacting amine 87 with acrylate NF to form lipid NF87. In certain embodiments, the lipid NF87 is of one of the formulae below:

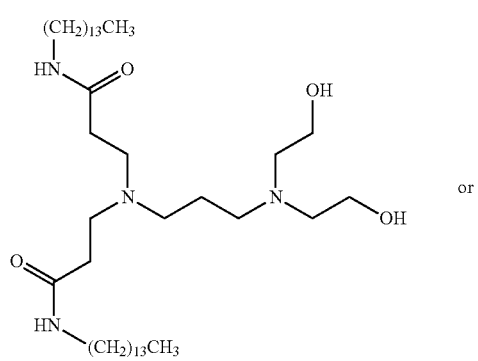

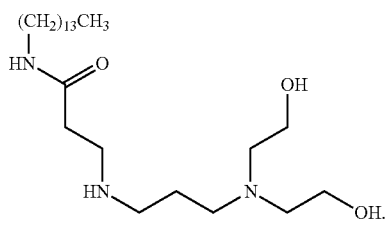

In other embodiments, the lipid is a composition of one or more of the above lipids.

In certain embodiments, the lipid is prepared by reacting amine 91 with acrylate NF to form lipid NF91. In certain embodiments, the lipid NF91 is of one of the formulae below:

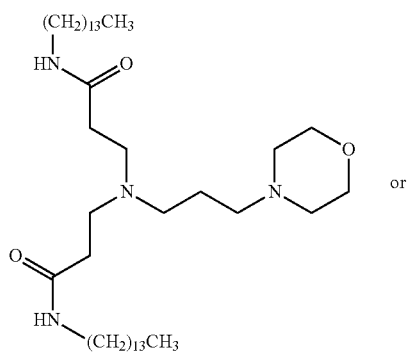

or

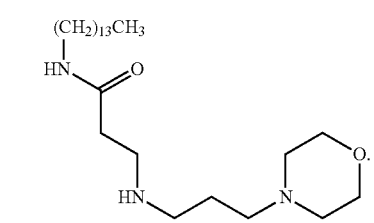

In other embodiments, the lipid is a composition of one or more of the above lipids.

In certain embodiments, the lipid is prepared by reacting amine 95 with acrylate NF to form lipid NF95. In certain embodiments, the lipid NF95 is of one of the formulae below:

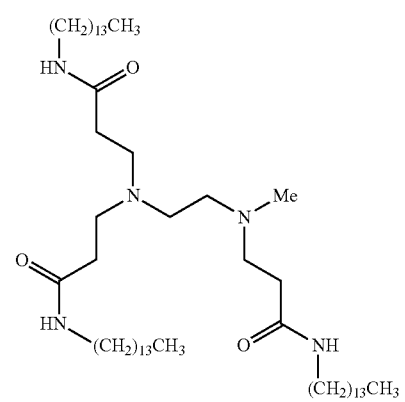

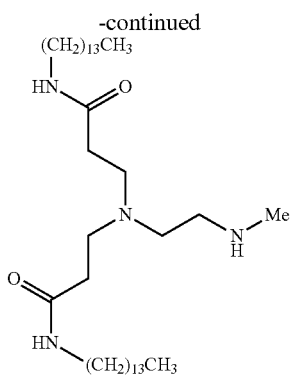

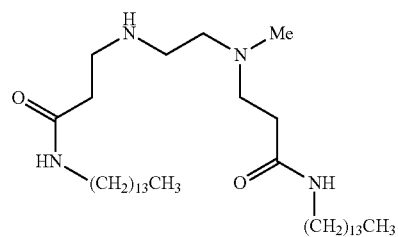

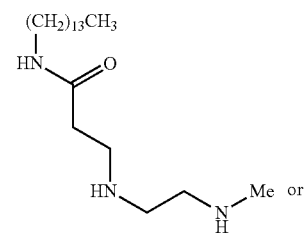

or

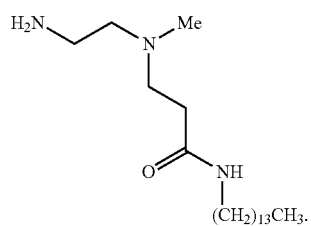

In other embodiments, the lipid is a composition of one or more of the above lipids.

In certain embodiments, the lipid is prepared by reacting amine 96 with acrylate NF to form lipid NF96. In certain embodiments, the lipid NF96 is of one of the formulae below:

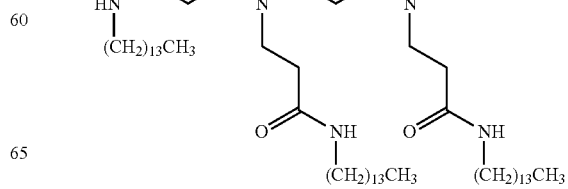

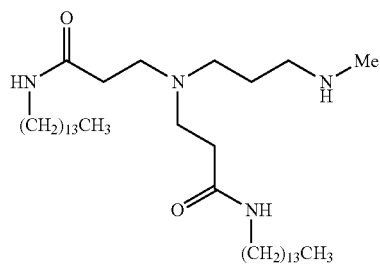
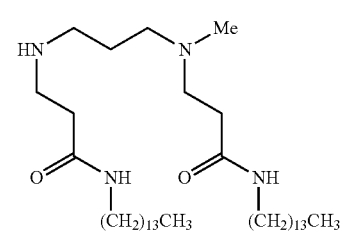
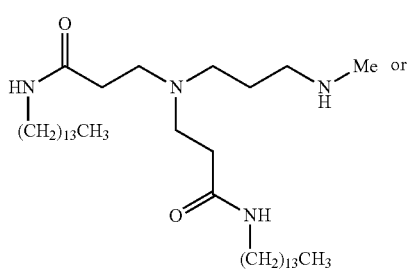
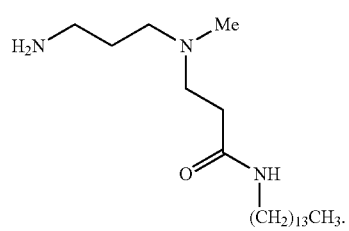
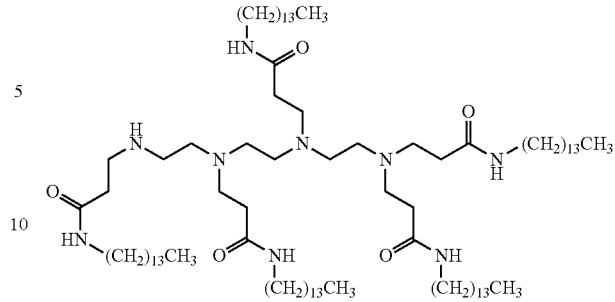
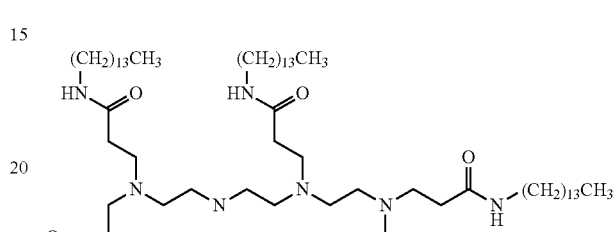
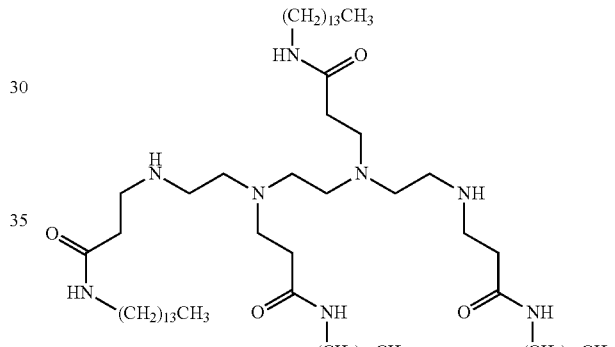
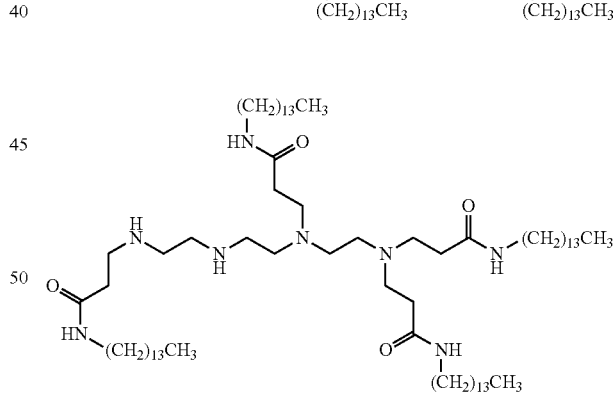
In other embodiments, the lipid is a composition of one or more of the above lipids.
In certain embodiments, the lipid is prepared by reacting amine 98 with acrylate NF to form lipid NF98. In certain embodiments, the lipid NF98 is of one of the formulae below:
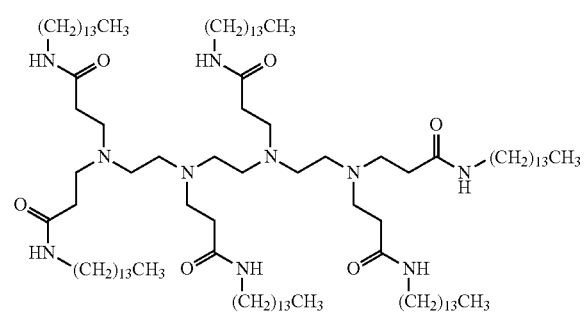
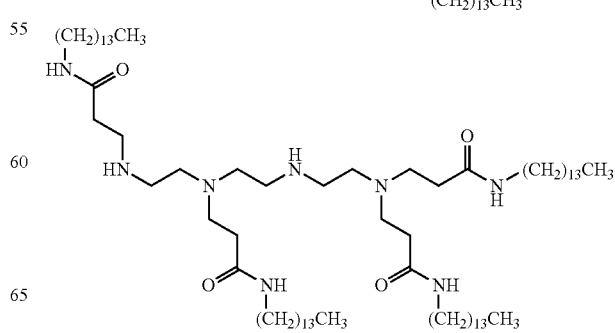

133
-continued
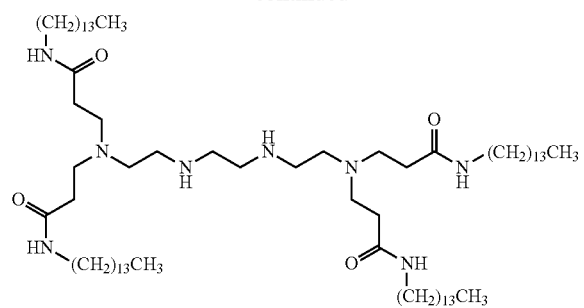
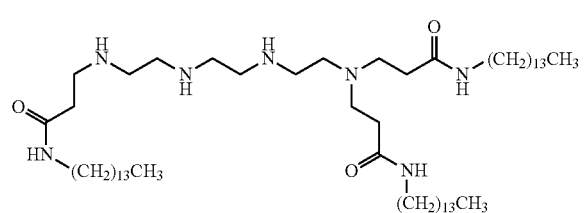
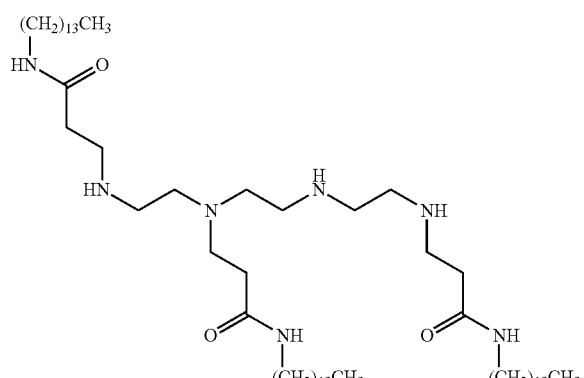
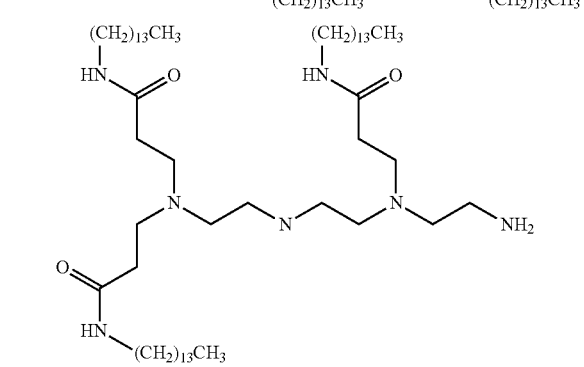
134
-continued
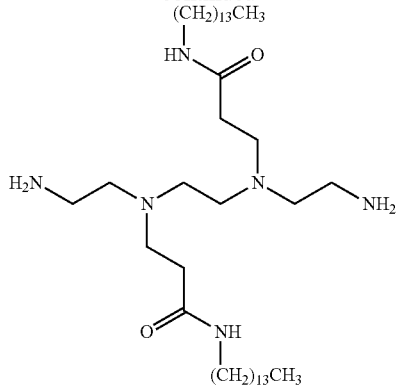
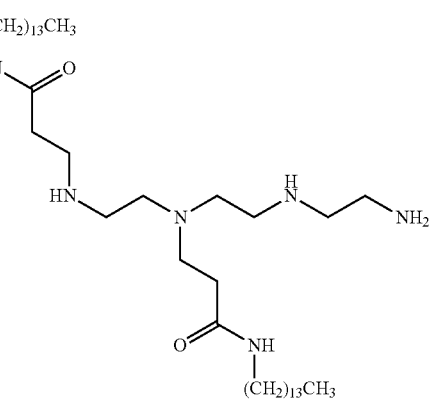
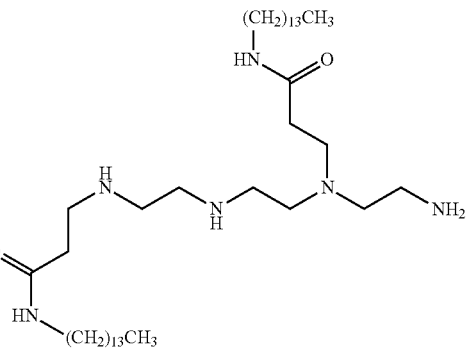
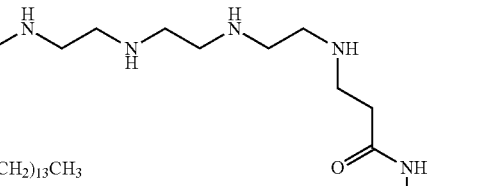
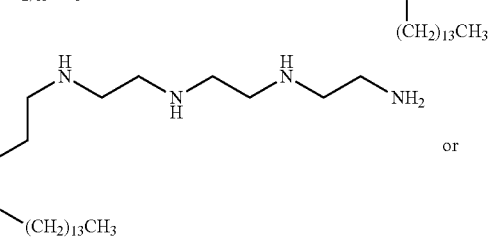
or -continued

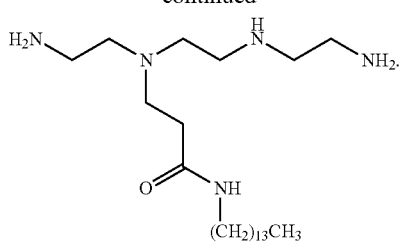

In other embodiments, the lipid is a composition of one or more of the above lipids.

In certain embodiments, the lipid is prepared by reacting amine 99 with acrylate NF to form lipid NF99. In certain embodiments, the lipid NF99 is of one of the formulae below:

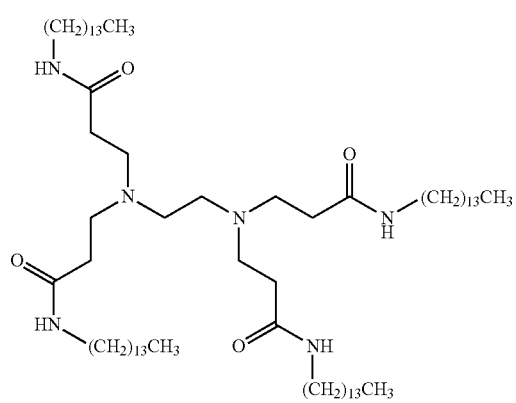

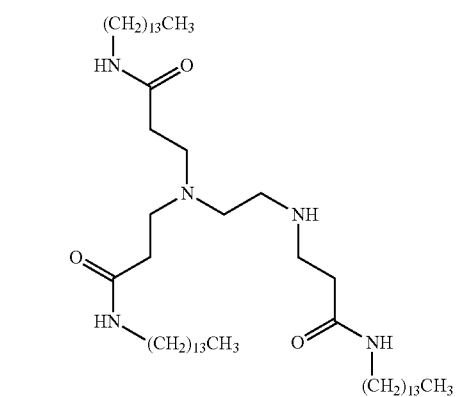

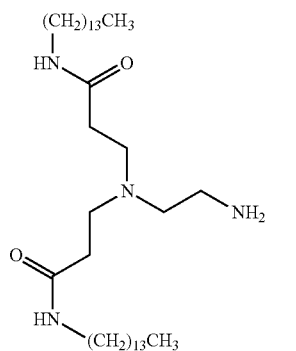

-continued

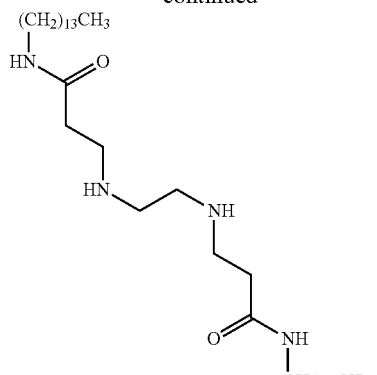

or

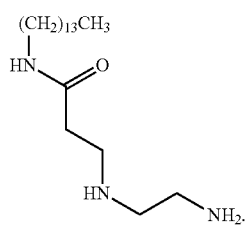

In other embodiments, the lipid is a composition of one or more of the above lipids. In certain embodiments, NF99 is treated with MeI or another alkylating agent to form lipids of the formula:

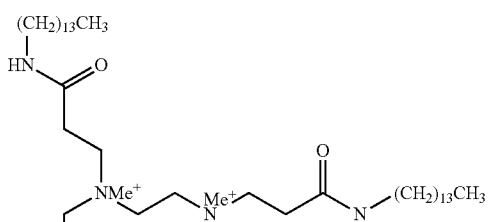

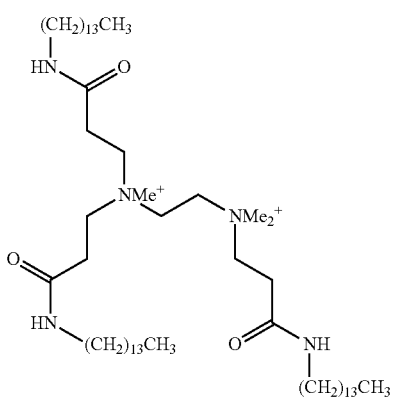

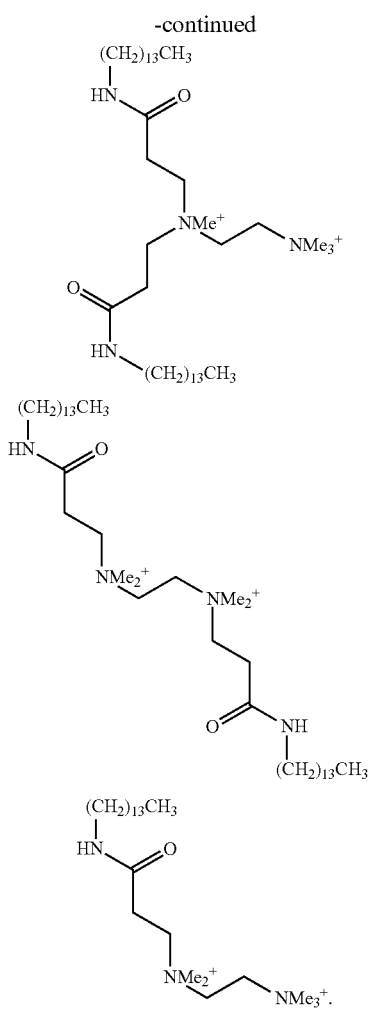

In certain embodiments, the lipid is prepared by reacting amine 100 with acrylate NF to form lipid NF100. In certain embodiments, the lipid NF100 is of one of the formulae below:

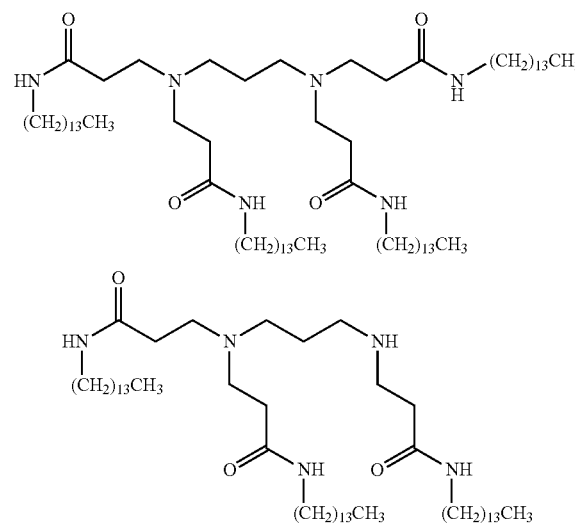

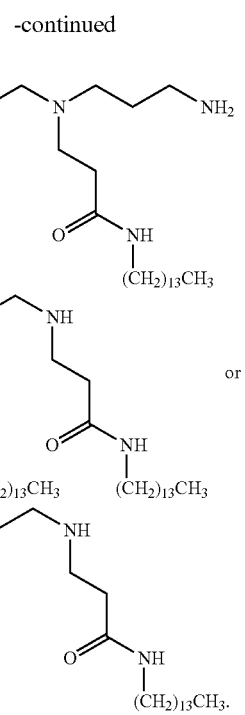

In other embodiments, the lipid is a composition of one or more of the above lipids.

In certain embodiments, the lipid is prepared by reacting amine 103 with acrylate NF to form lipid NF103. In certain embodiments, the lipid NE103 is of one of the formulae below:

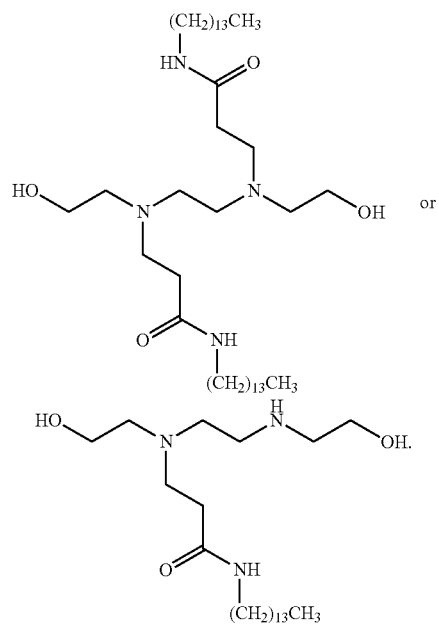

In other embodiments, the lipid is a composition of one or more of the above lipids.

In certain embodiments, the lipid is prepared by reacting amine 109 with acrylate NF to form lipid NF109. In certain embodiments, the lipid NF109 is of one of the formulae below:

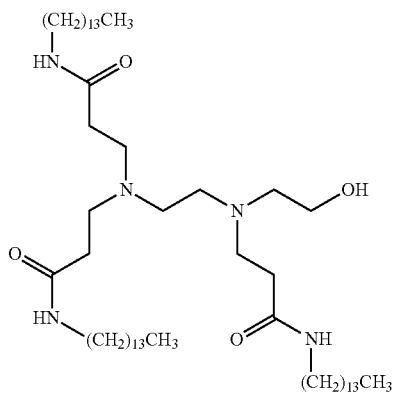

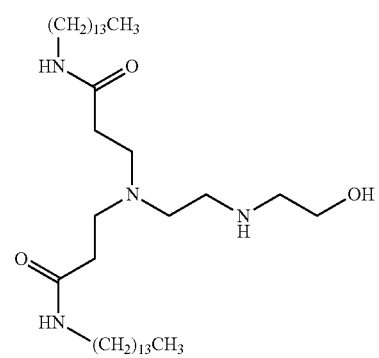

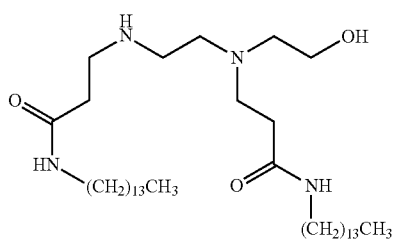

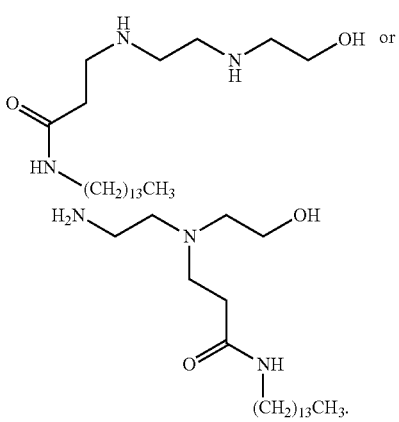

In other embodiments, the lipid is a composition of one or more of the above lipids.

In certain embodiments, the lipid is prepared by reacting amine 61 with acrylate NG to form lipid NG61. In certain embodiments, the lipid NG61 is of one of the formulae below:

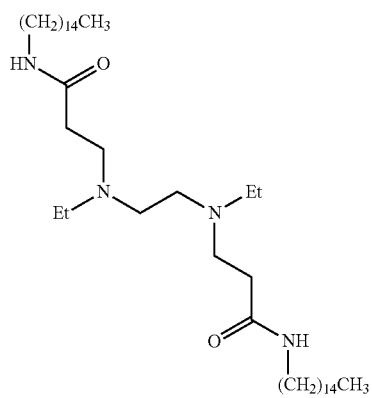

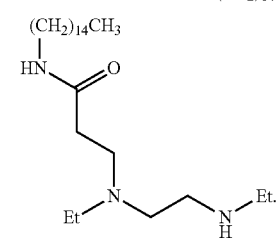

In other embodiments, the lipid is a composition of one or more of the above lipids.

In certain embodiments, the lipid is prepared by reacting amine 64 with acrylate NG to form lipid NG64. In certain embodiments, the lipid NG64 is of one of the formulae below:

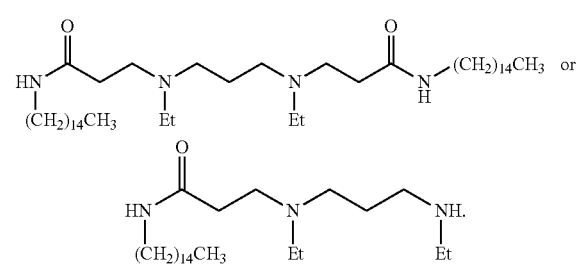

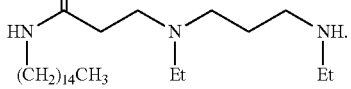

In other embodiments, the lipid is a composition of one or more of the above lipids.

In certain embodiments, the lipid is prepared by reacting amine 77 with acrylate NG to form lipid NG77. In certain embodiments, the lipid NG77 is of one of the formulae below:

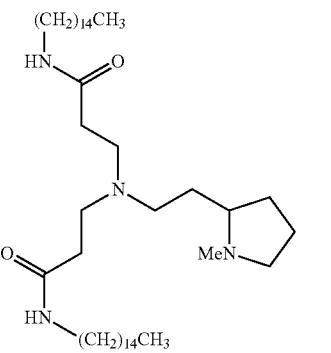

-continued

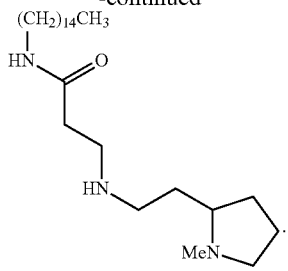

In other embodiments, the lipid is a composition of one or more of the above lipids.

In certain embodiments, the lipid is prepared by reacting amine 86 with acrylate NG to form lipid NG86. In certain embodiments, the lipid NG86 is of one of the formulae below:

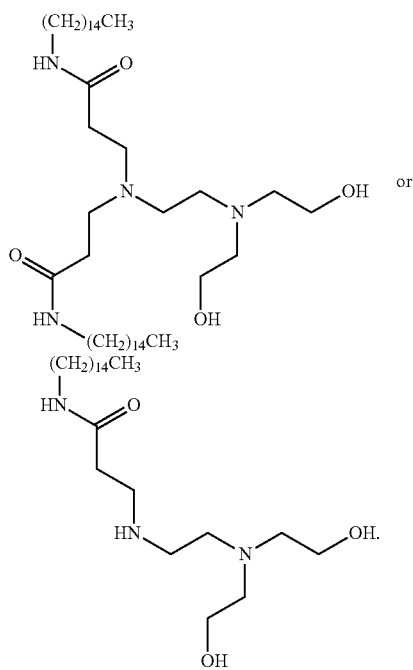

In other embodiments, the lipid is a composition of one or more of the above lipids.

In certain embodiments, the lipid is prepared by reacting amine 87 with acrylate NG to form lipid NG87. In certain embodiments, the lipid NG87 is of one of the formulae below:

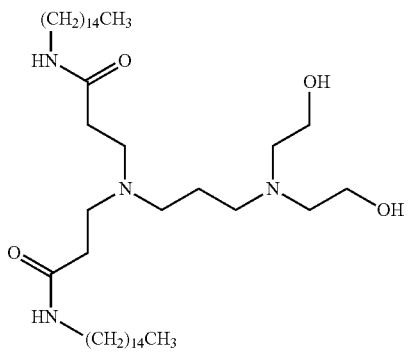

-continued

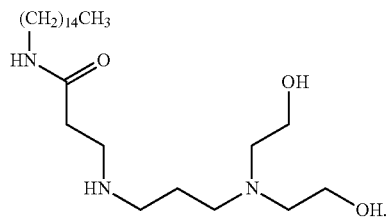

In other embodiments, the lipid is a composition of one or more of the above lipids.

In certain embodiments, the lipid is prepared by reacting amine 95 with acrylate NG to form lipid NG95. In certain embodiments, the lipid NG95 is of one of the formulae below:

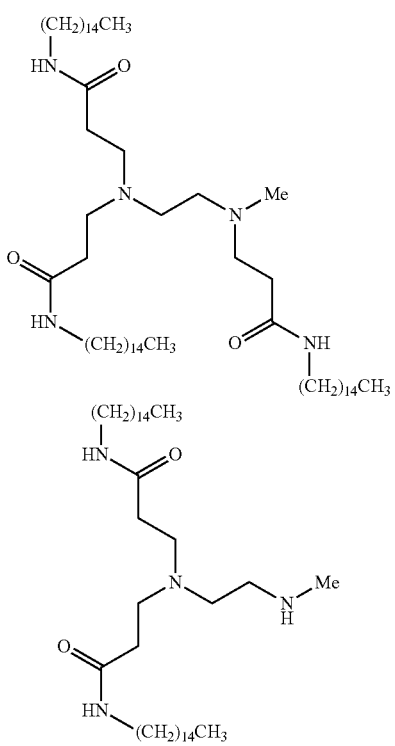

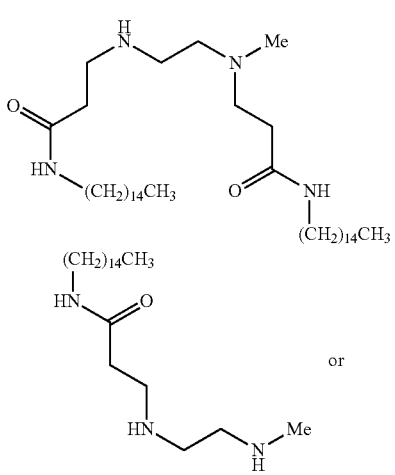

-continued

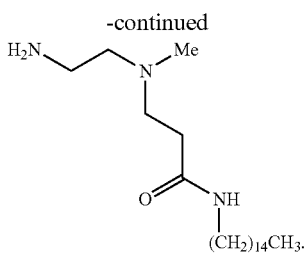

In other embodiments, the lipid is a composition of one or more of the above lipids.

In certain embodiments, the lipid is prepared by reacting amine 100 with acrylate NG to form lipid NG100. In certain embodiments, the lipid NG100 is of one of the formulae below:

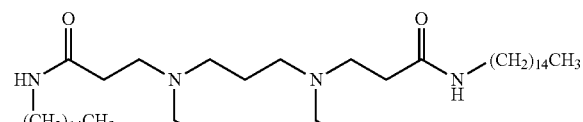

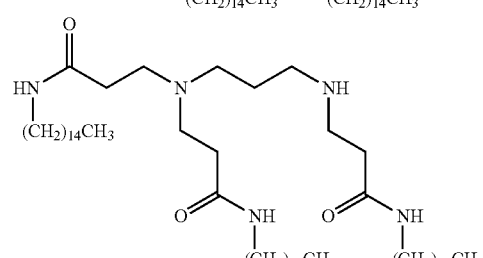

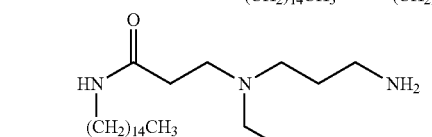

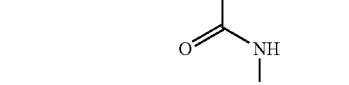

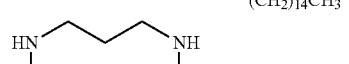

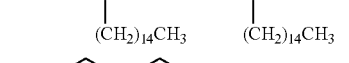

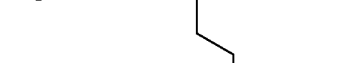

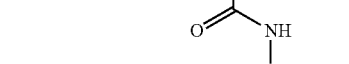

or

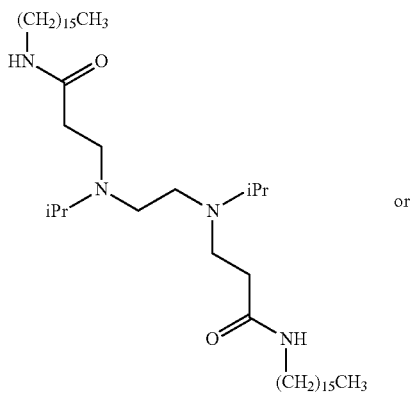

In other embodiments, the lipid is a composition of one or more of the above lipids. In certain embodiments, NG100 is alkylated with methyl iodide or another alkylating agent.

In certain embodiments, the lipid is prepared by reacting amine 62 with acrylate NP to form lipid NP62. In certain embodiments, the lipid NP62 is of one of the formulae below:

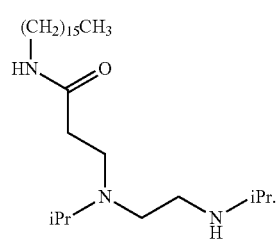

or

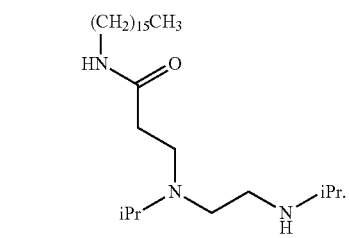

In other embodiments, the lipid is a composition of one or more of the above lipids.

In certain embodiments, the lipid is prepared by reacting amine 63 with acrylate NP to form lipid NP63. In certain embodiments, the lipid NP63 is of one of the formulae below:

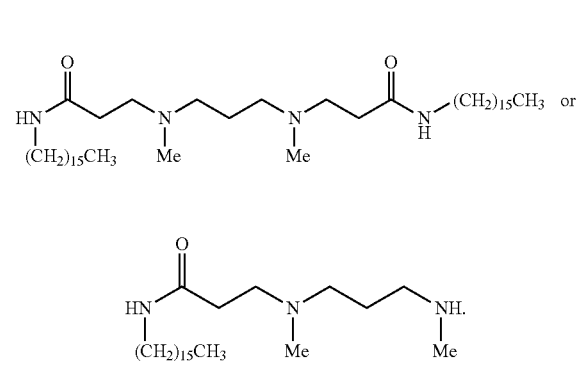

In other embodiments, the lipid is a composition of one or more of the above lipids.

In certain embodiments, the lipid is prepared by reacting amine 86 with acrylate NP to form lipid NP86. In certain embodiments, the lipid NP86 is of one of the formulae below:

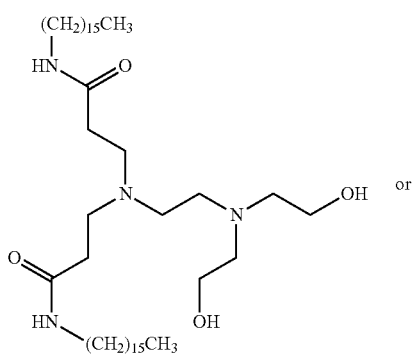

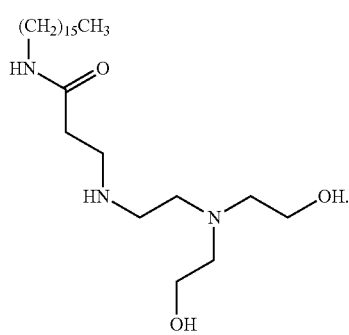

In other embodiments, the lipid is a composition of one or more of the above lipids.

In certain embodiments, the lipid is prepared by reacting amine 87 with acrylate NP to form lipid NP87. In certain embodiments, the lipid NP87 is of one of the formulae below:

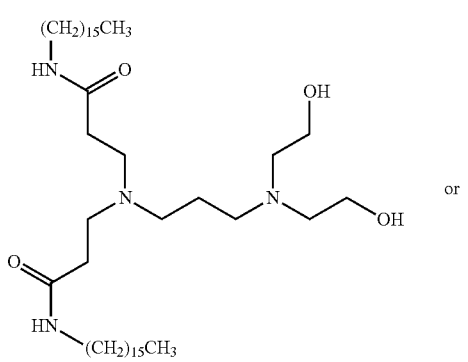

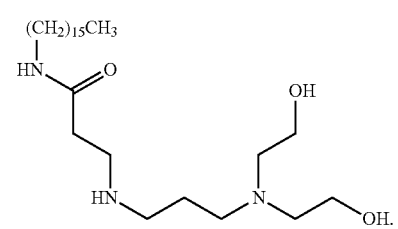

In other embodiments, the lipid is a composition of one or more of the above lipids.

In certain embodiments, the lipid is prepared by reacting amine 96 with acrylate NP to form lipid NP96. In certain embodiments, the lipid NP96 is of one of the formulae below:

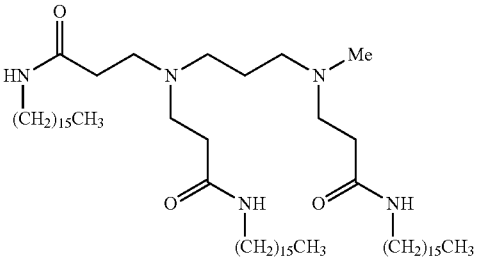

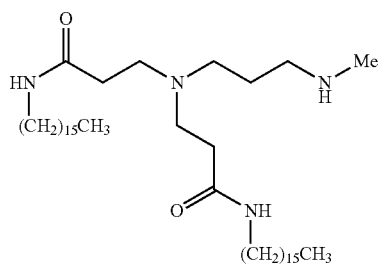

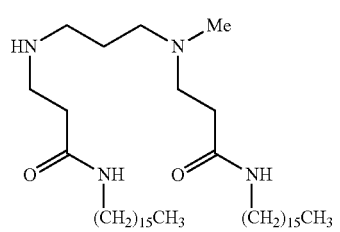

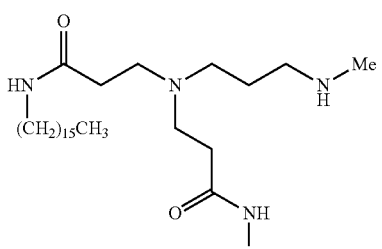

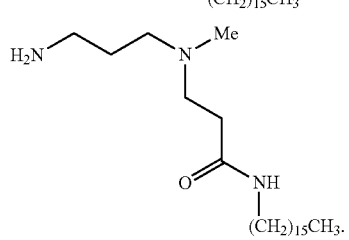

In other embodiments, the lipid is a composition of one or more of the above lipids.

In certain embodiments, the lipid is prepared by reacting amine 98 with acrylate NP to form lipid NP98. In certain embodiments, the lipid NP98 is of one of the formulae below:

147
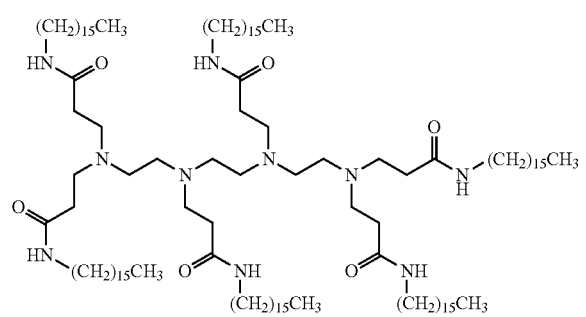
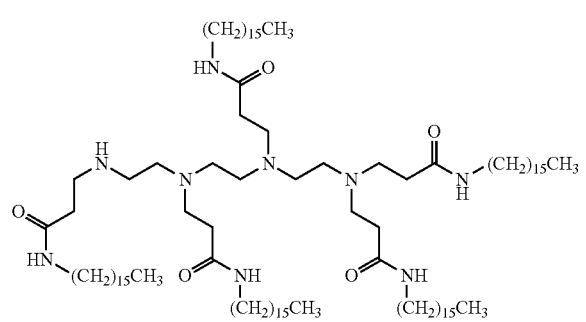
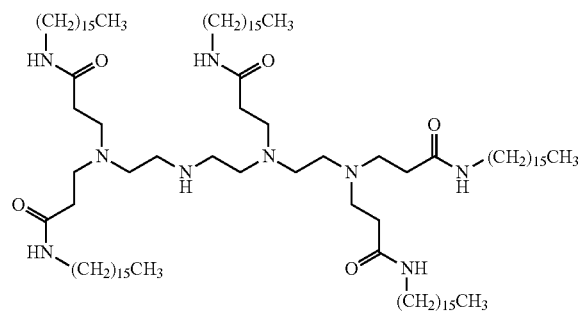
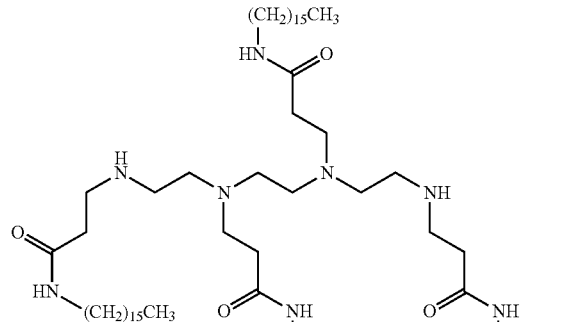
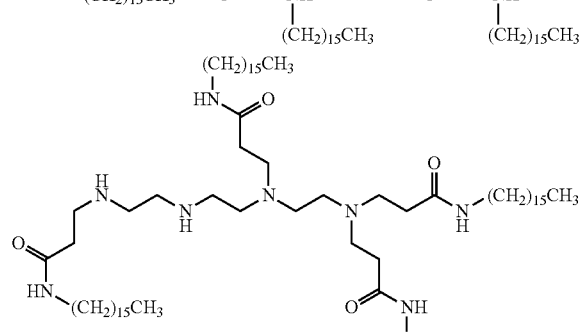
148
-continued
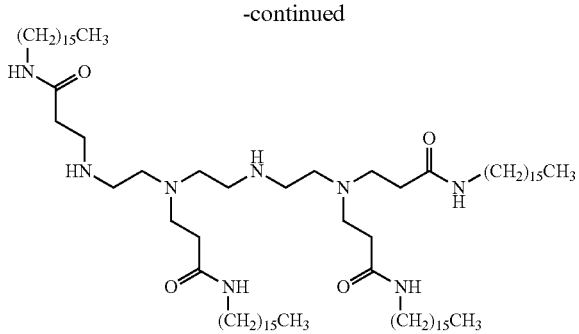
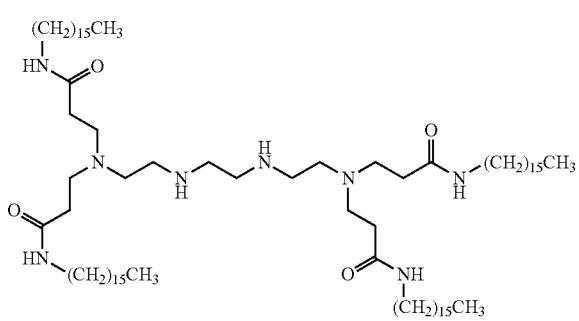
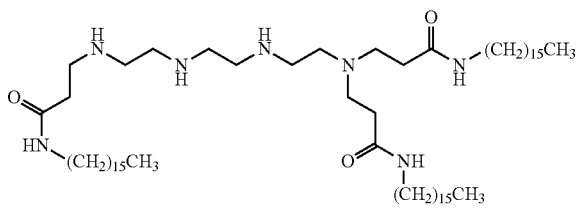
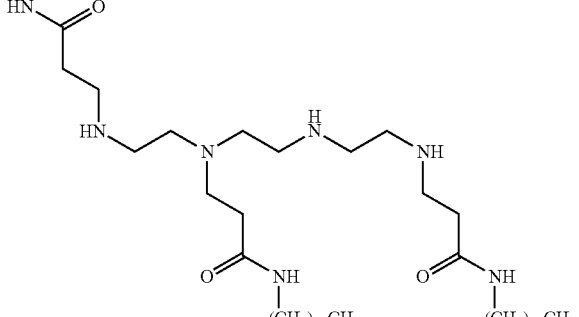
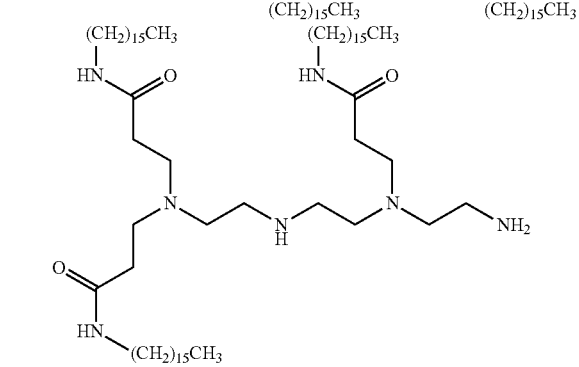

149
-continued
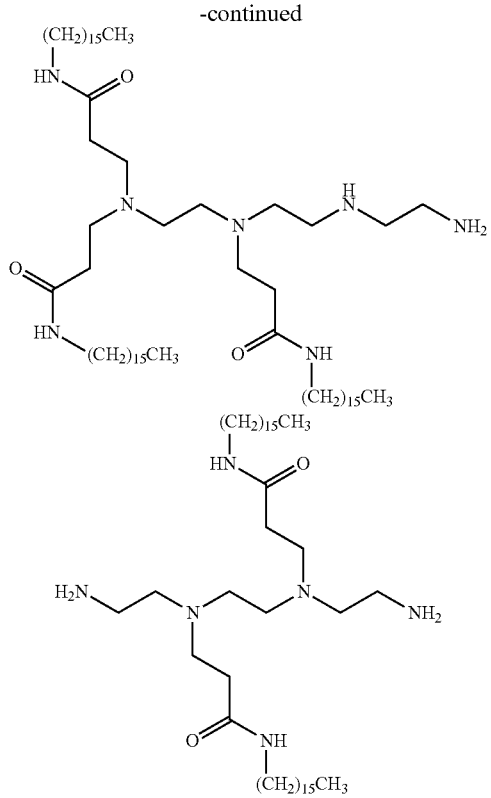
150
-continued
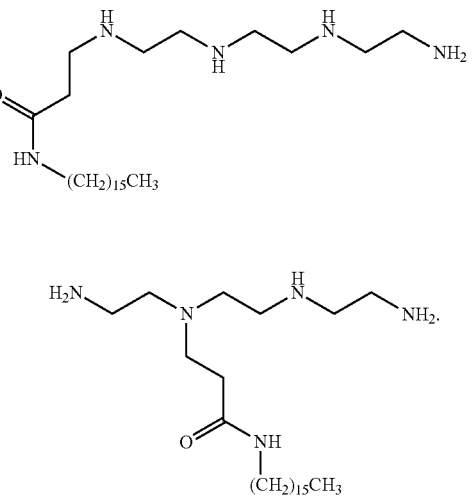
In other embodiments, the lipid is a composition of one or more of the above lipids.
In certain embodiments, the lipid is prepared by reacting amine 99 with acrylate NP to form lipid NP99. In certain embodiments, the lipid NP99 is of one of the formulae below:
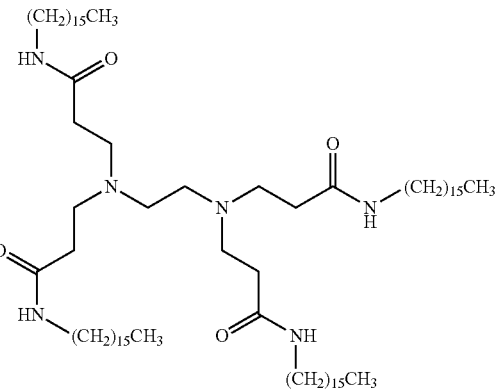
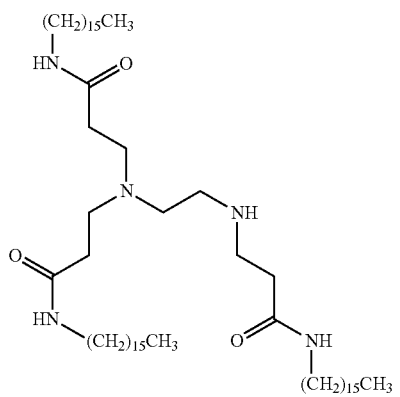

In other embodiments, the lipid is a composition of one or more of the above lipids. In certain embodiments, NF99 is treated with MeI or another alkylating agent to form lipids of the formula:

In certain embodiments, the lipid is prepared by reacting amine 100 with acrylate NP to form lipid NP100. In certain embodiments, the lipid NP100 is of one of the formulae below:

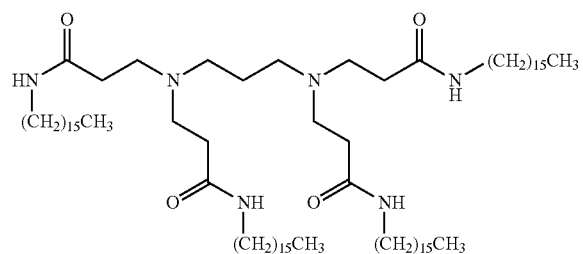

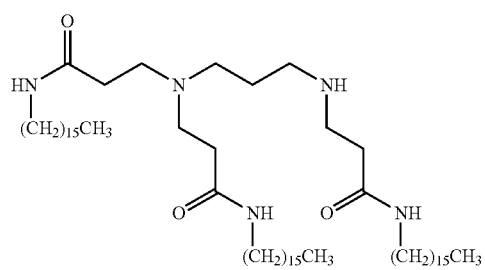

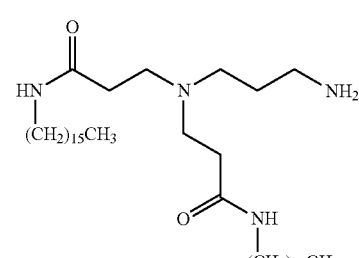

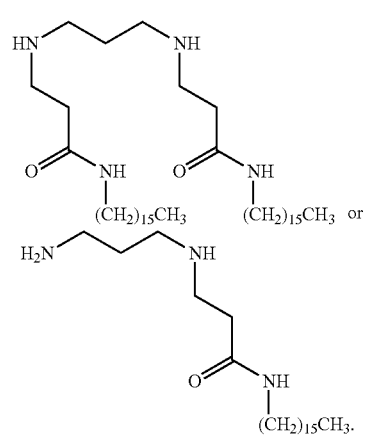

In other embodiments, the lipid is a composition of one or more of the above lipids.

In certain embodiments, the lipid is prepared by reacting amine 103 with acrylate NP to form lipid NP103. In certain embodiments, the lipid NP103 is of one of the formulae below:

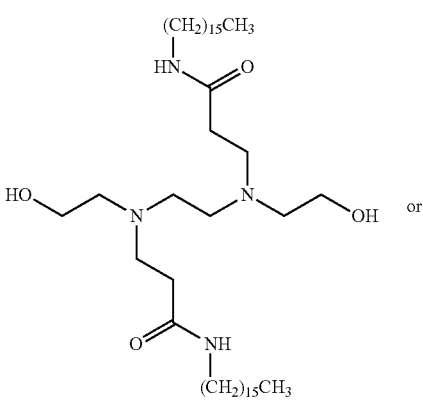

In other embodiments, the lipid is a composition of one or more of the above lipids.

In certain embodiments, the lipid is prepared by reacting amine 31 with acrylate LD to form lipid LD31. In certain embodiments, the lipid LD31 is of one of the formulae below:

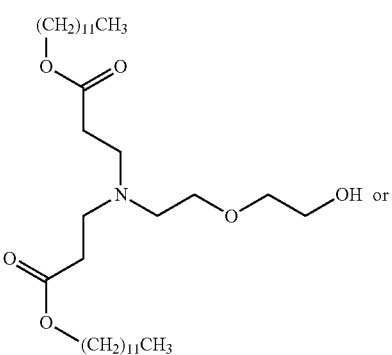

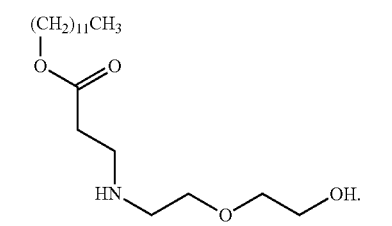

In other embodiments, the lipid is a composition of one or more of the above lipids.

In certain embodiments, the lipid is prepared by reacting amine 98 with acrylate LD to form lipid LD98. In certain embodiments, the lipid LD98 is of one of the formulae below:

155
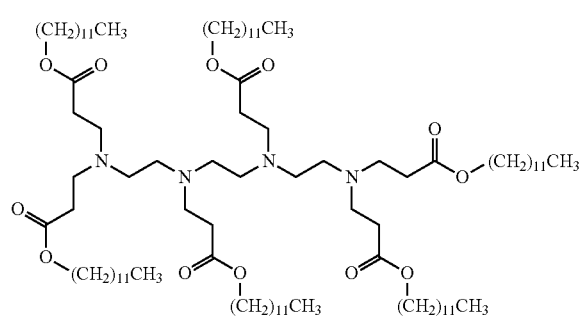
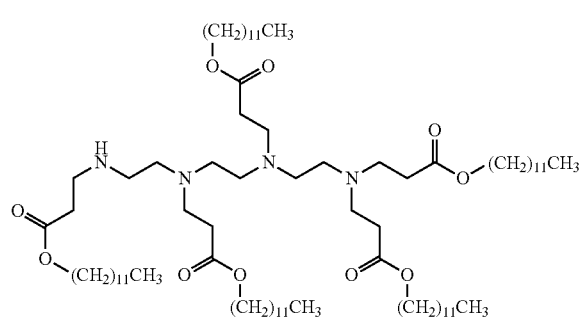
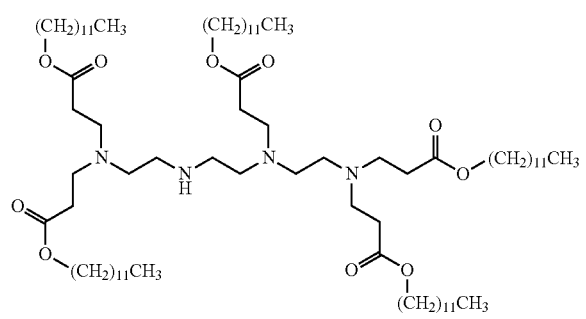
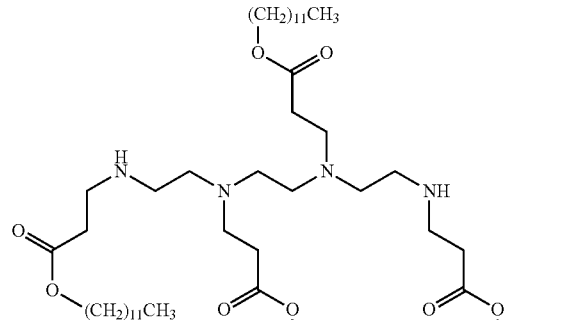
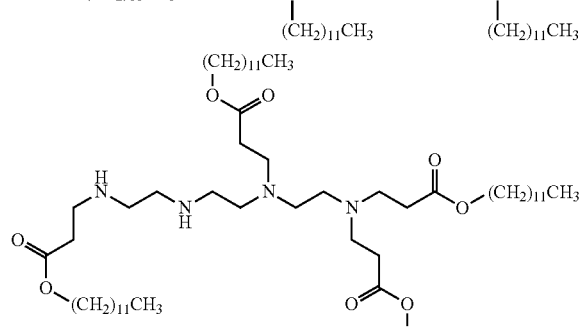
156
-continued
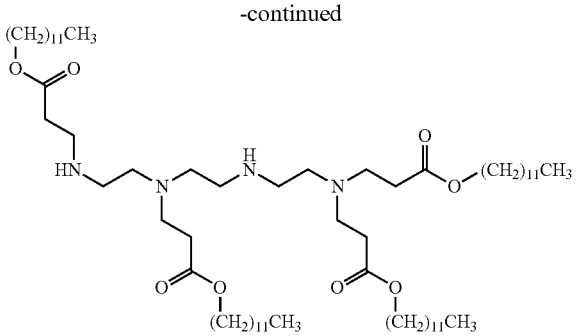
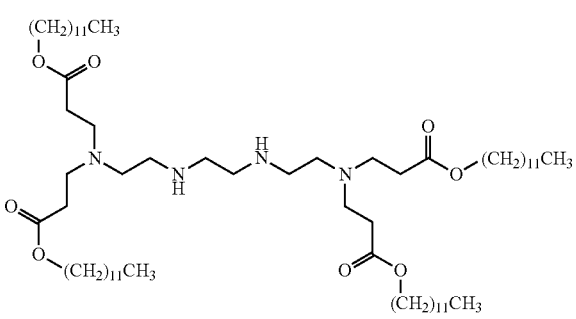
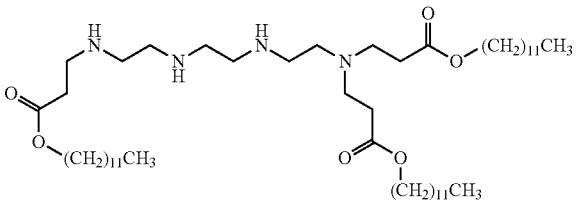
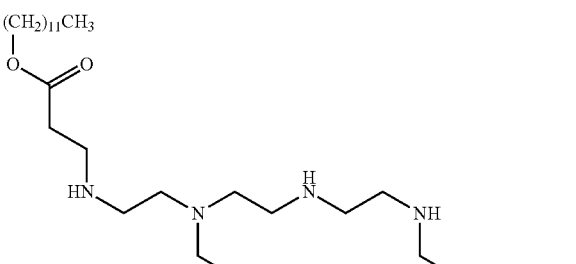
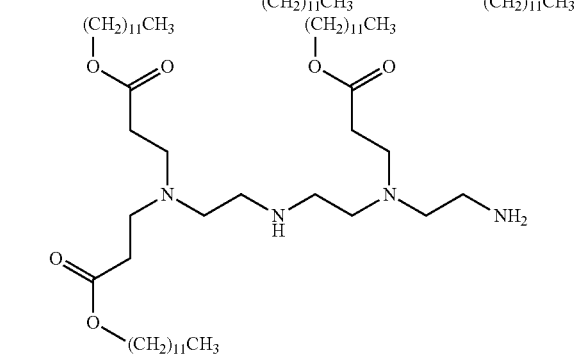

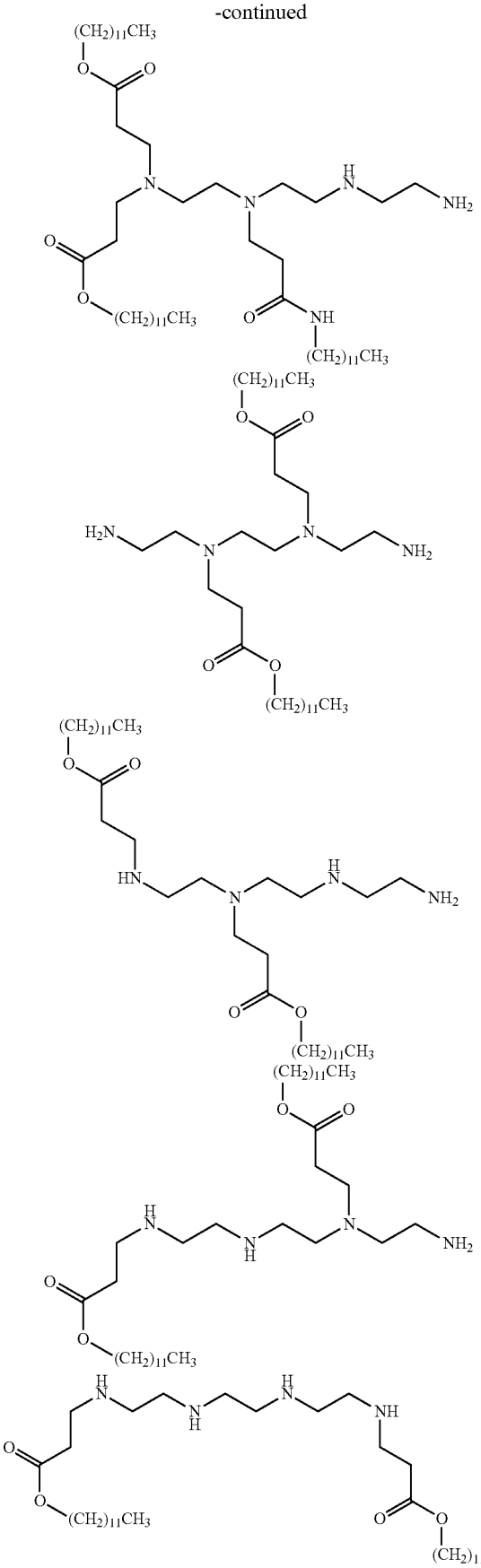
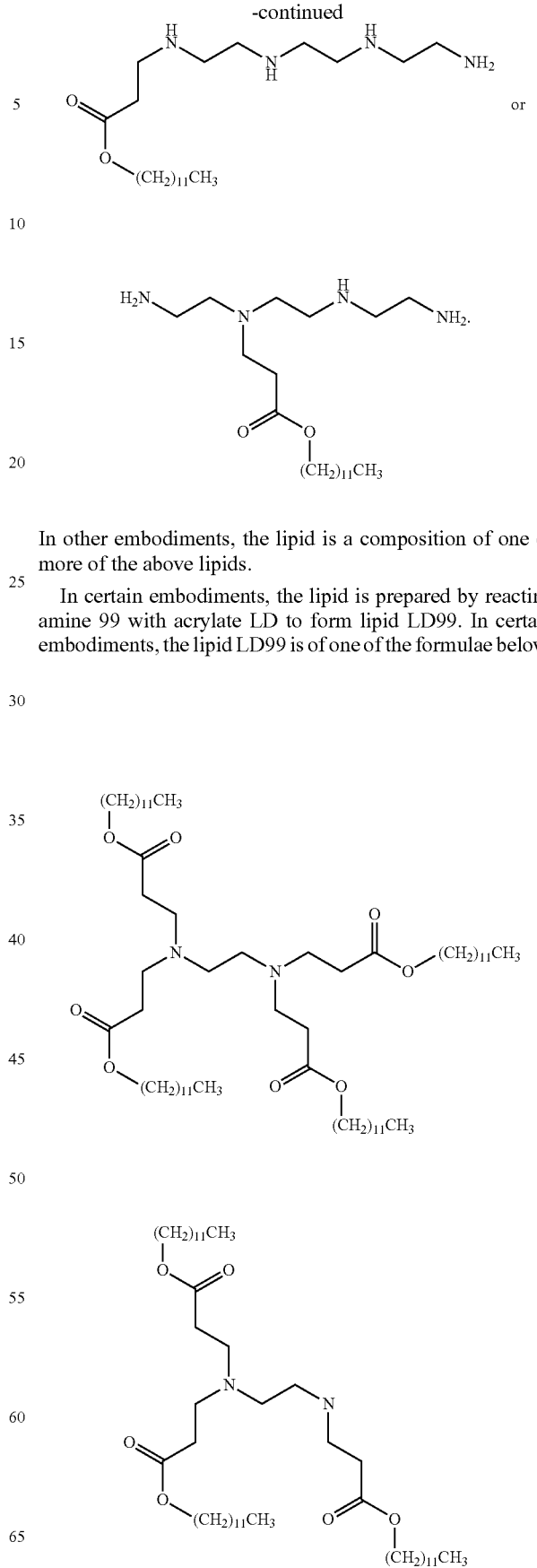
In other embodiments, the lipid is a composition of one or more of the above lipids.
In certain embodiments, the lipid is prepared by reacting amine 99 with acrylate LD to form lipid LD99. In certain embodiments, the lipid LD99 is of one of the formulae below:

-continued

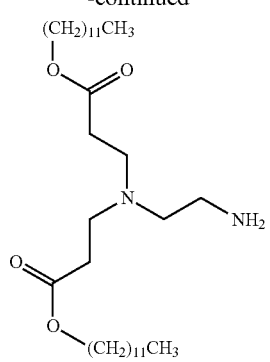

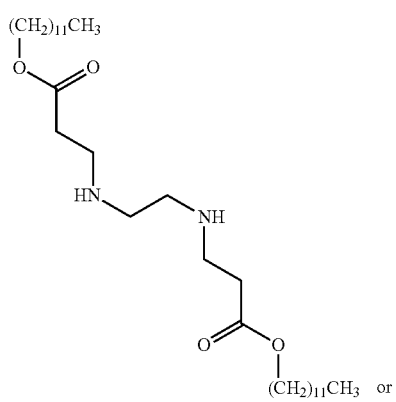

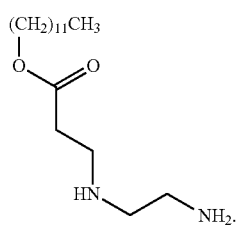

In other embodiments, the lipid is a composition of one or more of the above lipids. In certain embodiments, LD99 is treated with MeI or another alkylating agent to form lipids (QD99) of the formula:

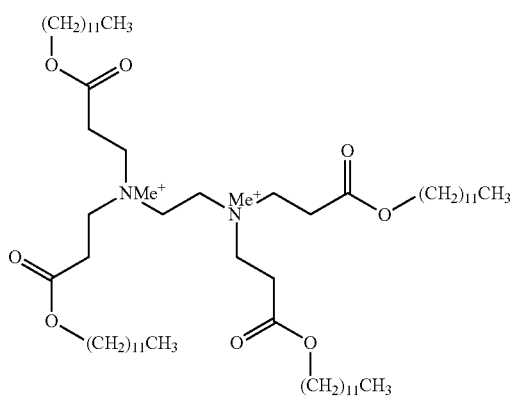

-continued

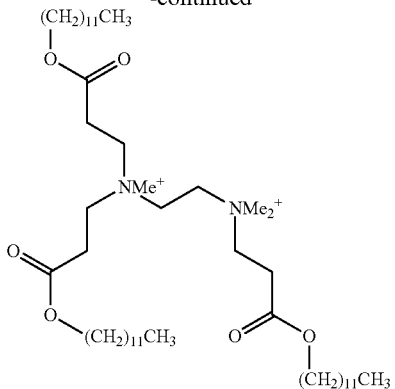

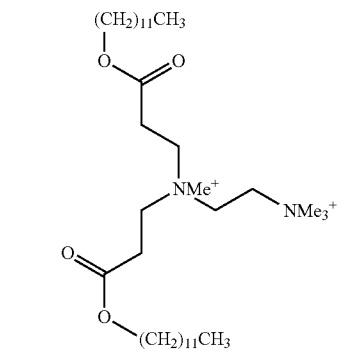

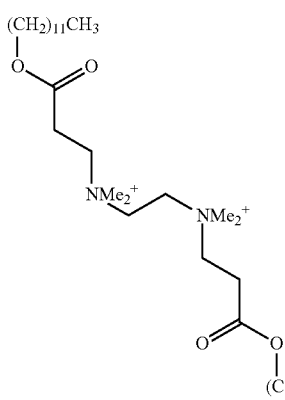

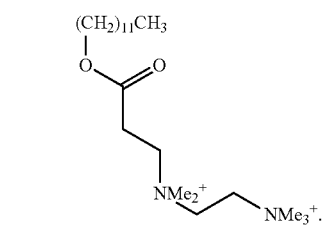

In certain embodiments, the lipid is prepared by reacting amine 100 with acrylate LD to form lipid LD100. In certain embodiments, the lipid LD100 is of one of the formulae below:

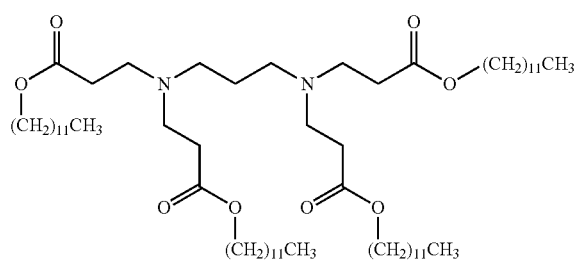
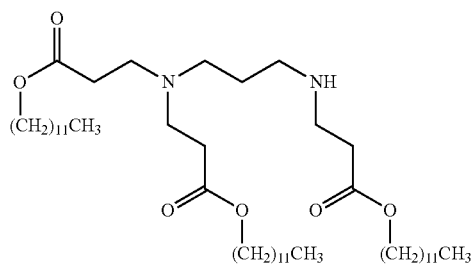
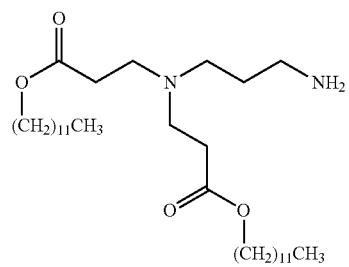
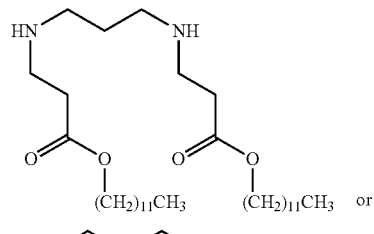
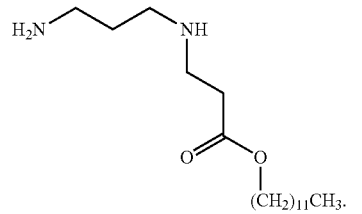
In other embodiments, the lipid is a composition of one or more of the above lipids. In certain embodiments, LD100 is treated with MeI or another alkylating agent to form lipids (QD100) of the formula:
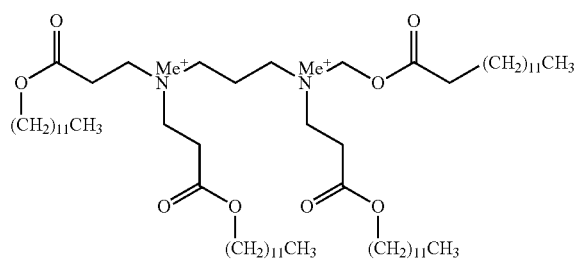
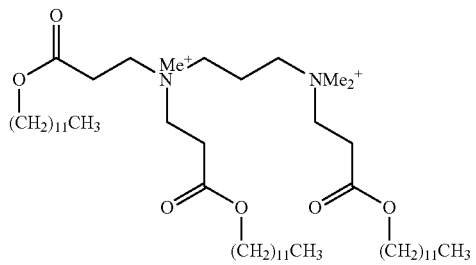
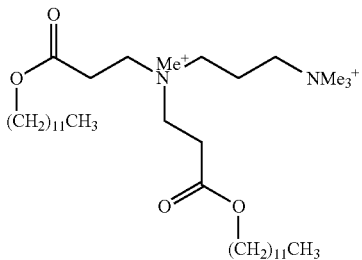
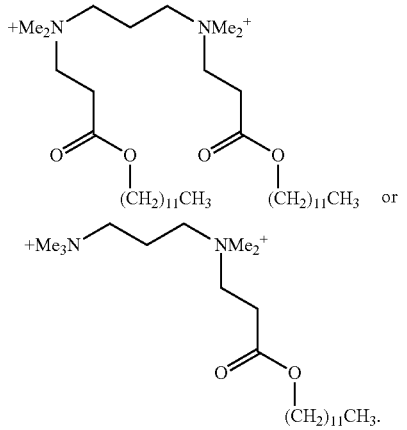
In certain embodiments, the lipid is prepared by reacting amine 87 with acrylate LE to form lipid LE87. In certain embodiments, the lipid LE87 is of one of the formulae below:
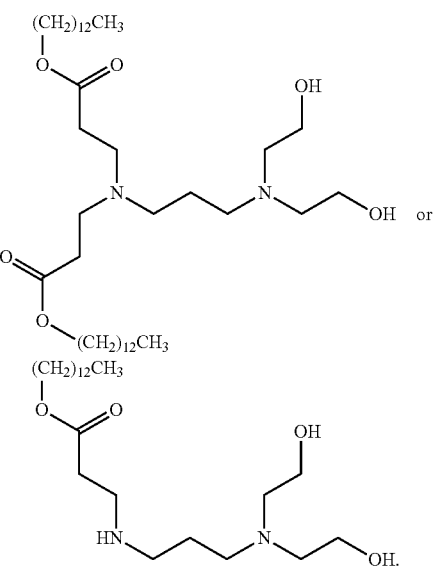

In other embodiments, the lipid is a composition of one or more of the above lipids.

In certain embodiments, the lipid is prepared by reacting amine 94 with acrylate LE to form lipid LE94. In certain embodiments, the lipid LE94 is of one of the formulae below:

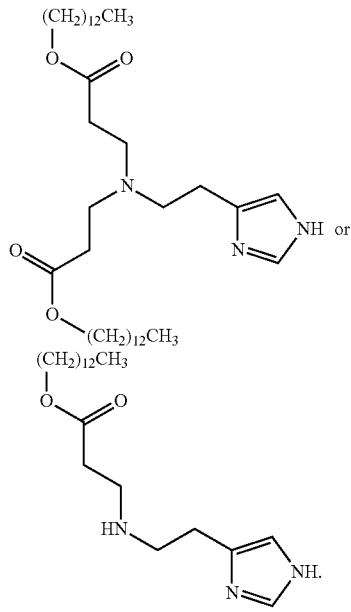

In other embodiments, the lipid is a composition of one or more of the above lipids.

In certain embodiments, the lipid is prepared by reacting amine 31 with acrylate LF to form lipid LF31. In certain embodiments, the lipid LF31 is of one of the formulae below:

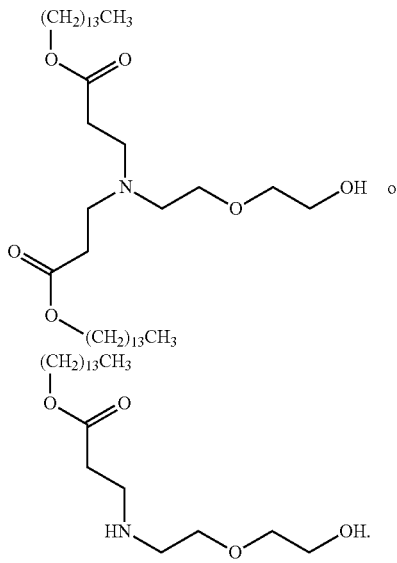

In other embodiments, the lipid is a composition of one or more of the above lipids.

In certain embodiments, the lipis is prepared by reacting amine 94 with acrylate LF to form lipid LF94. In certain embodiments, the lipid LF94 is of one of the formulae below:

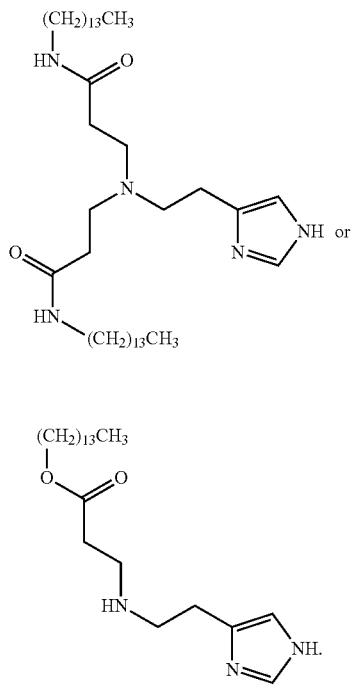

In other embodiments, the lipid is a composition of one or more of the above lipids.

In certain embodiments, the lipid is prepared by reacting amine 95 with acrylate LF to form lipid LF95. In certain embodiments, the lipid LF95 is of one of the formulae below:

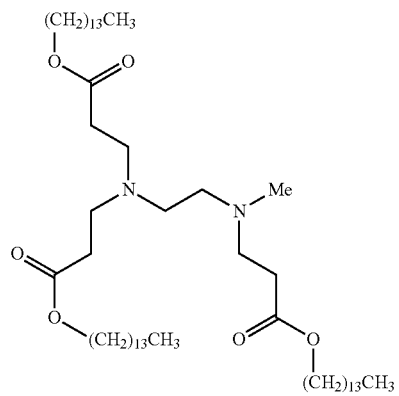

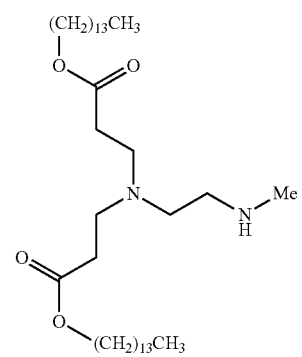

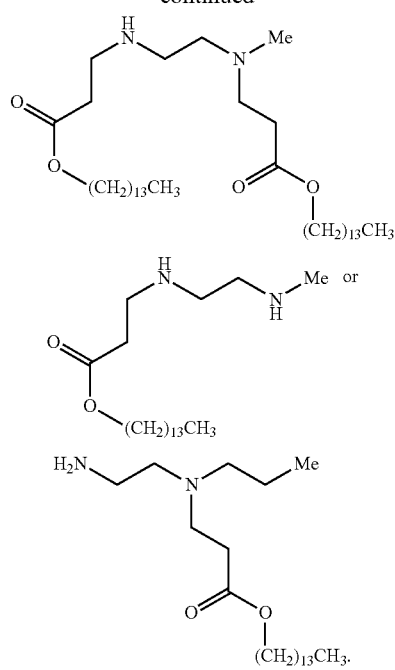

In other embodiments, the lipid is a composition of one or more of the above lipids.

In certain embodiments, the lipid is prepared by reacting amine 99 with acrylate LF to form lipid LF 99. In certain embodiments, the lipid LF99 is of one of the formulae below:

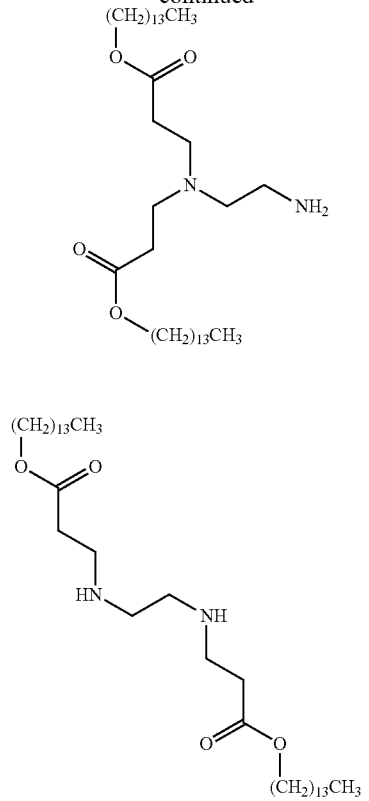

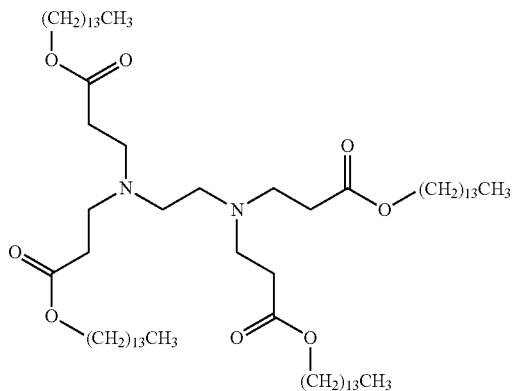

In other embodiments, the lipid is a composition of one or more of the above lipids. In certain embodiments, LF99 is treated with MeI or another alkylating agent to form lipid (QF99) of the formula:

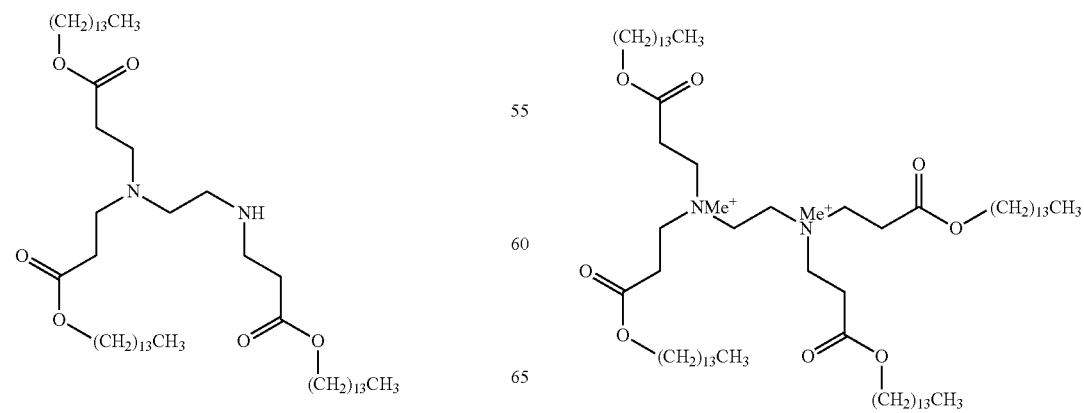

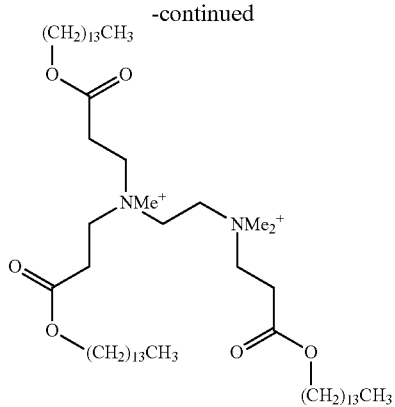

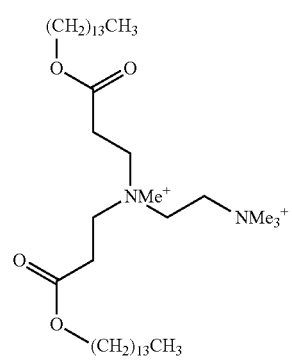

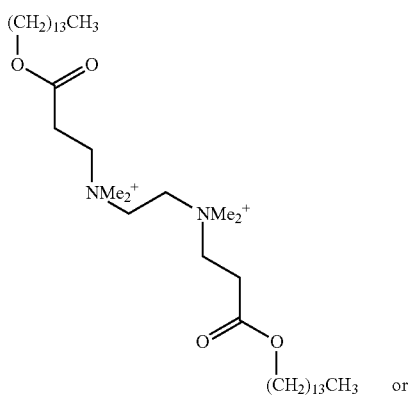

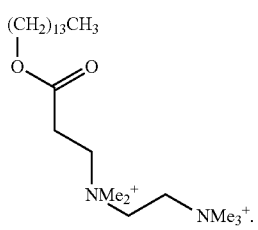

In certain embodiments, the lipid is prepared by reacting amine 32 with acrylate LG to form lipid LG32. In certain embodiments, the lipid LG32 is of one of the formulae below:

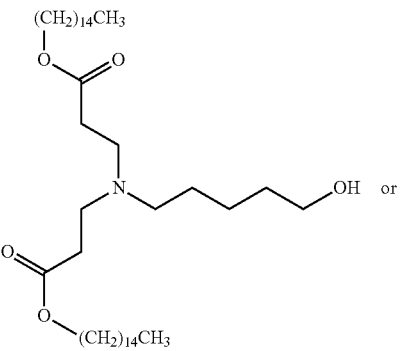

In other embodiments, the lipid is a composition of one or more of the above lipids.

In certain embodiments, the lipid is prepared by reacting amine 77 with acrylate LG to form lipid LG77. In certain embodiments, the lipid LG77 is of one of the formulae below:

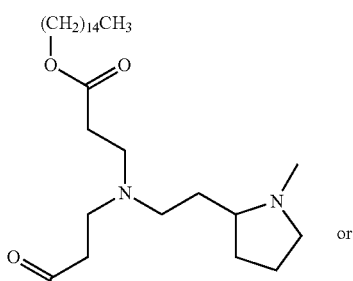

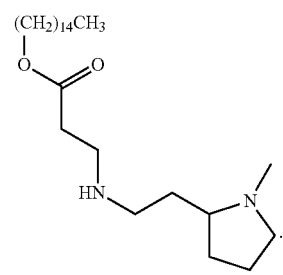

In other embodiments, the lipid is a composition of one or more of the above lipids.

In certain embodiments, the lipid is prepared by reacting amine 80 with acrylate LG to form lipid LG80. In certain embodiments, the lipid LG80 is of one of the formulae below:

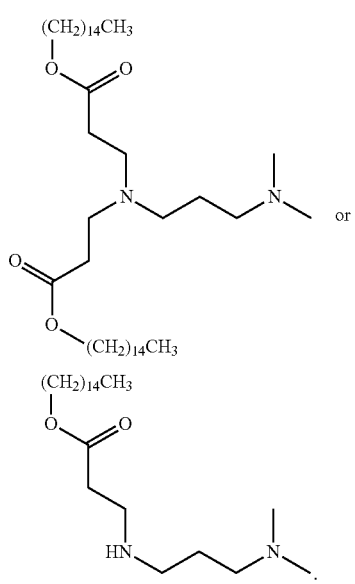

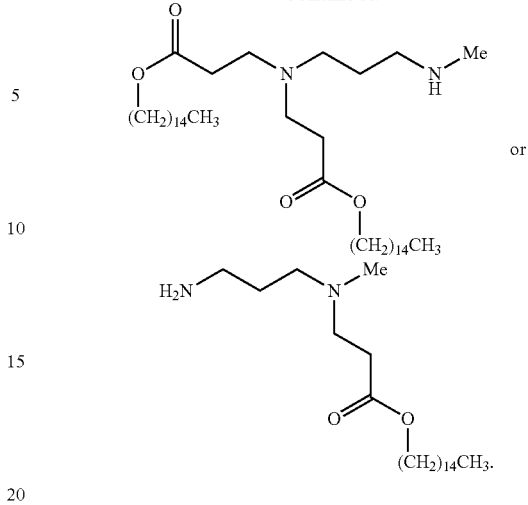

In other embodiments, the lipid is a composition of one or more of the above lipids.

In certain embodiments, the lipid is prepared by reacting amine 96 with acrylate LG to form lipid LG96. In certain embodiments, the lipid NG96 is of one of the formulae below:

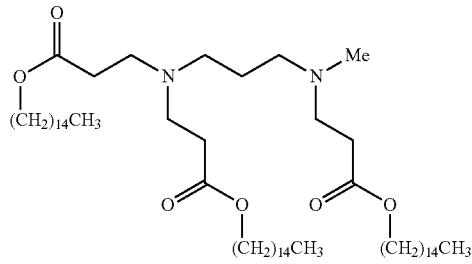

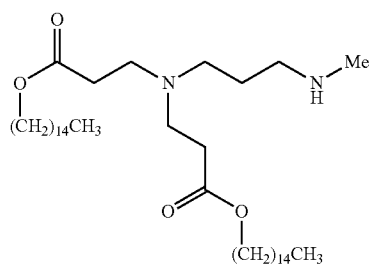

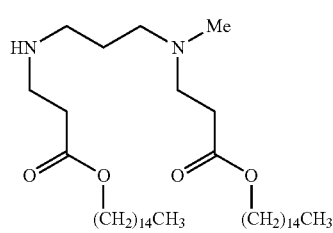

In other embodiments, the lipid is a composition of one or more of the above lipids.

In certain embodiments, the lipid is prepared by reacting amine 100 with acrylate LG to form lipid LG100. In certain embodiments, the lipid LG100 is of one of the formulae below:

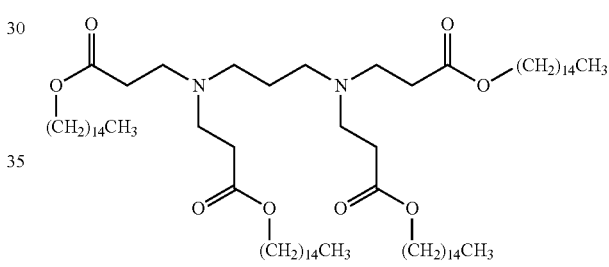

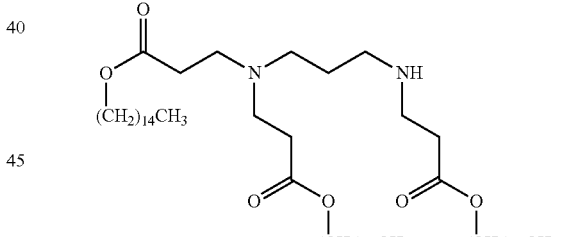

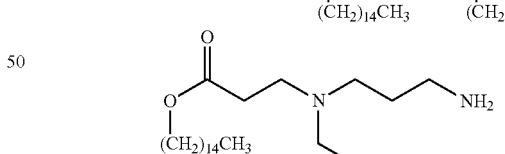

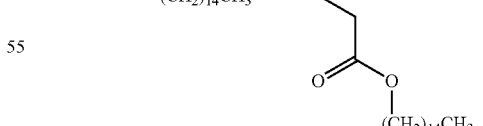

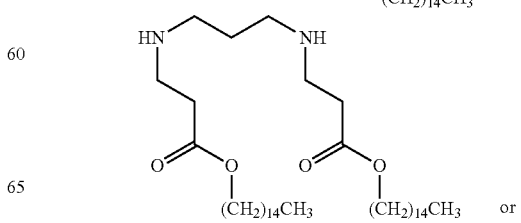

-continued

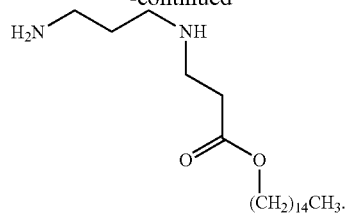

In other embodiments, the lipid is a composition of one or more of the above lipids. In certain embodiments, LG100 is treated with MeI or another alkylating agent to form lipids (QG100) of the formula:

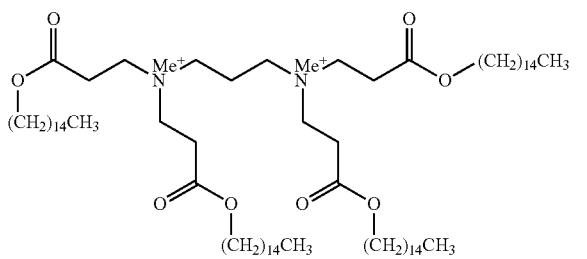

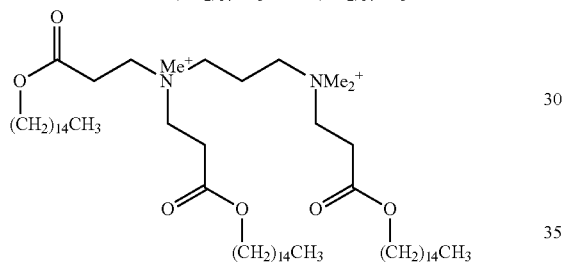

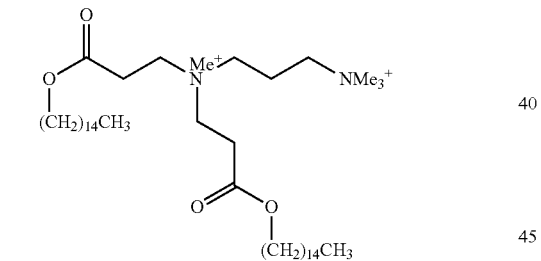

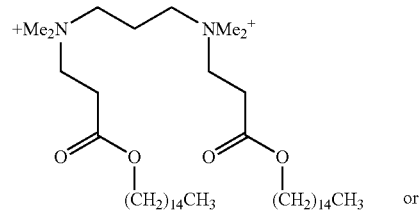

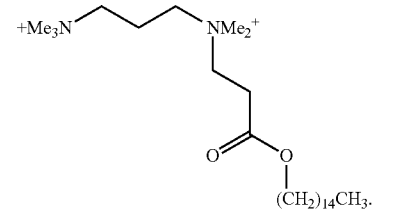 or

In certain embodiments, the lipid is prepared by reacting amine 109 with acrylate LG to form lipid LG109. In certain embodiments, the lipid NG109 is of one of the formulae below:

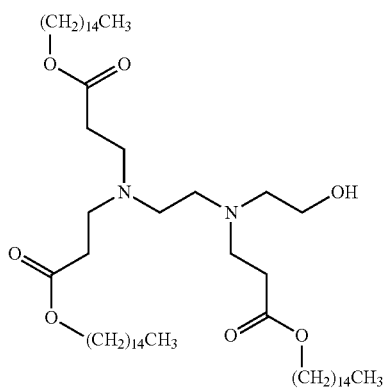

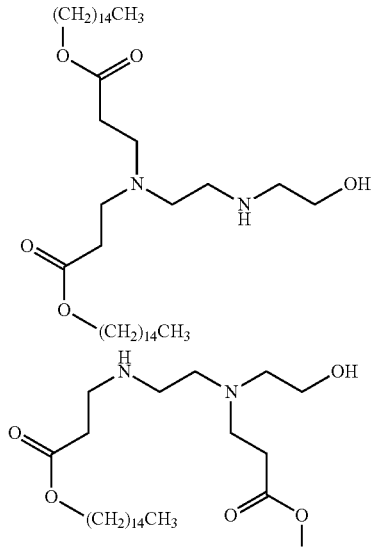

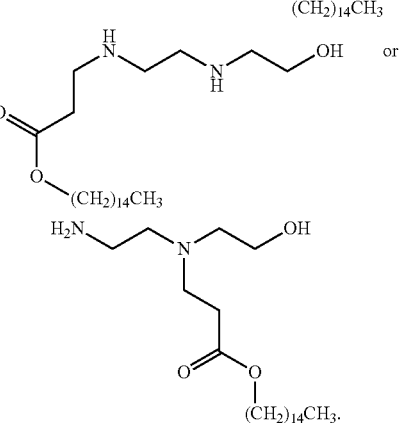

In other embodiments, the lipid is a composition of one or more of the above lipids.

In certain embodiments, the lipid is prepared by reacting amine 64 with acrylate LG to form lipid LG64. In certain embodiments, the lipid LG64 is of one of the formulae below:

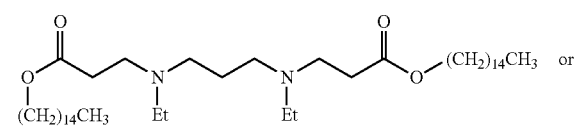 or

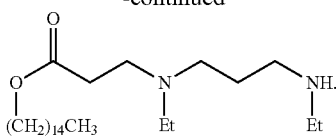

In other embodiments, the lipid is a composition of one or more of the above lipids.

In certain embodiments, the lipid is prepared by reacting amine 31 with acrylate LG to form lipid LG31. In certain embodiments, the lipid LG31 is of one of the formulae below:

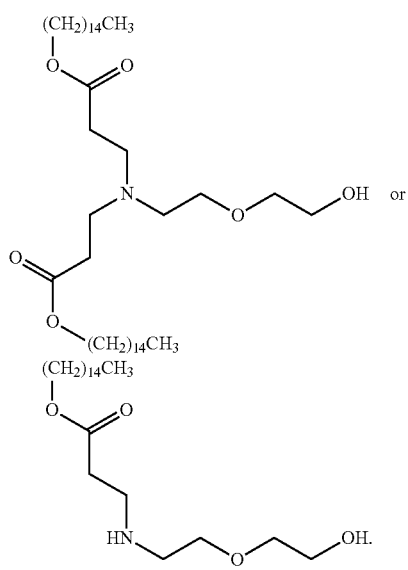

In other embodiments, the lipid is a composition of one or more of the above lipids.

In certain embodiments, the lipid is prepared by reacting amine 32 with acrylate LG to form lipid LG32. In certain embodiments, the lipid NG32 is of one of the formulae below:

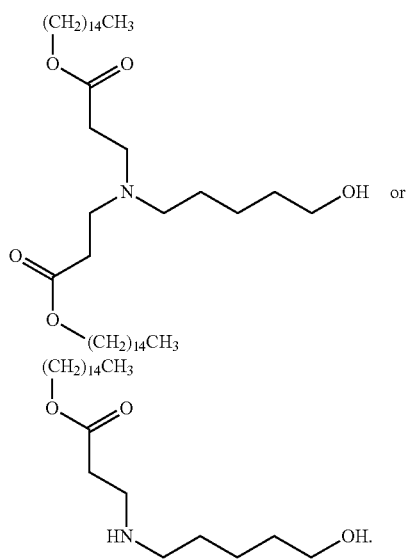

In other embodiments, the lipid is a composition of one or more of the above lipids.

Synthesis of Lipids

The inventive lipids may be prepared by any method known in the art. Preferably the lipids are prepared from commercially available starting materials, such acrylates or acrylamides, and amines. In another preferred embodiment, the lipids are prepared from easily and/or inexpensively prepared starting materials. As would be appreciated by one of skill in the art, the inventive lipids can be prepared by total synthesis starting from commercially available starting materials A particular lipid may be the desired final product of the synthesis, or a mixture of lipids may be the desired final product.

In a particularly preferred embodiment, the inventive lipid is prepared via the conjugate addition of primary amines to acrylates or acrylamides. An exemplary reaction scheme is shown below:

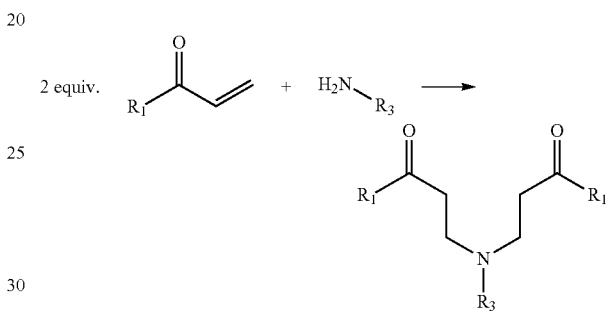

Any primary amine is useful in preparing inventive lipids. Primary amines useful in this invention include, but are not limited to, methylamine, ethylamine, isopropylamine, aniline, substituted anilines, and ethanolamine. The primary amine may be a bis(primary amine). Preferably, the amine is commercially available. In certain embodiments, the amine used in the synthesis of the lipid is of the formula:

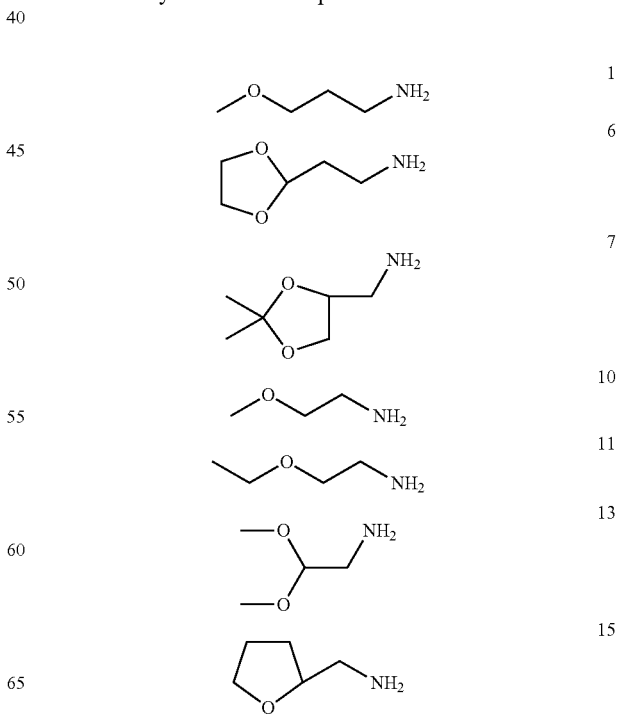

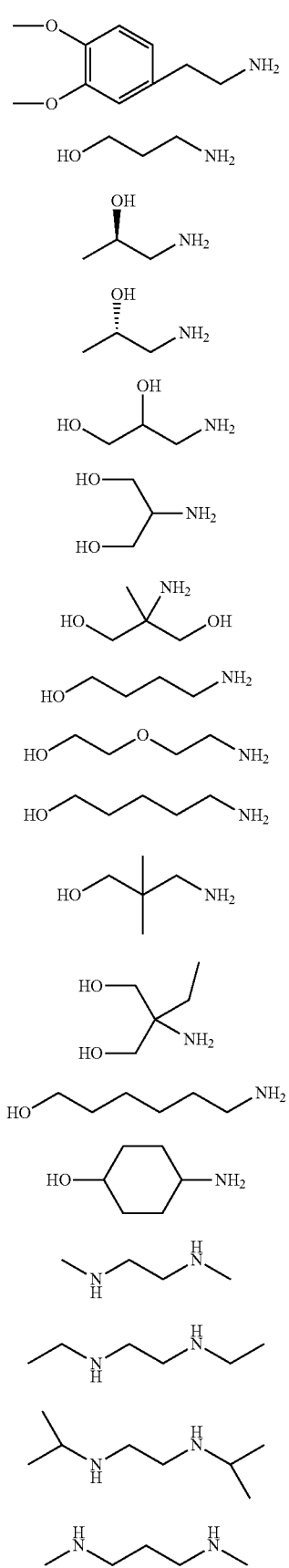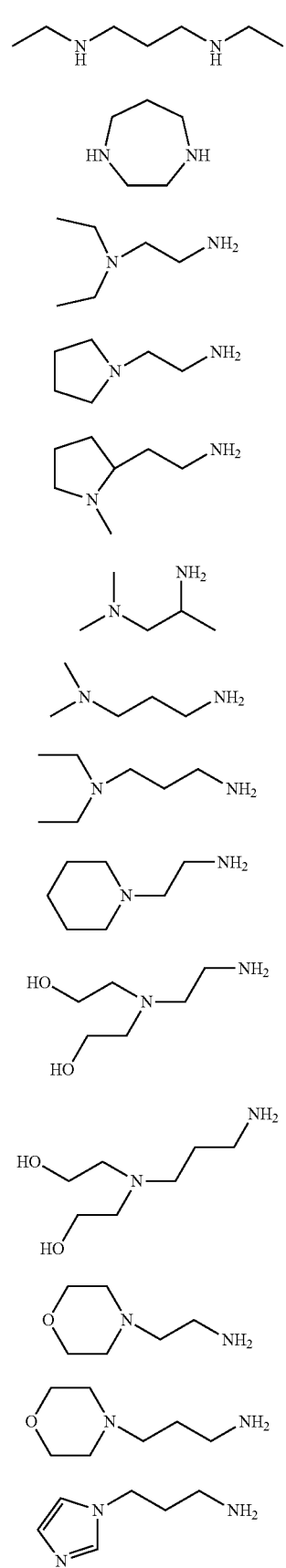

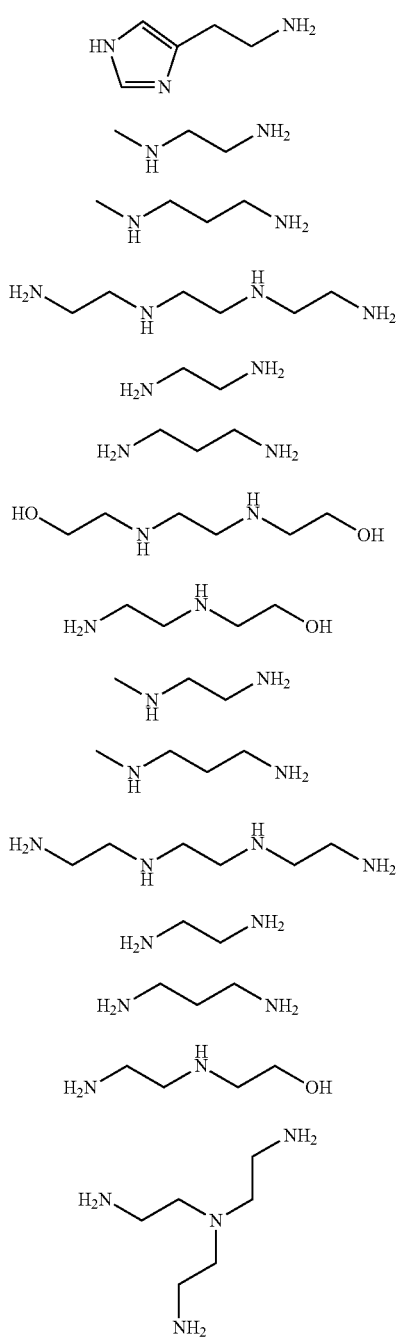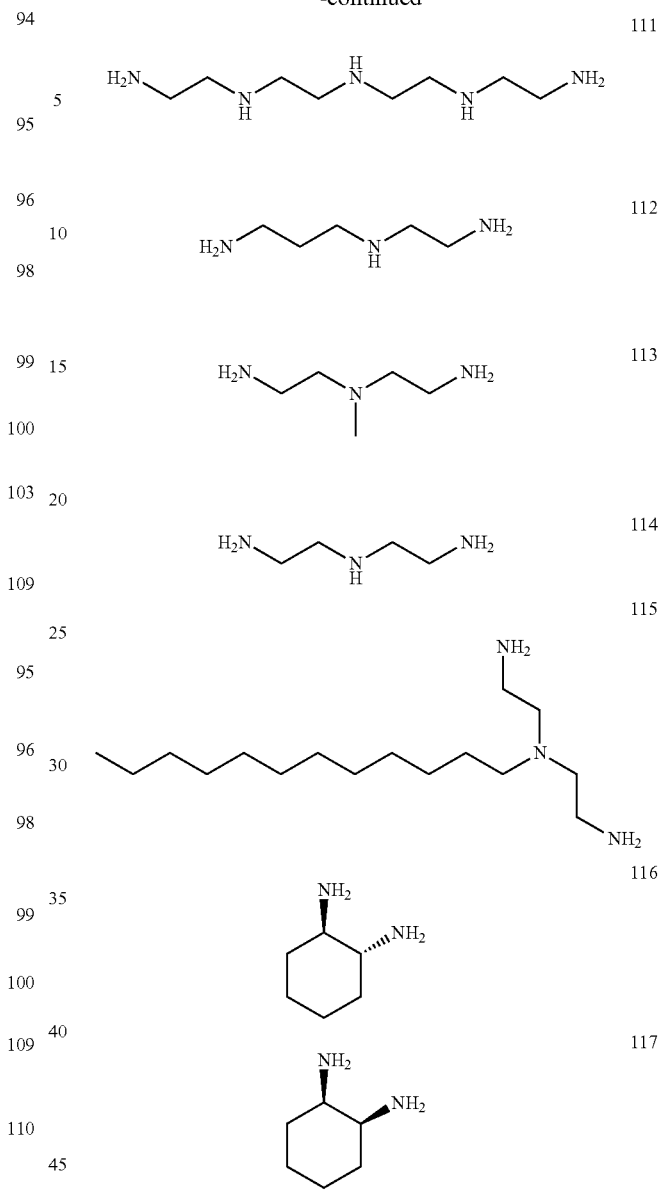
Acrylate or acrylamide monomers that are useful in the present invention include any acrylates and acrylamides In certain embodiments, the acrylates or acrylamides are acrylates or acrylamides of straight chain alkyl groups. In certain embodiments, the acrylate or acrylamide is of the formula:
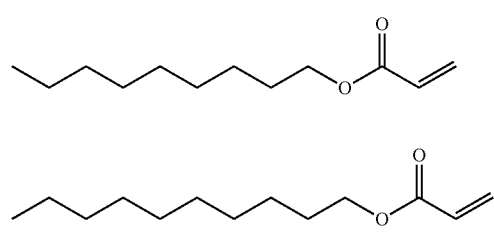

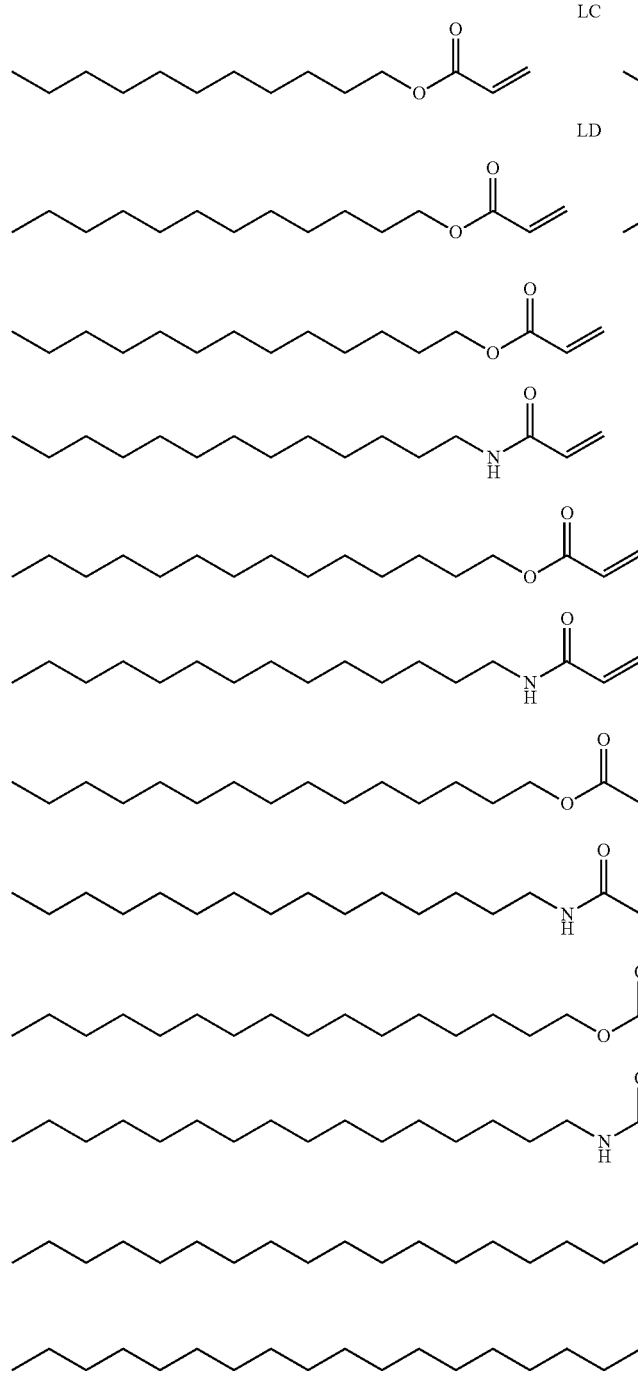

In other embodiments, the acrylate or acrylamide may include branched, substituted, or cyclic aliphatic or heteroaliphatic groups. In certain embodiments, the acrylate or acrylamide is substituted with C1-C6 alkyl group, halogens, amino groups, hydroxyl groups, alkoxy groups, etc.

In certain embodiments, the reaction is performed neat without the use of a solvent. In other embodiments, a solvent is used for the reaction. Both or one of the monomers is dissolved in an organic solvent (e.g., THF, $CH_2Cl_2$, MeOH, EtOH, $CHCl_3$, hexanes, toluene, benzene, $CCl_4$, glyme, diethyl ether, etc.). The resulting solutions are combined, and the reaction mixture is heated to yield the desired lipid. In a particularly preferred embodiment, the reaction mixture is heated to temperature ranging from 50-150° C. In another particularly preferred embodiment, the reaction mixture is heated to approximately 95° C. The reaction may also be catalyzed. For example, the reaction may be catalyzed by the addition of an acid, base, or metal. The reagents may be allowed to react for fours, days, or weeks. Preferably, the reaction is allowed to proceed from overnight (e.g., 8-2 hours) to 7 days.

In another particularly preferred embodiment, the inventive lipids are prepared by the conjugate addition of a bis(amine) to an acrylate. The bis(amine) may be a bis(secondary amine) or a bis(primary amine). En exemplary reaction scheme using bis(amines) is shown below:

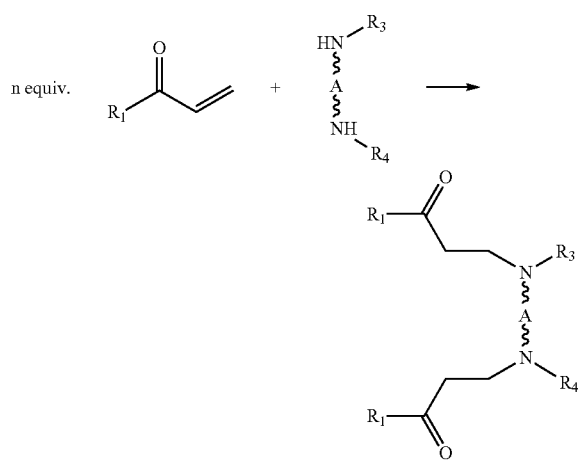

In certain embodiments, the reaction is performed neat without a solvent. In other embodiments, the reaction is performed in a solvent. One or both of the monomers are dissolved in an organic solvent (e.g., THF, $CH_2Cl_2$, MeOH, EtOH, $CHCl_3$, hexanes, $CCl_4$, glyme, diethyl ether, etc.). Organic solvents are preferred due to the susceptibility of polyesters to hydrolysis. The resulting solutions are combined, and the reaction mixture is heated to yield the desired lipid. In a particularly preferred embodiment, the reaction mixture is maintained at a temperature ranging from 50-150° C. In another particularly preferred embodiment, the reaction mixture is heated to approximately 95° C. The reaction may also be catalyzed. For example, the reaction may be catalyzed by the addition of an acid, base, or metal.

In yet another particularly preferred embodiment, the inventive lipids are prepared by the conjugate addition of a poly(amine) to an acrylate or acrylamide. The poly(amine) may include primary, secondary, tertiary, or quaternary amines. In certain embodiments, the poly(amine) contains only primary and secondary amines. An exemplary reaction scheme using poly(amines) is shown below:

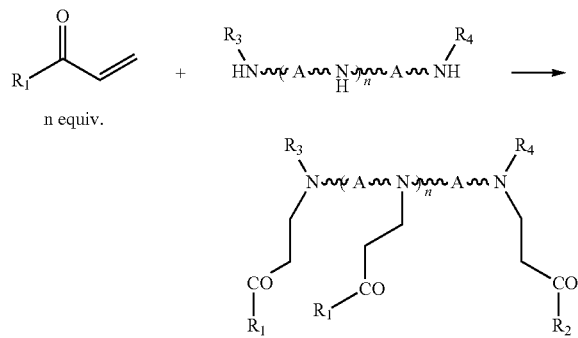

In certain embodiments, the reaction is performed with an excess of acrylate or acrylamide to fully funcationlize all amino groups of the poly(amine). In other embodiments, the equivalents of acrylate are limiting; therefore, all amino groups of the poly(amine) are not functionalized. In certain embodiments, the reaction is performed neat without a solvent. In other embodiments, the reaction is performed in a solvent. One or both of the monomers are dissolved in an organic solvent (e.g., THF, $CH_2Cl_2$, MeOH, EtOH, $CHCl_3$, hexanes, $CCl_4$, glyme, diethyl ether, etc.). Organic solvents are preferred due to the susceptibility of polyesters to hydrolysis. The resulting solutions are combined, and the reaction mixture is heated to yield the desired lipid. In a particularly preferred embodiment, the reaction mixture is maintained at a temperature ranging from 50-150° C. In another particularly preferred embodiment, the reaction mixture is heated to approximately 95° C. The reaction may also be catalyzed. For example, the reaction may be catalyzed by the addition of an acid, base, or metal.

The synthesized lipid may be purified by any technique known in the art including, but not limited to, precipitation, crystallization, chromatography, distillation, etc. In a particularly preferred embodiment, the lipid is purified through repeated precipitations in organic solvent (e.g., diethyl ether, hexane, etc.). In a particularly preferred embodiment, the lipid is isolated as a salt. The lipid is reacted with an acid (e.g., an organic acid or inorganic acid) to form the corresponding salt. In certain embodiments, the tertiary amine is alkylated to form a quaternary ammonium salt of the lipid. The tertiary amines may be alkylated with any alkylating agent, for example, alkyl halides such as methyl iodide may be used to from the quaternary amino groups. The anion associated with the quaternary amine may be any organic or inorganic anion. Preferably, the anion is a pharmaceutically acceptable anion.

In certain embodiments, the reaction mixture results in a mixture of isomers with varying numbers and positions of acrylate tails. Such mixtures of products may be used as is, or a single isomer may be purified from the reaction mixture. When an amine is not exhaustively alkylated, the resulting primary, secondary, or tertiary amines may be further reacted with another acrylate, acrylamide, or other electrophile. The resulting lipid may then be optionally purified.

In certain embodiments, a desired lipid is prepared by traditional total synthesis. In certain embodiments, a commercially available amine is the starting material. One or more amino groups of the amine are optionally protected. The unprotected amino groups are reacted with a acrylate or acrylamide. The product is optionally purified. Protecting groups are removed, and the free amino groups are optionally reacted with another acrylate, acrylamide, or other electrophile. Such a sequence may be repeated depending on the desired complexity of the inventive product being prepared. The final product may then be optionally purified.

In one embodiment, a library of different lipids is prepared in parallel. A different amine and/or acrylate is added to each vial in a set of vials or to each well of a multi-well plate used to prepare the library. The array of reaction mixtures is incubated at a temperature and length of time sufficient to allow formation of the lipids to occur. In one embodiment, the vials are incubated at approximately 95° C. overnight. In other embodiments, the vials are incubated from 1 to 7 days at approximately 95° C. The lipids may then be isolated and purified using techniques known in the art. The lipids may then be screened using high-throughput techniques to identify lipids with a desired characteristic (e.g., solubility in water, solubility at different pH, ability to bind polynucleotides, ability to bind heparin, ability to bind small molecules, ability to form microparticles, ability to increase transfection efficiency, etc.). In certain embodiments the lipids may be screened for properties or characteristics useful in gene therapy (e.g., ability to bind polynucleotides, increase in transfection efficiency).

Polynucleotide Complexes

The ability of cationic compounds to interact with negatively charged polynucleotides through electrostatic interactions is well known. Cationic lipids such as Lipofectamine have been prepared and studied for their ability to complex and transfect polynucleotides. The interaction of the lipid with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In a particularly preferred embodiment, the complex is slightly positively charged. In another particularly preferred embodiment, the complex has a positive c-potential, more preferably the $\xi$-potential is between +1 and +30.

The lipids of the present invention possess tertiary amines. Although these amines are hindered, they are available to interact with a polynucleotide (e.g., DNA, RNA, synthetic analogs of DNA and/or RNA, DNA/RNA hydrids, etc.). Polynucleotides or derivatives thereof are contacted with the inventive lipids under conditions suitable to form polynucleotide/lipid complexes. The lipid is preferably at least partially protonated so as to form a complex with the negatively charged polynucleotide. In a preferred embodiment, the polynucleotide/lipid complexes form nanoparticles that are useful in the delivery of polynucleotides to cells. In certain embodiments, multiple lipid molecules may be associated with a polynucleotide molecule. The complex may include 1-100 lipid molecules, 1-1000 lipid molecules, 10-1000 lipid molecules, or 100-10,000 lipid molecules. In certain embodiments, the complex may form a nanoparticle. In a particularly preferred embodiment, the diameter of the nanoparticles ranges from 10-500 nm, more preferably the diameter of the nanoparticles ranges from 10-1200 nm, and most preferably from 50-150 nm. The nanoparticles may be associated with a targeting agent as described below.

Polynucleotide

The polynucleotide to be complexed, encapsulated by the inventive lipids, or included in a composition with the inventive lipds may be any nucleic acid including but not limited to RNA and DNA. In certain embodiments, the polynucleotide is DNA. In other embodiments, the polynucleotide is RNA. In other embodiments, the polynucleotide is an siRNA. In other embodiments, the polynucleotide is an shRNA. The polynucleotides may be of any size or sequence, and they may be single- or double-stranded. In certain preferred embodiments, the polynucleotide is greater than 100 base pairs long. In certain other preferred embodiments, the polynucleotide is greater than 1000 base pairs long and may be greater than 10,000 base pairs long. The polynucleotide is preferably purified and substantially pure. Preferably, the polynucleotide is greater than 50% pure, more preferably greater than 75% pure, and most preferably greater than 95% pure. The polynucleotide may be provided by any means known in the art. In certain preferred embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press; 1989); each of which is incorporated herein by reference). The polynucleotide may also be obtained from natural sources and purified from contaminating components found normally in nature. The polynucleotide may also be chemically synthesized in a laboratory. In a preferred embodiment, the polynucleotide is synthesized using standard solid phase chemistry.

The polynucleotide may be modified by chemical or biological means. In certain preferred embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, $C_5$-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3"-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain preferred embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In other particularly preferred embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al. *Nature* 391: 806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10(2):123-126, discussion 127, 2000; *Methods in Enzymology* volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

In a particularly preferred embodiment, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health and can be found on the internet (http:/www.niaid.nih.gov/daids/vaccine/pdf/compendium.pdf, incorporated herein by reference; see also Allison *Dev. Biol. Stand.* 92:3-11, 1998; Unkeless et al. *Annu. Rev. Immunol.* 6:251-281, 1998; and Phillips et al. *Vaccine* 10:151-158, 1992, each of which is incorporated herein by reference).

The antigenic protein or peptides encoded by the polynucleotide may be derived from such bacterial organisms as *Streptococccus pneumoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Microparticles

The lipids of the present invention may also be used to form drug delivery devices. The inventive lipids may be used to encapsulate agents including polynucleotides, small molecules, proteins, peptides, metals, organometallic compounds, etc. The inventive lipids have several properties that make them particularly suitable in the preparation of drug delivery devices. These include 1) the ability of the lipid to complex and "protect" labile agents; 2) the ability to buffer the pH in the endosome; 3) the ability to act as a "proton sponge" and cause endosomolysis; and 4) the ability to neutralize the charge on negatively charged agents. In a preferred embodiment, the lipids are used to form microparticles containing the agent to be delivered. These microparticles may include other materials such as proteins, carbohydrates, synthetic polymers (e.g., PEG, PLGA), and natural polymers. In a particularly preferred embodiment, the diameter of the microparticles ranges from between 500 nm to 50 micrometers, more preferably from 1 micrometer to 20 micrometers, and most preferably from 1 micrometer to 10 micrometers. In another particularly preferred embodiment, the microparticles range from 1-5 micrometers.

Methods of Preparing Microparticles

The inventive microparticles may be prepared using any method known in this art. These include, but are not limited to, spray drying, single and double emulsion solvent evaporation, solvent extraction, phase separation, simple and complex coacervation, and other methods well known to those of ordinary skill in the art. Particularly preferred methods of preparing the particles are the double emulsion process and spray drying. The conditions used in preparing the microparticles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making microparticles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve deisirable surface properties (e.g., a particular charge).

Micelles and Liposomes

The lipids of the invention may be used to prepare micelles or liposomes. Many techniques for preparing micelles and liposomes are known in the art, and any method may be used with the inventive lipids to make micelles and liposomes. In addition, any agent including polynucleotides, small molecules, proteins, peptides, metals, organometallic compounds, etc. may be included in a micelle or liposome. Micelles and liposomes are particularly useful in delivering hydrophobic agents such as hydrophobic small molecules.

In certain embodiments, liposomes (lipid vesicles) are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). See Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al. "Comparative Properties and Methods of Preparation of Lipid Vesicles (Liposomes)" *Ann. Rev. Biophys. Bioeng.* 9:467-508, 1980; each of which is incorporated herein. The preparation of lipsomes involves preparing the lipid for hydration, hydrating the lipid with agitation, and sizing the vesicles to achieve a homogenous distribution of liposomes. Lipids are first dissolved in an organic solvent to assure a homogeneous mixture of lipids. The solvent is then removed to form a lipid film. This film is thoroughly dried to remove residual organic solvent by placing the vial or flask on a vaccuum pump overnight. Hydration of the lipid film/cake is accomplished by adding an aqueous medium to the container of dry lipid and agitating the mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm.

In certain embodiments of the invention, liposomes are formed comprising an inventive lipid, PEG-ceramide, cholesterol, and a polynucleotide. In certain embodiments, the polynucleotide is an RNA molecule (e.g., an RNAi molecule). In other embodiments, the polynucleotide is a DNA molecule. In certain embodiments, the lipid is ND98. In other embodiments, the lipid is ND28, ND32, LF94, ND99, ND95, NP103, NP98, ND25, $ND_{20}$, ND100, NF96, NF103, NF109, NF11, ND24, NF86, NP96, ND36, NF61, NF87, NF95, QG100, NF60, NP100, NF1, NP99, QD99, NF63, LG109, ND103, LF95, QF99, LG100, LF31, LG32, NF109, NF64, LE87, LG77, LG96, ND96, LD31, NG64, ND109, or LG80. In certain embodiments, the amount of lipid in the liposome ranges from 30-80 mol %, preferably 40-70 mol %, more preferably 60-70 mol %. In certain embodiments, the amount of PEG-ceramide in the liposomes ranges from 5-20 mol %, preferably 10-15 mol %, more preferably approximately 10 mol %. In certain embodiments, the amount of cholesterol in the liposome ranges from 5-25 mol %, preferably 10-20 mol %, more preferably approximately 15 mol %. In certain embodiments, the amount of cholesterol in the liposome is approximately 20 mol %. These liposomes may be prepared using any method known in the art. In certain embodiments (e.g., liposomes containing RNAi molecules), the liposomes are prepared by lipid extrusion.

Certain lipids can spontaneously self assemble around certain molecules, such as DNA and RNA, to form liposomes. For some applications such as the delivery of polynucleotides, these are preferred. Use of these lipids allows for simple assembly of liposomes without the need for additional steps or devices such as an extruder.

The following scientific papers described other methods for preparing liposomes and micelles: Narang et al. "Cationic Lipids with Increased DNA Binding Affinity for Nonviral Gene Transfer in Dividing and Nondividing Cells" *Bioconjugate Chem.* 16:156-68, 2005; Hofland et al. "Formation of stable cationic lipid/DNA complexes for gene transfer" *Proc. Natl. Acad. Sci. USA* 93:7305-7309, July 1996; Byk et al. "Synthesis, Activity, and Structure—Activity Relationship Studies of Novel Cationic Lipids for DNA Transfer" *J. Med. Chem.* 41(2):224-235, 1998; Wu et al. "Cationic Lipid Polymerization as a Novel Approach for Constructing New DNA Delivery Agents" *Bioconjugate Chem.* 12:251-57, 2001; Lukyanov et al. "Micelles from lipid derivatives of water-soluble polymers as delivery systems for poorly soluble drugs" *Advanced Drug Delivery Reviews* 56:1273-1289, 2004; Tranchant et al. "Physicochemical optimisation of plasmid delivery by cationic lipids" *J. Gene Med.* 6:S24-S35, 2004; van Balen et al. "Liposome/Water Lipophilicity: Methods, Information Content, and Pharmaceutical Applications" *Medicinal Research Rev.* 24(3):299-324, 2004; each of which is incorporated herein by reference.

Agent

The agents to be delivered by the system of the present invention may be therapeutic, diagnostic, or prophylactic agents. Any chemical compound to be administered to an individual may be delivered using the inventive comlexes, nanoparticles, or microparticles. The agent may be a small molecule, organometallic compound, nucleic acid, protein, peptide, polynucleotide, metal, an isotopically labeled chemical compound, drug, vaccine, immunological agent, etc.

In a preferred embodiment, the agents are organic compounds with pharmaceutical activity. In another embodiment of the invention, the agent is a clinically used drug. In a particularly preferred embodiment, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In a preferred embodiment of the present invention, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypano-*

*soma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents

The inventive complexes, liposomes, micelles, microparticles, and nanoparticles may be modified to include targeting agents since it is often desirable to target a particular cell, collection of cells, or tissue. A variety of targeting agents that direct pharmaceutical compositions to particular cells are known in the art (see, for example, Cotten et al. *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Pharmaceutical Compositions

Once the complexes, micelles, liposomes, microparticles, or nanoparticles have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the microparticles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

These and other aspects of the present invention will be further appreciated upon consideration of the following Examples, which are intended to illustrate certain particular embodiments of the invention but are not intended to limit its scope, as defined by the claims.

EXAMPLES

Example 1

Preparation and Testing of Amine-Containing Lipids

Lipid Synthesis.

Monomers were purchased from Aldrich (Milwaukee, Wis.), TCI (Portland, Oreg.), Pfaltz & Bauer (Waterbury, Conn.), Matrix Scientific (Columbia, S.C.), Acros-Fisher (Pittsburg, Pa.), Scientific Polymer (Ontario, N.Y.), Polysciences (Warrington, Pa.), and Dajac monomer-polymer (Feasterville, Pa.). The acrylate and amine monomers were used neat to prepare the lipids. All possible pair wise combinations of amine and acrylate monomers shown in FIG. 1 were prepared in sealed vials. The vials were then incubated overnight at approximately 95° C. with shaking. The synthesized lipids were used without further purification.

The molecular weights of the synthesized lipids were determined by mass spectroscopy and compared to predicted molecular weights to confirm synthesis of the lipid. Mass spectrometric data are shown in the table below.

TABLE 1

Mass-spectrometry data of amine-containing lipids.

| Lipid | Formula | Predicted MW | Actual MW |
|---|---|---|---|
| LF1 | $C_{38}H_{75}NO_5$ | 626.572 | 626.651 |
| LF6 | $C_{39}H_{75}NO_6$ | 654.5667 | 654.6604 |
| LF7 | $C_{40}H_{77}NO_6$ | 668.5824 | 668.6972 |
| LF10 | $C_{37}H_{73}NO_5$ | 612.5562 | 612.5917 |
| LF11 | $C_{38}H_{75}NO_5$ | 626.5718 | 626.6789 |
| LF15 | $C_{39}H_{76}NO_5$ | 638.5723 | 638.6649 |
| LF17 | $C_{44}H_{79}NO_6$ | 718.598 | 718.6921 |
| LF20 | $C_{37}H_{73}NO_5$ | 612.5562 | 612.5946 |
| LF21 | $C_{37}H_{73}NO_5$ | 612.556 | 612.5959 |
| LG1 | $C_{40}H_{79}NO_5$ | 654.6036 | 654.8644 |
| LG6 | $C_{41}H_{79}NO_6$ | 682.5985 | 682.8408 |
| LG7 | $C_{42}H_{81}NO_6$ | 696.6142 | 696.9988 |
| LG10 | $C_{39}H_{78}NO_5$ | 640.588 | 640.9817 |
| LG13 | $C_{40}H_{80}NO_6$ | 670.5985 | 670.9156 |
| LG15 | $C_{41}H_{79}NO_5$ | 666.6036 | 666.9696 |
| LG17 | $C_{46}H_{83}NO_5$ | 746.6298 | 746.9586 |
| LG20 | $C_{39}H_{77}NO_5$ | 640.588 | 640.9586 |
| LG21 | $C_{39}H_{77}NO_5$ | 640.588 | 640.9292 |
| LG22 | $C_{39}H_{77}NO_5$ | 640.588 | 640.8809 |
| LG24 | $C_{39}H_{77}NO_6$ | 656.5829 | 656.9402 |
| QF1 | $C_{39}H_{78}NO_5$ | 640.588 | 640.6866 |
| QF6 | $C_{40}H_{78}NO_6$ | 668.5829 | 668.7032 |
| QF7 | $C_{41}H_{80}NO_6$ | 682.5985 | 682.7867 |
| QF10 | $C_{38}H_{76}NO_5$ | 626.5723 | 626.6509 |
| QF11 | $C_{39}H_{78}NO_5$ | 640.588 | 640.6297 |
| ND25 | $C_{33}H_{67}N_3O_4$ | 570.5204 | 570.6493 |
| ND36 | $C_{36}H_{73}N_3O_3$ | 596.5725 | 596.6654 |
| ND75 | $C_{36}H_{74}N_4O_2$ | 595.5885 | 595.6977 |
| ND87 | $C_{37}H_{76}N_4O_4$ | 641.5939 | 641.7349 |
| NH32 | $C_{47}H_{96}N_3O_3$ | 750.7451 | 750.8913 |
| NH36 | $C_{48}H_{98}N_3O_3$ | 764.7608 | 764.8723 |
| NH60 | $C_{45}H_{93}N_4O_2$ | 735.7455 | 735.8695 |
| NH86 | $C_{48}H_{99}N_4O_4$ | 795.7666 | 795.804 |
| NH87 | $C_{49}H_{100}N_4O_4$ | 809.7822 | 809.8638 |

Q in the lipid name indicates that the amino groups of the lipid were quaternized using methyl iodide.
L indicates lipids prepared from the indicated acrylates and amines.
N indicates that the ester functional group of the acrylate has been replaced with an amide group.

Transfection Experiments.

14,000 cos-7 cells (ATCC, Manassas, Va.) were seeded into each well of a solid white or clear 96 well plate (Corning-Costar, Kennebunk, Me.) and allowed to attached overnight in growth medium, composed of: 500 ml phenol red minus DMEM, 50 ml heat inactivated FBS, 5 ml penicillin/streptomycin (Invitrogen, Carlsbad, Calif.).

A small liquot of lipid was tranferred to an Eppendorf tube. Based on the mass of the lipid in the tube, sterile 25 mM sodium acetate buffer was added to each tube to yield a concentration of 60 mg/ml. The resulting mixture was vortexed for approximately 20 minutes until the lipid was fully dissolved. DNA was prepared based on 300 ng DNA per well of a 96-well plate. 291 µg of Lc DNA was dissolved in 9210 µl of 25 mM sodium acetate buffer. Aliquots of 30 µl of DNA solution were added to each well expect for the last column which was reserved for the Lipo2000 standard. For the last column of the plate, 61 µg of DNA was added to 1940 µl Optimem. 150 µl of media/Optimem was added to each well of plates. 50 µl of lipid solution was aliquoted into wells of robot plate. The following amounts were aliquoted to obtain the correct ratios of DNA to lipid:

For 300 ng DNA well:

| w/w ratio | μl of lipid from robot plate | μl of NaOAc buffer |
|---|---|---|
| 2.5 | 5 | 195 |
| 5 | 10 | 190 |
| 10 | 20 | 180 |
| 15 | 30 | 170 |
| 20 | 40 | 160 |
| 25 | 50 | 150 |

In quadruplicate, 30 μl of lipid was aliquoted onto DNA in four rows for each ratio. For the Lipo2000 control (2.5 w/w ratio to DNA), 152.5 μg of Lipo sample was aliquoted into 1847.5 μl of Optimem. 30 μl of this solution was aliquoted onto DNA in the Optimem in the last columns of each plate. The plates were incubated for 15-20 minutes, and then 36.5 μl of lipid+DNA complexes was transferred into 150 μl of media/Optimem, then add to cells. The media was aspirated off the cells, and 105 μl of the lipid/DNA/media/Optimem solution was added to the cells. The luciferase assay was performed after 48 hours.

Luminescence was analyzed using bright-glo assay kits (Promega). Briefly, 100 μl of bright-glo solution was added to each well of the microtiter plate containing media and cells. Luminescence was measured using a Mithras Luminometer (Berthold, Oak Ridge, Tenn.). In some cases, a neutral density filter (Chroma, Brattleboro, Vt.) was used to prevent saturation of the luminometer. A standard curve for Luciferase was generated by titration of Luciferase enzyme (Promega) into growth media in white microtiter plates. Luciferase in ng per well are calculated for each of the lipids at 2.5 w/w, 5 w/w, 10 w/w, 15 w/w, 20 w/w, and 25 w/w lipid to DNA based on the standard curve. These data are shown in the table below. eGFP expression was examined using a Zeiss Aciovert 200 inverted microscope.

TABLE 2

Luciferase expression (measured in relative light units) as a percentage of that achieved using Lipofectamine ™ 2000 (ng per well) for lipids at specific lipid/DNA (w/w) ratios using 300 ng Luciferase DNA per well

| | 2.5 w/w | 5 w/w | 10 w/w | 15 w/w | 20 w/w | 25 w/w |
|---|---|---|---|---|---|---|
| QG7 | 0.4 | 0.3 | 0.5 | 0.3 | 0.4 | 0.3 |
| QB1 | 0.4 | 0.3 | 0.4 | 0.3 | 0.4 | 0.4 |
| QF1 | 0.4 | 0.3 | 0.4 | 0.3 | 0.3 | 0.3 |
| QG1 | 0.4 | 0.5 | 0.4 | 0.4 | 0.3 | 0.3 |
| QB77 | 0.4 | 0.4 | 0.4 | 0.3 | 0.3 | 0.3 |
| QF77 | 0.4 | 0.4 | 0.7 | 1.3 | 2.7 | 9.9 |
| QG77 | 0.5 | 0.6 | 1.5 | 5.6 | 18.8 | 29.5 |
| LD90 | 0.5 | 0.4 | 0.4 | 0.6 | 0.4 | 0.4 |
| LE90 | 0.5 | 0.3 | 0.4 | 0.4 | 0.4 | 0.4 |
| LF90 | 0.5 | 0.4 | 0.7 | 0.4 | 0.4 | 0.4 |
| LG90 | 0.6 | 0.6 | 0.4 | 0.4 | 0.4 | 0.4 |
| LB64 | 0.1 | 0.1 | 0.2 | 0.1 | 0.1 | 0.2 |
| LD64 | 0.1 | 0.1 | 0.1 | 0.1 | 0.1 | 0.1 |
| LE64 | 0.1 | 0.1 | 0.1 | 0.0 | 0.1 | 0.1 |
| LF64 | 0.1 | 0.1 | 0.4 | 0.1 | 0.2 | 0.1 |
| LG64 | 0.2 | 0.1 | 0.1 | 0.1 | 0.1 | 0.2 |
| LB31 | 1.2 | 0.8 | 8.3 | 1.9 | 1.3 | 4.2 |
| LD31 | 44.2 | 38.7 | 18.8 | 11.3 | 42.8 | 174.1 |
| LE31 | 1.0 | 1.0 | 0.9 | 2.5 | 2.9 | 9.5 |
| LF31 | 64.1 | 78.7 | 13.4 | 69.5 | 97.3 | 266.8 |
| LG31 | 19.6 | 27.6 | 34.0 | 8.5 | 14.3 | 94.0 |
| LB63 | 0.1 | 0.2 | 0.1 | 1.0 | 0.1 | 0.2 |
| ND28 | 124.8 | 116.0 | 28.9 | 0.0 | 0.0 | 0.0 |
| ND86 | 0.5 | 0.2 | 0.0 | 0.0 | 0.0 | 0.0 |
| ND87 | 0.0 | 0.0 | 0.0 | 0.0 | 0.0 | 0.0 |
| QB6 | 0.0 | 0.0 | 0.0 | 0.0 | 0.0 | 0.0 |
| QF6 | 0.0 | 0.0 | 0.0 | 0.0 | 0.0 | 0.0 |
| QG6 | 0.0 | 0.0 | 0.0 | 0.0 | 0.0 | 0.0 |
| QB7 | 0.0 | 0.0 | 0.0 | 0.0 | 0.0 | 0.0 |
| QF7 | 0.0 | 0.0 | 0.0 | 0.0 | 0.0 | 0.0 |
| LB1 | 0.1 | 0.1 | 0.1 | 0.1 | 0.1 | 0.2 |
| LB6 | 0.1 | 0.1 | 0.1 | 0.1 | 0.1 | 0.1 |
| LB7 | 0.1 | 0.1 | 0.1 | 0.1 | 0.1 | 0.2 |
| LB10 | 0.1 | 0.1 | 0.1 | 0.1 | 0.1 | 0.1 |
| LB11 | 0.1 | 0.1 | 0.1 | 0.1 | 0.1 | 0.1 |
| LB13 | 0.1 | 0.1 | 0.1 | 0.1 | 0.1 | 0.1 |
| LB15 | 0.1 | 0.1 | 0.1 | 0.1 | 0.1 | 0.1 |
| LB17 | 0.1 | 0.1 | 0.1 | 0.1 | 0.1 | 0.1 |
| LB20 | 0.1 | 0.1 | 0.4 | 0.2 | 0.3 | 0.7 |
| LB21 | 0.7 | 0.8 | 0.7 | 0.7 | 0.7 | 0.8 |
| LB22 | 0.3 | 0.3 | 0.4 | 0.4 | 0.4 | 0.4 |
| LB24 | 0.1 | 0.2 | 0.4 | 0.1 | 0.1 | 0.1 |
| LB25 | 0.8 | 2.4 | 2.6 | 3.3 | 2.3 | 1.8 |
| LB26 | 0.1 | 0.1 | 0.1 | 0.1 | 0.1 | 0.1 |
| LB28 | 0.1 | 0.1 | 0.1 | 0.1 | 0.1 | 0.1 |
| LB31 | 0.1 | 0.1 | 0.1 | 0.1 | 0.1 | 0.1 |
| LB32 | 0.1 | 0.1 | 0.1 | 0.1 | 0.1 | 0.1 |
| LB33 | 0.1 | 0.1 | 0.1 | 0.1 | 0.1 | 0.1 |
| LB34 | 0.1 | 0.1 | 0.2 | 0.4 | 0.1 | 0.1 |
| LB36 | 0.1 | 0.1 | 0.1 | 0.1 | 0.1 | 0.1 |
| LB38 | 0.7 | 0.8 | 0.7 | 0.8 | 0.7 | 0.8 |
| LB60 | 0.4 | 0.4 | 0.4 | 0.4 | 0.4 | 0.4 |
| LB61 | 0.1 | 0.1 | 0.1 | 0.1 | 0.1 | 0.1 |
| LB62 | 0.1 | 0.1 | 0.1 | 0.1 | 0.1 | 0.1 |
| LB63 | 0.1 | 0.1 | 0.1 | 0.1 | 0.1 | 0.1 |
| LB64 | 0.1 | 0.1 | 0.1 | 0.1 | 0.1 | 0.1 |
| LB70 | 0.1 | 0.1 | 0.1 | 0.1 | 0.1 | 0.1 |
| LB75 | 0.1 | 0.1 | 0.1 | 0.1 | 0.1 | 0.1 |
| LB76 | 0.1 | 0.1 | 0.1 | 0.1 | 0.1 | 0.1 |
| LB77 | 0.1 | 0.1 | 0.1 | 0.2 | 0.1 | 0.3 |
| LB79 | 0.1 | 0.1 | 0.1 | 0.1 | 0.1 | 0.1 |
| LB80 | 0.7 | 0.8 | 0.1 | 0.2 | 1.0 | 1.5 |
| LB81 | 0.4 | 0.4 | 0.2 | 0.3 | 0.4 | 0.5 |
| LF1 | 0.1 | 0.1 | 0.0 | 0.0 | 0.1 | 0.1 |
| LF64 | 0.1 | 0.1 | 0.0 | 0.0 | 0.1 | 0.1 |
| LF7 | 0.1 | 0.1 | 0.0 | 0.0 | 0.1 | 0.1 |
| LF10 | 0.1 | 0.1 | 0.0 | 0.0 | 0.1 | 0.1 |
| LF11 | 0.1 | 0.1 | 0.0 | 0.0 | 0.1 | 0.1 |
| LF13 | 0.1 | 0.1 | 0.0 | 0.0 | 0.1 | 0.1 |
| LF15 | 0.1 | 0.1 | 0.0 | 0.0 | 0.1 | 0.1 |
| LF17 | 0.1 | 0.1 | 0.1 | 0.1 | 0.1 | 0.1 |
| LF20 | 0.2 | 0.4 | 0.3 | 0.2 | 0.1 | 0.1 |
| LF21 | 0.4 | 0.4 | 0.4 | 0.4 | 0.4 | 0.4 |
| LD28 | | | 1.7 | 8.5 | | |
| LD86 | | | 29.6 | 16.0 | | |
| LD87 | | | 53.9 | 43.3 | | |
| LG34 | | | 1.4 | 0.8 | | |
| LG77 | | | 43.5 | 34.0 | | |
| LH28 | | | 0.2 | 0.2 | | |
| QD28 | | | 0.1 | 0.1 | | |
| QD86 | | | 2.0 | 2.0 | | |
| QD87 | | | 0.5 | 0.7 | | |
| LF22 | 0.1 | 0.1 | 0.1 | 0.1 | 0.1 | 0.1 |
| LF24 | 0.1 | 0.1 | 0.1 | 0.2 | 0.3 | 0.3 |
| LF25 | 0.1 | 0.2 | 0.3 | 0.4 | 0.9 | 1.5 |
| LF26 | 0.1 | 0.2 | 0.7 | 0.1 | 0.1 | 0.3 |
| LF28 | 0.1 | 0.1 | 0.1 | 0.2 | 0.3 | 0.4 |
| LF32 | 0.1 | 0.1 | 0.2 | 0.1 | 0.4 | 0.4 |
| LF33 | 0.1 | 0.1 | 0.1 | 0.1 | 0.1 | 0.1 |
| LF34 | 0.1 | 0.3 | 1.1 | 0.5 | 0.2 | 0.3 |
| LF36 | 0.1 | 0.1 | 0.1 | 0.1 | 0.1 | 0.1 |
| LF38 | 0.8 | 0.9 | 0.9 | 0.9 | 0.8 | 1.0 |
| LF60 | 0.4 | 0.4 | 0.5 | 0.5 | 0.5 | 0.5 |
| LF61 | 0.1 | 0.1 | 0.1 | 0.1 | 0.1 | 0.1 |
| LF62 | 0.1 | 0.1 | 0.2 | 0.1 | 0.4 | 0.2 |
| LF63 | 0.1 | 0.1 | 0.1 | 0.3 | 0.3 | 0.4 |

TABLE 2-continued

Luciferase expression (measured in relative light units) as a percentage of that achieved using Lipofectamine ™ 2000 (ng per well) for lipids at specific lipid/DNA (w/w) ratios using 300 ng Luciferase DNA per well

|  | 2.5 w/w | 5 w/w | 10 w/w | 15 w/w | 20 w/w | 25 w/w |
|---|---|---|---|---|---|---|
| LF64 | 0.1 | 0.1 | 0.1 | 0.1 | 0.1 | 0.1 |
| LF70 | 0.1 | 0.1 | 0.2 | 0.3 | 0.2 | 0.3 |
| LF75 | 0.7 | 1.0 | 0.7 | 1.9 | 1.7 | 1.7 |
| LF76 | 1.7 | 5.6 | 9.8 | 24.3 | 22.2 | 19.5 |
| LF77 | 3.7 | 25.1 | 28.2 | 24.1 | 17.0 | 22.1 |
| LF79 | 0.1 | 0.3 | 0.3 | 0.3 | 0.3 | 0.3 |
| LF80 | 2.5 | 35.1 | 35.5 | 34.3 | 19.9 | 14.8 |
| LF81 | 0.5 | 1.6 | 1.5 | 4.9 | 4.6 | 4.0 |
| LF82 | 0.4 | 0.3 | 0.7 | 0.5 | 0.6 | 0.8 |
| LF86 | 21.5 | 17.9 | 19.6 | 21.2 | 10.5 | 10.4 |
| LF87 | 19.4 | 11.3 | 30.2 | 13.3 | 11.0 | 10.0 |
| LF90 | 0.4 | 0.5 | 0.3 | 1.3 | 1.1 | 1.5 |
| LF91 | 0.5 | 0.5 | 0.8 | 1.4 | 1.3 | 1.6 |
| LF93 | 32.0 | 50.4 | 15.0 | 150.7 | 143.2 | 171.3 |
| LF94 | 41.8 | 37.7 | 96.3 | 114.7 | 99.0 | 98.6 |
| LF95 | 15.3 | 51.3 | 44.3 | 71.8 | 64.6 | 75.1 |
| LF96 | 52.4 | 62.8 | 79.3 | 47.7 | 64.4 | 36.0 |
| LF98 | 2.5 | 7.9 | 17.8 | 17.2 | 9.5 | 9.9 |
| LF99 | 32.2 | 49.8 | 26.5 | 10.7 | 6.0 | 6.2 |
| LF100 | 17.6 | 70.0 | 69.0 | 85.9 | 44.2 | 50.9 |
| LF103 | 43.9 | 11.6 | 65.4 | 91.8 | 61.6 | 61.4 |
| LF109 | 16.0 | 28.3 | 16.9 | 21.9 | 28.7 | 49.5 |
| LG1 | 0.0 | 0.0 | 0.0 | 0.0 | 0.0 | 0.0 |
| LG64 | 0.0 | 0.0 | 0.0 | 0.0 | 0.0 | 0.0 |
| LG77 | 0.0 | 0.0 | 0.0 | 0.0 | 0.0 | 0.0 |
| LG10 | 0.0 | 0.0 | 0.0 | 0.0 | 0.0 | 0.0 |
| LG11 | 0.0 | 0.0 | 0.0 | 0.0 | 0.0 | 0.0 |
| LG13 | 0.0 | 0.0 | 0.0 | 0.0 | 0.0 | 0.0 |
| LG15 | 0.7 | 0.8 | 0.5 | 0.6 | 0.7 | 0.8 |
| LG17 | 0.4 | 0.3 | 0.1 | 0.0 | 0.3 | 0.3 |
| LG20 | 2.0 | 2.5 | 0.4 | 0.2 | 0.1 | 0.1 |
| LG21 | 0.1 | 0.1 | 0.1 | 0.2 | 0.2 | 0.4 |
| LG22 | 0.2 | 0.3 | 0.4 | 0.5 | 0.4 | 0.7 |
| LG24 | 2.0 | 3.3 | 4.8 | 11.2 | 16.4 | 32.5 |
| LG25 | 15.9 | 32.0 | 43.2 | 56.9 | 42.1 | 63.9 |
| LG26 | 0.6 | 13.0 | 1.9 | 0.5 | 0.3 | 0.4 |
| LG28 | 0.2 | 0.5 | 0.2 | 0.2 | 0.1 | 0.2 |
| LG32 | 0.2 | 10.2 | 1.0 | 0.7 | 0.4 | 0.7 |
| LG33 | 0.1 | 0.1 | 0.1 | 0.1 | 0.1 | 0.1 |
| LG60 | 0.9 | 1.0 | 0.8 | 0.9 | 0.8 | 1.0 |
| LG61 | 0.4 | 0.5 | 0.4 | 0.4 | 0.4 | 0.5 |
| LG63* | 0.5 | 0.5 | 0.5 | 0.5 | 0.5 | 0.7 |
| LG64* | 0.3 | 0.3 | 1.8 | 1.8 | 1.2 | 1.6 |
| LG75* | 0.9 | 1.1 | 3.1 | 4.7 | 3.1 | 5.3 |
| LG76* | 6.2 | 14.1 | 21.4 | 48.6 | 54.1 | 92.5 |
| LG79* | 0.6 | 0.4 | 1.5 | 1.6 | 1.4 | 1.4 |
| LG93* | 45.0 | 43.8 | 310.5 | 281.8 | 185.9 | 183.8 |
| 160A* | 0.4 | 0.4 | 1.7 | 1.5 | 1.1 | 1.1 |
| 160B* | 0.8 | 0.8 | 1.1 | 1.1 | 0.9 | 0.9 |
| 160C* | 0.5 | 0.5 | 0.7 | 0.7 | 0.6 | 0.8 |
| 160D* | 0.5 | 0.3 | 0.4 | 0.4 | 0.3 | 0.3 |
| 160E* | 0.6 | 0.5 | 0.6 | 0.6 | 0.6 | 0.3 |
| LD109 | 9.3 | 18.6 | 31.1 | 20.7 | 7.0 | 2.0 |
| LD103 | 11.6 | 17.2 | 24.4 | 27.1 | 12.3 | 6.6 |
| LD100 | 3.9 | 1.5 | 12.0 | 15.3 | 6.9 | 1.3 |
| LD99 | 4.4 | 12.8 | 44.6 | 27.0 | 6.2 | 0.8 |
| LD98 | 0.2 | 0.7 | 0.8 | 1.0 | 0.8 | 0.6 |
| LD96 | 2.3 | 0.3 | 1.3 | 3.6 | 1.2 | 0.4 |
| LD95 | 1.2 | 19.5 | 3.6 | 9.1 | 9.4 | 5.9 |
| LD94 | 1.5 | 5.9 | 2.0 | 8.5 | 9.2 | 7.3 |
| LD93 | 1.8 | 4.2 | 3.9 | 24.6 | 15.8 | 10.8 |
| LD91 | 0.2 | 0.2 | 0.2 | 0.2 | 0.2 | 0.2 |
| LD90 | 0.4 | 0.4 | 0.4 | 0.4 | 0.5 | 0.5 |
| LD82 | 0.1 | 0.1 | 0.2 | 0.3 | 0.4 | 0.7 |
| LD81 | 0.1 | 0.1 | 15.2 | 7.6 | 5.4 | 2.3 |
| LD80 | 0.1 | 0.1 | 3.7 | 6.5 | 7.1 | 2.1 |
| LD79 | 0.1 | 0.1 | 0.1 | 0.2 | 0.3 | 0.2 |
| LD77 | 0.1 | 0.1 | 6.9 | 11.1 | 6.4 | 2.9 |
| LD76 | 0.1 | 0.1 | 0.2 | 0.3 | 0.2 | 0.4 |
| LD75 | 0.1 | 0.1 | 0.1 | 0.2 | 0.2 | 0.2 |
| LD70 | 0.1 | 0.1 | 0.6 | 0.6 | 0.6 | 0.6 |
| LD64 | 0.1 | 0.1 | 0.3 | 0.3 | 0.3 | 0.4 |
| LD63 | 0.7 | 0.8 | 0.3 | 0.3 | 0.4 | 0.6 |
| LD62 | 0.4 | 0.4 | 0.4 | 0.4 | 0.4 | 0.5 |
| LG109 | 16.3 | 36.0 | 23.4 | 37.9 | 25.7 | 34.5 |
| LG100 | 21.5 | 32.7 | 11.8 | 18.0 | 8.6 | 8.1 |
| LG98 | 0.7 | 2.3 | 13.2 | 9.8 | 6.8 | 7.8 |
| LG96 | 46.7 | 82.9 | 37.3 | 32.6 | 14.1 | 18.5 |
| LG93 | 3.6 | 9.2 | 19.8 | 37.3 | 24.0 | 24.6 |
| LG91 | 0.2 | 0.2 | 0.1 | 0.2 | 0.1 | 0.1 |
| LG90 | 0.1 | 0.1 | 0.0 | 0.0 | 0.1 | 0.0 |
| LG87 | 14.5 | 7.5 | 9.2 | 10.4 | 5.9 | 4.7 |
| LG82 | 0.2 | 0.2 | 0.6 | 0.8 | 0.5 | 1.2 |
| LG81 | 0.7 | 0.8 | 1.2 | 4.1 | 14.8 | 19.9 |
| LG80 | 2.2 | 11.9 | 19.8 | 31.3 | 21.9 | 17.4 |
| LH1 | 0.0 | 0.0 | 0.0 | 0.0 | 0.0 | 0.0 |
| LH6 | 0.0 | 0.0 | 0.0 | 0.0 | 0.0 | 0.0 |
| LH7 | 0.0 | 0.0 | 0.0 | 0.0 | 0.0 | 0.0 |
| LH10 | 0.0 | 0.0 | 0.0 | 0.0 | 0.0 | 0.0 |
| LH11 | 0.0 | 0.0 | 0.0 | 0.0 | 0.0 | 0.0 |
| LH13 | 0.0 | 0.0 | 0.0 | 0.0 | 0.0 | 0.0 |
| LH15 | 0.0 | 0.0 | 0.0 | 0.0 | 0.0 | 0.0 |
| LH17 | 0.0 | 0.0 | 0.0 | 0.0 | 0.0 | 0.0 |
| LH20 | 0.0 | 0.0 | 0.0 | 0.0 | 0.0 | 0.0 |
| LH21 | 0.0 | 0.0 | 0.0 | 0.0 | 0.0 | 0.0 |
| LH22 | 0.0 | 0.0 | 0.0 | 0.0 | 0.0 | 0.0 |

Q in the lipid name indicates that the tertiary amines of the lipid were quaternized using methyl iodide.
L indicates lipids prepared from the indicated acrylates and amines.
N indicates that the ester functional group of the acrylate has been replaced with an amide group.
*indicates 72 hours incubation before bright-glo.

The table below summarizes the data as a % of the luciferase activity obtained from the use of Lipofectamine 2000. The table indicates the best lipids for transfection.

TABLE 3

|  | 2.5 w/w | 5 w/w | 10 w/w | 15 w/w | 20 w/w | 25 w/w |
|---|---|---|---|---|---|---|
| LD28 |  |  | 1.7 | 8.5 |  |  |
| LD31 | 44.2 | 38.7 | 18.8 | 11.3 | 42.8 | 174.1 |
| LD77 | 0.1 | 0.1 | 6.9 | 11.1 | 6.4 | 2.9 |
| LD81 | 0.1 | 0.1 | 15.2 | 7.6 | 5.4 | 2.3 |
| LD86 |  |  | 29.6 | 16.0 |  |  |
| LD87 |  |  | 53.9 | 43.3 |  |  |
| LD93 | 1.8 | 4.2 | 3.9 | 24.6 | 15.8 | 10.8 |
| LD94 | 1.5 | 5.9 | 2.0 | 8.5 | 9.2 | 7.3 |
| LD95 | 1.2 | 19.5 | 3.6 | 9.1 | 9.4 | 5.9 |
| LD99 | 4.4 | 12.8 | 44.6 | 27.0 | 6.2 | 0.8 |
| LD100 | 3.9 | 1.5 | 12.0 | 15.3 | 6.9 | 1.3 |
| LD103 | 11.6 | 17.2 | 24.4 | 27.1 | 12.3 | 6.6 |
| LD109 | 9.3 | 18.6 | 31.1 | 20.7 | 7.0 | 2.0 |
| LE86 | 31.1 | 22.7 | 22.6 | 2.5 | 0.0 | 0.0 |
| LE87 | 10.5 | 9.0 | 38.4 | 4.3 | 0.0 | 0.0 |
| LE96 | 13.5 | 0.5 | 0.0 | 0.0 | 0.0 | 0.0 |
| LE99 | 9.9 | 5.4 | 13.7 | 2.7 | 0.0 | 0.0 |
| LE103 | 20.4 | 22.1 | 11.8 | 2.8 | 0.0 | 0.0 |
| LE109 | 1.5 | 5.3 | 28.7 | 18.0 | 1.8 | 0.6 |
| LF31 | 64.1 | 78.7 | 13.4 | 69.5 | 97.3 | 266.8 |
| LF76 | 1.7 | 5.6 | 9.8 | 24.3 | 22.2 | 19.5 |
| LF77 | 3.7 | 25.1 | 28.2 | 24.1 | 17.0 | 22.1 |
| LF80 | 2.5 | 35.1 | 35.5 | 34.3 | 19.9 | 14.8 |
| LF86 | 21.5 | 17.9 | 19.6 | 21.2 | 10.5 | 10.4 |
| LF87 | 19.4 | 11.3 | 30.2 | 13.3 | 11.0 | 10.0 |
| LF93 | 32.0 | 50.4 | 15.0 | 150.7 | 143.2 | 171.3 |
| LF94 | 41.8 | 37.7 | 96.3 | 114.7 | 99.0 | 98.6 |
| LF95 | 15.3 | 51.3 | 44.3 | 71.8 | 64.6 | 75.1 |
| LF96 | 52.4 | 62.8 | 79.3 | 47.7 | 64.4 | 36.0 |
| LF98 | 2.5 | 7.9 | 17.8 | 17.2 | 9.5 | 9.9 |
| LF99 | 32.2 | 49.8 | 26.5 | 10.7 | 6.0 | 6.2 |
| LF100 | 17.6 | 70.0 | 69.0 | 85.9 | 44.2 | 50.9 |
| LF103 | 43.9 | 11.6 | 65.4 | 91.8 | 61.6 | 61.4 |
| LF109 | 16.0 | 28.3 | 16.9 | 21.9 | 28.7 | 49.5 |

TABLE 3-continued

|       | 2.5 w/w | 5 w/w | 10 w/w | 15 w/w | 20 w/w | 25 w/w |
|-------|---------|-------|--------|--------|--------|--------|
| LG25  | 15.9    | 32.0  | 43.2   | 56.9   | 42.1   | 63.9   |
| LG31  | 19.6    | 27.6  | 34.0   | 8.5    | 14.3   | 94.0   |
| LG32  | 0.2     | 10.2  | 1.0    | 0.7    | 0.4    | 0.7    |
| LG76* | 6.2     | 14.1  | 21.4   | 48.6   | 54.1   | 92.5   |
| LG77  |         |       |        | 43.5   | 34.0   |        |
| LG80  | 2.2     | 11.9  | 19.8   | 31.3   | 21.9   | 17.4   |
| LG81  | 0.7     | 0.8   | 1.2    | 4.1    | 14.8   | 19.9   |
| LG87  | 14.5    | 7.5   | 9.2    | 10.4   | 5.9    | 4.7    |
| LG93* | 3.6     | 9.2   | 19.8   | 37.3   | 24.0   | 24.6   |
| LG96  | 46.7    | 82.9  | 37.3   | 32.6   | 14.1   | 18.5   |
| LG98  | 0.7     | 2.3   | 13.2   | 9.8    | 6.8    | 7.8    |
| LG100 | 21.5    | 32.7  | 11.8   | 18.0   | 8.6    | 8.1    |
| LG109 | 16.3    | 36.0  | 23.4   | 37.9   | 25.7   | 34.5   |
| LG93  | 45.0    | 43.8  | 310.5  | 281.8  | 185.9  | 183.8  |
| ND28  | 124.8   | 116.0 | 28.9   | 0.0    | 0.0    | 0.0    |
| QG75  | 10.0    | 20.6  | 34.0   | 2.7    | 1.0    | 0.8    |
| QG76  | 5.6     | 16.9  | 20.7   | 2.5    | 0.0    | 0.0    |
| QG80  | 1.3     | 4.9   | 32.2   | 68.4   | 36.2   | 24.5   |
| QG81  | 0.7     | 3.6   | 41.1   | 15.5   | 2.4    | 1.4    |
| QG82  | 25.0    | 24.6  | 32.6   | 8.6    | 2.3    | 1.4    |
| QG87  | 89.0    | 94.0  | 42.4   | 64.7   | 62.1   | 44.1   |
| QG90  | 1.1     | 4.3   | 7.7    | 17.4   | 7.3    | 5.4    |
| QG91  | 0.4     | 3.3   | 25.9   | 45.2   | 18.5   | 2.8    |

TABLE 3-continued

|        | 2.5 w/w | 5 w/w | 10 w/w | 15 w/w | 20 w/w | 25 w/w |
|--------|---------|-------|--------|--------|--------|--------|
| QG98   | 2.1     | 10.3  | 22.3   | 14.9   | 9.3    | 4.5    |
| QG100  | 11.2    | 32.1  | 57.1   | 102.6  | 93.0   | 94.5   |
| QG109  | 29.9    | 40.6  | 31.3   | 52.6   | 51.3   | 46.6   |

Q in the lipid name indicates that the tertiary amines of the lipid were quaternized using methyl iodide.
L indicates lipids prepared from the indicated acrylates and amines.
N indicates that the ester functional group of the acrylate has been replaced with an amide group.
*indicates 72 hour incubuation before bright-glo.

Example 2

Testing of Lipids for RNA Delivery

Reporter-protein knockdown achieved by the top transfecting lipids relative to Lipofectamine™ 2000 (where negative values indicate improved knockdown). The assay accounts for toxicity, monitoring expression of both renilla and firefly luciferases, where the latter serves as viability control. For each lipid, 50 ng of siRNA was added per well at specific lipid/RNA w/w ratios (from top to bottom: 2.5, 5, 10, 15).

| ND95     | ND98     | ND99     | ND100    | NF96    | LD31     | LE87     | LF31     | LF95     | LG32     |
|----------|----------|----------|----------|---------|----------|----------|----------|----------|----------|
| 19.8058  | −4.00473 | −10.1961 | 10.88263 | −6.262  | 15.3558  | 5.504325 | 50.09235 | 36.29344 | 58.10496 |
| 8.318854 | −4.48242 | −9.86007 | −7.54577 | −2.03466| −7.89703 | −6.92331 | 11.94445 | 28.86141 | 41.51079 |
| −5.20544 | −4.63444 | −18.2728 | −21.4945 | 63.19863| −15.5821 | −8.53319 | −0.82516 | −2.22361 | 44.71105 |
| −7.16345 | −13.9514 | −20.0273 | −8.3303  | 90.8142 | −16.8831 | −15.2929 | −10.5366 | −8.09928 | −13.6483 |

| LG77     | LG80     | LG96     | LG100    | LG109    | QD99     | QF99     | NG64     | QF100    | LG31     |
|----------|----------|----------|----------|----------|----------|----------|----------|----------|----------|
| 71.00772 | 2.006687 | 27.952   | 33.5374  | 55.7409  | 11.53579 | 9.026287 | −11.7697 | 24.82954 | 41.00232 |
| −0.05414 | −9.08975 | −20.9722 | 15.36957 | 43.90063 | 5.050401 | −1.83976 | −34.6712 | 1.751482 | 21.06244 |
| −7.72114 | −15.9409 | −38.0741 | −21.8017 | −5.23097 | −27.9145 | −8.99917 | 3.073073 | −0.8059  | −2.71354 |
| −21.3897 | −21.0263 | −31.1828 | −20.7012 | −11.1255 | −22.3471 | −34.0996 | 1.439032 | 0.212713 | −5.76419 |

Example 3

Testing of Lipids for DNA Delivery

Raw values for luciferase expression (relative lights units) of best-transfecting lipids at lipid/DNA (w/w) ratios listed. 300 ng of DNA was added per well.

|          | 2.5 w/w  | 5 w/w    |          | 10 w/w   | 15 w/w   |
|----------|----------|----------|----------|----------|----------|
| ND20     | 6868960  | 4880532  |          |          |          |
| ND21     | 1170534  | 1213862  |          |          |          |
| ND22     | 721270   | 1083569  |          |          |          |
| LIPO2000 | 2467624  | 1754800  |          |          |          |
| ND24     | 5256861  | 1231973  |          |          |          |
| ND25     | 7548491  | 5088120  |          |          |          |
| ND28     | 20925873 | 1299887  |          |          |          |
| ND32     | 17713202 | 2745231  | ND31     | 1154404  | 936815   |
| ND36     | 4517622  | 2945357  | ND36     | 2043526  | 658985   |
| LIPO2000 | 3334772  | 4043316  | LIPO2000 | 2424297  | 2086728  |
|          |          |          | ND66     | 835433   | 1291599  |
|          |          |          | LIPO2000 | 30344816 | 28204810 |
| ND94     | 774425   | 1382667  |          |          |          |
| ND95     | 2875811  | 4619654  | ND95     | 7977064  | 10279185 |
| ND96     | 2910700  | 42837    |          |          |          |
| ND98     | 5649897  | 791660   |          |          |          |
| LIPO2000 | 25489210 | 14945620 | LIPO2000 | 21192523 | 19239706 |
| ND99     | 10252260 | 9886021  |          |          |          |
| ND100    | 2713327  | 294518   |          |          |          |
| ND109    | 2197484  | 2087995  |          |          |          |
| NF1      | 778473   | 227587   |          |          |          |
| NF10     | 1192178  | 838283   |          |          |          |
| LIPO2000 | 13040527 | 10774995 |          |          |          |

-continued

| | | | | | |
|---|---|---|---|---|---|
| NF20 | 1814886 | 1801431 | | | |
| NF25 | 2473702 | 1366194 | | | |
| LIPO2000 | 19020395 | 15427061 | | | |
| NF61 | 4332331 | 3689556 | NF60 | 2401570 | 3739668 |
| NF63 | 1141469 | 865897 | NF63 | 3031718 | 1138429 |
| NF64 | 384317 | 2283250 | NF70 | 1605749 | 887500 |
| LIPO2000 | 6776111 | 5451663 | LIPO2000 | 8309497 | 7617169 |
| NF86 | 4798383 | 4087285 | | | |
| NF87 | 3904993 | 3436007 | | | |
| NF91 | 1993690 | 1670695 | | | |
| LIPO2000 | 8463204 | 7664209 | | | |
| NF95 | 1839462 | 2082965 | NF95 | 1906488 | 918612 |
| NF96 | 3095896 | 650770 | | | |
| NF100 | 1061441 | 8015 | | | |
| NF103 | 2559344 | 347240 | | | |
| NF109 | 2867865 | 678968 | | | |
| LIPO2000 | 1397825 | 1469076 | LIPO2000 | 1897360 | 2712535 |
| NG61 | 1452027 | 765795 | | | |
| NG64 | 2585784 | 1972838 | | | |
| LIPO2000 | 7992593 | 9351046 | | | |
| NG77 | 972002 | 1184771 | | | |
| NG86 | 1357355 | 1521687 | NG86 | 1513703 | 1223360 |
| NG87 | 823764 | 1005875 | | | |
| LIPO2000 | 6188050 | 5383340 | LIPO2000 | 4484218 | 6094431 |
| | | | NG95 | 834849 | 1208120 |
| | | | LIPO2000 | 2308433 | 3627875 |
| NP62 | 1443678 | 33188 | | | |
| NP63 | 1180418 | 1543275 | NP63 | 1388102 | 798342 |
| LIPO2000 | 15535841 | 14019561 | LIPO2000 | 15019226 | 14524819 |
| | | | NP86 | 595340 | 1323915 |
| | | | NP87 | 1207376 | 1192838 |
| | | | LIPO2000 | 8746668 | 10523338 |
| NP96 | 4598787 | 288439 | | | |
| NP98 | 7860614 | 24812 | | | |
| NP99 | 3202948 | 9767 | | | |
| NP103 | 8798627 | 308844 | | | |
| NP109 | 37952 | 19829 | | | |
| NF95 | 12051 | 3775212 | | | |
| NF103 | 19086 | 7008052 | NF103 | 2886271 | 772518 |
| NF109 | 85471 | 3352713 | NF109 | 1151621 | 108854 |
| LIPO2000 | 10602791 | 11196771 | LIPO2000 | 11152535 | 11535693 |
| ND20 | 7521540 | 435731 | | | |
| ND98 | 6947385 | 5165088 | ND98 | 1824773 | 643862 |
| ND99 | 11757295 | 7656193 | | | |
| ND100 | 5544902 | 2936058 | | | |
| NF61 | 458095 | 3053999 | | | |
| NF96 | 7037710 | 3202668 | NF96 | 2048655 | 167043 |
| NF103 | 5865613 | 4028907 | | | |
| NF109 | 6605163 | 1767496 | | | |
| LIPO2000 | 8861025 | 7852498 | LIPO2000 | 7017261 | 6964853 |

| | 2.5 w/w | 5 w/w | 10 w/w | 15 w/w | 20 w/w | 25 w/w | |
|---|---|---|---|---|---|---|---|
| LD31 | 44.2 | 38.7 | 18.8 | 11.3 | 42.8 | 174.1 | |
| LD87 | | | 53.9 | 43.3 | | | |
| LF31 | 64.1 | 78.7 | 13.4 | 69.5 | 97.3 | 266.8 | |
| LF93 | 32.0 | 50.4 | 15.0 | 150.7 | 143.2 | 171.3 | |
| LF94 | 41.8 | 37.7 | 96.3 | 114.7 | 99.0 | 98.6 | |
| LF95 | 15.3 | 51.3 | 44.3 | 71.8 | 64.6 | 75.1 | |
| LF96 | 52.4 | 62.8 | 79.3 | 47.7 | 64.4 | 36.0 | |
| LF99 | 32.2 | 49.8 | 26.5 | 10.7 | 6.0 | 6.2 | |
| LF100 | 17.6 | 70.0 | 69.0 | 85.9 | 44.2 | 50.9 | |
| LF103 | 43.9 | 11.6 | 65.4 | 91.8 | 61.6 | 61.4 | |
| LF109 | 16.0 | 28.3 | 16.9 | 21.9 | 28.7 | 49.5 | |
| LG25 | 15.9 | 32.0 | 43.2 | 56.9 | 42.1 | 63.9 | |
| LG31 | 19.6 | 27.6 | 34.0 | 8.5 | 14.3 | 94.0 | |
| LG76 | 6.2 | 14.1 | 21.4 | 48.6 | 54.1 | 92.5 | * 72 hours incubation before bright-glo |
| LG96 | 46.7 | 82.9 | 37.3 | 32.6 | 14.1 | 18.5 | |
| LG93 | 45.0 | 43.8 | 310.5 | 281.8 | 185.9 | 183.8 | * 72 hours incubation before bright-glo |
| ND28 | 124.8 | 116.0 | 28.9 | 0.0 | 0.0 | 0.0 | |
| QF80 | 0.4 | 1.4 | 10.9 | 52.7 | 35.1 | 20.8 | |
| QF86 | 61.1 | 58.1 | 53.2 | 27.8 | 22.2 | 19.6 | |
| QF87 | 11.7 | 41.8 | 57.2 | 64.0 | 53.5 | 45.4 | |
| QF91 | 0.3 | 2.1 | 36.4 | 51.2 | 23.0 | 12.1 | |
| QF94 | 34.2 | 37.6 | 42.5 | 53.6 | 47.7 | 35.6 | |
| QD99 | 5.1 | 22.9 | 16.9 | 83.1 | 91.7 | 96.9 | |
| QD109 | 40.3 | 65.7 | 71.0 | 60.5 | 44.0 | 32.9 | |
| LB100 | 0.0 | 0.9 | 13.2 | 39.9 | 46.6 | 29.0 | |
| LB109 | 0.0 | 0.9 | 1.9 | 13.5 | 47.1 | 61.6 | |

-continued

| | | | | | | | | | | |
|---|---|---|---|---|---|---|---|---|---|---|
| QG80 | 1.3 | 4.9 | 32.2 | 68.4 | 36.2 | 24.5 | | | | |
| QG87 | 89.0 | 94.0 | 42.4 | 64.7 | 62.1 | 44.1 | | | | |
| QG100 | 11.2 | 32.1 | 57.1 | 102.6 | 93.0 | 94.5 | | | | |
| QG109 | 29.9 | 40.6 | 31.3 | 52.6 | 51.3 | 46.6 | | | | |
| ND20 | 278.4 | 278.1 | 0.2 | 0.1 | 0.0 | 0.0 | ND20 | 84.9 | 5.5 | 0.1 | 0.0 |
| ND21 | 47.4 | 69.2 | 18.7 | 2.6 | 0.1 | 0.4 | | | | |
| ND22 | 29.2 | 61.7 | 48.0 | 4.4 | 0.4 | 0.2 | | | | |
| ND24 | 157.6 | 30.5 | 2.4 | 0.2 | 0.0 | 0.0 | | | | |
| ND25 | 226.4 | 125.8 | 19.5 | 0.5 | 0.0 | 0.0 | | | | |
| ND26 | 13.4 | 2.3 | 0.1 | 0.0 | 0.0 | 0.0 | | | | |
| ND28 | 627.5 | 32.1 | 0.1 | 0.1 | 0.0 | 0.0 | | | | |
| ND31 | 7.7 | 5.6 | 47.6 | 44.9 | 7.6 | 19.7 | | | | |
| ND32 | 531.2 | 67.9 | 1.1 | 0.1 | 0.0 | 0.0 | | | | |
| ND36 | 135.5 | 72.8 | 84.3 | 31.6 | 0.8 | 0.0 | | | | |
| ND95 | 11.3 | 30.9 | 37.6 | 53.4 | 37.8 | 54.0 | | | | |
| ND98 | 22.2 | 5.3 | 0.5 | 0.4 | 0.4 | 0.3 | ND98 | 78.4 | 65.8 | 26.0 | 9.2 |
| ND99 | 16.8 | 36.5 | 78.6 | 91.7 | | | ND99 | 132.7 | 97.5 | 6.8 | 2.2 |
| ND100 | 45.7 | 48.0 | 20.8 | 2.7 | | | ND100 | 62.6 | 37.4 | 2.5 | 0.6 |
| NF60 | 6.8 | 21.9 | 28.9 | 49.1 | | | NF61 | 5.2 | 38.9 | 8.6 | 1.1 |
| NF61 | 63.9 | 67.7 | 7.0 | 2.9 | | | | | | | |
| NF64 | 5.7 | 41.9 | 0.3 | 0.1 | | | | | | | |
| NF86 | 56.7 | 53.3 | 4.5 | 2.3 | | | | | | | |
| NF87 | 46.1 | 44.8 | 0.3 | 0.0 | | | | | | | |
| NF95 | 131.6 | 141.8 | 100.5 | 33.9 | | | NF95 | 6.0 | 9.4 | 4.7 | 12.1 |
| NF96 | 221.5 | 44.3 | 0.2 | 0.1 | | | NF96 | 79.4 | 40.8 | 29.2 | 2.4 |
| NF100 | 75.9 | 0.5 | 0.0 | 0.0 | | | | | | | |
| NF103 | 183.1 | 23.6 | 0.0 | 0.0 | | | NF103 | 66.2 | 51.3 | 0.6 | 0.0 |
| NF109 | 205.2 | 46.2 | 1.7 | 0.0 | | | NF109 | 74.5 | 22.5 | 3.9 | 1.6 |
| NP96 | 43.4 | 2.6 | 7.1 | 8.2 | | | | | | | |
| NP98 | 74.1 | 0.2 | 0.3 | 0.4 | | | NP98 | 0.4 | 0.3 | 0.3 | 0.2 |
| NP103 | 83.0 | 2.8 | 0.0 | 1.5 | | | NP103 | 2.1 | 2.3 | 3.8 | 1.4 |

The data in the second set of columns represents is a replicate set of data for certain experiments.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A compound of formula:

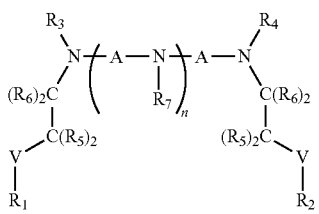

or a salt thereof;
wherein:
A is acyclic, substituted or unsubstituted, branched or unbranched aliphatic; or acyclic, substituted or unsubstituted, branched or unbranched heteroaliphatic;
V is $C=O$;
$R_1$ is cyclic or acyclic, substituted or unsubstituted, branched or unbranched aliphatic; substituted or unsubstituted aryl; substituted or unsubstituted heteroaryl; $-OR_A$; $-SR_A$; or $-NHR_A$; wherein each occurrence of $R_A$ is independently cyclic or acyclic, substituted or unsubstituted, branched or unbranched $C_9$-$C_{16}$ aliphatic; substituted or unsubstituted aryl; or substituted or unsubstituted heteroaryl;
$R_2$ is cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR_B$; $-SR_B$; or $-NHR_B$; wherein each occurrence of $R_B$ is independently cyclic or acyclic, substituted or unsubstituted, branched or unbranched $C_9$-$C_{16}$ aliphatic; substituted or unsubstituted aryl; or substituted or unsubstituted heteroaryl;
$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR_C$; $-C(=O)R_C$; $-CO_2R_C$; $-CN$; $-SCN$; $-SR_C$; $-SOR_C$; $-SO_2R_C$; $-NO_2$; $-N_3$; $-N(R_C)_2$; $-NHC(=O)R_C$; $-NR_CC(=O)N(R_C)_2$; $-OC(=O)OR_C$; $-OC(=O)R_C$; $-OC(=O)N(R_C)_2$; $-NR_CC(=O)OR_C$; or $-C(R_C)_3$; wherein each occurrence of $R_C$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted, heteroaryl; or $-CH_2CH_2C(=O)R_1$;
$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$_D$; —C(=O)R$_D$; —CO$_2$R$_D$; —CN; —SCN; —SR$_D$; —SOR$_D$; —SO$_2$R$_D$; —NO$_2$; —N$_3$; —N(R$_D$)$_2$; —NHC(=O)R$_D$; —NR$_C$C(=O)N(R$_D$)$_2$; —OC(=O)OR$_D$; —OC(=O)R$_D$; —OC(=O)N(R$_D$)$_2$; —NR$_C$C(=O)OR$_D$; or —C(R$_D$)$_3$; wherein each occurrence of R$_D$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; or —CH$_2$CH$_2$C(=O)R$_1$;

wherein at least one of R$_3$, R$_4$, or R$_7$ is —CH$_2$CH$_2$C(=O)R$_1$;

each occurrence of R$_5$ is independently selected from the group consisting of hydrogen and C$_1$-C$_6$ alkyl;

each occurrence of R$_6$ is independently selected from the group consisting of hydrogen and C$_1$-C$_6$ alkyl;

R$_7$ is hydrogen; halogen; substituted or unsubstituted, branched or unbranched acyl; substituted or unsubstituted aryl; substituted or unsubstituted heteroaryl; —OR$_G$; —C(=O)R$_G$; —CO$_2$R$_G$; —CN; —SCN; —SR$_G$; —SOR$_G$; —SO$_2$R$_G$; —NO$_2$; —N$_3$; —N(R$_G$)$_2$; —NHC(=O)R$_G$; —NR$_G$C(=O)N(R$_G$)$_2$; —OC(=O)OR$_G$; —OC(=O)R$_G$; —OC(=O)N(R$_G$)$_2$; —NR$_G$C(=O)OR$_G$; or —CH$_2$CH$_2$C(=O)R$_1$; wherein each occurrence of R$_G$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; an acyl moiety; alkoxy; aryloxy; alkylthio; arylthio; amino, alkylamino, dialkylamino, heteroaryloxy; or heteroarylthio moiety;

n is an integer between 1 and 10, inclusive; and wherein each instance of substituted refers to the replacement of one, two, three, or more of the hydrogen atoms of an aliphatic, heteroaliphatic, aryl, or heteroaryl group with one, two, three, or more substituents independently selected from the group consisting of aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CO(O)R$_x$; —OCO$_2$R$_x$; —OCON(R$_x$)$_2$; —N(R$_x$)$_2$; —N(R$_x$)$_2$; —S(O)$_2$R$_x$; and —NR$_x$(CO)R$_x$, wherein each occurrence of R$_x$ independently is selected from the group consisting of aliphatic, heteroaliphatic, aryl, heteroaryl, arylalkyl, and heteroarylalkyl and salts thereof.

2. The compound of claim 1, wherein

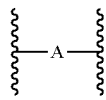

is selected from the group consisting of:

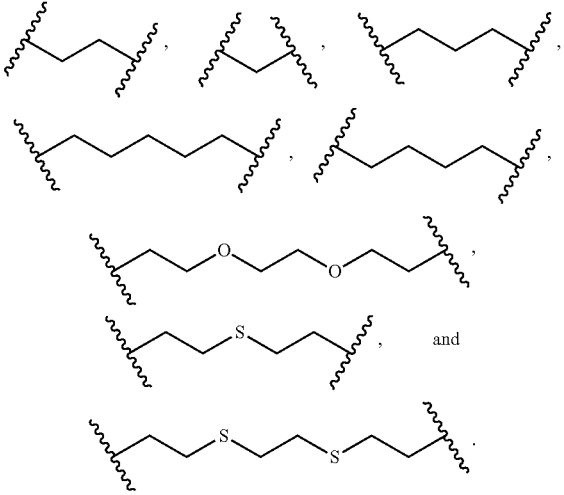

3. A compound of formula:

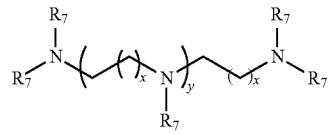

or a salt thereof;

wherein:
each occurrence of x is an integer between 1 and 10, inclusive;
y is an integer between 1 and 10, inclusive;
each occurrence of R$_7$ is independently hydrogen or —CH$_2$CH$_2$C(=O)R$_1$;
wherein at least one of R$_7$ is —CH$_2$CH$_2$C(=O)R$_1$;
each occurrence of R$_1$ is independently cyclic or acyclic, substituted or unsubstituted, branched or unbranched aliphatic; substituted or unsubstituted aryl; substituted or unsubstituted heteroaryl; —OR$_A$; —SR$_A$; or —NHR$_A$; wherein each occurrence of R$_A$ is independently cyclic or acyclic, substituted or unsubstituted, branched or unbranched C$_9$-C$_{16}$ aliphatic; substituted or unsubstituted aryl; or substituted or unsubstituted heteroaryl;
wherein each instance of substituted refers to the replacement of one, two, three, or more of the hydrogen atoms of an aliphatic, heteroaliphatic, aryl, or heteroaryl group with one, two, three, or more substituents independently selected from the group consisting of aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —OC(O)R$_x$; —OCO$_2$R$_x$; —OCON(R$_x$)$_2$; —N(R$_x$)$_2$; —S(O)$_2$R$_x$; and —NR$_x$(CO)R$_x$, wherein each occurrence of R$_x$ independently is selected from the group consisting of aliphatic, heteroaliphatic, aryl, heteroaryl, arylalkyl, and heteroarylalkyl.

4. The compound of claim 3, wherein each occurrence of R$_7$ is independently selected from the group consisting of:

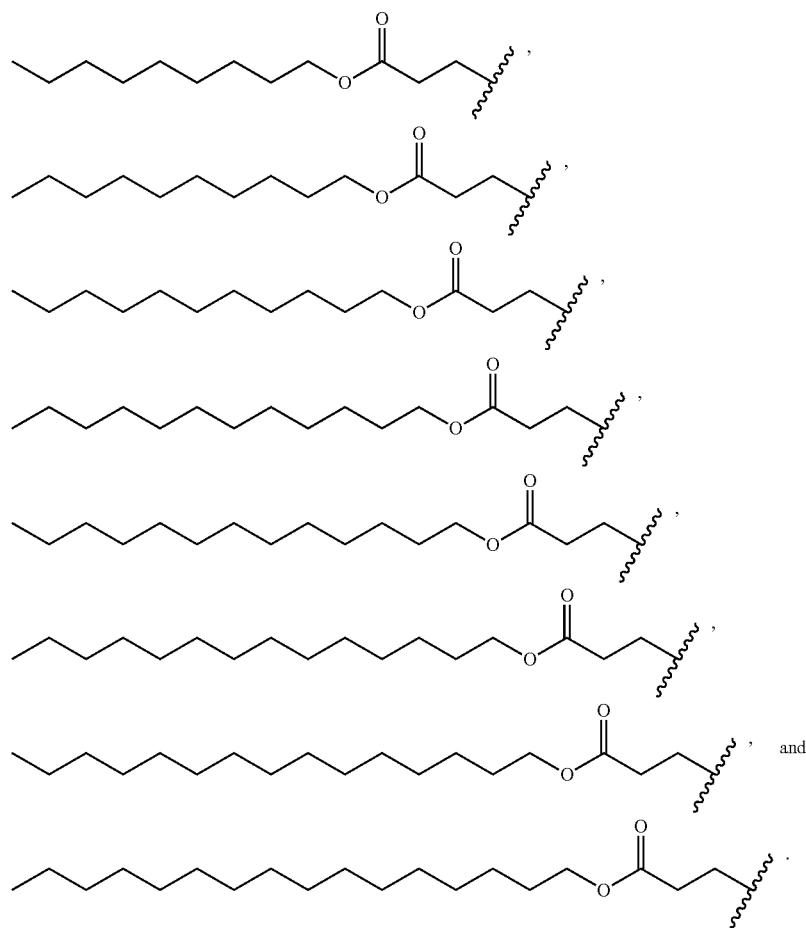
5. The compound of claim 3, wherein each occurrence of $R_7$ is independently selected from the group consisting of:
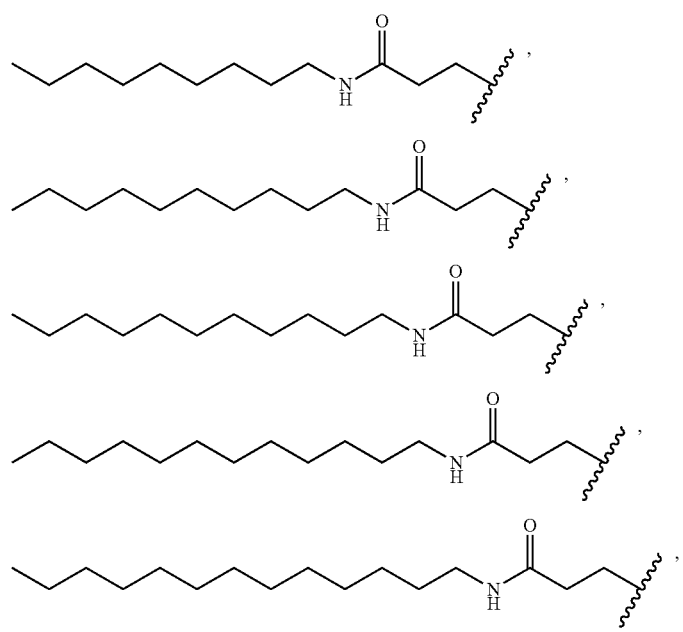

-continued

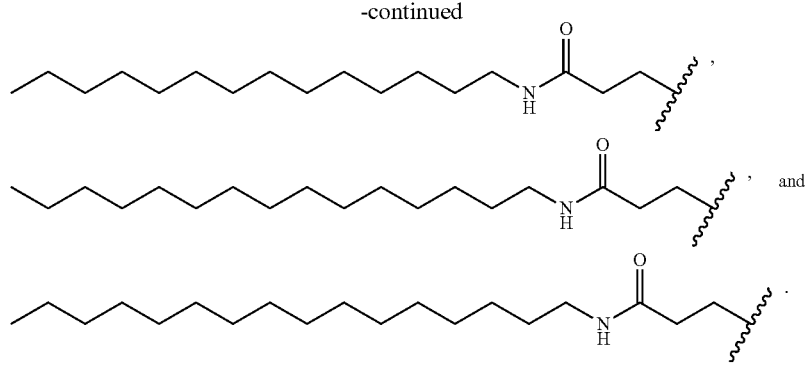

6. The compound of claim 3 of the formula:

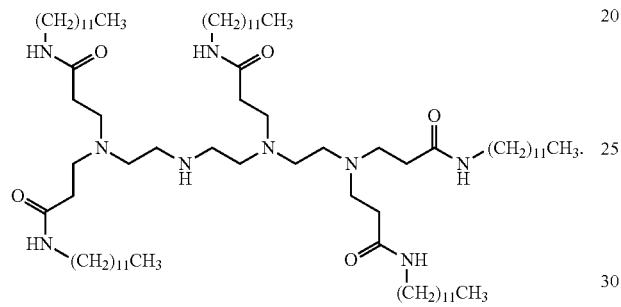

7. A compound of the formula:

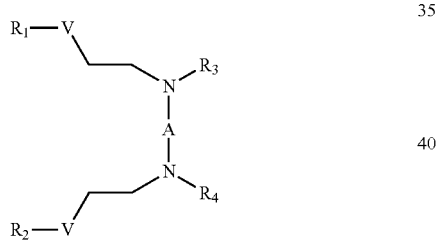

or a salt thereof;
wherein:
A is acyclic, substituted or unsubstituted, branched or unbranched heteroaliphatic;
V is C=O;
$R_1$ is cyclic or acyclic, substituted or unsubstituted, branched or unbranched aliphatic; substituted or unsubstituted aryl; substituted or unsubstituted heteroaryl; —$SR_A$; and —$NHR_A$; wherein each occurrence of $R_A$ is independently cyclic or acyclic, substituted or unsubstituted, branched or unbranched $C_9$-$C_{16}$ aliphatic; substituted or unsubstituted aryl; or substituted or unsubstituted heteroaryl;
$R_2$ is cyclic or acyclic, substituted or unsubstituted, branched or unbranched aliphatic; substituted or unsubstituted aryl; substituted or unsubstituted heteroaryl; —$SR_B$; or —$NHR_B$; wherein each occurrence of $R_B$ is independently a cyclic or acyclic, substituted or unsubstituted, branched or unbranched $C_9$-$C_{16}$ aliphatic; substituted or unsubstituted aryl; or substituted or unsubstituted heteroaryl;
$R_3$ is hydrogen; halogen; cyclic or acyclic substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR_C$; —$C(=O)R_C$; —$CO_2R_C$; —CN; —SCN; —$SR_C$; —$SOR_C$; —$NO_2$; —$N_3$; —$N(R_C)_2$; —$NHC(=O)R_C$; —$NR_CC(=O)N(R_C)_2$; —$OC(=O)OR_C$; —$OC(=O)R_c$; —$OC(=O)N(R_C)_2$; —$NR_CC(=O)OR_C$; or —$C(R_C)_3$; wherein each occurrence of $R_C$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; or substituted or unsubstituted heteroaryl;
$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR_D$; —$C(=O)R_D$; —$CO_2R_D$; —CN; —SCN; —$SR_D$; —$SOR_D$; —$SO_2R_D$; —$NO_2$; —$N_3$; —$N(R_D)_2$; —$NHC(=O)R_D$; —$NR_CC(=O)N(R_D)_2$; —$OC(=O)OR_D$; —$OC(=O)R_D$; —$OC(=O)N(R_D)_2$; —$NR_CC(=O)OR_D$; or —$C(R_D)_3$; wherein each occurrence of $R_D$ is independently a hydrogen; a protecting group; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; or substituted or unsubstituted heteroaryl;
provided that at least one of $R^3$ and $R^4$ is a substituted aliphatic;
wherein each instance of substituted refers to the replacement of one, two, three, or more of the hydrogen atoms of an aliphatic, heteroaliphatic, aryl, or heteroaryl group with one, two, three, or more substituents independently selected from the group consisting of aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$OC(O)R_x$; —$OCO_2R_x$; —$OCON(R_x)_2$; —$N(R_x)_2$; —$S(O)_2R_x$; and —$NR_x(CO)R_x$ wherein each occurrence of $R_x$ independently is selected from the group consisting of aliphatic, heteroaliphatic, aryl, heteroaryl, arylalkyl, and heteroarylalkyl.
8. The compound of claim 7, wherein
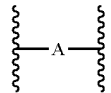
is selected from the group consisting of:
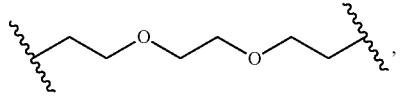,
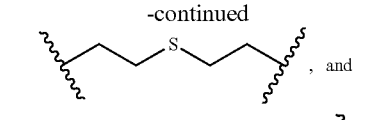, and
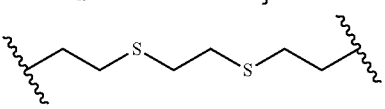.
9. The compound of claim 1, wherein
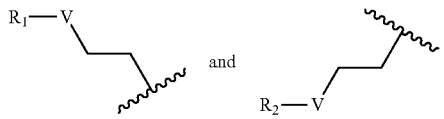
are independently selected from the group consisting of:
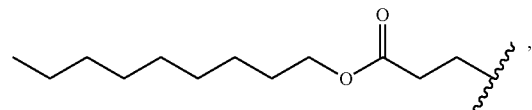,
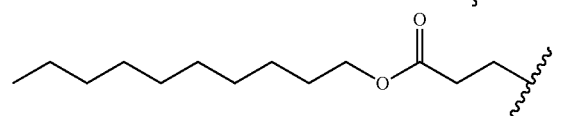,
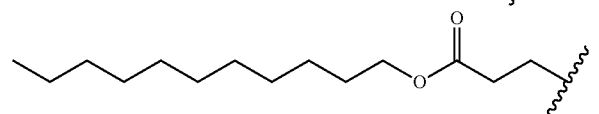,
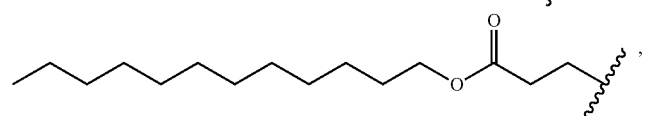,
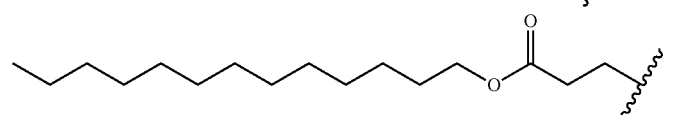,
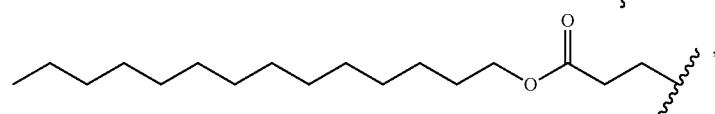,
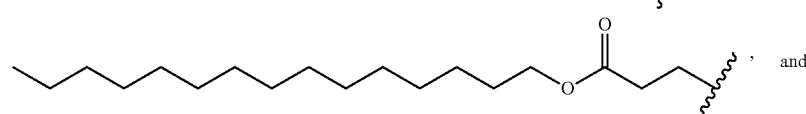, and
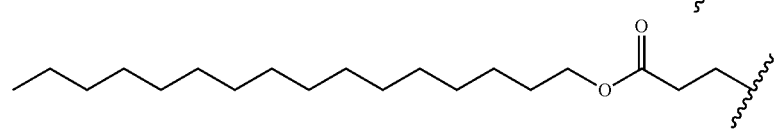.
10. The compound of claim 1, wherein
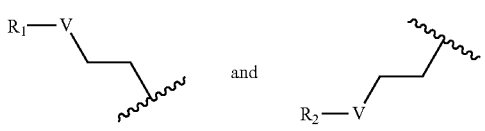
are independently selected from the group consisting of:

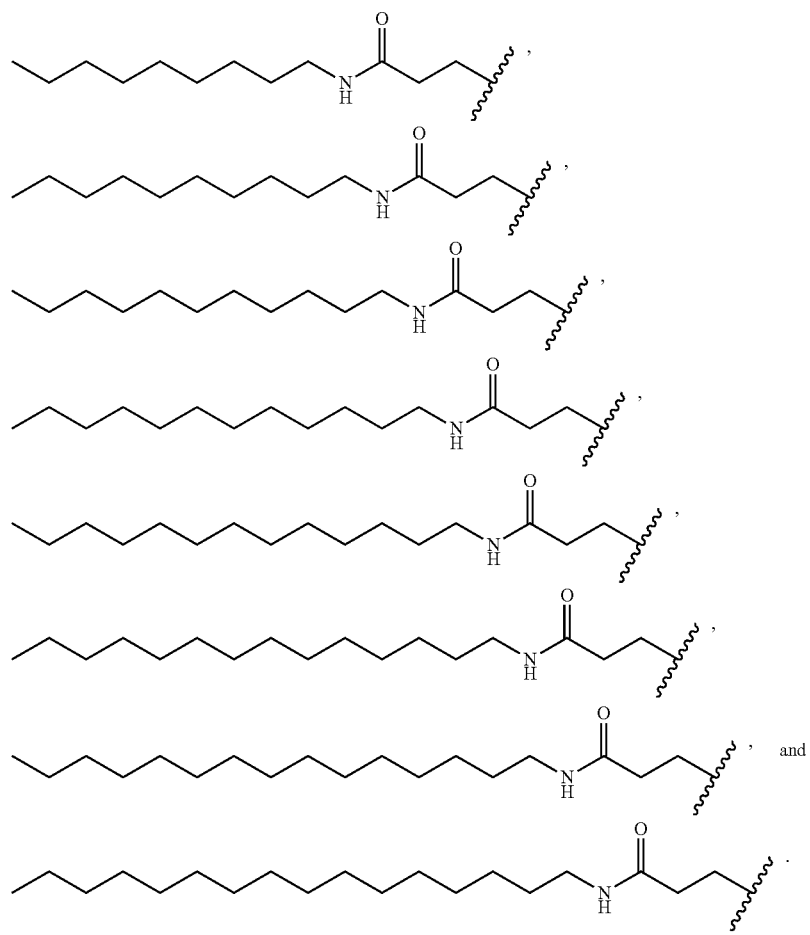
11. The compound of claim 3, wherein each occurrence of $R_7$ is independently selected from the group consisting of hydrogen,
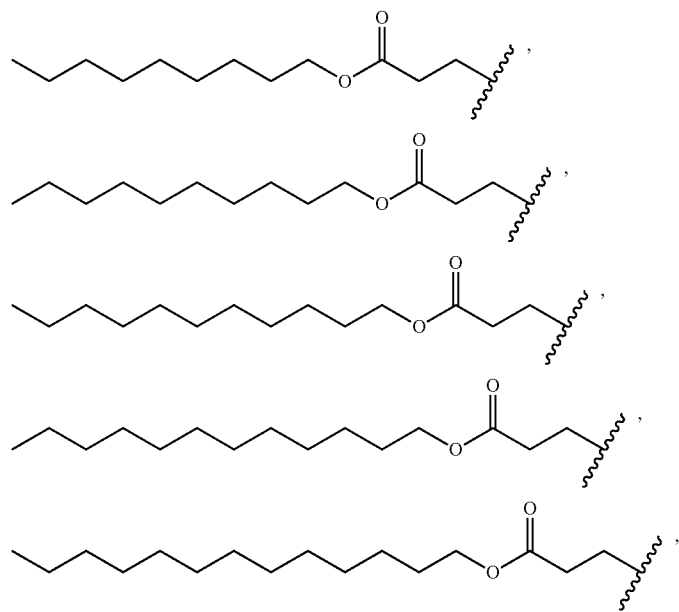

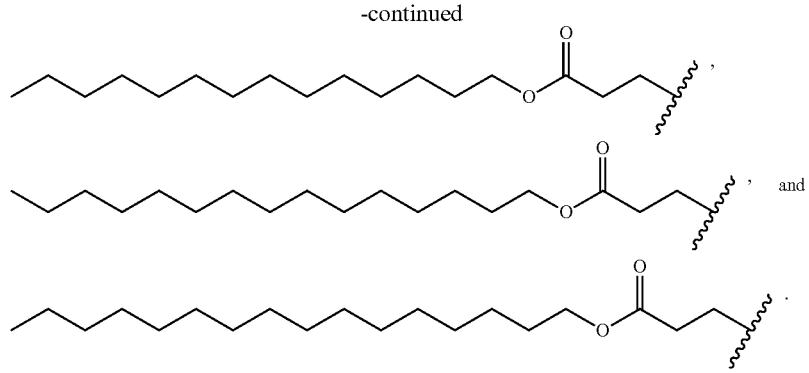
12. The compound of claim 3, wherein each occurrence of $R_7$ is independently selected from the group consisting of hydrogen,
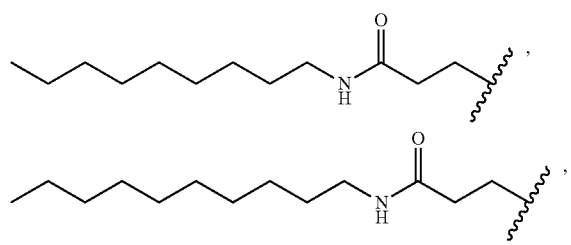
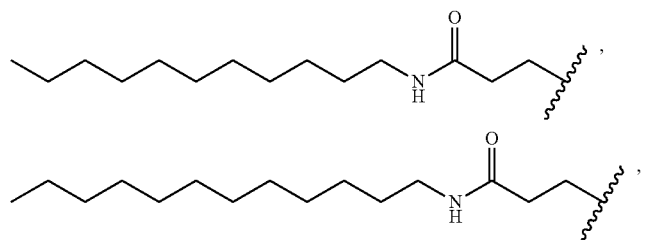
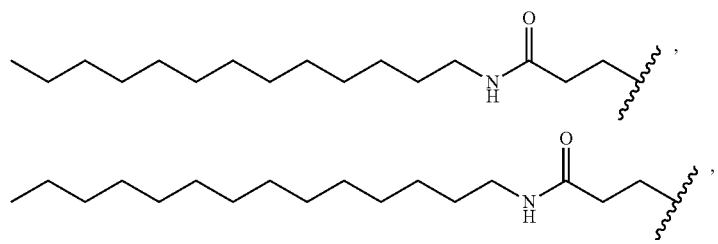
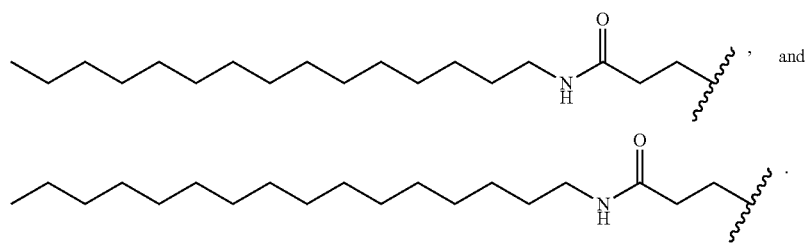

13. The compound of claim 3 selected from the group consisting of:
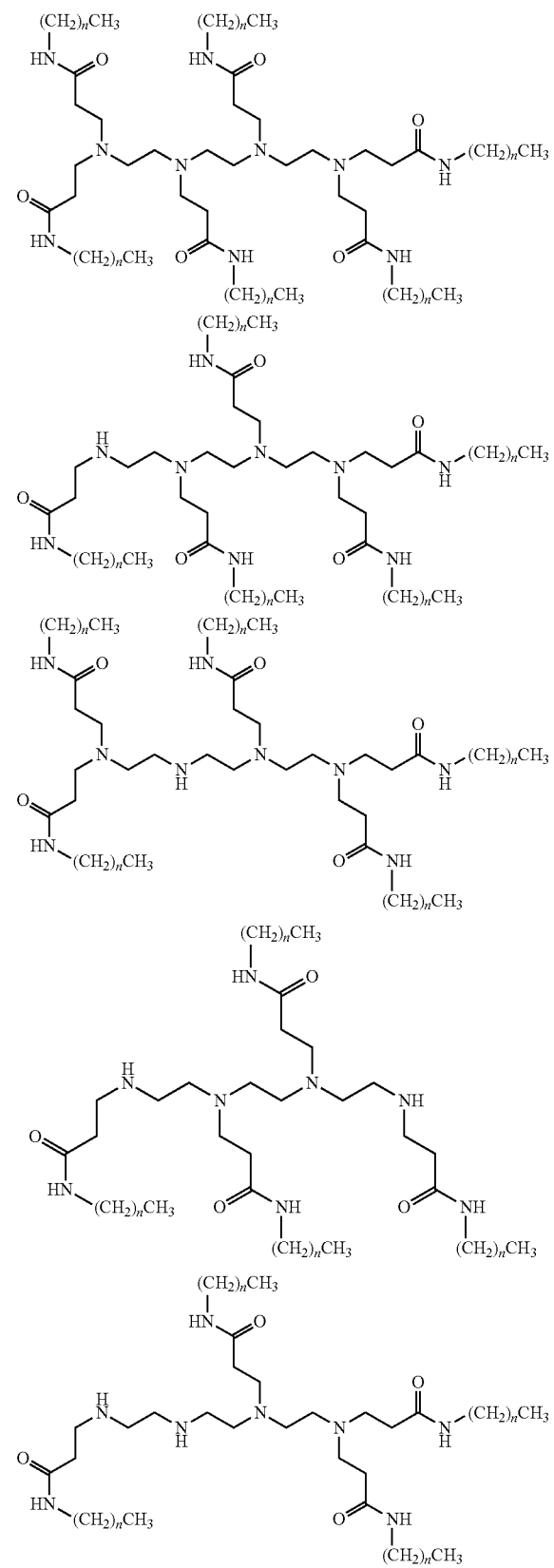
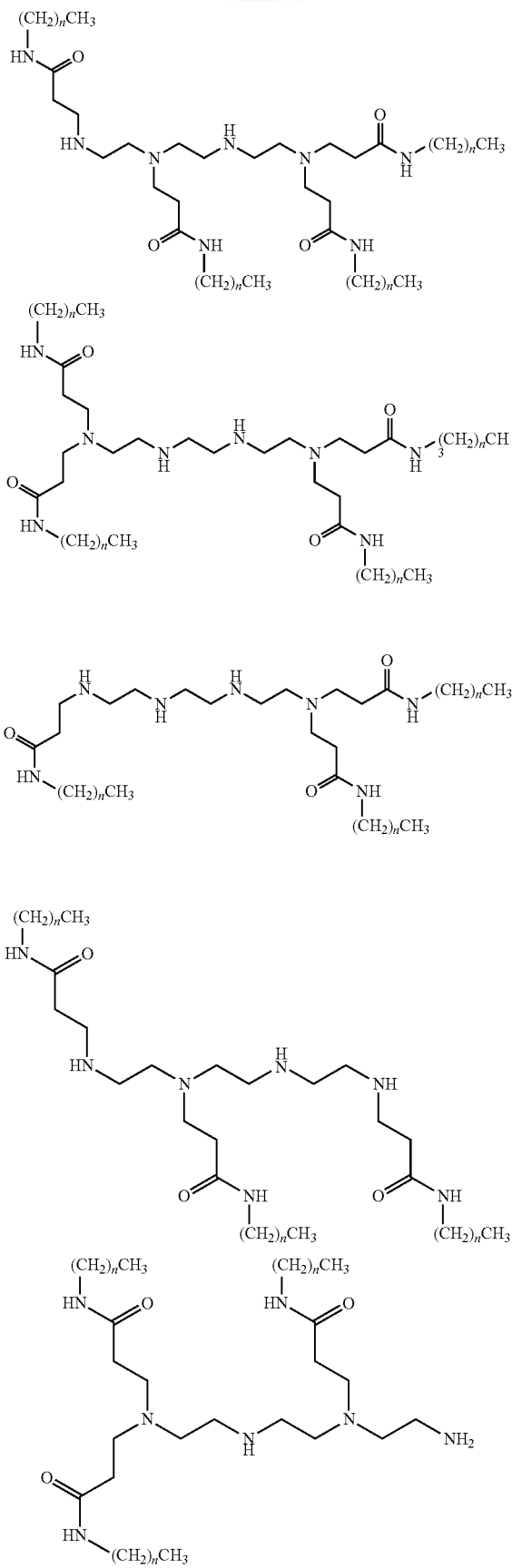

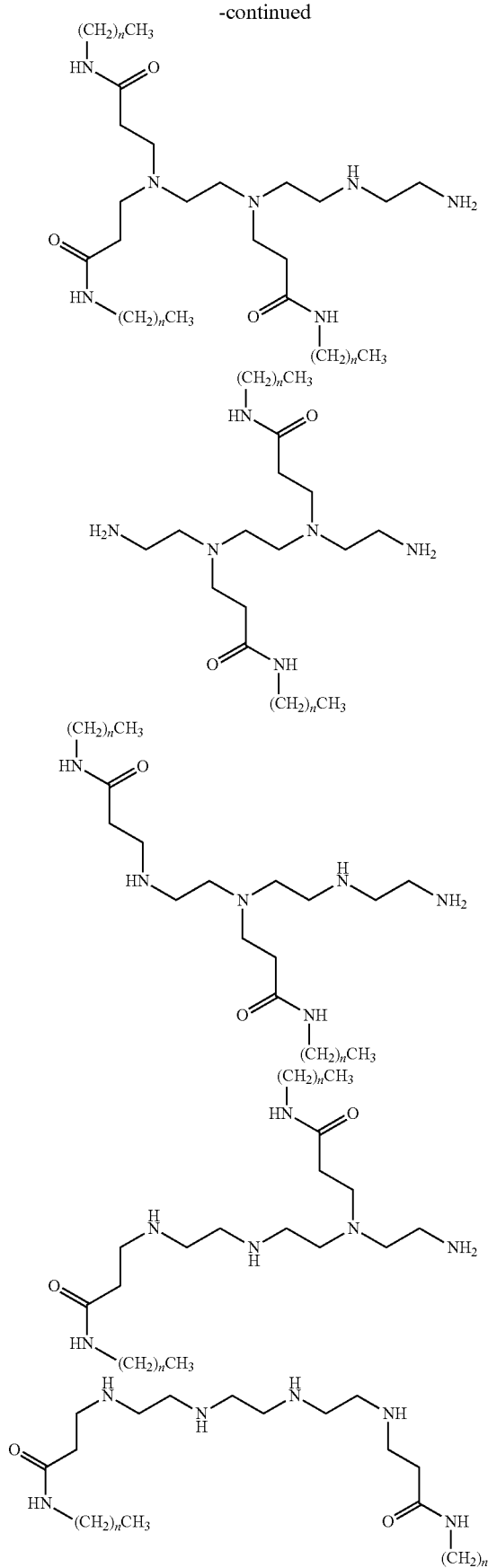
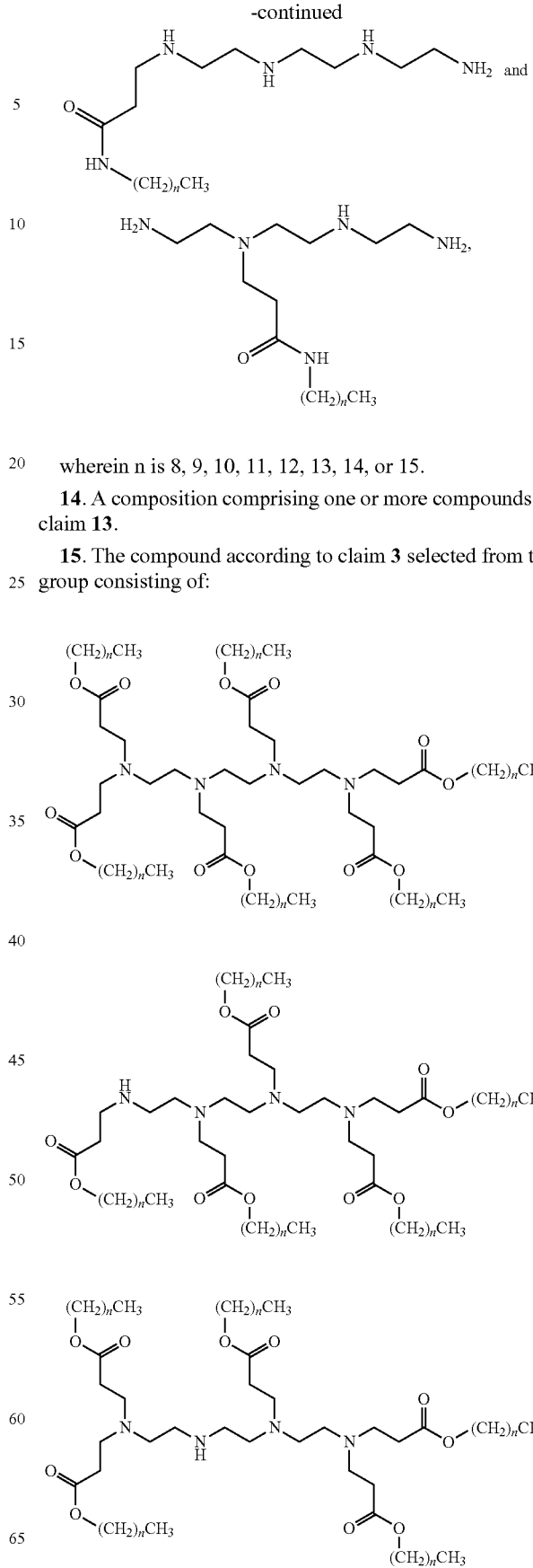
wherein n is 8, 9, 10, 11, 12, 13, 14, or 15.
14. A composition comprising one or more compounds of claim 13.
15. The compound according to claim 3 selected from the group consisting of:

219
-continued
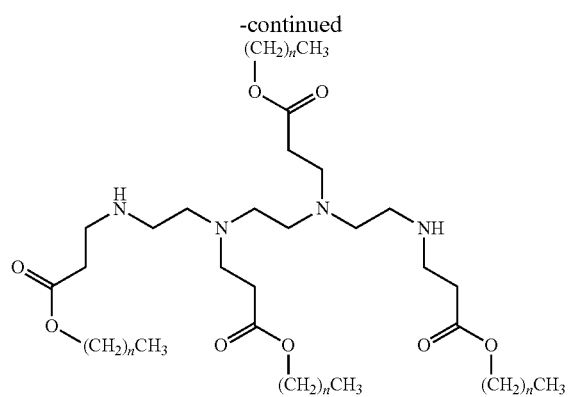
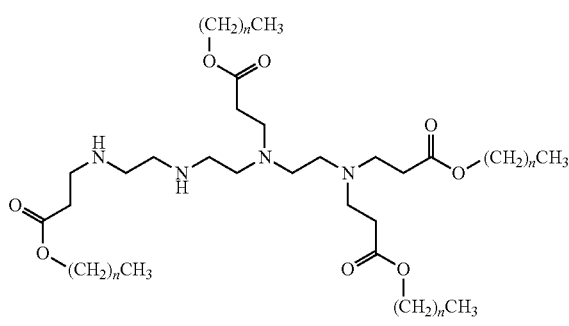
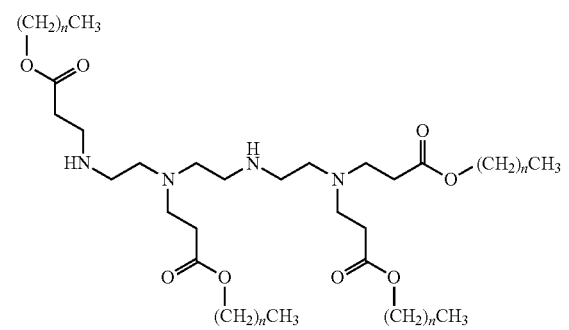
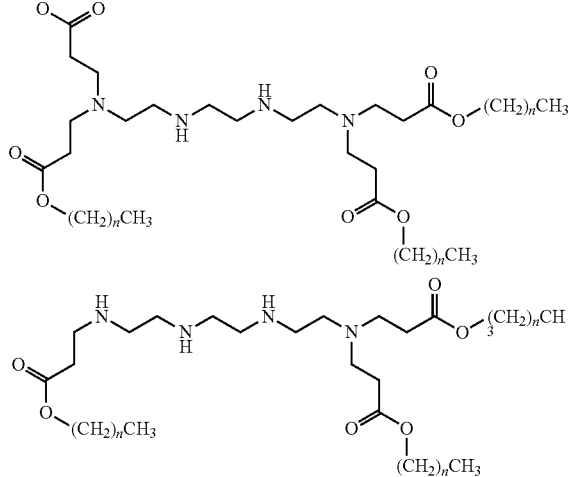
220
-continued
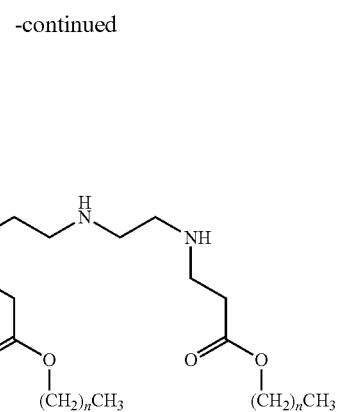
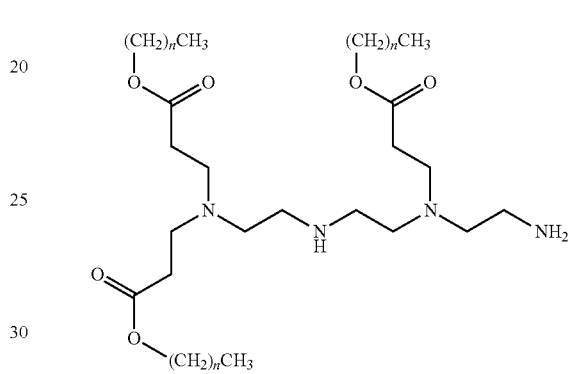
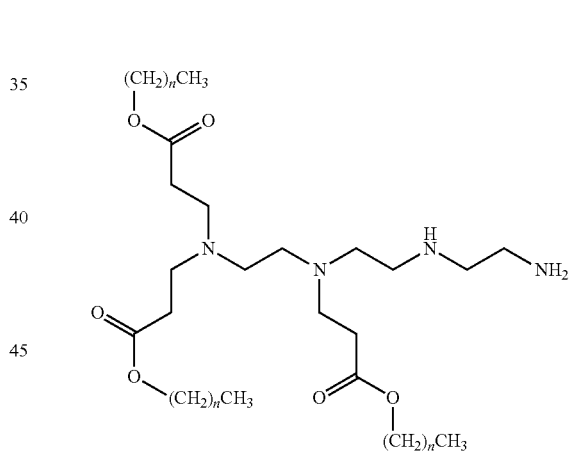
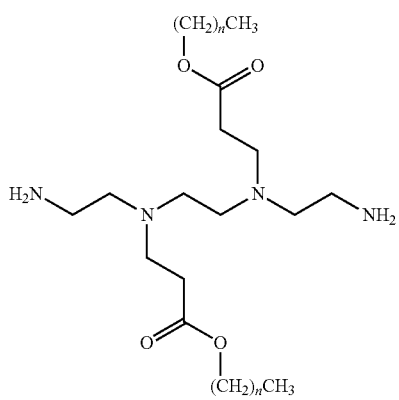

-continued
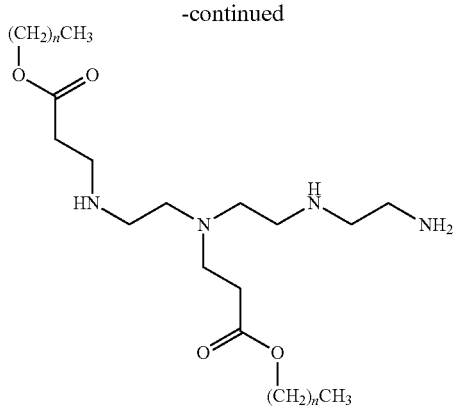
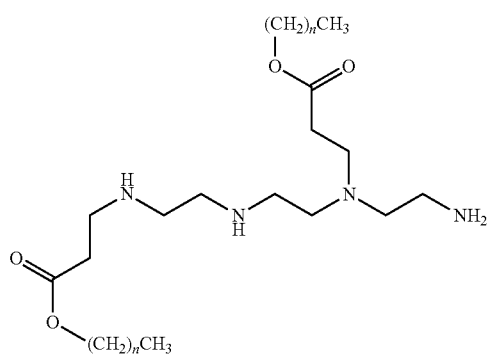
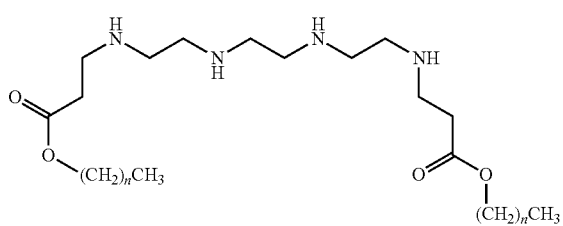
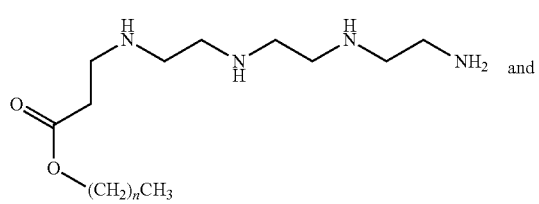
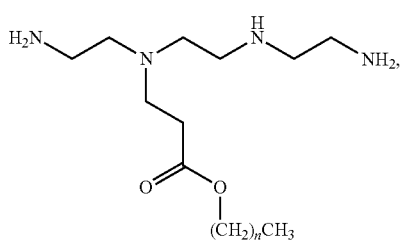
wherein n is 8, 9, 10, 11, 12, 13, 14, or 15.
16. A composition comprising one or more compounds of claim 15.
17. The compound of claim 13 selected from the group consisting of:
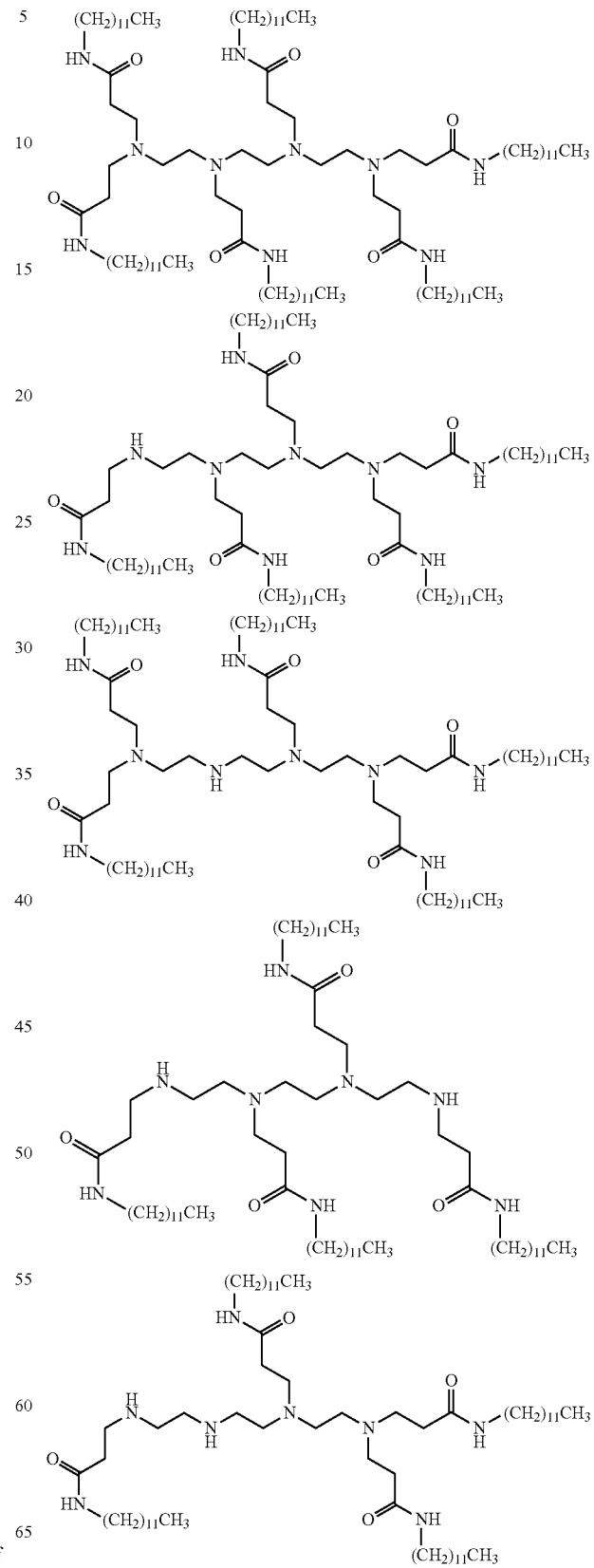

223
-continued
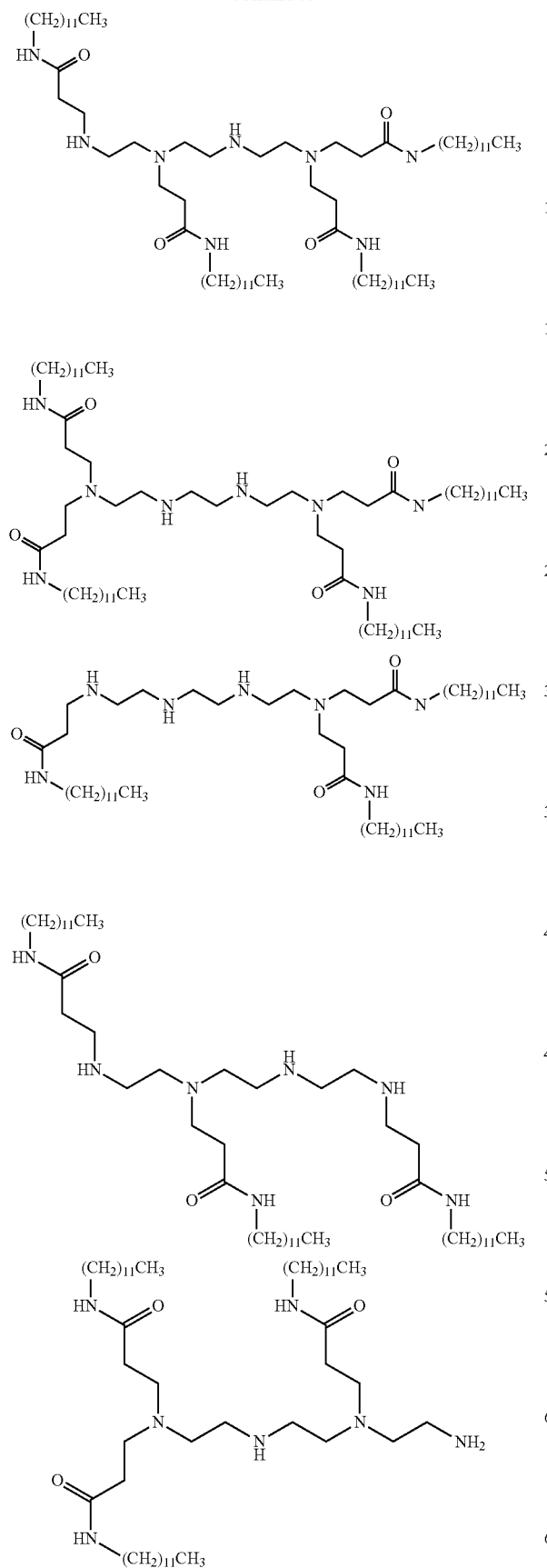
224
-continued
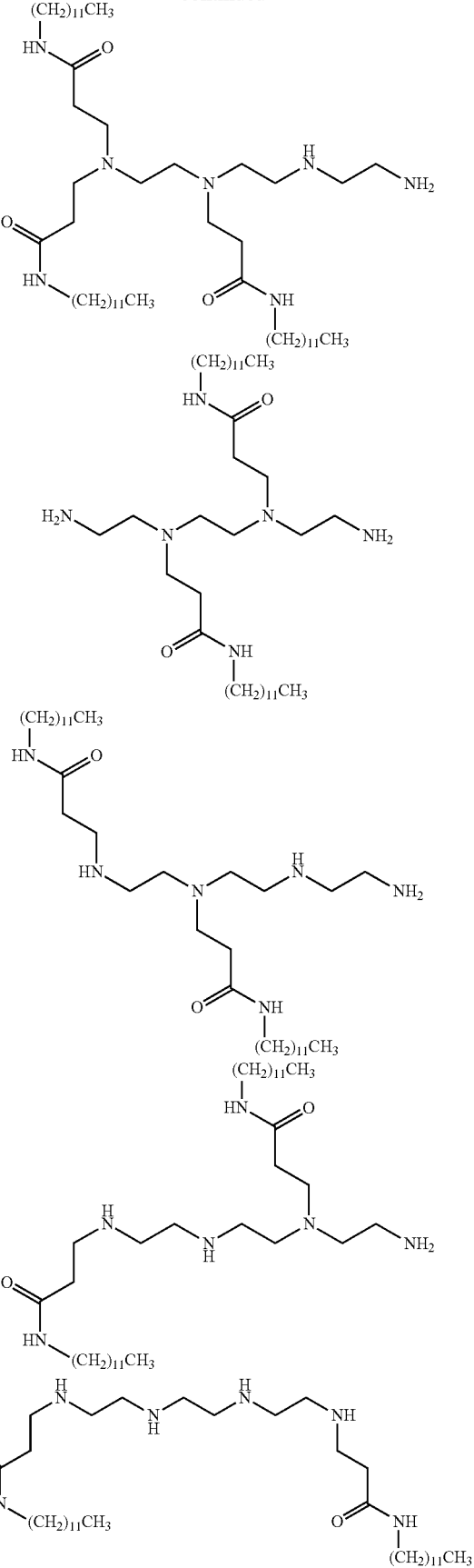

-continued

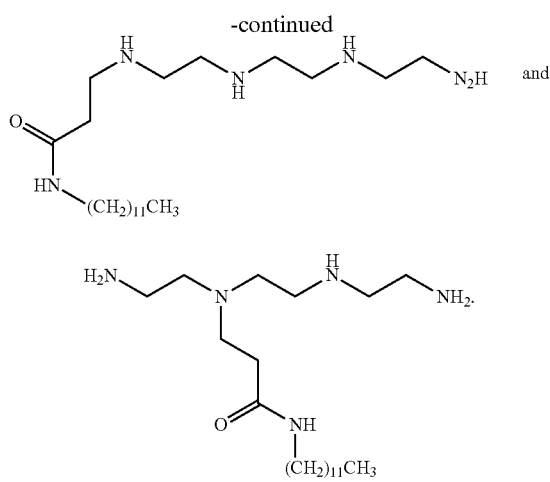

and

18. A composition comprising one or more compounds of claim 17.

19. The composition of claim 14 or 16 further comprising an agent to be delivered.

20. The composition of claim 19, wherein the agent is a polynucleotide, a protein, a peptide, or a small molecule.

21. The composition of claim 20, wherein the agent is a polynucleotide.

22. The composition of claim 21, wherein the polypeptide is DNA.

23. The composition of claim 21, wherein the polypeptide is RNA.

24. The composition of claim 21, wherein the polypeptide is siRNA, shRNA, antisense RNA, or a polypeptide encoding a protein or peptide.

25. The composition of claim 24, wherein the polypeptide is a polypeptide encoding a protein or peptide.

* * * * *

UNITED STATES PATENT AND TRADEMARK OFFICE
CERTIFICATE OF CORRECTION

PATENT NO. : 9,006,487 B2
APPLICATION NO. : 11/453222
DATED : April 14, 2015
INVENTOR(S) : Anderson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this
Nineteenth Day of January, 2016

Michelle K. Lee
*Director of the United States Patent and Trademark Office*

UNITED STATES PATENT AND TRADEMARK OFFICE
CERTIFICATE OF CORRECTION

Page 1 of 4

PATENT NO. : 9,006,487 B2
APPLICATION NO. : 11/453222
DATED : April 14, 2015
INVENTOR(S) : Anderson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1724 days.

In the Claims:

In claim 13, at column 216, lines 14-26, the formula:

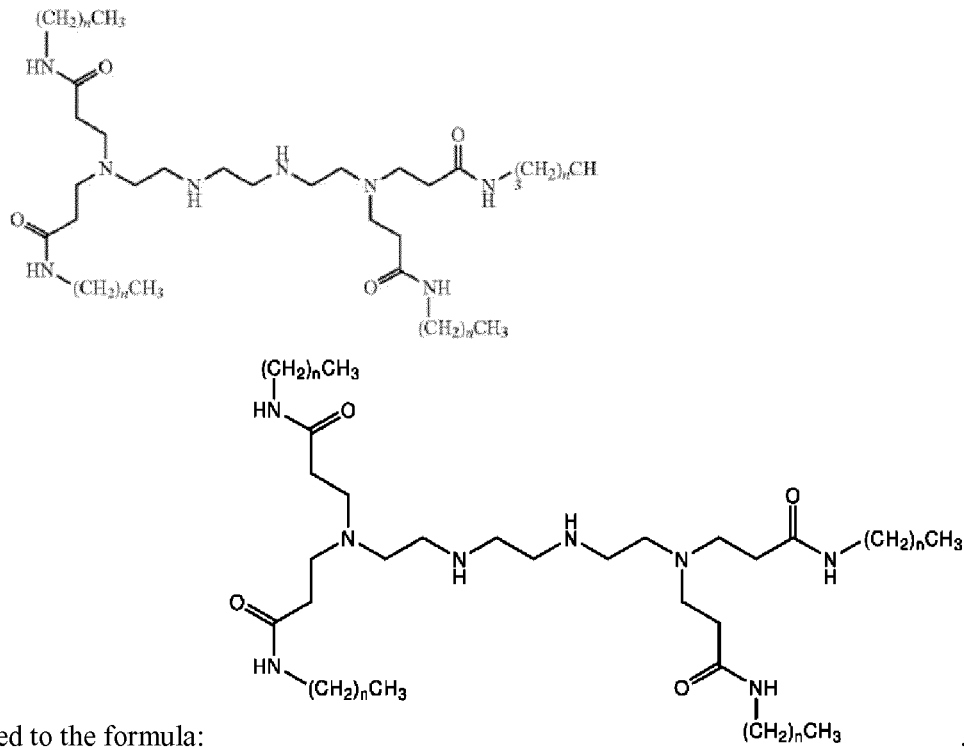

should be changed to the formula:

Signed and Sealed this
Twenty-sixth Day of April, 2016

Michelle K. Lee
*Director of the United States Patent and Trademark Office*

CERTIFICATE OF CORRECTION (continued)
U.S. Pat. No. 9,006,487 B2

In claim 15, at column 219, lines 58-66, the formula:

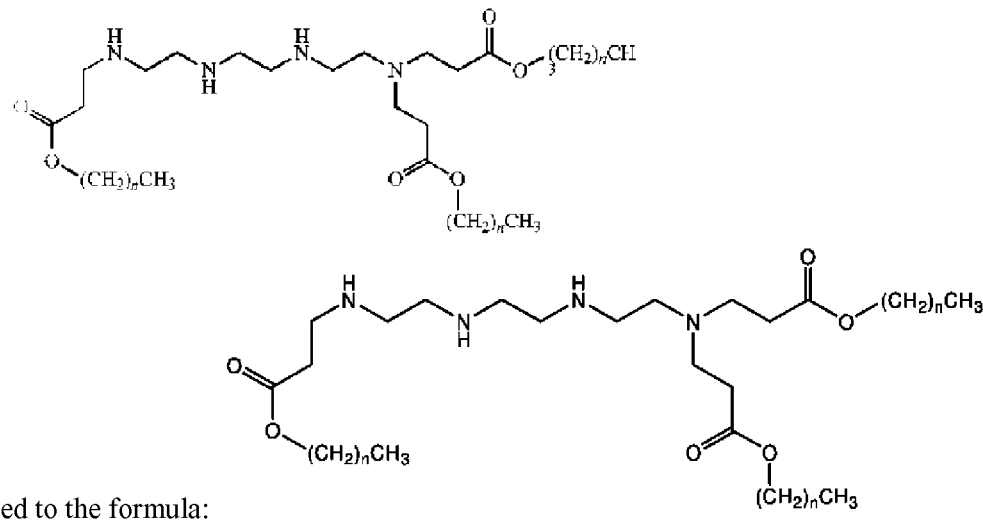

should be changed to the formula:

In claim 17, at column 223, lines 1-13, the formula:

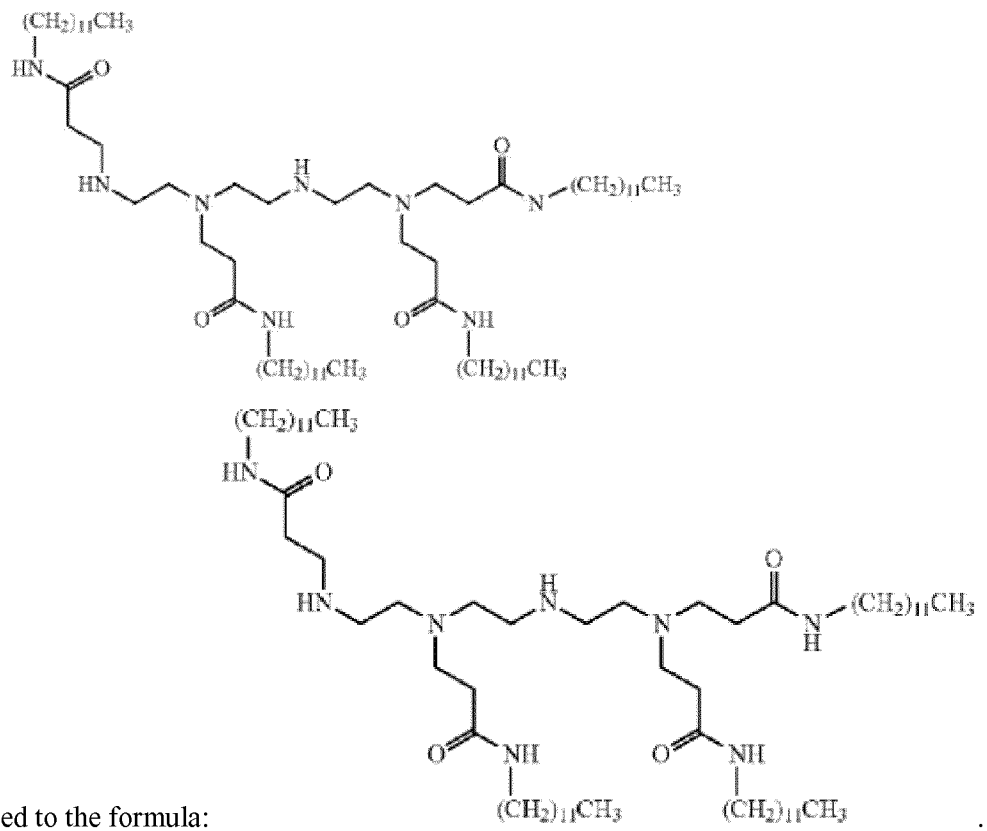

should be changed to the formula:

CERTIFICATE OF CORRECTION (continued)
U.S. Pat. No. 9,006,487 B2

In claim 17, at column 223, lines 16-28, the formula:

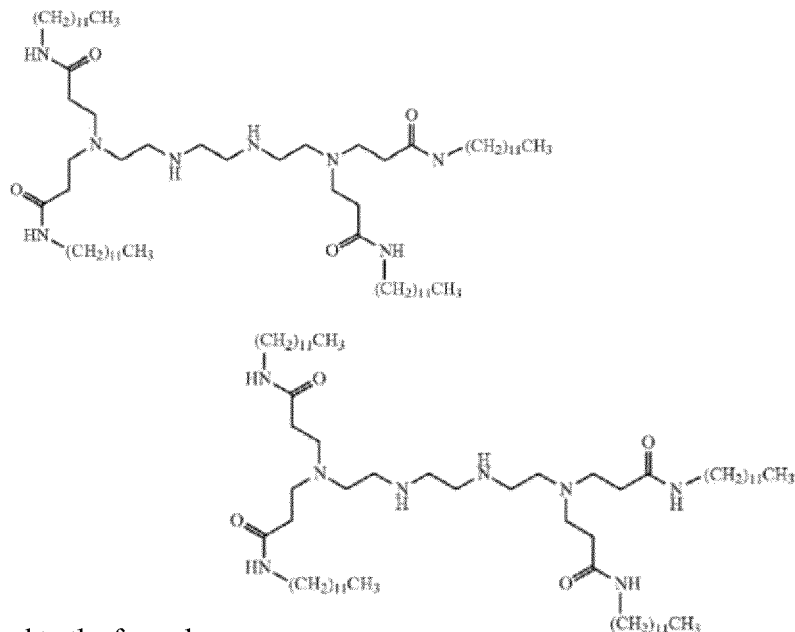

should be changed to the formula:

In claim 17, at column 223, lines 29-36, the formula:

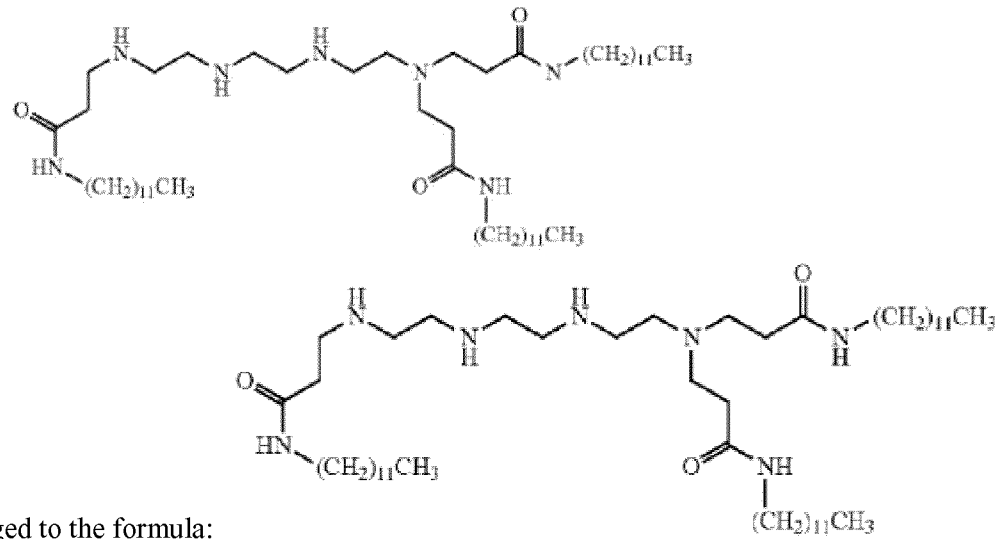

should be changed to the formula:

In claim 17, at column 225, lines 1-8, the formula:

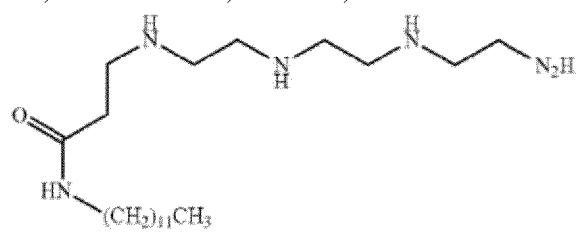

CERTIFICATE OF CORRECTION (continued)
U.S. Pat. No. 9,006,487 B2 should be changed to the formula: 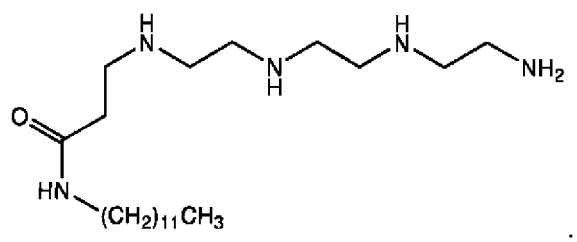 .